US009505782B2

(12) United States Patent
Grembecka et al.

(10) Patent No.: US 9,505,782 B2
(45) Date of Patent: Nov. 29, 2016

(54) COMPOSITIONS COMPRISING THIENOPYRIMIDINE AND THIENOPYRIDINE COMPOUNDS AND METHODS OF USE THEREOF

(71) Applicant: THE REGENTS OF THE UNIVERSITY OF MICHIGAN, Ann Arbor, MI (US)

(72) Inventors: Jolanta Grembecka, Ann Arbor, MI (US); Tomasz Cierpicki, Ann Arbor, MI (US); Dmitry Borkin, Ann Arbor, MI (US); Jay L. Hess, Ann Arbor, MI (US); Duxin Sun, Ann Arbor, MI (US); Xiaoqin Li, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/937,421

(22) Filed: Nov. 10, 2015

(65) Prior Publication Data
US 2016/0137665 A1 May 19, 2016

Related U.S. Application Data

(63) Continuation of application No. 14/203,233, filed on Mar. 10, 2014, now Pat. No. 9,216,993.

(60) Provisional application No. 61/780,099, filed on Mar. 13, 2013.

(51) Int. Cl.
*C07D 495/04* (2006.01)
*C07D 495/16* (2006.01)
*C07D 519/00* (2006.01)

(52) U.S. Cl.
CPC ........... *C07D 495/04* (2013.01); *C07D 495/16* (2013.01); *C07D 519/00* (2013.01)

(58) Field of Classification Search
CPC . C07D 495/04; C07D 495/16; C07D 519/00
See application file for complete search history.

(56) References Cited

U.S. PATENT DOCUMENTS

| 8,207,174 B2 | 6/2012 | Tasler et al. |
| 8,993,552 B2 | 3/2015 | Grembecka et al. |
| 9,216,993 B2 | 12/2015 | Grembecka et al. |
| 2003/0153556 A1* | 8/2003 | Levy .................. C07D 495/04 514/218 |
| 2011/0065690 A1 | 3/2011 | Grembecka et al. |
| 2014/0275070 A1 | 9/2014 | Grembecka et al. |

FOREIGN PATENT DOCUMENTS

WO WO-2013024291 A2 2/2013

OTHER PUBLICATIONS

Agarawal et al., "Menin molecular interactions: insights into normal functions and tumorigenesis," Horm Matab Res, 37(6):369-374 (2005).
Chen et al., "The tumor suppressor menin regulates hematopoiesis and myeloid transformation by influencing Hox gene expression," Proc Natl Acad Sci USA, 103(4): 1018-1023 (2006).
Cox et al., "Chromosomal aberration of the 11q23 locus in acute leukemia and frequency of MLL gene translocation: results in 378 adult patients," Am J Clin Pathol, 122(2): 298-306 (2004).
Eguchi et al., "The role of the MLL gene in infant leukemia," Int J Hematol, 78(5):390-401 (2003).
Marx, "Molecular genetics of multiple endocrine neoplasia types 1 and 2," Nat Rev Cancer, 5(5):367-75 (2005).
Slany, "When epigenetics kills: MLL fusion proteins in leukemia," Hematol Oncol, 23(1):1-9 (2005).
Sorensen et al., "Molecular rearrangements of the MLL gene are present in most cases of infant acute myeloid leukemia and are strongly correlated with monocytic or myelomonocytic phenotypes," J Clin Invest, 93(1):429-437 (1994).
Yokoyama et al., "The menin tumor suppressor protein is an essential oncogenic cofactor for MLL-associated leukemogenesis," Cell, 123(2), pp. 207-218 (2005).
U.S. Appl. No. 14/773,686, filed Sep. 8, 2015.
International search report and written opinion dated Aug. 28, 2014 for PCT/US2014/022750.
Notice of allowance dated Sep. 10, 2015 for U.S. Appl. No. 14/203,233.
Office action dated Apr. 16, 2015 for U.S. Appl. No. 14/203,233.

* cited by examiner

*Primary Examiner* — Valerie Rodriguez-Garcia
(74) *Attorney, Agent, or Firm* — Casimir Jones SC; David W. Staple

(57) ABSTRACT

The present disclosure relates generally to thienopyrimidine and thienopyridine compounds and methods of use thereof. In particular embodiments, the present disclosure provides compositions comprising thienopyrimidine and thienopyridine compounds of Formula 2:

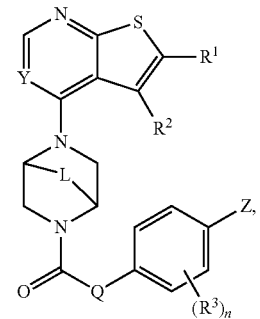

and methods of use to inhibit the interaction of menin with MLL1, MLL2 and MLL-fusion oncoproteins.

26 Claims, 18 Drawing Sheets

MLL-AF9 BMC

Compound 108

Compound 44

Compound 175

Compound 206

Compound 175

COMPOSITIONS COMPRISING THIENOPYRIMIDINE AND THIENOPYRIDINE COMPOUNDS AND METHODS OF USE THEREOF

The present application is a continuation of U.S. patent application Ser. No. 14/203,233, filed Mar. 10, 2014, now U.S. Pat. No. 9,216,993, which claims priority to U.S. Provisional Patent Application Ser. No. 61/780,099, filed Mar. 13, 2013, each of which are herein incorporated by reference in their entirety.

STATEMENT REGARDING FEDERALLY SPONSORED RESEARCH OR DEVELOPMENT

This invention was made with government support under R01 CA160467-01 awarded by the National Institutes of Health. The government has certain rights in the invention.

FIELD OF THE INVENTION

The present invention relates generally to thienopyrimidine and thienopyridine class compounds and methods of use thereof. In particular embodiments, the present invention provides compositions comprising thienopyrimidine and thienopyridine class compounds and methods of use to inhibit the interaction of menin with MLL1, MLL2 and MLL-fusion oncoproteins (e.g., for the treatment of leukemia, solid cancers and other diseases dependent on activity of MLL1 and MLL2 or menin).

BACKGROUND OF THE INVENTION

Chromosomal translocations that affect the proto-oncogene Mixed Lineage Leukemia (MLL) occur in aggressive human acute leukemias, both in children and adults (Sorensen et al., J Clin Invest., 1994.93(1): p. 429-37., Cox, et al., Am J Clin Pathol., 2004. 122(2): p. 298-306., herein incorporated by reference in their entireties). They are particularly common in infants with acute myeloblastic leukemia (AML) and acute lymphoblastic leukemia (ALL) and constitute up to 80% of all infant acute leukemia cases. Fusion of MLL with one of 60 partner genes forms a chimeric oncogene which upregulates HOX genes resulting in a blockage of blood cell differentiation that ultimately leads to acute leukemia (Eguchi et al. Int J Hematol., 2003. 78(5): p. 390-401., herein incorporated by reference in its entirety). Patients with leukemias harboring MLL translocations have a very poor prognosis (35% five year survival) and it is clear that novel therapeutic strategies are urgently needed to treat these leukemias (Slany. Hematol Oncol., 2005. 23(1): p. 1-9., herein incorporated by reference in its entirety). Menin is a critical cofactor in MLL-associated leukemias. Menin is a tumor-suppressor protein encoded by the Multiple Endocrine Neoplasia (MEN) gene. Menin is a ubiquitously expressed nuclear protein that is engaged in interactions with a cohort of transcription factors, chromatin modifying proteins, and DNA processing and repair proteins (Agarwal et al. Horm Metab Res., 2005. 37(6): p. 369-74., herein incorporated by reference in its entirety). The biological function of menin remains unclear and is context dependent. It functions as a tumor suppressor in endocrine organs (Marx. Nat Rev Cancer., 2005. 5(5): p. 367-75., herein incorporated by reference in its entirety) but has an oncogenic role in myeloid cells (Yokoyama et al., Cell., 2005.123(2): p. 207-18., herein incorporated by reference in its entirety). Association of menin with oncogenic MLL fusion proteins constitutively up-regulates expression of HOX genes and impairs proliferation and differentiation of hematopoietic cells leading to leukemia development. Myeloid cells transformed with oncogenic MLL-AF9 fusion protein require menin for efficient proliferation (Chen et al., Proc Natl Acad Sci USA., 2006.103(4): p. 1018-23., herein incorporated by reference in its entirety). Menin is also required to maintain oncogenic transformation induced by other MLL translocations, including MLL-ENL, MLL-GAS7 and MLL-AF6 (Yokoyama et al., Cell., 2005.123(2): p. 207-18., herein incorporated by reference in its entirety), demonstrating that menin functions as a general oncogenic cofactor in MLL-related leukemias and implies the interaction of menin with MLL fusions and MLL is a valuable target for molecular therapy. The leukemogenic activity of MLL fusion oncoproteins is dependent on association with menin. Therefore, selective targeting of this interaction could provide an attractive therapeutic approach to develop novel drugs for leukemias with translocations of MLL gene and other leukemias with upregulation of HOX genes.

SUMMARY OF THE INVENTION

In some embodiments, the present invention provides compositions for the treatment of leukemia which inhibit binding of one or more MLL fusion proteins to menin and/or MLL wild type to menin. In some embodiments, the composition comprises a thienopyrimidine and thienopyridine class compounds.

In some embodiments, the thienopyrimidine and thienopyridine class compound is of the general formula:

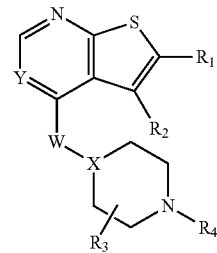

wherein X, Y, W, R1, R2, R3, and R4 are independently selected from any of the respective substituents described herein or depicted in any of Tables 1-8, in any combination. For example, in some embodiments, $R_1$-$R_4$ each independently consist of or comprise: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., mono-, di-, tetra-,penta- and trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, alkyl-substituted cycloalkyl group, cycloalkoxy group, cyclolkylamine, etc.), a halogen (e.g., F, Cl, Br, I, and At), a ketone, a carbocyclic ring, an aromatic ring (e.g., heteroaryl), a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring (e.g., heteroaryl), a multi-ring system comprising a combination of elements selected from aromatic rings, cycloalkane, heterocyclic rings, alkyl chains, and suitable C—, N—, O—, S—, and/or halogen-containing substituents (e.g., substituted heteroaryl), or a hydrogen bond donor or a hydrogen bond acceptor, and/or combinations thereof.

In some embodiments, the thienopyrimidine and thienopyridine class compound is of a general formula of:

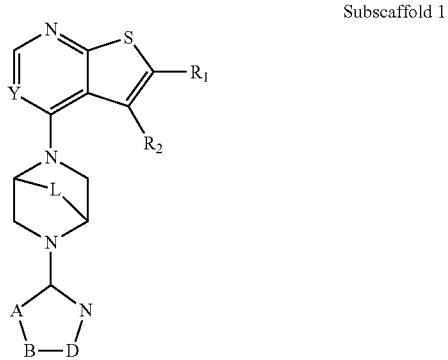

Subscaffold 1 wherein R1 and R2 both independently comprise or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., mono-, di-, tetra-,penta- and trihaloethane (e.g., trifluoroethane), halomethane (e.g., fluoromethane), dihalomethane (e.g., difluoromethane), trihalomethane (e.g., trifluoromethane), 1-trihalo, 2-halo-ethane, trihalobutane, etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, alkyl-substituted cycloalkyl group, cycloalkoxy group, cyclolkylamine, etc.), a halogen (e.g., F, Cl, Br, I, and At), a ketone, a carbocyclic ring, an aromatic ring (e.g., heteroaryl), a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring (e.g., heteroaryl), a multi-ring system comprising a combination of elements selected from aromatic rings, cycloalkane, heterocyclic rings, alkyl chains, and suitable C—, N—, O—, S—, and/or halogen-containing substituents (e.g., substituted heteroaryl), or a hydrogen bond donor or a hydrogen bond acceptor, and/or combinations thereof; and wherein A, B, and D each independently comprise or consist of: C, N, O, or S; wherein when one or more of A, B, and/or D comprise O or S, there is no further substitution at that respective position; wherein when one or more of A, B, and/or D comprise N or C that respective position is optionally substituted, wherein the substituent at that respective position comprises or consists of: alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor, a heterocyclic non-aromatic ring (e.g., comprising carbon and one or more nitrogen, oxygen and/or sulfur members), carbocyclic or heterocyclic aromatic ring (e.g., heteroaryl) comprising carbon atoms and one or more nitrogen, oxygen and/or sulfur members fused to another aromatic ring, a multi-ring system comprising a combination of elements selected from aromatic rings (e.g., heteroaryl), cycloalkane, heterocyclic rings, alkyl chains, and suitable C—, N—, O—, S—, and/or halogen-containing substituents, or a hydrogen bond donor or a hydrogen bond acceptor, and/or combinations thereof; and wherein Y is N or C, and wherein when Y is C the Y position may be substituted with R$^a$, with R$^a$ consisting of or comprising an H, alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl ($(CH_2)_2CF_3$), trihalobutyl group (e.g., trifluorobutyl group ($(CH_2)_3CF_3$)), 1-trifluoro, 2-ethanol, alcohol (e.g., $(CH_2)_nOH$, wherein n=0-10), alkoxy (e.g., $(CH_2)_n$—OR, wherein n=0-10, wherein R is alkyl, $(CH_2)_n$-aryl, $(CH_2)_n$-aromatic, $(CH_2)_n$-heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, heterocycle, aromatic, combinations thereof, etc.; and wherein L is present or absent and comprises alkylene (e.g. methylene, —$CH_2$—, ethylene, —$CH_2$—$CH_2$—, etc) or oxalkylene (e.g. —O—, —$CH_2$—O—$CH_2$) groups.

In some embodiments, R1 of subscaffold 1 is selected from an alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group, See, e.g., compound 1), trihalopropyl (e.g., trifluoropropyl ($(CH_2)_2CF_3$), trihalobutyl group (e.g., trifluorobutyl group ($(CH_2)_3CF_3$)), trihaloisopropyl (e.g., trifluoroisopropyl (See, e.g., compound 38)), 1-fluoro, 2-trifluoro, ethane (See, e.g., compound 21), 1-trifluoro, 2-ethanol (See, e.g., compound 23)), alcohol, amino (e.g., alkyl amine, amino alkyl, etc.), cyano, sulfonyl, methoxy, aldehyde, heterocycle, aromatic, combinations thereof, etc.

In some embodiments, R2 of subscaffold 1 is selected from a halogen (e.g., Cl, F, Br, I), alkyl (e.g., branched, straight chain (e.g., methyl), cycloalkyl, heteroalkyl, alkyl-substituted aryl, substituted alkyl (e.g., halo-substituted alkyl, alcohol, amino, etc.), OH, SH, $NH_2$, etc.

In some embodiments, A of subscaffold 1 is selected from C, N, O, or S; wherein when A is O or S, there is no further substitution at that respective position; wherein, when A is N, it is optionally substituted with one substituent that comprises or consists of: alkyl (e.g., branched (e.g., isopropyl), straight chain (e.g., methyl, propyl), cycloalkyl (e.g., cyclopropane, cyclopentante, cyclohexane)), heteroalkyl (e.g., methyl propyl ether ($CH_2O(CH_2)_2CH_3$), methylamine ($CH_2NH_2$), aminomethyl ($CH_2NH$), etc.), alkyl-substituted aryl (e.g., methylbenzene, ethylbenzene, propylbenzene, butylbenzene, etc.), substituted alkyl (e.g., halo-substituted alkyl (e.g., trihalomethyl group (e.g., trifluoromethyl group), trihaloethyl group (e.g., trifluoroethyl group), trihalopropyl (e.g., trifluoropropyl), trihalobutyl group (e.g., trifluorobutyl group), trihaloisopropyl (e.g., trifluoroisopropyl), 1-fluoro, 2-trifluoro, ethane, trifluoroethanol), alcohol-substituted alkyl, amino-substituted alkyl, substituted cycloalkyl, substituted aromatic ring (e.g., propylbenzene, 1-ethyl-4methoxybenzene, 1-propyl-4-methoxy-benzene, etc.)), alcohol, amino, and/or combinations thereof; wherein when A is C, it is optionally substituted with one or two substituents that comprises or consists of: alkyl (e.g., branched (e.g., isopropyl), straight chain (e.g., methyl, propyl), cycloalkyl (e.g., cyclopropane, cyclopentante, cyclohexane)), heteroalkyl (e.g., methyl propyl ether, methylamino, etc.), alkyl-substituted aryl (e.g., methylbenzene, ethylbenzene, propylbenzene, butylbenzene, etc.), substituted alkyl (e.g., halo-substituted alkyl (e.g., trihalomethyl group (e.g., trifluoromethyl group), trihaloethyl group (e.g., trifluoroethyl group), trihalopropyl (e.g., trifluoropropyl), trihalobutyl group (e.g., trifluorobutyl group), trihaloisopropyl (e.g., trifluoroisopropyl), 1-fluoro, 2-trifluoro, ethane, trifluoroethanol), alcohol-substituted alkyl, amino-substituted alkyl, substituted cycloalkyl, substituted aromatic ring (e.g., propylbenzene, 1-ethyl-4methoxybenzene, 1-propyl-4-methoxy-benzene, etc.)), alcohol, amino, and/or combinations thereof.

In some embodiments, B of subscaffold 1 is selected from C, N, O, or S; wherein when B is O or S, there is no further substitution at that respective position; wherein, when B is N, it is optionally substituted with one substituent that comprises or consists of: alkyl (e.g., branched (e.g., isopropyl), straight chain (e.g., methyl, propyl), cycloalkyl (e.g., cyclopropane, cyclopentante, cyclohexane)), heteroalkyl (e.g., methyl propyl ether, methylamino, etc.), alkyl-substituted aryl (e.g., methylbenzene, ethylbenzene, propylbenzene, butylbenzene, etc.), substituted alkyl (e.g., halo-substituted alkyl (e.g., trihalomethyl group (e.g., trifluoromethyl group), trihaloethyl group (e.g., trifluoroethyl group), trihalopropyl (e.g., trifluoropropyl), trihalobutyl group (e.g., trifluorobutyl group), trihaloisopropyl (e.g., trifluoroisopropyl), 1-fluoro, 2-trifluoro, ethane, trifluoroethanol), alcohol-substituted alkyl, amino-substituted alkyl, substituted cycloalkyl, substituted aromatic ring (e.g., propylbenzene, 1-ethyl-4-methoxybenzene, 1-propyl-4-methoxy-benzene, etc.)), alcohol, amino, and/or combinations thereof; wherein when B is C, it is optionally substituted with one or two substituents that comprises or consists of: alkyl (e.g., branched (e.g., isopropyl), straight chain (e.g., methyl, propyl), cycloalkyl (e.g., cyclopropane, cyclopentante, cyclohexane)), alkyl-substituted cycloalkyl (e.g. methylcyclohexyl), heteroalkyl (e.g., methyl propyl ether, methylamino, etc.), alkyl-substituted aryl (e.g., methylbenzene, ethylbenzene, propylbenzene, butylbenzene, etc.), substituted alkyl (e.g., halo-substituted alkyl (e.g., trihalomethyl group (e.g., trifluoromethyl group), dihalomethyl group (e.g. difluoromethyl group), monohalomethyl group (3.g. monofluoromethyl group)), trihaloethyl group (e.g., trifluoroethyl group), trihalopropyl (e.g., trifluoropropyl), trihalobutyl group (e.g., trifluorobutyl group), trihaloisopropyl (e.g., trifluoroisopropyl), 1-fluoro, 2-trifluoro, ethane (See, e.g., compound 21), trifluoroethanol), alcohol-substituted alkyl, amino-substituted alkyl, substituted cycloalkyl, substituted aromatic ring (e.g., propylbenzene, 1-ethyl-4methoxybenzene, 1-propyl-4-methoxybenzene, etc.)), alcohol, amino, and/or combinations thereof (See, e.g., Table 1).

In some embodiments, D of subscaffold 1 is selected from C, N, O, or S; wherein when D is O or S, there is no further substitution at that respective position; wherein, when D is N, it is optionally substituted with one substituent that comprises or consists of: alkyl (e.g., branched (e.g., isopropyl), straight chain (e.g., methyl, propyl), cycloalkyl (e.g., cyclopropane, cyclopentante, cyclohexane)), heteroalkyl (e.g., methyl propyl ether, methylamino, etc.), alkyl-substituted aryl (e.g., methylbenzene, ethylbenzene, propylbenzene, butylbenzene, etc.), substituted alkyl (e.g., halo-substituted alkyl (e.g., trihalomethyl group (e.g., trifluoromethyl group), trihaloethyl group (e.g., trifluoroethyl group), trihalopropyl (e.g., trifluoropropyl), trihalobutyl group (e.g., trifluorobutyl group), trihaloisopropyl (e.g., trifluoroisopropyl), 1-fluoro, 2-trifluoro, ethane, trifluoroethanol), alcohol-substituted alkyl, amino-substituted alkyl, substituted cycloalkyl, substituted aromatic ring (e.g., propylbenzene, 1-ethyl-4methoxybenzene, 1-propyl-4-methoxy-benzene, etc.)), alcohol, amino, and/or combinations thereof; wherein when D is C, it is optionally substituted with one or two substituents that comprises or consists of: alkyl (e.g., branched (e.g., isopropyl), straight chain (e.g., methyl, propyl), cycloalkyl (e.g., cyclopropane, cyclopentante, cyclohexane)), heteroalkyl (e.g., methyl propyl ether, methylamino, etc.), alkyl-substituted aryl (e.g., methylbenzene, ethylbenzene, propylbenzene, butylbenzene, etc.), substituted alkyl (e.g., halo-substituted alkyl (e.g., trihalomethyl group (e.g., trifluoromethyl group), trihaloethyl group (e.g., trifluoroethyl group), trihalopropyl (e.g., trifluoropropyl), trihalobutyl group (e.g., trifluorobutyl group), trihaloisopropyl (e.g., trifluoroisopropyl), 1-fluoro, 2-trifluoro, ethane, trifluoroethanol), alcohol-substituted alkyl, amino-substituted alkyl, substituted cycloalkyl, substituted aromatic ring (e.g., propylbenzene, 1-ethyl-4methoxybenzene, 1-propyl-4-methoxy-benzene, etc.)), alcohol, amino, and/or combinations thereof (See, e.g., Table 1).

In some embodiments, Y of subscaffold 1 is selected from N or C.

In some embodiments, L of subscaffold 1 is alkylene (e.g. methylene, —CH$_2$—, ethylene, —CH$_2$—CH$_2$—, etc).

In some embodiments, compositions comprising one or more of compound 1-42 of Table 1 are provided.

In some embodiments, the thienopyrimidine class compound is of a general formula of:

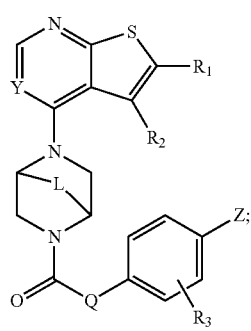

Subscaffold 2 wherein R1 and R2 both independently comprise or consist of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., mono-, di-, tetra-,penta- and trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, or a hydrogen bond donor or a hydrogen bond acceptor, and/or combinations thereof; wherein R3 comprises or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, a hydrogen bond donor or a hydrogen bond acceptor, a sulfur-containing group (e.g., thiol, sulfide, disulfide, sulfoxide, sulfone (e.g., dimethyl sulfone, sulfonyl-amino ($SO_2NH_2$), sulfonyl-methane ($SO_2CH_3$), amino-sulfonyl-methane ($NHSO_2CH_3$), amino-sulfonyl-amino ($NHSO_2NH_2$), methy-sulfonyl-amino ($CH_2SO_2NH_2$; See, e.g. compound 96), methyl-sulfonyl-methane ($CH_2SO_2CH_3$), methyl-sulfonyl-halomethane ($CH_2SO_2CH_3$)) and/or combinations thereof; wherein R3 is present at 1-4 positions on the phenyl ring;

wherein L is present or absent and comprises alkylene (e.g. methylene, —CH$_2$—, ethylene, —CH$_2$—CH$_2$—, etc) or oxalkylene (e.g. —O—, —CH$_2$—O—CH$_2$) groups;

wherein Q comprises alkyl ($C_1$-5) or heteroalkyl with one or more N, O atoms;

wherein Y is N or C, and wherein when Y is C the Y position may be substituted with $R^a$, with $R^a$ consisting of or comprising an alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl (($CH_2$)$_2CF_3$), trihalobutyl group (e.g., trifluorobutyl group (($CH_2$)$_3CF_3$)), trihaloisopropyl (e.g., trifluoroisopropyl, 1-fluoro, 2-trifluoro, ethane, 1-trifluoro, 2-ethanol, alcohol (e.g., ($CH_2$)$_n$OH, wherein n=0-10), alkoxy (e.g., ($CH_2$)$_n$—OR, wherein n=0-10, wherein R is alkyl, ($CH_2$)$_n$-aryl, ($CH_2$)$_n$-aromatic, ($CH_2$)$_n$-heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, heterocycle, aromatic, combinations thereof, etc.; wherein Z comprises or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, a hydrogen bond donor or a hydrogen bond acceptor, a sulfur-containing group (e.g., thiol, sulfide, disulfide, sulfoxide, sulfone), a group selected from CHR$^4$SO$_2$R$^5$ or NR$^4$SO$_2$R$^5$, in which R$^4$ comprises or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), alkylnitrile group (e.g. ethanenitryle group, $CH_2CN$), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), a carbocyclic ring, a substituted cycloalkyl group (e.g., halogen-substituted cycloalkyl group, alkyl-substituted cycloalkyl group, cycloalkoxy group, cyclolkylamine, etc.) and R$^5$ comprises or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, a substituted cycloalkyl group (e.g., halogen-substituted cycloalkyl group, cycloalkoxy group, cycloalkylamine, etc.), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, a hydrogen bond donor or a hydrogen bond acceptor, and/or combinations thereof, R$^5$ might also be a part of the 3-8 member aromatic or non-aromatic ring comprising C, N, O, S (e.g. compounds 52,53,55). In some embodiments, Z comprises:

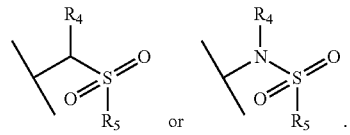

In some embodiments, Z is selected from: dimethyl sulfone, amino-sulfonyl-methane (NHSO$_2$CH$_3$), amino-sulfonyl-amine (NHSO$_2$NH$_2$), methyl-sulfonyl-amino (CH$_3$SO$_2$NH$_2$, methylamino-sulfonyl-methane (NCH$_3$SO$_2$CH$_3$; See e.g., compound 46), amino-sulfonyl-amino-methane (NHSO$_2$NHCH3), amino-sulfonyl-ethane-2-amine (NHSO$_2$CH$_2$CH$_2$NH$_2$), amino-sulfonyl-ethane (NHSO$_2$CH$_2$CH$_3$), amino-sulfonyl-dimethylamine (NHSO$_2$N(CH3)$_2$; See, e.g., compound 51), amino-sulfonyl-isopropane (NHSO$_2$$^i$Pr), amino-sulfonyl-heterocycloalkane (e.g., amino-sulfonyl-1-pyridine, amino-sulfonyl-1-oxazine, amino-sulfonyl-1-pyrazine, etc.), amino-sulfonyl-alkyl (e.g., amino-sulfonyl-methane (NHSO$_2$CH$_3$), amino-sulfonyl-ethane (NHSO$_2$CH$_2$CH$_3$), amino-sulfonyl-propane (NHSO$_2$(CH$_2$)$_2$CH$_3$), amino-sulfonyl-butane (NHSO2(CH$_2$)$_3$CH$_3$), etc.), sulfinic acid, thiocyanate, etc.), and/or combinations thereof.

In some embodiments, R1 of subscaffold 2 is selected from an alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), trihaloethyl group (e.g., trifluoroethyl group), trihalopropyl (e.g., trifluoropropyl), trihalobutyl group (e.g., trifluorobutyl group), trihaloisopropyl (e.g., trifluoroisopropyl), 1-fluoro, 2-trifluoro, ethane, trifluoroethanol), alcohol, amino, etc. (See, e.g., Table 2).

In some embodiments, R2 of subscaffold 2 is selected from a halogen (e.g., Cl, F, Br, I), alkyl (e.g., branched, straight chain (e.g., methyl), cycloalkyl, heteroalkyl, etc.), alkyl-substituted aryl, substituted alkyl (e.g., halo-substituted alkyl, alcohol, amino, etc.), alcohol (e.g. OH, methanol, ethanol, etc), SH, $NH_2$, etc.

In some embodiments, R3 of subscaffold 2 is selected from hydrogen, alkyl ($C_1$-$C_5$), haloalkyl (e.g. $CF_3$), alcohol (e.g., OH, methanol, ethanol, isopropanol, etc.), alkoxy (e.g. methoxy, ethoxy, etc), amine (e.g. —NH2), halogen (Cl, Br, F, I), methyl-sulfonyl-amine ($CH_2SO_2NH_2$), etc. (See, e.g., Table 2). In some embodiments, R3 can be present at more than 1 position of the phenyl ring.

In some embodiments, R3 of subscaffold 2 is present at the ortho or meta positions of the benzene ring. In some embodiments, R3 groups are present at two or more positions on the benzene.

In some embodiments, Z of subscaffold 2 comprises an H, alkyl group, amino group (e.g., primary, secondary, alkylamine, aminoalkyl, etc.), halogen, heterocycle, sulfone-containing group (see e.g., Table 2), $CHR^4SO_2R^5$ or $NR^4SO_2R^5$ in which R4 and R5 are independently selected from an alkyl (e.g., branched, straight chain (e.g., methyl), cycloalkyl, heteroalkyl, etc.), substituted or non-substituted heterocycle comprising one or more N, C, O or S, thrihaloalkane, amino, alcohol, alkyl-substituted aryl, substituted or non-substituted heterocyclic ring, substituted alkyl (e.g., halo-substituted alkyl, alcohol, amino, cyano, aryl, heterocyclic ring, etc.), cyano, etc.

In some embodiments, R3 and Z groups (e.g., $(CH)_2NH$ in compound 81) bridge two positions of the benzene ring of subscaffold 2.

In some embodiments, L of subscaffold 2 is alkylene (e.g. ethylene, —$CH_2$—$CH_2$—, etc).

In some embodiments, Q of subscaffold 2 is alkylene (e.g. C1-C5) or oxyalkylene (e.g. —$CH_2$—O—$CH_2$—).

In some embodiments, compositions comprising one or more of compound 43-104 of Table 2 are provided.

In some embodiments, the thienopyrimidine class compound is of a general formula of:

Subscaffold 3

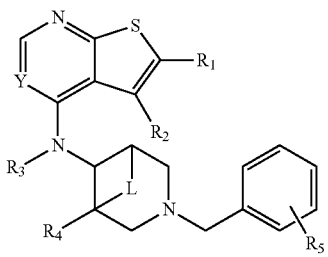

wherein R1, R2, R3, and R4 independently comprise or consist of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., mono-, di-, tetra-,penta- and trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, or a hydrogen bond donor or a hydrogen bond acceptor, and/or combinations thereof; wherein R5 comprises or consists of: H, alkyl group (e.g., straight-chain alkyl (e.g., methane, ethane, propane, butane, pentane, hexane, etc.), branched alkyl group (e.g., iso-propanol, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), amide, alkylamide, a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, or a hydrogen bond donor or a hydrogen bond acceptor, and/or combinations thereof. In some embodiments, R5 is present at the ortho, meta, or para position of the benzene ring of subscaffold 3. In some embodiments, the benzene ring of subscaffold 3 comprises R5 groups at two or more (e.g., 2, 3, 4, or 5) positions. In some embodiments, an R5 group bridges two positions of the benzene ring of subscaffold 3 (See e.g., 3-keto, 4-aminopropane of compound 136 of Table 3); and wherein Y is N or C, and wherein when Y is C the Y position may be substituted with $R^a$, with $R^a$ consisting of or comprising an alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl ($(CH_2)_2CF_3$), trihalobutyl group (e.g., trifluorobutyl group ($(CH_2)_3CF_3$)), trihaloisopropyl (e.g., trifluoroisopropyl, 1-fluoro, 2-trifluoro, ethane, 1-trifluoro, 2-ethanol, alcohol (e.g., $(CH_2)_nOH$, wherein n=0-10), alkoxy (e.g., $(CH_2)_n$—OR, wherein n=0-10, wherein R is alkyl, $(CH_2)_n$-aryl, $(CH_2)_n$-aromatic, $(CH_2)_n$-heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, heterocycle, aromatic, combinations thereof, etc.; and wherein L is present or absent and comprises alkylene (e.g. methylene, —$CH_2$—, ethylene, —$CH_2$—$CH_2$—, propylene, —$CH_2$—$CH_2$—$CH_2$—, etc) or oxalkylene (e.g. —O—, —$CH_2$—O—$CH_2$) groups.

In some embodiments, R1 of subscaffold 3 comprises or consists of trifluoroethane. In some embodiments, R1 of subscaffold 3 comprises or consists of trihaloethane (e.g., trifluoroethane), 2-dihalo-4-butanol (e.g., 2-difluoro-4-butanol, etc.), an alkyl chain (e.g., straight chain alkyl (e.g., methane, ethane, propane, butane, etc.), branched alkyl, cycloalkyl, or combinations thereof), 2-dihalo-propane (e.g., 2-difluoro-propane, etc.), etc. (See Table 3).

In some embodiments, R2 of subscaffold 3 is selected from a halogen (e.g., Cl, F, Br, I), alkyl (e.g., branched, straight chain (e.g., methyl), cycloalkyl, heteroalkyl, etc.), alkyl-substituted aryl, substituted alkyl (e.g., halo-substituted alkyl, alcohol, amino, etc.), alcohol (—OH, —$CH_2OH$, etc) SH, $NH_2$, etc.

In some embodiments, R3 of subscaffold 3 consists of H. In some embodiments, R3 of subscaffold 3 comprises or consists of an alkyl (e.g., methane, ethane, propane, butane, etc.), amine (e.g., $NH_2$, NH-alkyl (e.g., NH-methyl, NH-ethyl, NH—$CH_2$-Ph, etc.), NH-alcohol (e.g., NH—$CH_2$—$CH_2$—OH), etc.), alcohol (e.g., methanol, ethanol, butanol, propanol, —$CH_2$—$CHOHCH_2OH$, etc.), halo-substituted alkyl, combinations thereof, etc. (See Table 3). In some embodiments, R3 is fused in a ring with R2 (See, e.g. compound 158).

In some embodiments, R4 of subscaffold 4 comprises or consists of an amine (e.g., $NH_2$, alkylamine (e.g., methylamine, ethylamine, propylamine, etc.), aminoalkyl (e.g., straight chain alkyl, cycloalkyl, or combinations thereof (See, e.g., compound 171)), amino-alkyl-phenyl (e.g., amino-methyl-phenyl, amino-ethyl-phenyl, etc.), etc.), alcohol (e.g., OH, methanol, ethanol, propanol, isopropanol, etc.), substituted amine (—$NHR^3$) or substituted alcohol (—$OR^3$), in which $R^3$ is alkyl, alkyl-aryl (substituted and non-substituted), alkyl-cycloalkyl (substituted and non-substituted), alkyl-aromatic ring substituted or non-substituted, akyl-non aromatic ring (C, N, O, S) substituted or non-substituted, or any of the R4 groups depicted in Tables 4, 5, or 7. In some embodiments, R4 comprises or consists of aminomethyl phenyl (See, e.g. compound 167), aminoethyl phenyl (See, e.g., compound 168), amino-methyl-cyclopentane (See, e.g., compound 169), aminomethyl, n-methanal pyrrolidine, aminoethyl cyclopentane, aminomethyl ($NHCH_3$), methylamine ($CH_2NH_2$), n-sulfonyl-methyl pyrrolidine (See, e.g., compound 173), O-methyl phenyl (See, e.g. compound 174), etc., see Table 4.

In some embodiments, R5 of subscaffold 3 comprises or consists of: H, an alcohol (e.g., OH, methanol, ethanol, etc.), alkane, cycloalkane (e.g., substituted cycloalkane (e.g., cyanocyclopropane)), amine, halogen (e.g., chlorine, fluorine, bromine, iodine, etc.), heterocyclic ring (e.g., attached at any position on the heterocyclic ring: morpholine, piperidine, methylpiperidine, pyrrole, thiophene, piperazine, etc.), alkylamine (e.g., methylamine, ethylamine, propylamine, 1,4-dimethyl-piperazine, etc.), alkylalkohol (e.g. —$CH_2OH$), alkoxy, carboxamido, O-dihalomethane, sulfonyl-amine, trihalomethane (e.g., trifluoromethane), etc. In some embodiments, the benzene ring of subscaffold 3 comprises R5 groups at two or more (e.g., 2, 3, 4, or 5) positions.

In some embodiments, L of subscaffold 3 is alkylene (e.g. ethylene, —$CH_2$—$CH_2$—, compound 135).

In some embodiments, compositions comprising one or more of compound 105-159 of Table 3, 165-174 of Table 4 and 280 and 282 of Table 7 are provided.

In some embodiments, the thienopyrimidine class compound is of a general formula of:

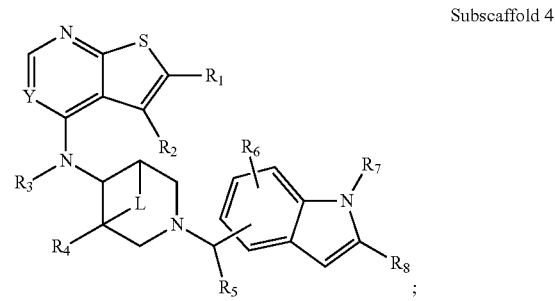

Subscaffold 4 wherein R1, R2, R3, R4, R5, R6, R7, R8 each independently comprise or consist of: H, alkyl group (e.g., straight-chain alkyl (e.g., methane, ethane, propane, butane, pentane, hexane, etc.), branched alkyl group (e.g., iso-propanel, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), amine, alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, an amide, an alkylamide, a cyano group, methyl carbonitrile (e.g. $CH_2CN$), —$SO_2CH_3$ group, sulfonyl group, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a substituted or non-substituted heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, or a hydrogen bond donor or a hydrogen bond acceptor, and/or combinations thereof; and wherein any of the H atoms, R6, R7 and R8 on the indole of subscaffold 4 may be replaced with one of: halogen (e.g., F, Cl, Br, I, etc.), alcohol (e.g., OH, methanol, ethanol, etc.), alkyl (C1-C5), alkoxy (e.g. methoxy, ethoxy, etc), amine (e.g. $NH_2$, methylamine, ethylamine, etc), cyano group (e.g., CN, methyl carbonitrile, ethyl carbonitrile, etc.), an amide (e.g. $CONH_2$, acetamide, etc), —$SO_2CH_3$ group; wherein R6 can be present on either the phenyl and/or pyrrole portion of the indole ring, and wherein R6 can be present at one or more of the positions of the phenyl and/or pyrrole portion of the indole ring that are not otherwise occupied by a substituent; and wherein Y is N or C, and wherein when Y is C the Y position may be substituted with $R^a$, with $R^a$ consisting of or comprising an alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl (($CH_2)_2CF_3$), trihalobutyl group (e.g., trifluorobutyl group (($CH_2)_3CF_3$)), trihaloisopropyl (e.g., trifluoroisopropyl, 1-fluoro, 2-trifluoro, ethane, 1-trifluoro, 2-ethanol), alcohol (e.g., $(CH_2)_nOH$, wherein n=0-10), alkoxy (e.g., $(CH_2)_n$—OR, wherein n=0-10, wherein R is alkyl, $(CH_2)_n$-aryl, $(CH_2)_n$-aromatic, $(CH_2)_n$-heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, heterocycle, aromatic, combinations thereof, etc.;

wherein L is present or absent, and if present it comprises alkylene (e.g. methylene, —$CH_2$—, ethylene, —$CH_2$—$CH_2$—, propylene, —$CH_2$—$CH_2$—$CH_2$—, etc) or oxalkylene (e.g. —O—, —$CH_2$—O—$CH_2$) groups.

In some embodiments, R1 of subscaffold 4 comprises or consists of trihaloethane (e.g., trifluoroethane) group, (see Table 5).

In some embodiments R2 is H or another R2 substituent described herein.

In some embodiments R3 of subscaffold 4 comprises or consists of an alkyl (e.g., methane, ethane, propane, butane, etc.), amine (e.g., $NH_2$, NH-alkyl (e.g., NH-methyl, NH-ethyl, NH—$CH_2$-Ph, etc.), NH-alcohol (e.g., NH—$CH_2$—$CH_2$—OH), etc.), an alcohol (e.g., methanol, ethanol, butanol, propanol, $CH_2CHOHCH_2OH$, etc.), a heterocyclic ring, an alkyl-heterocyclic ring (e.g., ethyl-morpholine (see compound 238), propyl-indole, etc.), etc. In some embodiments, R3 is fused in a ring with R2 (See, e.g. compound 158).

In some embodiments R4 comprises or consists of amine (e.g. —$NH_2$), aminomethyl, n-methanal pyrrolidine (see compound 161 in Table 5), —$CH_2$—OH (see compounds 163-164 in Table 5).

In some embodiments, R5 is —$CH_2$—OH (see compound 211, Table 5).

In some embodiments, R6 is an alkyl (e.g., methane, ethane, propane, butane, etc.), halogen (e.g., Br, F, Cl, I, etc.), haloalkane, amine (e.g., $NH_2$, NH-alkyl (e.g., NH-methyl, NH-ethyl, NH—$CH_2$-Ph, etc.), O-alkyl (e.g., $OCH_3$, $OCH_2CH_3$, etc.), NH-alcohol (e.g., NH—$CH_2$—$CH_2$—OH), etc.), an alcohol (e.g., methanol, ethanol, butanol, propanol, $CH_2CHOHCH_2OH$, etc.), or any R6 group of Tables 4, 5, or 7. In some embodiments, R6 is present on either the phenyl and/or pyrrole portions of the indole ring. In some embodiments R6 on indole ring is present at more than one position on the phenyl and/or pyrrole portions of the indole ring.

In some embodiments, R7 is H, alkyl (e.g., methyl, ethyl, propyl, butyl, etc.), haloalkane, cycloalkyl (e.g., cyclopropane (e.g., methyl cyclopropane), cyclobutane, cyclopentane, cyclohexane, etc.), an alcohol (e.g., OH, methanol, ethanol, propanol, butanol, etc.), a substituted or non-substituted heteroaromatic ring (e.g., pyrazole, triazole (e.g., 1,2,4 triazole), isoxazole (e.g., dimethyl isoxazole), $(CH_2)_n$—OR (wherein n=1-10 and R is an aromatic ring, heteroaromatic ring, cycloalkyl, heterocycle, substituted ring, etc.), $(CH_2)_n$—R (wherein n=1-10 and R is an aromatic ring, heteroaromatic ring, cycloalkyl, heterocycle, substituted ring, etc.), $(CH_2)_n$—O—$(CH_2)_m$—R (wherein n=1-10, m=1-10, and R is an aromatic ring, heteroaromatic ring, cycloalkyl, heterocycle, substituted ring, etc.), alkyl-heteroaromatic ring (e.g. $CH_2$-pyrazole, $CH_2$-triazole, $CH_2$—$CH_2$-triazole, etc), amide (e.g. acetamide, see, e.g. compound 189), amine (e.g., $NH_2$, NH-alkyl (e.g., NH-methyl, NH-ethyl, NH—$CH_2$-Ph, etc., NH-alcohol (e.g., NH—$CH_2$—$CH_2$—OH), etc.), substituted or non-substituted alcohol (e.g., methanol, ethanol, butanol, propanol, $CH_2CHOHCH_2OH$, etc.), or any R7 substituents in the compounds of Tables 4, 5, or 7.

In some embodiments, R8 of subscaffold 4 comprises or consists of: H, alkyl (e.g., methyl, ethyl, propyl, butyl, etc.), cycloalkyl (e.g., cyclopropane (e.g., methyl cyclopropane), cyclobutane, cyclopentane, cyclohexane, etc.), a primary alcohol (e.g., OH, methanol, ethanol, propanol, butanol, etc.), a secondary alcohol, a substituted or non-substituted heteroaromatic ring (e.g., pyrazole, triazole (e.g., 1,2,4 triazole), isoxazole, isopropylisopropanolamine ($CH_2CHOHCH_2NHCH(CH_3)_2$); sulfonamide, a cyano group (e.g., CN, methyl carbonitrile, ethyl carbonitrile, propyl carbonitrile, etc.), amide (e.g., $CONH_2$, methylcarboxamido (e.g., $CH_2CONH_2$), ethyl carboxamido ($CH_2CH_2CONH_2$), carboxyamido-methane (e.g., $CONHCH_3$ or $NHCOCH_3$), etc.), methylsulfonyl, sulfonamide, ketone (e.g., =O), or any R8 substituents in the compounds of Tables 4, 5, or 7.

In some embodiments, the substituted indole ring of subscaffold 4 is: cyano substituted (e.g., 1-carbonitrile, 2-carbonitrile, etc.), methyl-carbonitrile substituted (e.g., 5-methyl-carbonitrile, etc.), methylcyclopropane substituted (e.g., 1-methylcyclopropane), halo-substituted (e.g., 3-halo (e.g., 3-fluoro, 4-fluoro, 6-fluoro, etc.)), alkyl substituted (e.g., 1-alkyl (e.g., 1-methyl, 1-ethyl, 1-propyl, etc.)), alcohol-substituted (e.g., OH substituted (e.g., 6-OH), methanol substituted (e.g., 1-methanol), ethanol substituted (e.g., 1-ethanol), etc.), O-methyl substituted (e.g., 4-O-methyl, 6-O-methyl, etc.), alkoxy substituted (e.g. 1-O-methoxy, 1-O-ethoxy, etc), heterocyclic aromatic ring (or ring system) substituted (e.g., imidazole), amine substituted (e.g., $NH_2$, methylamine, ethylamine (e.g., 1-ethylamine, etc.), aminomethyl, etc.), dihydroxy substituted (e.g., 1,2-propanediol, etc.), amide substituted (e.g., 1-propanamide), acetamide, 1-methyl 1,2,3-triazole substituted, 1-ethyl imidazole substituted, heterocycle substituted, carboxamido substituted (e.g., 1-carboxamido), sulfonyl substituted (e.g., 1-sulfonyl methyl ($SO_2CH_3$), ether substituted (e.g., isopropanol methyl ether ($CH_2CHOHCH_2CH_3$), keto-substituted (e.g., 1-keto), isopropanol-amine-isopropyl substituted ($CH_2CHOHCH_2NHCH(CH_3)_2$), combinations thereof depicted in Table 4, or combinations thereof not depicted in Table 4).

In some embodiments, L is absent.

In some embodiments, compositions comprising one or more of compound 160-164 (Table 4) and 175-252 of Table 5 and compounds 278, 279, 281 of Table 7 are provided.

In some embodiments, the thienopyrimidine class compound is of a general formula of:

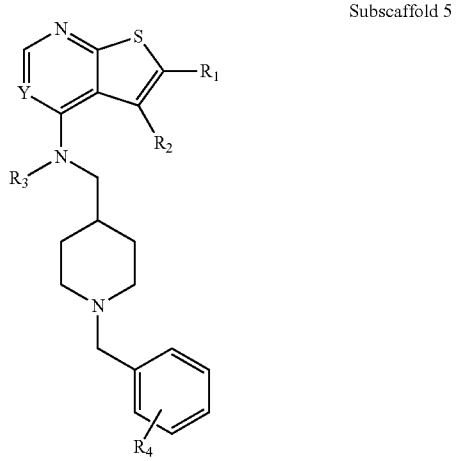

Subscaffold 5 wherein R1, R2, R3 and R4 independently comprise or consist of: H,
alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, or a hydrogen bond donor or a hydrogen bond acceptor, and/or combinations thereof; and wherein any of the H atoms on the benzene ring of subscaffold 5 may be replaced with one of: halogen (e.g., F, Cl, Br, I, etc.), alcohol (e.g., OH, methanol, ethanol, etc.), cyano group (e.g., CN, methyl carbonitrile, ethyl carbonitrile, etc.), amine (e.g. $NH_2$, methylamine, ethylamine, etc.), trifluoromethane, alkyl (e.g., methane, ethane, propane, etc.), alkoxy (e.g. methoxy, ethoxy, etc), halogen substituted alkoxy (e.g. trifluoromethoxy), ketone, sulfonyl group (e.g. slufonamide), substituted or non-substituted heterocyclic ring (e.g. comprising carbon and one or more nitrogen oxygen and/or sulfur members), etc.; and wherein Y is N or C, and wherein when Y is C the Y position may be substituted with $R^a$, with $R^a$ consisting of or comprising an alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl (($CH_2)_2CF_3$), trihalobutyl group (e.g., trifluorobutyl group (($CH_2)_3CF_3$)), trihaloisopropyl (e.g., trifluoroisopropyl, 1-fluoro, 2-trifluoro, ethane, 1-trifluoro, 2-ethanol), alcohol (e.g., $(CH_2)_nOH$, wherein n=0-10), alkoxy (e.g., $(CH_2)_n$—OR, wherein n=0-10, wherein R is alkyl, $(CH_2)_n$-aryl, $(CH_2)_n$-aromatic, $(CH_2)_n$-heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, heterocycle, aromatic, combinations thereof, etc.;

In some embodiments, R1 of subscaffold 5 comprises or consists of: H, trifluoroethane, or another R1 group provided herein.

In some embodiments, R2 of subscaffold 5 comprises or consists of H.

In some embodiments, R3 of subscaffold 5 comprises or consists of alkyl group (e.g. n-buthyl, compound 264).

In some embodiments, R4 of subscaffold 5 comprises or consists of: H, aminosulfonyl, halogen (e.g., Cl, Br, F, I, etc.), a substituted or non-substituted heterocycle (e.g., piperidine, 1,4-oxazinane, piperazine, morpholine), cyano group (e.g., CN, cyanomethane, cyanoethane, etc.), alkoxy (e.g. O-methyl), amine (e.g. NH$_2$, methylamine, ethylamine, etc.), alcohol (e.g., OH, methanol, ethanol, etc.), trifluoromethane, ketone (e.g. acetyl), halogen substituted alkoxy (e.g. O-trifluoromethane, OCF$_3$, alkyl (e.g., methane, ethane, propane, etc.), etc.

In some embodiments, compositions comprising one or more of compound 253-277 of Table 6 are provided.

In some embodiments, the thienopyrimidine class compound is of a general formula of:

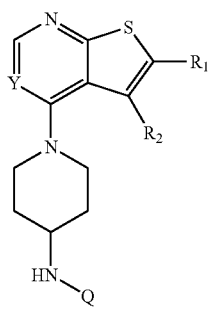

Subscaffold 6 wherein Q, R1 and R2 comprises or consists of: H, an alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyloctane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, or a hydrogen bond donor or a hydrogen bond acceptor, and/or combinations thereof; and wherein Y is N or C, and wherein when Y is C the Y position may be substituted with R$^a$, with R$^a$ consisting of or comprising an H, alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl ((CH$_2$)$_2$CF$_3$), trihalobutyl group (e.g., trifluorobutyl group ((CH$_2$)$_3$CF$_3$)), trihaloisopropyl (e.g., trifluoroisopropyl), 1-fluoro, 2-trifluoro, ethane, 1-trifluoro, 2-ethanol), alcohol (e.g., (CH$_2$)$_n$OH, wherein n=0-10), alkoxy (e.g., (CH$_2$)$_n$—OR, wherein n=0-10, wherein R is alkyl, (CH$_2$)$_n$-aryl, (CH$_2$)$_n$-aromatic, (CH$_2$)$_n$-heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, heterocycle, aromatic, combinations thereof, etc.; and wherein L is present or absent and comprises alkylene (e.g. methylene, —CH$_2$—, ethylene, —CH$_2$—CH$_2$—, etc) or oxalkylene (e.g. —O—, —CH$_2$—O—CH$_2$) groups.

In some embodiments, the present invention provides a composition comprising a compound having the structure of one or subscaffolds 1-6; wherein any of R1-R5, A, B, D, Q, L, W, X, Y, and Z each independently comprise organic substituents comprising fewer than 40 atoms selected from C, H, N, O, P, S, Cl, Br, F, and I. In some embodiments, the compound is selected from compounds 1-283. In some embodiments, R1 is CH$_2$CF$_3$.

In some embodiments, a compound of the present invention has a general structure of one of:

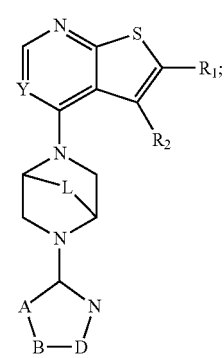

Subscaffold 1

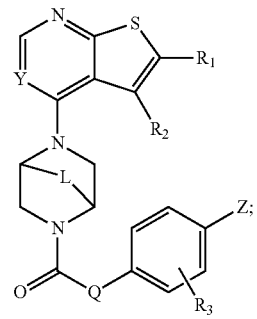

Subscaffold 2

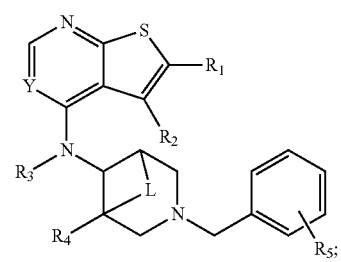

Subscaffold 3

-continued

Subscaffold 4

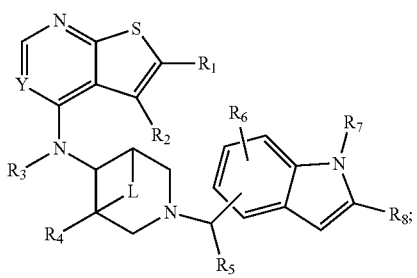

Subscaffold 5

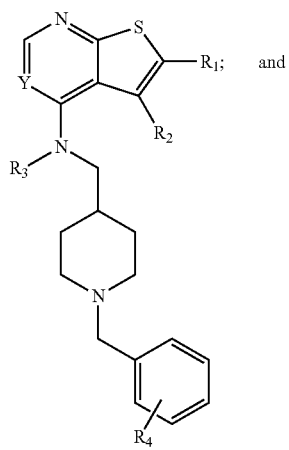

and

Subscaffold 6

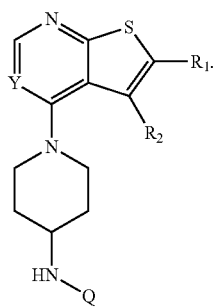

In some embodiments, all substituents (e.g., R1-R8, A, B, D, L, Q, X, Y, and Z) independently consist of or comprise any of the functional groups set forth herein, and in any suitable combination.

In some embodiments, R1-R8, when present on a sub-scaffold, each independently comprise or consist of any suitable combination of: $C_1$-$C_{10}$ alkanes (e.g., straight, branched, or cyclic), halogens (e.g., Cl, Br, F, or I), OH groups (e.g., alkyl-OH), O-alkyl groups, $NH_2$ groups, N-dialkyl, NH-alkyl groups, CN groups, heteroalkyl groups, aromatic groups, heteroaromatic groups, a sulfone-containing group, (e.g., $CH_2SO_2CH_3$, $CH_2SO_2NH_2$, $NHSO_2CH_3$, $NCH_3SO_2CH_3$, $NHSO_2NHCH_3$, $NHSO_2CH_2CH_3$, $NHSO_2(CH_2)_2NH_2$, $NHSO_2N(CH_3)_2$, $NHSO_2(CH_2)_{1-5}CH_3$, and $NHSO_2(CH_2)_2NHCOCH_3$), S, O, or N atoms, and combinations thereof.

In some embodiments, R1-R8 are independently selected from any of the respective substituents described herein or depicted in any of Tables 1-8, in any combination. For example, in some embodiments, R1-R8, when present on a subscaffold, each independently comprise or consist of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., mono-, di-, tetra-,penta- and trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, alkyl-substituted cycloalkyl group, cycloalkoxy group, cyclolkylamine, etc.), a halogen (e.g., F, Cl, Br, I, and At), a ketone, a carbocyclic ring, an aromatic ring (e.g., heteroaryl), a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring (e.g., heteroaryl), a multi-ring system comprising a combination of elements selected from aromatic rings, cycloalkane, heterocyclic rings, alkyl chains, and suitable C—, N—, O—, S—, and/or halogen-containing substituents (e.g., substituted heteroaryl), or a hydrogen bond donor or a hydrogen bond acceptor, and/or combinations thereof.

In some embodiments, A comprises or consists of: C, N, O, or S; wherein when A comprises O or S, there is no further substitution at that respective position; wherein when A comprises N or C that respective position is optionally substituted, wherein the substituent at that respective position comprises or consists of: alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor, a heterocyclic non-aromatic ring (e.g., comprising carbon and one or more nitrogen, oxygen and/or sulfur members), carbocyclic or heterocyclic aromatic ring (e.g., heteroaryl) comprising carbon atoms and one or more nitrogen, oxygen and/or sulfur members fused to another aromatic ring, a multi-ring system comprising a combination of elements selected from aromatic rings (e.g., heteroaryl), cycloalkane, heterocyclic rings, alkyl chains, and suitable C—, N—, O—, S—, and/or halogen-containing substituents, or a hydrogen bond donor or a hydrogen bond acceptor, and/or combinations thereof In some embodiments, B comprises or consists of: C, N, O, or S; wherein when B comprises O or S, there is no further substitution at that respective position; wherein when B comprises N or C that respective position is optionally substituted, wherein the substituent at that respective position comprises or consists of: alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor, a heterocyclic non-aromatic ring (e.g., comprising carbon and one or more nitrogen, oxygen and/or sulfur members), carbocyclic or heterocyclic aromatic ring (e.g., heteroaryl) comprising carbon atoms and one or more nitrogen, oxygen and/or sulfur members fused to another aromatic ring, a multi-ring system comprising a combination of elements selected from aromatic rings (e.g., heteroaryl), cycloalkane, heterocyclic rings, alkyl chains, and suitable C—, N—, O—, S—, and/or halogen-containing substituents, or a hydrogen bond donor or a hydrogen bond acceptor, and/or combinations thereof In some embodiments, D comprises or consists of: C, N, O, or S; wherein when D comprises O or S, there is no further substitution at that respective position; wherein D comprises N or C that respective position is optionally substituted, wherein the substituent at that respective position comprises or consists of: alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, combinations thereof, etc.), a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor, a heterocyclic non-aromatic ring (e.g., comprising carbon and one or more nitrogen, oxygen and/or sulfur members), carbocyclic or heterocyclic aromatic ring (e.g., heteroaryl) comprising carbon atoms and one or more nitrogen, oxygen and/or sulfur members fused to another aromatic ring, a multi-ring system comprising a combination of elements selected from aromatic rings (e.g., heteroaryl), cycloalkane, heterocyclic rings, alkyl chains, and suitable C—, N—, O—, S—, and/or halogen-containing substituents, or a hydrogen bond donor or a hydrogen bond acceptor, and/or combinations thereof In some embodiments, L is present or absent, and when present comprises or consists of: wherein L is present or absent and comprises alkylene (e.g. methylene, —$CH_2$—, ethylene, —$CH_2$—$CH_2$—, etc) or oxalkylene (e.g. —O—, —$CH_2$—O—$CH_2$) groups.

In some embodiments, Q comprises or consists of: alkyl ($C_{1-5}$) or heteroalkyl with one or more N, O, or S atoms.

In some embodiments, Y comprises or consists of: O, S, N or C, and wherein when Y is N or C the Y position may be substituted with $R^a$, with $R^a$ consisting of or comprising an alkyl (e.g., branched (e.g., isopropyl), straight chain (e.g., propyl), cycloalkyl (e.g., cyclopropyl)), heteroalkyl (e.g., methyl propyl ether), alkyl-substituted aryl (e.g., ethylbenzene), substituted alkyl (e.g., halo-substituted alkyl (e.g., trihalomethyl group (e.g., trifluoromethyl group), monohaloalkyl group (e.g. monofluoroethyl group), dihaloalkyl group (e.g. difluoroethyl group), trihaloethyl group (e.g., trifluoroethyl group), trihalopropyl (e.g., trifluoropropyl (($CH_2$)$_2CF_3$), trihalobutyl group (e.g., trifluorobutyl group (($CH_2$)$_3CF_3$)), trihaloisopropyl (e.g., trifluoroisopropyl (See, e.g., compound 38)), 1-fluoro, 2-trifluoro, ethane (See, e.g., compound 21), 1-trifluoro, 2-ethanol (See, e.g., compound 23)), alcohol (e.g., ($CH_2$)$_n$OH, wherein n=0-10), alkoxy (e.g., ($CH_2$)$_n$—OR, wherein n=0-10, wherein R is alkyl, ($CH_2$)$_n$-aryl, ($CH_2$)$_n$-aromatic, ($CH_2$)$_n$-heterocycle, substituted or non-substituted aryl, aromatic or non-aromatic heterocycle with one or more N, S, O, etc.), amino (e.g., alkyl amine, amino alkyl, etc.), cyano, sulfonyl, methoxy, aldehyde, heterocycle, aromatic, combinations thereof, etc.; and wherein L is present or absent and comprises alkylene (e.g. methylene, —$CH_2$—, ethylene, —$CH_2$—$CH_2$—, propylene, —CH₂—CH₂—CH₂—, etc) or oxalkylene (e.g. —O—, —CH₂—O—CH₂) groups.

In some embodiments, Z comprises or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, isopropylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, a substituted cycloalkyl group (e.g., halogen-substituted cycloalkyl group, cycloalkoxy group, cycloalkylamine, etc.), a halogen (e.g., F, Cl, Br, I, and At), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, a hydrogen bond donor or a hydrogen bond acceptor, a sulfur-containing group (e.g., thiol, sulfide, disulfide, sulfoxide, sulfone), a group selected from CHR⁴SO₂R⁵ or NR⁴SO₂R⁵, in which R⁴ comprises or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), alkylnitrile group (e.g. ethanenitryle group, CH₂CN), alkoxy group (e.g., ether, alcohol, etc.), alkylamine (e.g., primary amine (e.g., ethylamine, iso-butylamine, n-propylamine, sec-butylamine, iso-propylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), a carbocyclic ring, a substituted cycloalkyl group (e.g., halogen-substituted cycloalkyl group, alkyl-substituted cycloalkyl group, cycloalkoxy group, cyclolkylamine, etc.) and R⁵ comprises or consists of: H, alkyl group (e.g., straight-chain alkyl (e.g., methane, ethane, propane, butane, pentane, hexane, etc.), branched alkyl group (e.g., iso-propane, 2-methyl-hexane, 3-methyl, 2-propyl-octane, etc.), cycloalkyl (e.g., cyclopropane, cyclobutane, cyclopentane, cyclohexane, cyclooctane, etc.), branched cyclic alkyl (e.g., methylcyclohexane, ethylcyclobutane, propylcyclohexane, etc.)), a substituted alkyl group (e.g., halogen-substituted alkyl group (e.g., trihaloethane (e.g., trifluoroethane), halomethane (e.g., fluoromethane), dihalomethane (e.g., difluoromethane), trihalomethane (e.g., trifluoromethane), etc.), alkoxy group (e.g., ether, alcohol, etc.), alkylamine (e.g., primary amine (e.g., ethylamine, iso-butylamine, n-propylamine, sec-butylamine, isopropylamine, iso-amylamine, methylamine, dimethylamine, n-amylamine, etc.), secondary amines (e.g., dimethylamine, methylethanolamine, diphenylamine, etc.), tertiary amine (e.g., trimethylamine, triphenylamine, etc.), thioalkyl, a substituted cycloalkyl group (e.g., halogen-substituted cycloalkyl group, cycloalkoxy group, cycloalkylamine, etc.), a ketone, a carbocyclic ring, an aromatic ring, a substituted aromatic ring (e.g., branched aromatic ring (e.g., ethylbenzene, methyl benzene, etc.), halobenzene (e.g., chlorobenzene, fluorobenzene, etc.)), a heterocyclic aromatic ring (e.g., comprising one or more nitrogen, oxygen and/or sulfur members which may be non-substituted or substituted with alkyl, aryl, halogen, hydrogen bond donor or acceptor), a heterocyclic non-aromatic ring (e.g., comprising carbon and one or more nitrogen, oxygen and/or sulfur members), carbocyclic or heterocyclic aromatic ring comprising carbon atoms and one or more nitrogen, oxygen and/or sulfur members fused to another aromatic ring, a multi-ring system comprising a combination of elements selected from aromatic rings, cycloalkane, heterocyclic rings, alkyl chains, and suitable C—, N—, O—, S—, and/or halogen-containing substituents, a hydrogen bond donor or a hydrogen bond acceptor, and/or combinations thereof, R⁵ might also be a part of the 3-8 member aromatic or non-aromatic ring comprising C, N, O, or S.

In some embodiments, the present invention provides methods for the treatment of a disease or condition comprising: administering a thienopyrimidine or thienopyridine class compound to a subject suffering from said disease or condition. In some embodiments, the thienopyrimidine or thienopyridine class compounds comprise one of subscaffolds 1-6. In some embodiments, the thienopyrimidine or thienopyridine class compounds comprise one or compound 1-283. In some embodiments, the disease or condition comprises leukemia or a solid tumor cancer (e.g., breast cancer, prostate cancer, lung cancer, liver cancer, pancreatic cancer, glioblastoma and melanoma, etc.). In some embodiments, the leukemia comprises acute leukemias, chronic leukemias, lymphoblastic leukemias, lymphocytic leukemias, myeloid leukemias, myelogenous leukemias, Acute lymphoblastic leukemia (ALL), Chronic lymphocytic leukemia (CLL), Acute myelogenous leukemia (AML), Chronic myelogenous leukemia (CML), Hairy cell leukemia (HCL), T-cell prolymphocytic leukemia (T-PLL), Large granular lymphocytic leukemia, MLL-positive leukemias, MLL-induced leukemias, MLL-rearranged leukemias, etc.

In some embodiments, the present invention provides methods of inhibiting the interaction of MLL (MLL1 and MLL2) and menin comprising: (a) providing: (i) a sample comprising MLL (or MLL fusion proteins) and menin; and (ii) a thienopyrimidine and thienopyridine class compounds; (b) administering said composition to said sample; and (c) inhibiting the interaction between said MLL and said menin, or said MLL fusion proteins and said menin. In some embodiments, the thienopyrimidine or thienopyridine class compounds comprises one of subscaffolds 1-6. In some embodiments, the thienopyrimidine or thienopyridine class compound comprises one of compound 1-283.

The compositions may comprise combinations of any of the above compounds with one another or with other compounds of interest. Stereoisomers, salts, and derivates of the compounds are further contemplated.

In some embodiments, the present invention provides a method comprising administering a composition for the treatment of leukemia (e.g., which inhibits binding of one or more MLL fusion proteins to menin or MLL wild type to menin) to a subject suffering from leukemia. In some embodiments, the leukemia comprises AML or ALL. In some embodiments, the composition comprises a thienopyrimidine or thienopyridine class compound. In some embodiments, the composition comprises a compound of the general structure of one or subscaffolds 1, 2, 3, 4, 5, or 6. In some embodiments, the composition comprises one of compounds 1-283 and/or a derivative thereof.

In some embodiments, the present invention provides a method of screening compounds effective in treating leukemia comprising assaying one or more compounds for inhibition of the interaction between MLL and menin. In some embodiments, the screening is performed in vitro. In some embodiments, the screening is performed in vivo. In some embodiments, the assaying comprises a fluorescence polarization assay. In some embodiments, the assaying comprises a time-resolved fluorescence resonance energy transfer assay. In some embodiments, the assaying comprises a nuclear magnetic resonance (NMR) methods. In some embodiments, the assaying comprises cellular assays and/or animal (e.g., mice) studies.

In some embodiments, the present invention provides a method of inhibiting the interaction of MLL and menin comprising: (a) providing: (i) a sample comprising MLL and menin and (ii) a composition configured to inhibit the interaction of MLL and menin, (b) administering the composition to the sample, (c) contacting MLL and/or menin with the composition, and (d) inhibiting the interaction between MLL and menin, and between MLL fusion proteins and menin. In some embodiments, the sample comprises cells from a subject suffering from leukemia. In some embodiments, the subject is a human subject or a human patient. In some embodiments, the cells are within a subject suffering from leukemia. In some embodiments, the composition comprises a thienopyrimidine and thienopyridine class compound. In some embodiments, the present invention comprises any structural derivatives of Compounds 1-283.

In some embodiments, the present invention provides methods comprising the use of a composition and/or compound described herein (e.g., a derivative of one of Subscaffolds 1-6, one of compounds 1-283, etc.). In some embodiments, the present invention provides methods comprising the use of a composition and/or compound described herein (e.g., a derivative of one of Subscaffolds 1-6, one of compounds 1-283, etc.) for the treatment of leukemia.

DEFINITIONS

Figure 1:
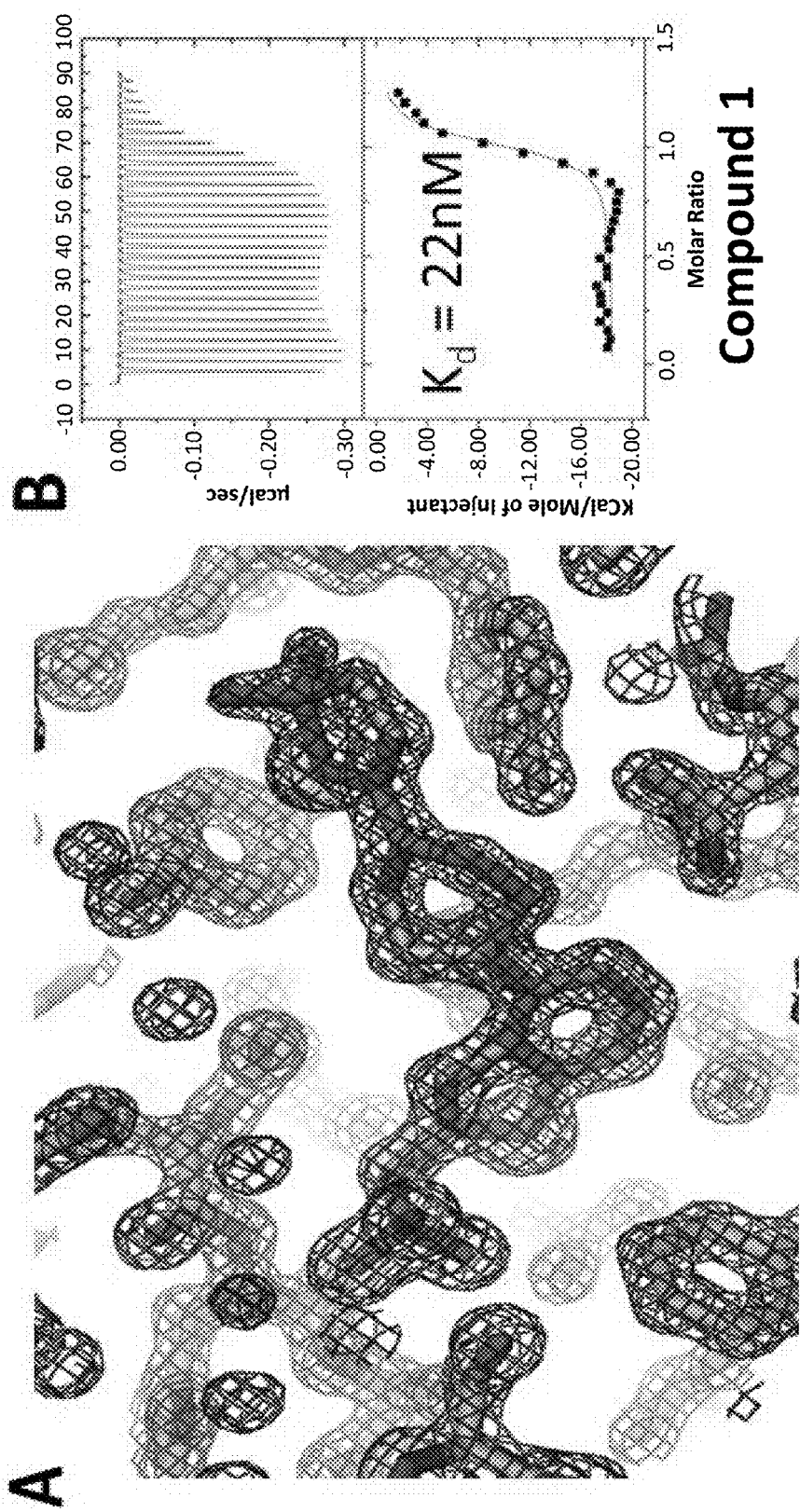
FIG. 1. Validation of direct binding of thienopyrimidine compounds to menin: a) X-ray structure of menin in complex with compound 1; b) Isothermal Titration Calorimetry (ITC) for binding of compound 1 to menin.

The nomenclature used herein for referring to substituents is either IUPAC format or a modified format in which functional groups within a substituent are read in the order in which they branch from the scaffold or main structure. For example, in the modified nomenclature, methyl-sulfonyl-propanol refers to $CH_2SO_2CH_2CH_2CH_2OH$ or:

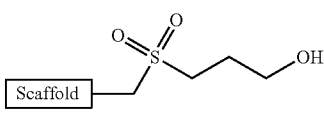

As another example, according to the modified nomenclature, a methyl-amine substituent is:

while an amino-methyl substituent is:

All chemical names of substituents should be interpreted in light of IUPAC and/or the modified nomenclature and with reference to the chemical structures depicted and/or described herein.

The term "system" refers a group of objects, compounds, methods, and/or devices that form a network for performing a desired objective.

As used herein a "sample" refers to anything capable of being subjected to the compositions and methods provided herein. The sample may be in vitro or in vivo. In some embodiments, samples are "mixture" samples, which samples from more than one subject or individual. In some embodiments, the methods provided herein comprise purifying or isolating the sample. In some embodiments, the sample is purified or unpurified protein. In some embodiments, a sample may be from a clinical or research setting. In some embodiments, a sample may comprise cells, fluids (e.g. blood, urine, cytoplasm, etc.), tissues, organs, lysed cells, whole organisms, etc. In some embodiments, a sample may be derived from a subject. In some embodiments, a sample may comprise one or more partial or whole subjects.

As used herein, the term "subject" refers to any animal including, but not limited to, humans, non-human primates, bovines, equines, felines, canines, pigs, rodents (e.g., mice), and the like. The terms "subject" and "patient" may be used interchangeably, wherein the term "patient" generally refers to a human subject seeking or receiving treatment or preventative measures from a clinician or health care provider.

As used herein, the terms "subject at risk for cancer" or "subject at risk for leukemia" refer to a subject with one or more risk factors for developing cancer and/or leukemia. Risk factors include, but are not limited to, gender, age, genetic predisposition, environmental exposure, and previous incidents of cancer, preexisting non-cancer diseases, and lifestyle.

As used herein, the terms "characterizing cancer in subject" "characterizing leukemia in subject" refers to the identification of one or more properties of a cancer and/or leukemia sample in a subject, including but not limited to, the presence of benign, pre-cancerous or cancerous tissue or cells and the stage of the cancer (e.g., leukemia). Cancers (e.g., leukemia) may be characterized by identifying cancer cells with the compositions and methods of the present invention.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "effective amount" refers to the amount of a compound (e.g., a compound having a structure presented above or elsewhere described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., a compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions characterized by viral infection (e.g., providing dosing, route of administration, decision trees for treating physicians for correlating patient-specific characteristics with therapeutic courses of action). The compounds of the present invention (e.g. as shown in structures above and elsewhere presented herein) can be packaged into a kit, which may include instructions for administering the compounds to a subject.

As used herein, the term "alkyl" refers to a moiety consisting of carbon and hydrogen containing no double or triple bonds. An alkyl may be linear, branched, cyclic, or a combination thereof, and may contain from one to fifty carbon atoms. Examples of alkyl groups include but are not limited to methyl, ethyl, propyl, isopropyl, cyclopropyl, butyl isomers (e.g. n-butyl, iso-butyl, tert-butyl, etc.) cyclobutyl isomers (e.g. cyclobutyl, methylcyclopropyl, etc.), pentyl isomers, cyclopentane isomers, hexyl isomers, cyclohexane isomers, and the like. Unless specified otherwise (e.g., substituted alkyl group, heteroalkyl, alkoxy group, haloalkyl, alkylamine, thioalkyl, etc.), an alkyl group contains carbon and hydrogen atoms only.

As used herein, the term "linear alkyl" refers to a chain of carbon and hydrogen atoms (e.g., ethane, propane, butane, pentane, hexane, etc.). A linear alkyl group may be referred to by the designation $—(CH_2)_qCH_3$, where q is 0-49. The designation "$C_{1-12}$ alkyl" or a similar designation, refers to alkyl having from 1 to 12 carbon atoms such as methyl, ethyl, propyl isomers (e.g. n-propyl, isopropyl, etc.), butyl isomers, cyclobutyl isomers (e.g. cyclobutyl, methylcyclopropyl, etc.), pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. Similar designations refer to alkyl with a number of carbon atoms in a different range.

As used herein, the term "branched alkyl" refers to a chain of carbon and hydrogen atoms, without double or triple bonds, that contains a fork, branch, and/or split in the chain (e.g., 3,5-dimethyl-2-ethylhexane, 2-methyl-pentane, 1-methyl-cyclobutane, ortho-diethyl-cyclohexane, etc.). "Branching" refers to the divergence of a carbon chain, whereas "substitution" refers to the presence of non-carbon/non-hydrogen atoms in a moiety. Unless specified otherwise (e.g., substituted branched alkyl group, branched heteroalkyl, branched alkoxy group, branched haloalkyl, branched alkylamine, branched thioalkyl, etc.), a branched alkyl group contains carbon and hydrogen atoms only.

As used herein, the term "cycloalkyl" refers to a completely saturated mono- or multi-cyclic hydrocarbon ring system. When composed of two or more rings, the rings may be joined together in a fused, bridged or spiro-connected fashion. Cycloalkyl groups of the present application may range from three to ten carbons ($C_3$ to $C_{10}$). A cycloalkyl group may be unsubstituted, substituted, branched, and/or unbranched. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. Unless specified otherwise (e.g., substituted cycloalkyl group, heterocyclyl, cycloalkoxy group, halocycloalkyl, cycloalkylamine, thiocycloalkyl, etc.), an alkyl group contains carbon and hydrogen atoms only.

As used herein, the term "heteroalkyl" refers to an alkyl group, as defined herein, wherein one or more carbon atoms are independently replaced by one or more heteroatoms (e.g., oxygen, sulfur, nitrogen, phosphorus, silicon, or combinations thereof). The alkyl group containing the non-carbon substitution(s) may be a linear alkyl, branched alkyl, cycloalkyl (e.g., cycloheteroalkyl), or combinations thereof. Non-carbons may be at terminal locations (e.g., 2-hexanol) or integral to an alkyl group (e.g., diethyl ether).

As used herein, the term "substituted" (e.g., substituted alyklene) means that the referenced group (e.g., alkyl, aryl, etc.) comprises a substituent group (e.g., carbon/hydrogen-only substituent, heterosubstituent, halosubstituent, etc.). The term "optionally substituted", as used herein, means that the referenced group (e.g., alkyl, cycloalkyl, etc.) may or may not be substituted with one or more additional group(s). Substituent groups may be selected from, but are not limited to: alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of substituents include, halo, —CN, —OR, —C(O)R, —OC(O)R, —C(O)OR, OC(O)NHR, —C(O)N(R)$_2$, —SR—, —S(=O)R, —S(=O)$_2$R, —NHR, —N(R)$_2$, —NHC(O)—, NHC(O)O—, —C(O)NH—, S(=O)$_2$NHR, —S(O)$_2$N(R)$_2$, —NHS(=O)$_2$, —NHS(O)$_2$R, $C^1$-$C^6$alkyl, $C^1$-$C^6$alkoxy, aryl, heteroaryl, cycloalkyl, heterocycloalkyl, halo-substituted $C^1$-$C^6$alkyl, halo-substituted $C^1$-$C^6$alkoxy, where each R is independently selected from H, halo, $C^1$-$C^6$alkyl, $C^1$-$C^6$alkoxy, aryl, heteroaryl, cycloalkyl, heterocycloalkyl, halo-substituted $C^1$-$C^6$alkyl, halo-substituted $C^1$-$C^6$alkoxy.

As used herein, the term "substituted alkyl" refers to an alkyl group, as defined herein, displaying one or more non-carbon-atom-containing moieties (e.g., a group containing non-carbon atoms, possibly in addition to carbon atoms). The non-carbon-atom-containing moieties atoms may comprise: oxygen, sulfur, nitrogen, phosphorus, silicon, halogens (e.g. chlorine, bromine, flourine, iodine, etc.), or combinations thereof). The non-carbon-atom-containing moieties may also comprise carbon and hydrogen. The alkyl group containing the non-carbon substitution(s) may be a linear alkyl, branched alkyl, cycloalkyl (e.g., cycloheteroalkyl), or combinations thereof. Examples of substituted alky groups include: 2-hexanol, diethyl ether (also a heteroalkyl), 1-chloro-propane, etc.

As used herein, the terms "heteroaryl" or "heteroaromatic" refer to monocyclic, bicyclic, tricyclic, and other multicyclic ring systems (e.g., having four or greater ring members), wherein at least one ring in the system is aromatic, at least one ring in the system contains one or more heteroatoms selected from nitrogen, oxygen and sulfur, and wherein each ring in the system contains 3 to 7 ring members. Unless otherwise defined herein, suitable substituents on the unsaturated carbon atom of a heteroaryl group are generally selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)O$_2$NHC(O)R, phenyl (Ph) optionally substituted with R, —O(Ph) optionally substituted with R, —(CH$_2$)1-2(Ph), optionally substituted with R, or —CH=CH(Ph), optionally substituted with R, wherein each independent occurrence of R is selected from hydrogen, optionally substituted C$^1$-C$^6$alkyl, optionally substituted C$^1$-C$^6$alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl. Any substituents depicted in structures or examples herein, should be viewed as suitable substituents for use in embodiments of the present invention.

As used herein, the terms "heterocycloalkyl" of "heterocycle" refer to a cycloalkyl, as defined herein, wherein one or more of the ring carbons are replaced by a moiety selected from —O—, —N=, —NR—, —C(O)—, —S—, —S(O)— or —S(O)$_2$—, wherein R is hydrogen, C$^1$-C$^8$alkyl or a nitrogen protecting group, with the proviso that the ring of said group does not contain two adjacent O or S atoms. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

DETAILED DESCRIPTION

The present invention provides thienopyrimidine and thienopyridine class compounds. In certain embodiments, thienopyrimidine compounds are provided for the treatment or prevention of one or more diseases or conditions (e.g., leukemia). Embodiments of the present invention directed toward the treatment and/or prevention of leukemia or recurrence thereof are described herein; however, it should be understood that the compositions and methods described herein are not limited to the leukemia application. Rather, in some embodiments, the compositions and methods described herein should be understood to also be useful for the treatment and/or prevention of other cancers, including but not limited to breast, pancreatic, prostate and colon cancers, glioblastoma, diabetes etc. The compounds provided herein are not limited to therapeutic uses; any additional uses for this class of compounds are also contemplated.

In some embodiments, thienopyrimidine and thienopyridine class compounds of the present invention comprise a general formula of:

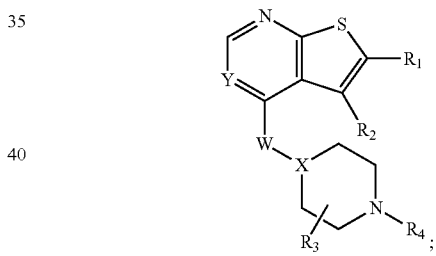

wherein W, X, Y, and R1-R4 independently comprise any suitable substituents described herein, or otherwise understood to one of skill in the art. In some embodiments, a thienopyrimidine class compound of the present invention comprises a general formula of one of:

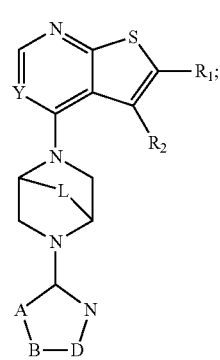

Subscaffold 1

-continued

Subscaffold 2

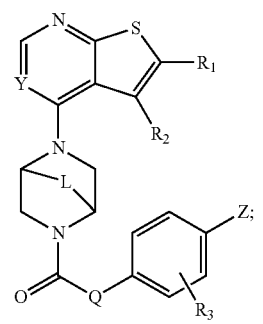

Subscaffold 3

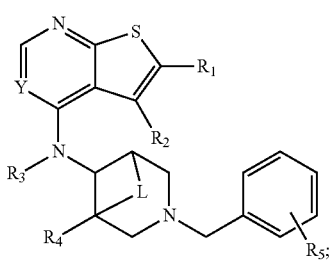

Subscaffold 4

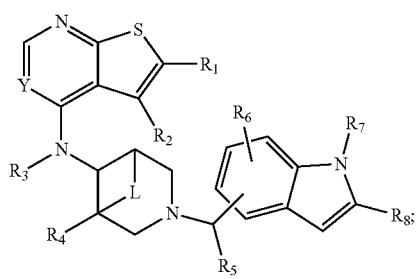

Subscaffold 5

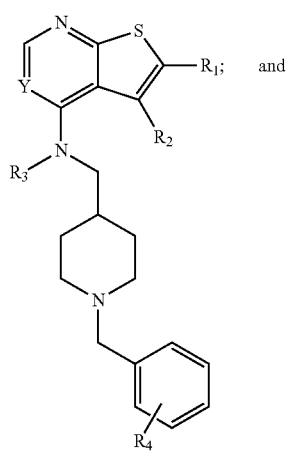 and

Subscaffold 6

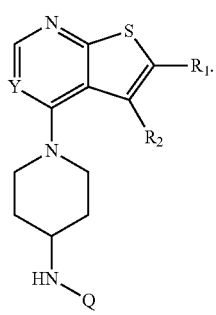

In some embodiments, the R1-R8, A, B, D, Q, L, X, Y, and Z of the above structures each independently comprise or consist of one or any combination of the following moieties:

Single atoms: H, Cl, Br, F, or I;

Alkanes (alkyl groups): methane (methyl), ethane (ethyl), propane (propyl), butane (butyl), pentane (pentyl), hexane (hexyl), or any suitable straight chain or branched $C^1$-$C^{20}$ alkane;

Alkenes: methene, ethene, propene, butene, pentene, hexene, or any suitable $C^7$-$C^{20}$ alkene;

Alkynes: methyne, ethyne, propyne, butyne, pentyne, hexyne, or any suitable $C^7$-$C^{20}$ alkyne;

Cycloalkanes: cyclopropane, cyclobutane, cyclopentane, cyclohexane, or any suitable $C^7$-$C^{20}$ cycloalkane;

Aromatic rings (e.g., carbon-only or heteroaromatics (e.g., heteroaryl)): furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, triazine (e.g., 1,2,3-triazine; 1,2,4-triazine; 1,3,5 triazine), thiadiazole, etc.;

Haloalkanes: halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) an halogens (e.g., Cl, Br, F, I, etc.);

Alcohols: OH, methanol, ethanol, propanol, butanol, pentanol, hexanol, cyclic alcohols (e.g., cyclohexanol), aromatic alcohols (e.g., phenol), or any other suitable combination of an OH moiety with a second moiety;

Ketones: methyl ketone (acetone), methyl ethyl ketone (butanone), propyl ethyl ketone (pentanone), or any other suitable combination of alkyl chains with =O;

Aldehydes: methanal, ethanal, propanal, butanal, pentanal, hexanal, or any other suitable combination of alkyl chain with =O;

Carboxylates: methanoate, ethanoate, propanote, butanoate, pentanoate, hexanoate, or any other suitable combination of alkyl chain with $OO^-$;

Carboxylic acids: methanoic acid, ethanoic acid, propanoic acid, butanoic acid, pentanoic acid, hexanoic acid, or any other suitable combination of alkyl chain with OOH;

Ethers: methoxy, ethoxy, methylmethoxy, ethylmethoxy, or any other suitable combination of alkyl chains surrounding an O;

Amides: methanamide ($CONH_2$), ethanamide ($CH_2CONH_2$), propanamide (($CH_2)_2CONH_2$), alkan″amide (($CH_2)_nCONH_2$), n-methyl alkan″amide (($CH_2)_nCONHCH_3$), c-methyl alkan″amide (($CH_2)_nNHCOCH_3$), n-alkyl alkan″amide (($CH_2)_nCONH(CH_2)_mCH_3$), c-methyl alkan″amide (($CH_2)_nNHCO(CH_2)_mCH_3$), etc.;

Primary amines: $NH_2$, methylamine, ethylamine, cyclopropylamine, etc.;

Secondary amines: aminomethyl ($NHCH_3$), aminoethyl ($NHCH_2CH_3$), methyl-aminomethyl ($CH_2NHCH_3$; aka methylamine-methane), alkyl″-aminomethane (($CH_2)_nNHCH_3$), etc.;

Tertiary amines: dimethylamine ($N(CH_3)_2$), dimethylamine ($N(CH_3)_2$), methyl-ethyl-amine ($NCH_3CH_2CH_3$), methane-diethylamine ($CH_2N(CH_2CH_3)_2$; aka methylamine-diethane), etc.;

Azides: methyl azide ($CH_2NNN$), ethyl azide ($(CH_2)_2NNN$), alkyl″ azide ($(CH_2)_nNNN$), etc.

Cyanates: methyl cyanate ($CH_2OCN$), ethyl cyanate ($(CH_2)_2OCN$), alkyl″ cyanate ($(CH_2)_nOCN$), etc.

Cyanos: methyl carbonitrile ($CH_2CN$), ethyl carbonitrile ($(CH_2)_2CN$), alkyl″ carbonitrile ($(CH_2)_nCN$), etc.

Thiols: methanethiol ($CH_2SH$), ethanethiol ($(CH_2)_2SH$), alkan″ethiol ($(CH_2)_nSH$), etc.

Sulfides: dimethyl sulfide ($CH_2SCH_3$), methyl-ethyl sulfide ($CH_2SCH_2CH_3$), alkyl″-alkyl‴ sulfide ($(CH_2)_nS(CH_2)_{m-1}CH_3$), etc.;

Sulfoxides: dimethyl sulfoxide ($CH_2SOCH_3$), methyl-ethyl sulfoxide ($CH_2SOCH_2CH_3$), alkyl″-alkyl‴ sulfoxide ($(CH_2)_nSO(CH_2)_{m-1}CH_3$), etc.;

Sulfone: dimethyl sulfone ($CH_2SO_2CH_3$; aka methyl-sulfone-methyl), methyl-ethyl sulfone ($CH_2SO_2CH_2CH_3$; aka methyl-sulfone-ethyl), alkyl″-alkyl‴ sulfone ($(CH_2)_nSO_2(CH_2)_{m-1}CH_3$; aka alkyl″-sulfone-alkyl‴), $R^xSO_2R^y$ (wherein Rx and Ry are independently selected from any of the moieties provided in this list or combinations thereof), etc.;

Sulfinic acids: $SO_2H$, methyl sulfinic acid ($CH_2SO_2H$), ethyl sulfinic acid ($(CH_2)_2SO_2H$), alkyl″ sulfinic acid ($(CH_2)_nSO_2H$), etc.;

Thiocyanate: SCN, methyl thiocyanate ($CH_2SCN$), ethyl thiocyanate ($(CH_2)_2SCN$), alkyl″ thiocyanate ($(CH_2)_nSCN$), etc.;

Phosphates: $OP(=O)(OH)_2$, methyl phosphate ($CH_2OP(=O)(OH)_2$), ethyl phosphate ($(CH_2)_2OP(=O)(OH)_2$), alkyl″ phosphate ($(CH_2)_nOP(=O)(OH)_2$), etc.

In various embodiments, the above listed moieties are attached at the X, Y, Z, A, B, D, and/or R positions in any suitable conformation. In some embodiments, the above listed functional groups are combined to produce the substituents depicted in compounds 1-283 of Tables 1-8.

TABLE 1

Examples of subscaffold 1 inhibitors of menin-MLL.

| compound # | Structure | [MH]$^+$ | LC-MS RT, min. or TLC R$_f$ |
|---|---|---|---|
| Inhibitors with IC50 0.01 nM-0.1 μM | | | |
| 1 | [structure] | 416.1 | 0.5 |
| 2 | [structure] | 442.1 | 0.6 |

TABLE 1-continued
Examples of subscaffold 1 inhibitors of menin-MLL.
| compound # | Structure | [MH]+ | LC-MS RT, min. or TLC R_f |
|---|---|---|---|
| | Inhibitors with IC50 0.1 uM-0.5 μM | | |
| 3 | 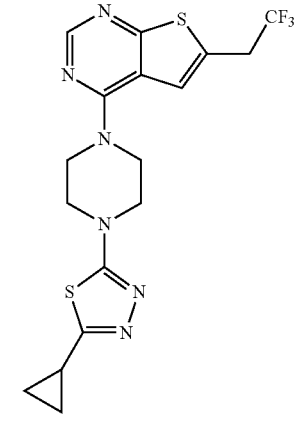 [SMILES: FC(F)(F)Cc1cc2c(N3CCN(c4nnc(C5CC5)s4)CC3)ncnc2s1] | 427.3 | 1.71 min |
| 4 | 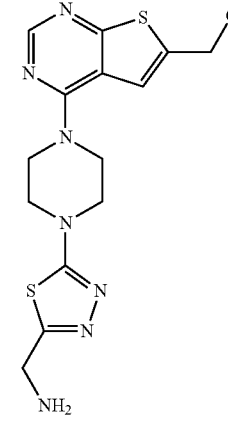 | 399.1 | 1.13 min |
| 5 | 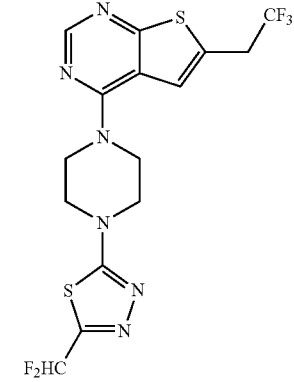 [SMILES: FC(F)c1nnc(N2CCN(c3ncnc4sc(CC(F)(F)F)cc34)CC2)s1] | 437.2 | 2.03 min |

TABLE 1-continued

Examples of subscaffold 1 inhibitors of menin-MLL.

| compound # | Structure | [MH]+ | LC-MS RT, min. or TLC R_f |
|---|---|---|---|
| 6 | 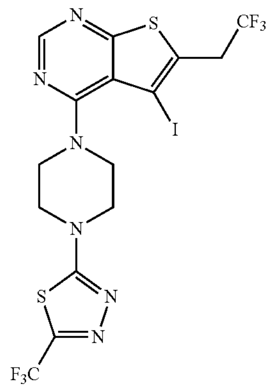 [SMILES: FC(F)(F)Cc1sc2ncnc(N3CCN(c4nnc(C(F)(F)F)s4)CC3)c2c1I] | 581.2 | 2.51 min |
| 7 | 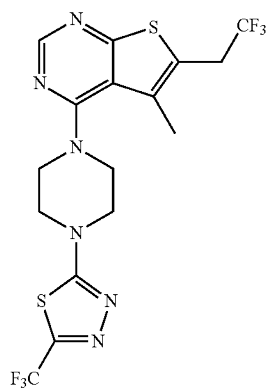 [SMILES: Cc1c(CC(F)(F)F)sc2ncnc(N3CCN(c4nnc(C(F)(F)F)s4)CC3)c12] | 469.3 | 2.78 min |
| 8 | 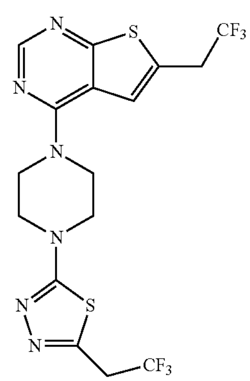 [SMILES: FC(F)(F)Cc1cc2c(N3CCN(c4nnc(CC(F)(F)F)s4)CC3)ncnc2s1] | 469.3 | 2.22 min |
| 9 | 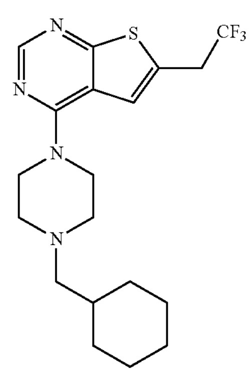 [SMILES: FC(F)(F)Cc1cc2c(N3CCN(CC4CCCCC4)CC3)ncnc2s1] | 399.0 | 1.64 min |

TABLE 1-continued

Examples of subscaffold 1 inhibitors of menin-MLL.

| compound # | Structure | [MH]+ | LC-MS RT, min. or TLC $R_f$ |
|---|---|---|---|
| 10 | 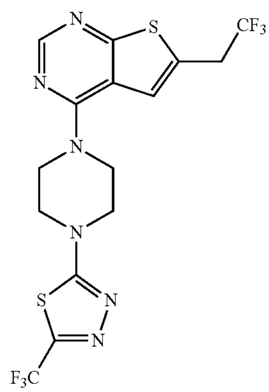 [SMILES: FC(F)(F)Cc1cc2c(N3CCN(c4nnc(C(F)(F)F)s4)CC3)ncnc2s1] | 455.1 | 0.5 |
| 11 | 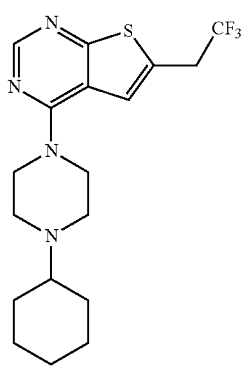 [SMILES: FC(F)(F)Cc1cc2c(N3CCN(C4CCCCC4)CC3)ncnc2s1] | 385.5 | 1.42 min |
| 12 | 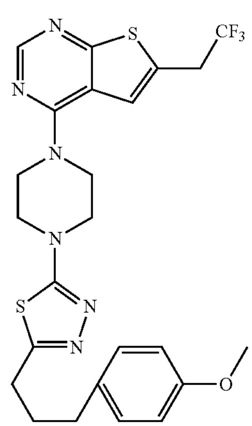 [SMILES: COc1ccc(CCCc2nnc(N3CCN(c4ncnc5sc(CC(F)(F)F)cc45)CC3)s2)cc1] | 535.2 | 0.6 |

TABLE 1-continued

Examples of subscaffold 1 inhibitors of menin-MLL.

| compound # | Structure | [MH]+ | LC-MS RT, min. or TLC R$_f$ |
|---|---|---|---|
| 13 | 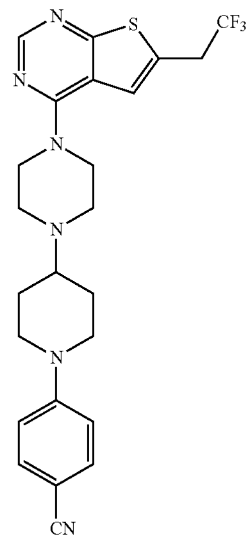 [SMILES: N#Cc1ccc(N2CCC(N3CCN(c4ncnc5sc(CC(F)(F)F)cc45)CC3)CC2)cc1] | 487.2 | 0.3 |
| 14 | AND Enantiomer | 427.1 | 0.5 |

Inhibitors with IC50 0.5 μM-2 μM

| | | | |
|---|---|---|---|
| 15 | | 419.2 | 1.89 min |

TABLE 1-continued

Examples of subscaffold 1 inhibitors of menin-MLL.

| compound # | Structure | [MH]+ | LC-MS RT, min. or TLC R_f |
|---|---|---|---|
| 16 | (thieno[3,2-d]pyrimidine with CF3, piperazine, 5-methyl-1,3,4-thiadiazole) | 401.2 | 1.51 min |
| 17 | (thieno[3,2-d]pyrimidine with CF3, piperazine, 1,3,4-thiadiazole with propyl-cyclohexyl) | 511.3 | 2.56 min |
| 18 | (thieno[3,2-d]pyrimidine with CF3, piperazine, 1,3,4-thiadiazole with CH2CH2CF3) | 483.4 | 1.89 min |

TABLE 1-continued

Examples of subscaffold 1 inhibitors of menin-MLL.

| compound # | Structure | [MH]+ | LC-MS RT, min. or TLC $R_f$ |
|---|---|---|---|
| 19 | 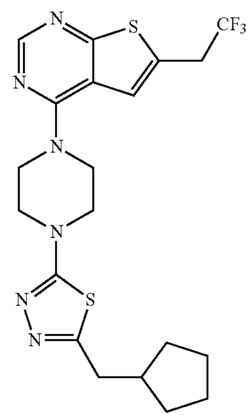 [SMILES: FC(F)(F)Cc1cc2c(N3CCN(c4nnc(CC5CCCC5)s4)CC3)ncnc2s1] | 469.3 | 2.50 min |
| 20 | 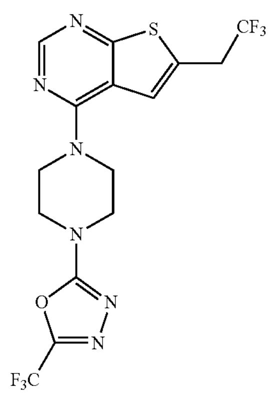 [SMILES: FC(F)(F)Cc1cc2c(N3CCN(c4nnc(C(F)(F)F)o4)CC3)ncnc2s1] | 439.0 | 2.30 min |
| 21 | 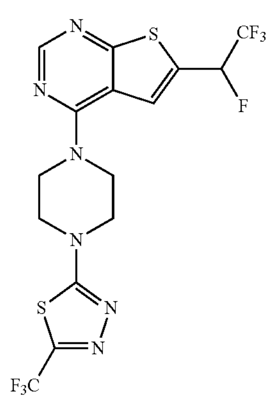 [SMILES: FC(c1cc2c(N3CCN(c4nnc(C(F)(F)F)s4)CC3)ncnc2s1)C(F)(F)F] | 473.2 | 2.48 min |

TABLE 1-continued
Examples of subscaffold 1 inhibitors of menin-MLL.
| compound # | Structure | [MH]+ | LC-MS RT, min. or TLC R_f |
|---|---|---|---|
| 22 | 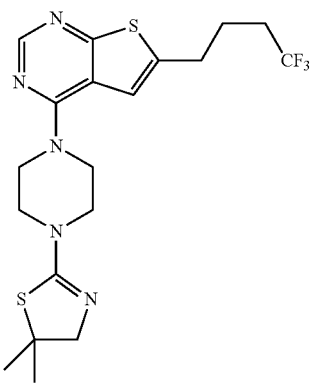 [SMILES: CC1(C)CN=C(N2CCN(c3ncnc4sc(CCCC(F)(F)F)cc34)CC2)S1] | | |
| 23 | 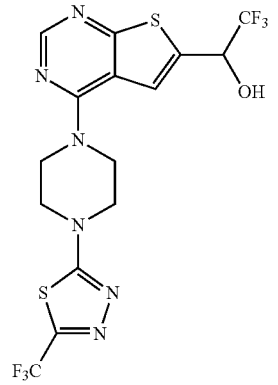 [SMILES: OC(c1cc2c(N3CCN(c4nnc(C(F)(F)F)s4)CC3)ncnc2s1)C(F)(F)F] | 471.5 | 1.93 min |
| 24 | 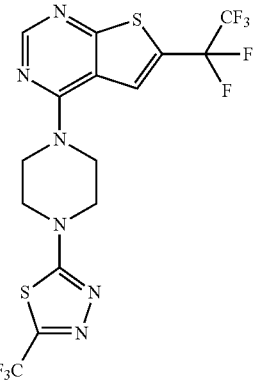 | 491.0 | 2.73 min |

TABLE 1-continued

Examples of subscaffold 1 inhibitors of menin-MLL.

| compound # | Structure | [MH]+ | LC-MS RT, min. or TLC $R_f$ |
|---|---|---|---|
| 25 | 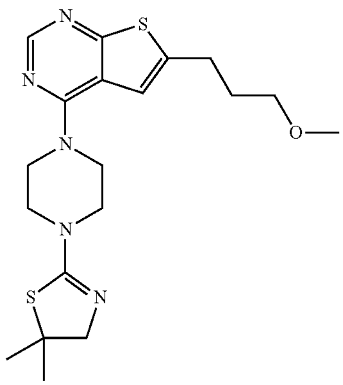 | 406.5 | 1.25 min |
| 26 | 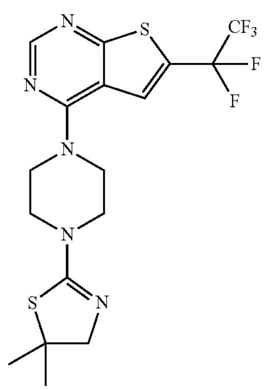 [SMILES: CC1(C)CN=C(N2CCN(c3ncnc4sc(C(F)(F)C(F)(F)F)cc34)CC2)S1] | 452.0 | 1.87 min |
| 27 | 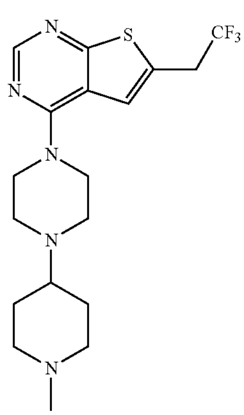 [SMILES: CN1CCC(N2CCN(c3ncnc4sc(CC(F)(F)F)cc34)CC2)CC1] | | |

TABLE 1-continued

Examples of subscaffold 1 inhibitors of menin-MLL.

| compound # | Structure | [MH]+ | LC-MS RT, min. or TLC R$_f$ |
|---|---|---|---|
| 28 | 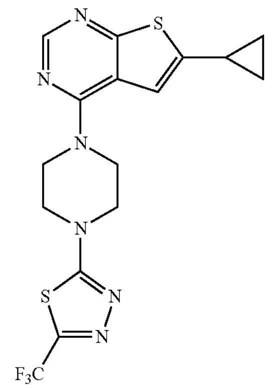 [SMILES: FC(F)(F)c1nnc(N2CCN(c3ncnc4sc(C5CC5)cc34)CC2)s1] | 413.0 | 2.01 min |
| 29 | 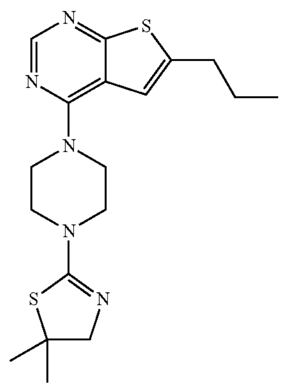 [SMILES: CCCc1cc2c(N3CCN(C4=NCC(C)(C)S4)CC3)ncnc2s1] | 327.5 | 1.42 min |
| 30 | 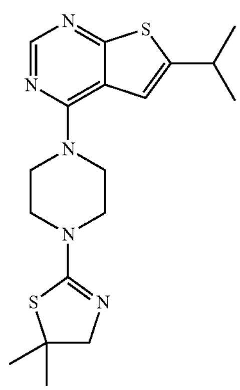 [SMILES: CC(C)c1cc2c(N3CCN(C4=NCC(C)(C)S4)CC3)ncnc2s1] | 376.5 | 1.42 min |
| 31 | 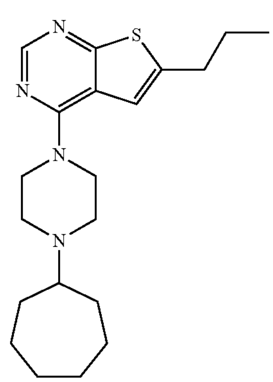 [SMILES: CCCc1cc2c(N3CCN(C4CCCCCC4)CC3)ncnc2s1] | 359.5 | 1.61 min |

TABLE 1-continued
Examples of subscaffold 1 inhibitors of menin-MLL.
| compound # | Structure | [MH]+ | LC-MS RT, min. or TLC R$_f$ |
|---|---|---|---|
| 32 | 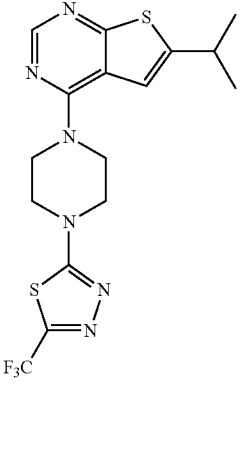 | 415.6 | 2.07 min |
| 33 | 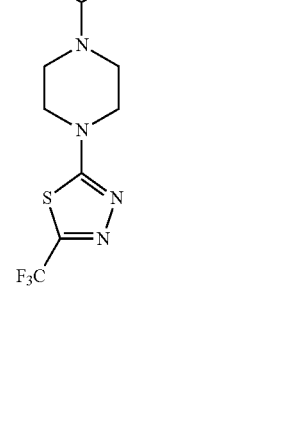 | 415.6 | 2.09 min |
| 34 | 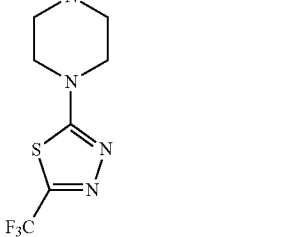 | 429.4 | 2.26 min |

TABLE 1-continued

Examples of subscaffold 1 inhibitors of menin-MLL.

| compound # | Structure | [MH]+ | LC-MS RT, min. or TLC $R_f$ |
|---|---|---|---|
| 35 | 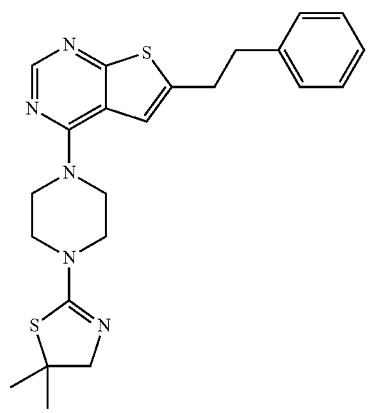 [SMILES: CC1(C)CN=C(N2CCN(c3ncnc4sc(CCc5ccccc5)cc34)CC2)S1] | 438.2 | 0.6 |
| 36 | 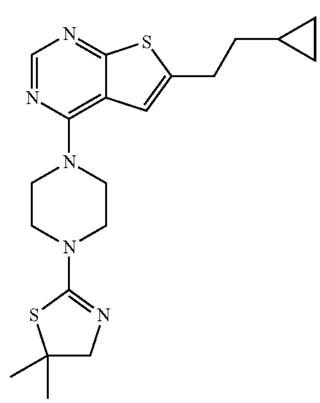 [SMILES: CC1(C)CN=C(N2CCN(c3ncnc4sc(CCC5CC5)cc34)CC2)S1] | 402.2 | 0.6 |
| 37 | 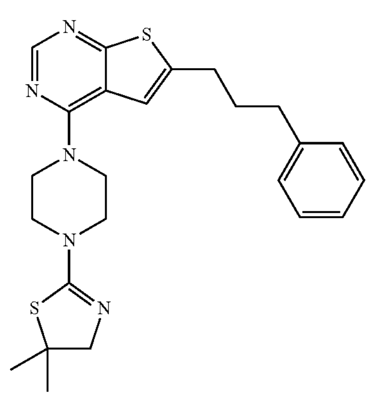 [SMILES: CC1(C)CN=C(N2CCN(c3ncnc4sc(CCCc5ccccc5)cc34)CC2)S1] | 452.2 | 0.6 |

TABLE 1-continued
Examples of subscaffold 1 inhibitors of menin-MLL.
| compound # | Structure | [MH]+ | LC-MS RT, min. or TLC R_f |
|---|---|---|---|
| 38 | 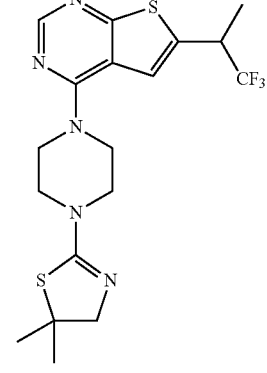 | 430.1 | 0.7 |
| 39 | 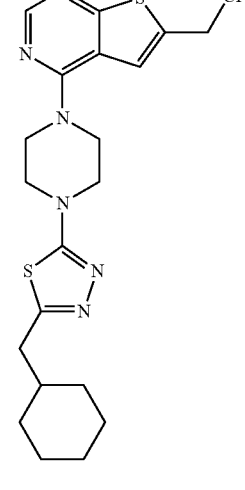 | 483.2 | 0.6 |
| 40 | 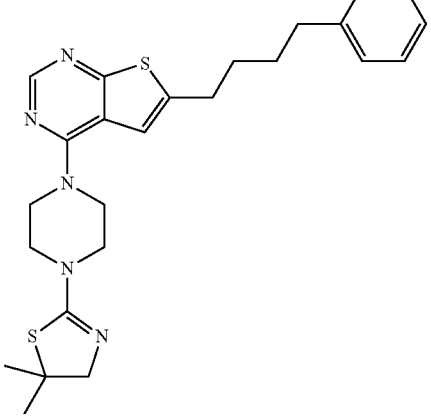 | 466.2 | 0.6 |

TABLE 1-continued

Examples of subscaffold 1 inhibitors of menin-MLL.

| compound # | Structure | [MH]+ | LC-MS RT, min. or TLC $R_f$ |
|---|---|---|---|
| 41 | 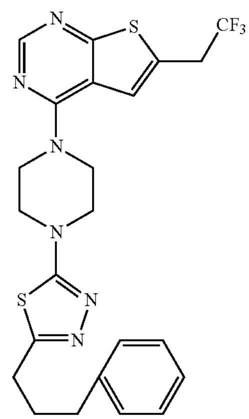 [SMILES: FC(F)(F)Cc1cc2c(N3CCN(c4nnc(CCCc5ccccc5)s4)CC3)ncnc2s1] | 505.2 | 0.6 |
| 42 | 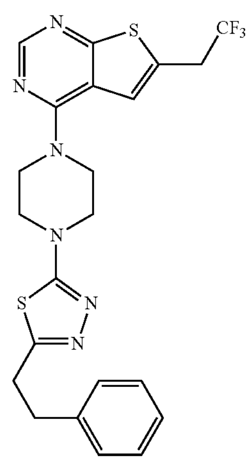 [SMILES: FC(F)(F)Cc1cc2c(N3CCN(c4nnc(CCc5ccccc5)s4)CC3)ncnc2s1] | 491.1 | 0.6 |

LC-MS conditions:

Column type: Phenomenex Kinetex 2.6 u C18

Column dimensions: 3.0 mm × 50 mm

Temperature: 60° C.

Solvent A: 0.1% TFA in water

Solvent B: 0.1% TFA in MeCN

Gradient program: 5% to 100% B/6 min

UV wavelength: 254 nm

TLC conditions:

Plates: Pre-coated Silica Gel 60 $F_{254}$

Developing solvent: DCM:MeOH:NH$_3$•H$_2$O, 20:1:0.1

TABLE 2
Examples of subscaffold 2 inhibitors of menin-MLL.
| Compound # | Structure | [MH]+ | LC-MS RT, min. or TLC R_f |
|---|---|---|---|
| | Inhibitors with IC50 0.01 nM-0.1 μM | | |
| 43 | 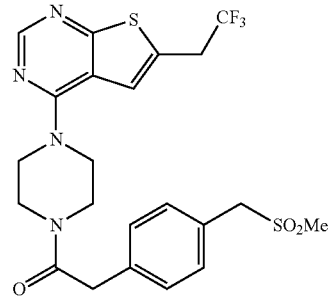 [SMILES: CS(=O)(=O)Cc1ccc(CC(=O)N2CCN(c3ncnc4sc(CC(F)(F)F)cc34)CC2)cc1] | 513.1 | 0.4 |
| 44 | 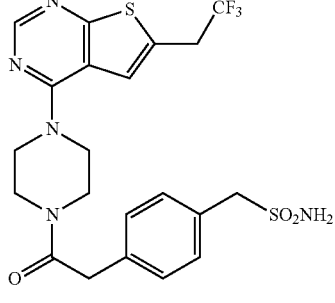 | 514.1 | 0.2 |
| 45 | 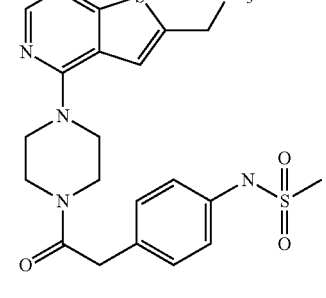 | 514.3 | 1.76 min |
| 46 | 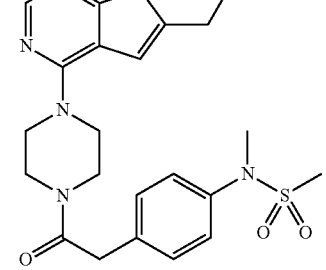 | 528.1 | 1.70 min |

TABLE 2-continued

Examples of subscaffold 2 inhibitors of menin-MLL.

| Compound # | Structure | [MH]+ | LC-MS RT, min. or TLC $R_f$ |
|---|---|---|---|
| 47 | 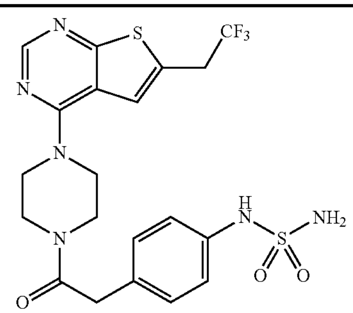 | 515.2 | 1.44 min |
| 48 | 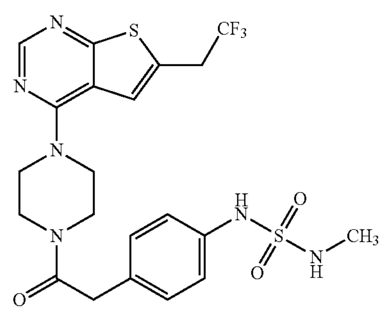 [SMILES: CNS(=O)(=O)Nc1ccc(CC(=O)N2CCN(c3ncnc4sc(CC(F)(F)F)cc34)CC2)cc1] | 529.0 | 1.69 min |
| 49 | 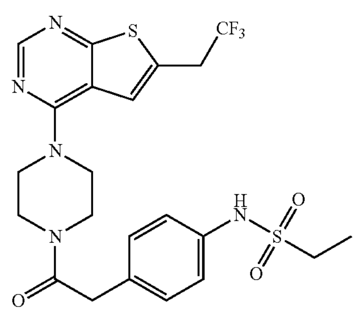 [SMILES: CCS(=O)(=O)Nc1ccc(CC(=O)N2CCN(c3ncnc4sc(CC(F)(F)F)cc34)CC2)cc1] | 528.1 | 1.85 min |
| 50 | 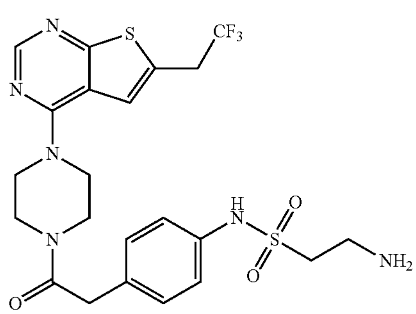 [SMILES: NCCS(=O)(=O)Nc1ccc(CC(=O)N2CCN(c3ncnc4sc(CC(F)(F)F)cc34)CC2)cc1] | 543.4 | 1.57 min |
| 51 | 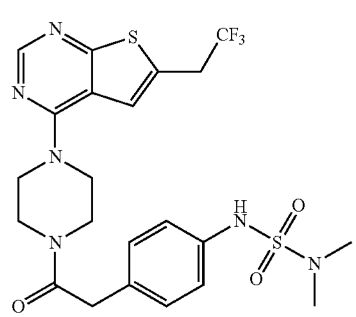 [SMILES: CN(C)S(=O)(=O)Nc1ccc(CC(=O)N2CCN(c3ncnc4sc(CC(F)(F)F)cc34)CC2)cc1] | 543.4 | 1.90 min |

TABLE 2-continued
Examples of subscaffold 2 inhibitors of menin-MLL.
| Compound # | Structure | [MH]+ | LC-MS RT, min. or TLC $R_f$ |
|---|---|---|---|
| 52 | 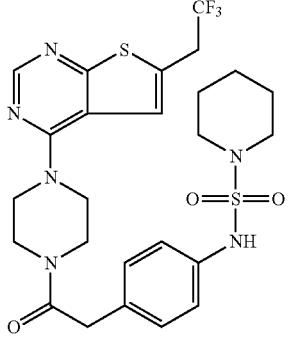 [SMILES: O=C(Cc1ccc(NS(=O)(=O)N2CCCCC2)cc1)N1CCN(c2ncnc3sc(CC(F)(F)F)cc23)CC1] | 583.0 | 2.04 min |
| 53 | 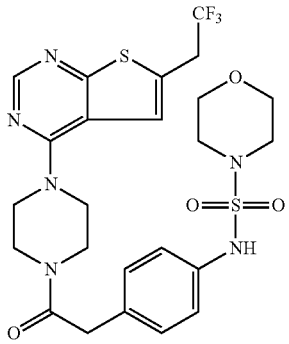 [SMILES: O=C(Cc1ccc(NS(=O)(=O)N2CCOCC2)cc1)N1CCN(c2ncnc3sc(CC(F)(F)F)cc23)CC1] | 585.1 | 1.73 min |
| 54 | 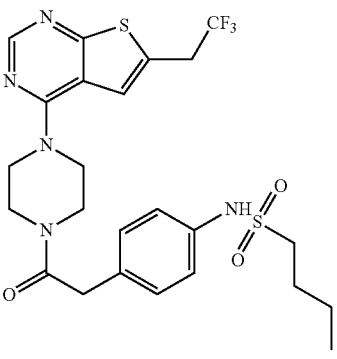 | 556.3 | 1.99 min |
| 55 | 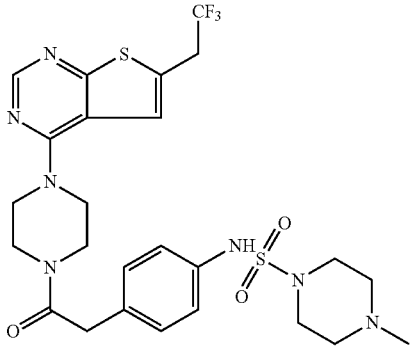 | 598.0 | 1.52 min |

TABLE 2-continued

Examples of subscaffold 2 inhibitors of menin-MLL.

| Compound # | Structure | [MH]+ | LC-MS RT, min. or TLC $R_f$ |
|---|---|---|---|
| 56 | 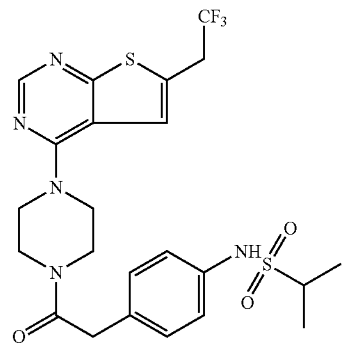 | 542.2 | 1.82 min |
| 57 | 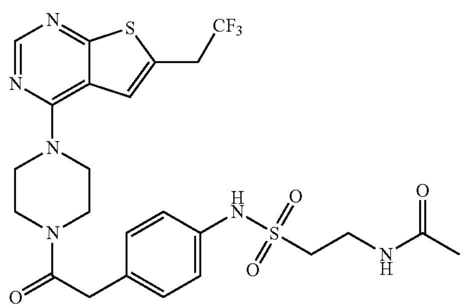 [SMILES: CC(=O)NCCS(=O)(=O)Nc1ccc(CC(=O)N2CCN(c3ncnc4sc(CC(F)(F)F)cc34)CC2)cc1] | 585.1 | 1.57 min |
| 58 | 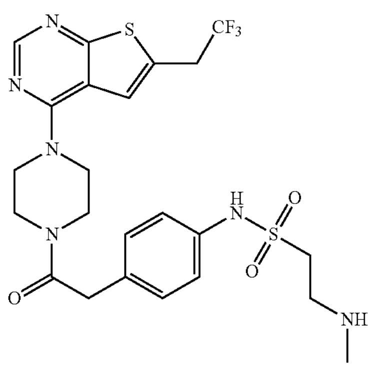 [SMILES: CNCCS(=O)(=O)Nc1ccc(CC(=O)N2CCN(c3ncnc4sc(CC(F)(F)F)cc34)CC2)cc1] | 556.9 | 1.43 min |
| 59 | 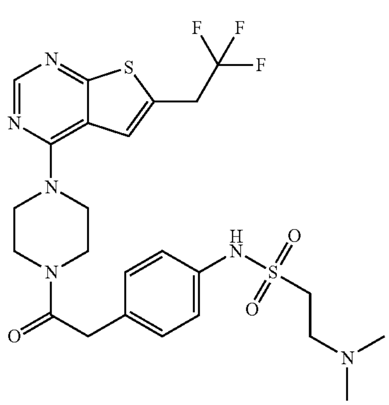 [SMILES: CN(C)CCS(=O)(=O)Nc1ccc(CC(=O)N2CCN(c3ncnc4sc(CC(F)(F)F)cc34)CC2)cc1] | 571.3 | 1.45 min |

TABLE 2-continued

Examples of subscaffold 2 inhibitors of menin-MLL.

| Compound # | Structure | [MH]+ | LC-MS RT, min. or TLC $R_f$ |
|---|---|---|---|
| 60 | 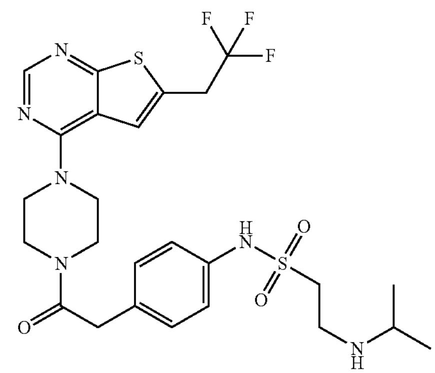 [SMILES: CC(C)NCCS(=O)(=O)Nc1ccc(CC(=O)N2CCN(c3ncnc4sc(CC(F)(F)F)cc34)CC2)cc1] | 585.1 | 1.51 min |
| 61 | 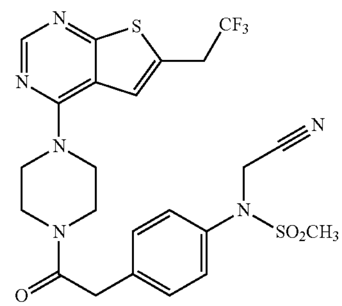 [SMILES: CS(=O)(=O)N(CC#N)c1ccc(CC(=O)N2CCN(c3ncnc4sc(CC(F)(F)F)cc34)CC2)cc1] | 553.0 | 1.77 min |
| 62 | 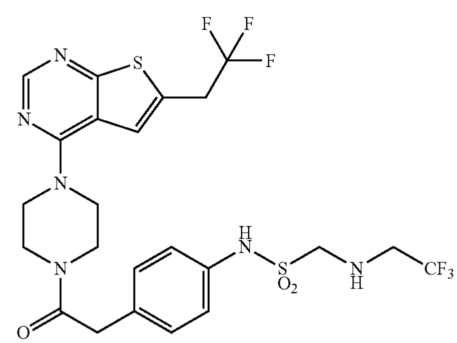 [SMILES: O=C(Cc1ccc(NS(=O)(=O)CNCC(F)(F)F)cc1)N1CCN(c2ncnc3sc(CC(F)(F)F)cc23)CC1] | 625.4 | 1.74 min |
| 63 | 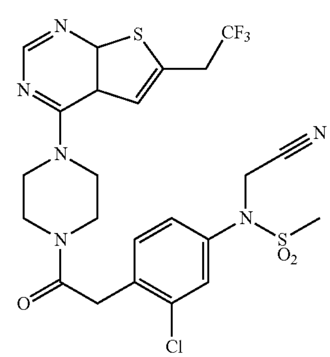 [SMILES: CS(=O)(=O)N(CC#N)c1ccc(CC(=O)N2CCN(C3=NC=NC4SC(CC(F)(F)F)=CC34)CC2)c(Cl)c1] | 587.0 | 2.15 min |

TABLE 2-continued

Examples of subscaffold 2 inhibitors of menin-MLL.

| Compound # | Structure | [MH]+ | LC-MS RT, min. or TLC R<sub>f</sub> |
|---|---|---|---|
| 64 | 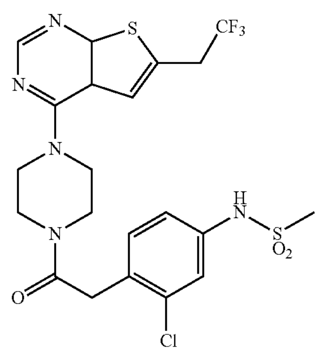 [SMILES: CS(=O)(=O)Nc1ccc(CC(=O)N2CCN(C3=NC=NC4SC(CC(F)(F)F)=CC34)CC2)c(Cl)c1] | 547.9 | 2.02 min |
| 65 | 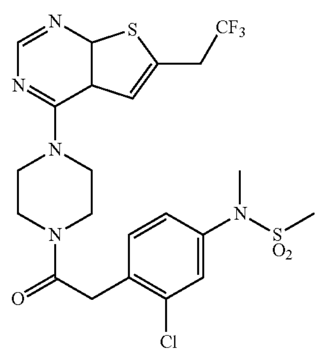 [SMILES: CN(c1ccc(CC(=O)N2CCN(C3=NC=NC4SC(CC(F)(F)F)=CC34)CC2)c(Cl)c1)S(C)(=O)=O] | 562.0 | 2.07 min |
| 66 | 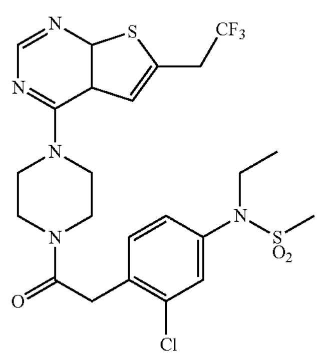 [SMILES: CCN(c1ccc(CC(=O)N2CCN(C3=NC=NC4SC(CC(F)(F)F)=CC34)CC2)c(Cl)c1)S(C)(=O)=O] | 576.1 | 2.13 min |

Inhibitors with IC50 0.1 μM-0.5 μM

| 67 | | 421.1 | 0.6 |

TABLE 2-continued
Examples of subscaffold 2 inhibitors of menin-MLL.
| Compound # | Structure | [MH]+ | LC-MS RT, min. or TLC R_f |
|---|---|---|---|
| 68 | 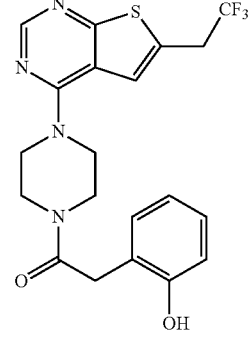 | 437.1 | 0.5 |
| 69 | 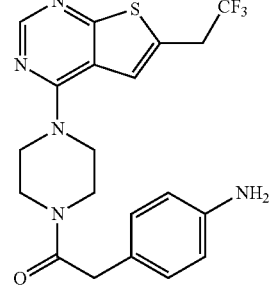 | 436.1 | 0.5 |
| 70 | 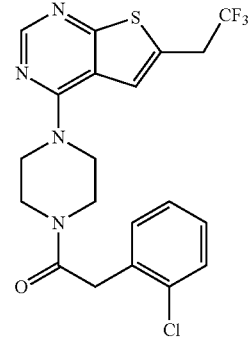 [SMILES: O=C(Cc1ccccc1Cl)N1CCN(c2ncnc3sc(CC(F)(F)F)cc23)CC1] | 455.1 | 0.6 |
| 71 | 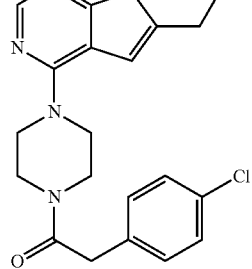 | 455.1 | 0.6 |

TABLE 2-continued

Examples of subscaffold 2 inhibitors of menin-MLL.

| Compound # | Structure | [MH]+ | LC-MS RT, min. or TLC R_f |
|---|---|---|---|
| 72 | 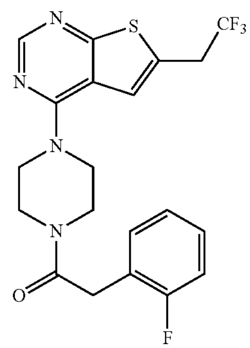 [SMILES: O=C(Cc1ccccc1F)N1CCN(c2ncnc3sc(CC(F)(F)F)cc23)CC1] | 439.1 | 0.6 |
| 73 | 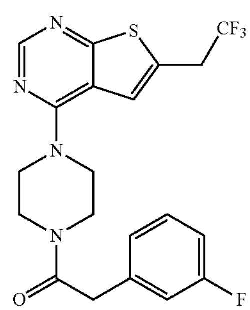 [SMILES: O=C(Cc1cccc(F)c1)N1CCN(c2ncnc3sc(CC(F)(F)F)cc23)CC1] | 439.1 | 0.6 |
| 74 | 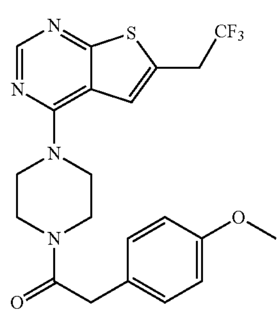 [SMILES: COc1ccc(CC(=O)N2CCN(c3ncnc4sc(CC(F)(F)F)cc34)CC2)cc1] | 451.1 | 0.5 |
| 75 | 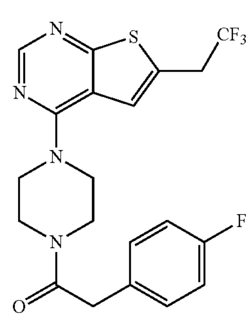 [SMILES: O=C(Cc1ccc(F)cc1)N1CCN(c2ncnc3sc(CC(F)(F)F)cc23)CC1] | 439.1 | 0.6 |

TABLE 2-continued

Examples of subscaffold 2 inhibitors of menin-MLL.

| Compound # | Structure | [MH]+ | LC-MS RT, min. or TLC $R_f$ |
|---|---|---|---|
| 76 | 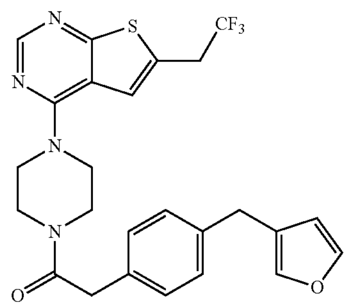 [SMILES: O=C(Cc1ccc(Cc2ccoc2)cc1)N1CCN(c2ncnc3sc(CC(F)(F)F)cc23)CC1] | 501.2 | 0.6 |
| 77 | 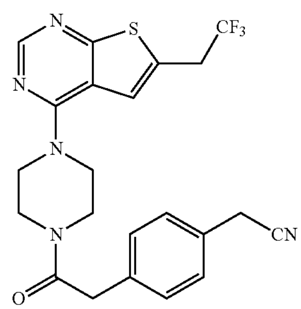 [SMILES: N#CCc1ccc(CC(=O)N2CCN(c3ncnc4sc(CC(F)(F)F)cc34)CC2)cc1] | 460.1 | 0.5 |
| 78 | 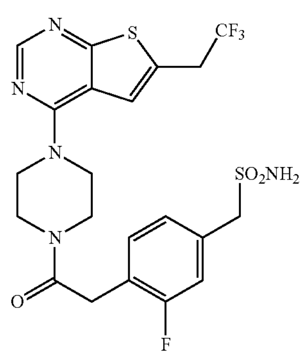 [SMILES: NS(=O)(=O)Cc1ccc(CC(=O)N2CCN(c3ncnc4sc(CC(F)(F)F)cc34)CC2)c(F)c1] | 532.1 | 0.2 |
| 79 | 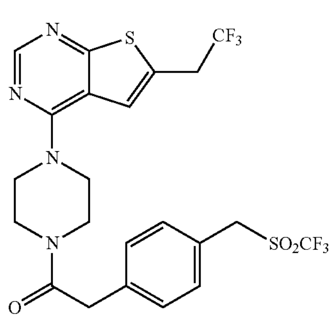 | 567.1 | 0.4 |

TABLE 2-continued

Examples of subscaffold 2 inhibitors of menin-MLL.

| Compound # | Structure | [MH]+ | LC-MS RT, min. or TLC R_f |
|---|---|---|---|
| 80 | 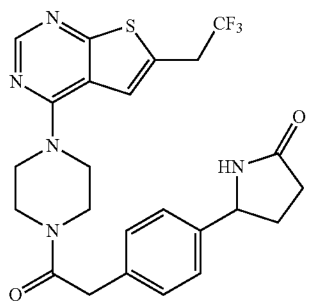 [SMILES: O=C1CCC(c2ccc(CC(=O)N3CCN(c4ncnc5sc(CC(F)(F)F)cc45)CC3)cc2)N1] | 504.1 | 1.50 min |
| 81 | 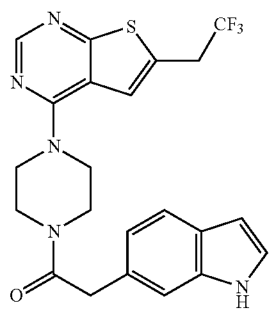 [SMILES: O=C(Cc1ccc2cc[nH]c2c1)N1CCN(c2ncnc3sc(CC(F)(F)F)cc23)CC1] | 460.0 | 1.76 min |
| 82 | 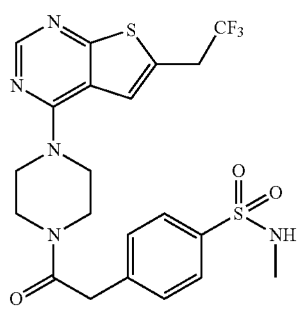 [SMILES: CNS(=O)(=O)c1ccc(CC(=O)N2CCN(c3ncnc4sc(CC(F)(F)F)cc34)CC2)cc1] | 514.3 | 1.60 min |
| 83 | 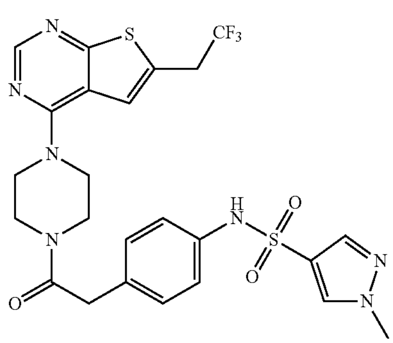 [SMILES: Cn1cc(S(=O)(=O)Nc2ccc(CC(=O)N3CCN(c4ncnc5sc(CC(F)(F)F)cc45)CC3)cc2)cn1] | 580.0 | 1.71 min |

TABLE 2-continued

Examples of subscaffold 2 inhibitors of menin-MLL.

| Compound # | Structure | [MH]+ | LC-MS RT, min. or TLC R_f |
|---|---|---|---|
| 84 | 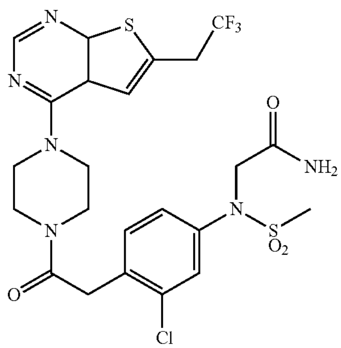 [SMILES: CS(=O)(=O)N(CC(N)=O)c1ccc(CC(=O)N2CCN(C3=NC=NC4SC(CC(F)(F)F)=CC34)CC2)c(Cl)c1] | 605.3 | 1.90 min |
| 85 | 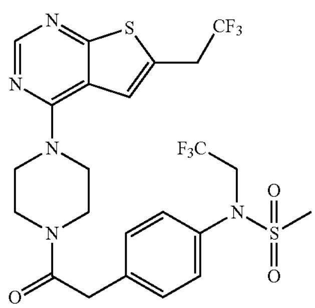 [SMILES: CS(=O)(=O)N(CC(F)(F)F)c1ccc(CC(=O)N2CCN(c3ncnc4sc(CC(F)(F)F)cc34)CC2)cc1] | 596.3 | 2.23 min |
| Inhibitors with IC50 0.5 μM-2 μM | | | |
| 86 | 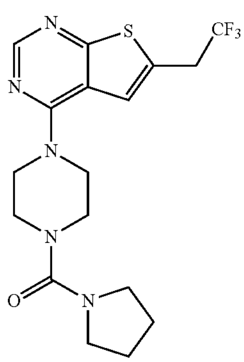 [SMILES: O=C(N1CCCC1)N1CCN(c2ncnc3sc(CC(F)(F)F)cc23)CC1] | 400.1 | 0.4 |
| 87 | 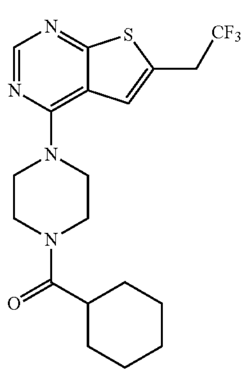 [SMILES: O=C(C1CCCCC1)N1CCN(c2ncnc3sc(CC(F)(F)F)cc23)CC1] | 413.2 | 0.5 |

TABLE 2-continued

Examples of subscaffold 2 inhibitors of menin-MLL.

| Compound # | Structure | [MH]+ | LC-MS RT, min. or TLC R_f |
|---|---|---|---|
| 88 | 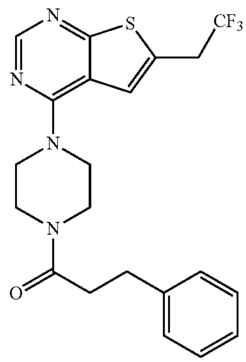 [SMILES: O=C(CCc1ccccc1)N1CCN(c2ncnc3sc(CC(F)(F)F)cc23)CC1] | 435.1 | 0.6 |
| 89 | 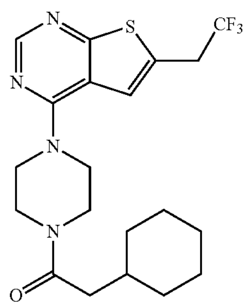 [SMILES: O=C(CC1CCCCC1)N1CCN(c2ncnc3sc(CC(F)(F)F)cc23)CC1] | 427.2 | 0.6 |
| 90 | 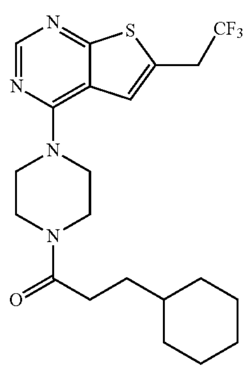 [SMILES: O=C(CCC1CCCCC1)N1CCN(c2ncnc3sc(CC(F)(F)F)cc23)CC1] | 441.2 | 0.6 |
| 91 | 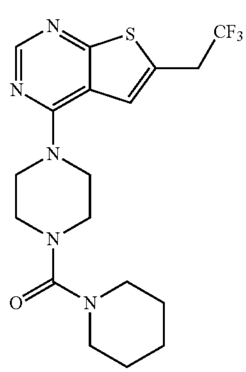 [SMILES: O=C(N1CCCCC1)N1CCN(c2ncnc3sc(CC(F)(F)F)cc23)CC1] | 414.2 | 0.4 |

TABLE 2-continued
Examples of subscaffold 2 inhibitors of menin-MLL.
| Compound # | Structure | [MH]+ | LC-MS RT, min. or TLC R_f |
|---|---|---|---|
| 92 | 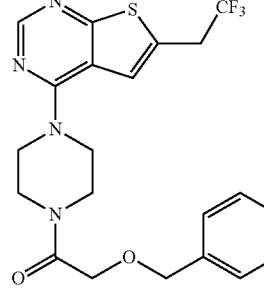 | 451.1 | 0.5 |
| 93 | 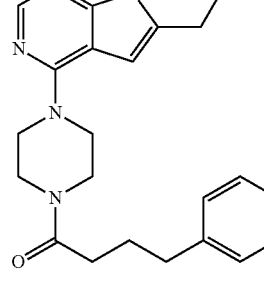 | 449.2 | 0.6 |
| 94 | 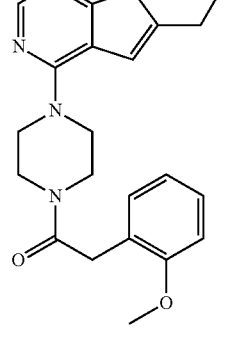 | 451.1 | 0.5 |
| 95 | 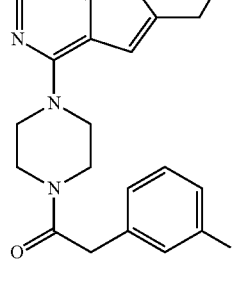 | 451.1 | 0.5 |

TABLE 2-continued

Examples of subscaffold 2 inhibitors of menin-MLL.

| Compound # | Structure | [MH]+ | LC-MS RT, min. or TLC R_f |
|---|---|---|---|
| 96 | 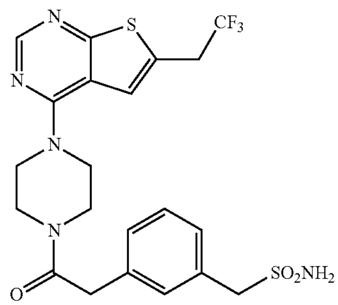 [SMILES: NS(=O)(=O)Cc1cccc(CC(=O)N2CCN(c3ncnc4sc(CC(F)(F)F)cc34)CC2)c1] | 514.1 | 0.2 |
| 97 | 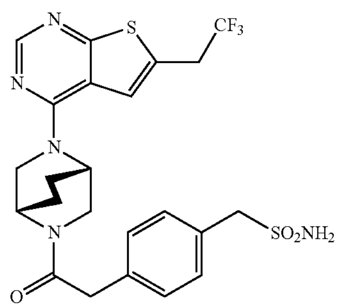 | 540.1 | 0.2 |
| 98 | 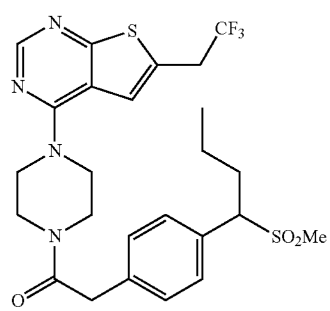 [SMILES: CCCC(c1ccc(CC(=O)N2CCN(c3ncnc4sc(CC(F)(F)F)cc34)CC2)cc1)S(C)(=O)=O] | 555.2 | 0.4 |
| 99 | 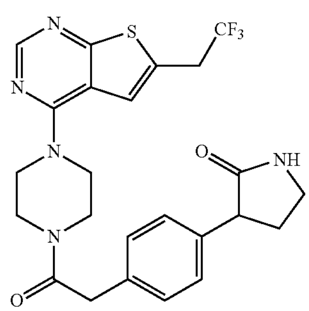 [SMILES: O=C1NCCC1c1ccc(CC(=O)N2CCN(c3ncnc4sc(CC(F)(F)F)cc34)CC2)cc1] | 504.4 | 1.60 min |
| 100 | 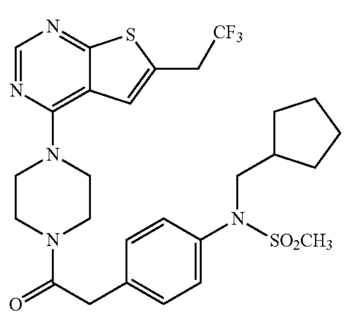 [SMILES: CS(=O)(=O)N(CC1CCCC1)c1ccc(CC(=O)N2CCN(c3ncnc4sc(CC(F)(F)F)cc34)CC2)cc1] | 596.3 | 2.26 min |

TABLE 2-continued

Examples of subscaffold 2 inhibitors of menin-MLL.

| Compound # | Structure | [MH]+ | LC-MS RT, min. or TLC R_f |
|---|---|---|---|
| 101 | 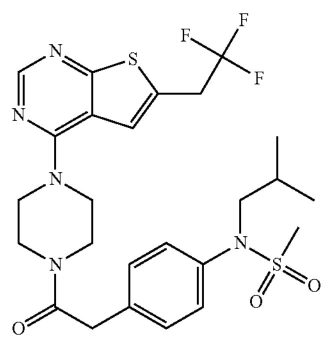 [SMILES: CC(C)CN(c1ccc(CC(=O)N2CCN(c3ncnc4sc(CC(F)(F)F)cc34)CC2)cc1)S(C)(=O)=O] | 570.1 | 2.11 min |
| 102 | 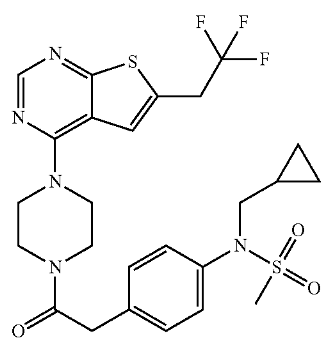 [SMILES: CS(=O)(=O)N(CC1CC1)c1ccc(CC(=O)N2CCN(c3ncnc4sc(CC(F)(F)F)cc34)CC2)cc1] | 568.3 | 2.10 min |
| 103 | 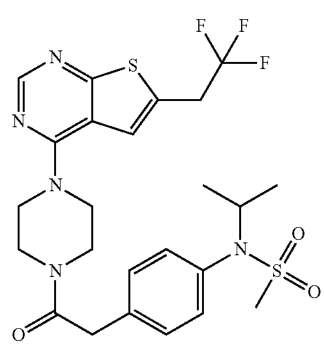 [SMILES: CC(C)N(c1ccc(CC(=O)N2CCN(c3ncnc4sc(CC(F)(F)F)cc34)CC2)cc1)S(C)(=O)=O] | 556.0 | 1.99 min |
| 104 | 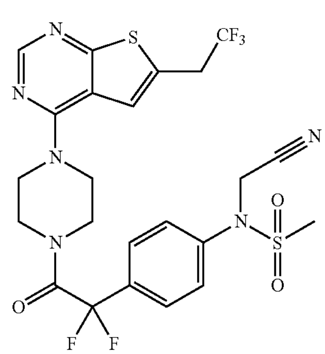 [SMILES: CS(=O)(=O)N(CC#N)c1ccc(C(F)(F)C(=O)N2CCN(c3ncnc4sc(CC(F)(F)F)cc34)CC2)cc1] | 589.1 | 2.30 min |

TABLE 3

Examples of subscaffold 3 inhibitors of menin-MLL.

| Compound# | Structure | [MH]+ | LC-MS RT, min. or TLC Rf |
|---|---|---|---|
| Inhibitors with IC50 0.01 nM-0.1 μM | | | |
| 105 | 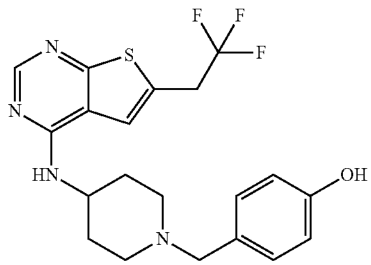 [SMILES: Oc1ccc(CN2CCC(Nc3ncnc4sc(CC(F)(F)F)cc34)CC2)cc1] | 423.1458 | 0.3 |
| 106 | 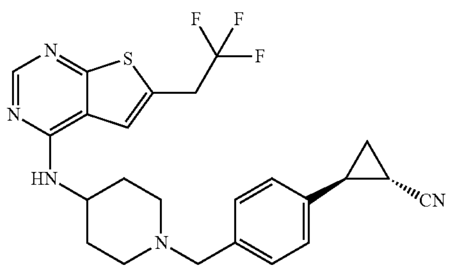 [SMILES: N#C[C@H]1C[C@@H]1c1ccc(CN2CCC(Nc3ncnc4sc(CC(F)(F)F)cc34)CC2)cc1] | 472.31 | 1.46 min |
| Inhibitors with IC50 0.1 uM-0.5 μM | | | |
| 107 | 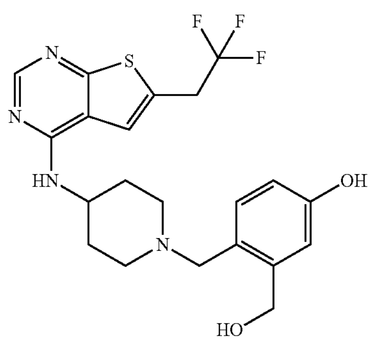 [SMILES: OCc1cc(O)ccc1CN1CCC(Nc2ncnc3sc(CC(F)(F)F)cc23)CC1] | 453.1 | 1.25 min |
| 108 | 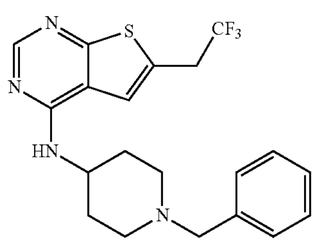 [SMILES: FC(F)(F)Cc1cc2c(NC3CCN(Cc4ccccc4)CC3)ncnc2s1] | 407.5 | 1.72 min |
| 109 | 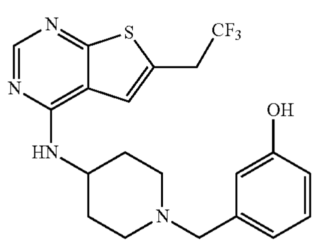 [SMILES: Oc1cccc(CN2CCC(Nc3ncnc4sc(CC(F)(F)F)cc34)CC2)c1] | 423.1 | 1.31 min |

TABLE 3-continued

Examples of subscaffold 3 inhibitors of menin-MLL.

| Compound# | Structure | [MH]+ | LC-MS RT, min. or TLC R$_f$ |
|---|---|---|---|
| 110 | 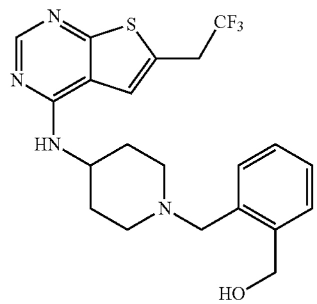 [SMILES: OCc1ccccc1CN1CCC(Nc2ncnc3sc(CC(F)(F)F)cc23)CC1] | 437.2 | 1.32 min |
| 111 | 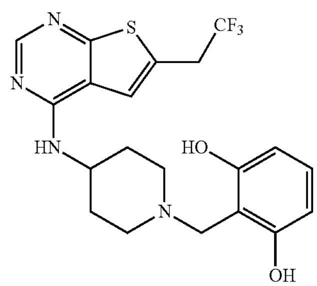 [SMILES: Oc1cccc(O)c1CN1CCC(Nc2ncnc3sc(CC(F)(F)F)cc23)CC1] | 439.3 | 1.28 min |
| 112 | 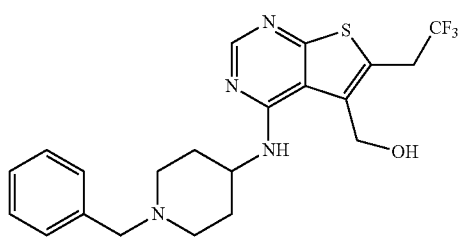 [SMILES: OCc1c(CC(F)(F)F)sc2ncnc(NC3CCN(Cc4ccccc4)CC3)c12] | 437.2 | 1.31 min |
| 113 | 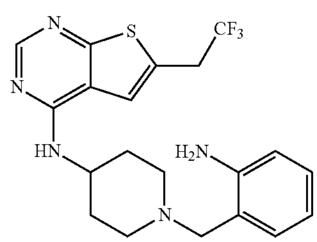 [SMILES: Nc1ccccc1CN1CCC(Nc2ncnc3sc(CC(F)(F)F)cc23)CC1] | 422.2 | 1.61 min |
| 114 | 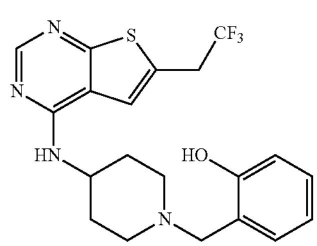 [SMILES: Oc1ccccc1CN1CCC(Nc2ncnc3sc(CC(F)(F)F)cc23)CC1] | 423.2 | 1.30 min |

TABLE 3-continued

Examples of subscaffold 3 inhibitors of menin-MLL.

| Compound# | Structure | [MH]+ | LC-MS RT, min. or TLC Rf |
|---|---|---|---|
| 115 | 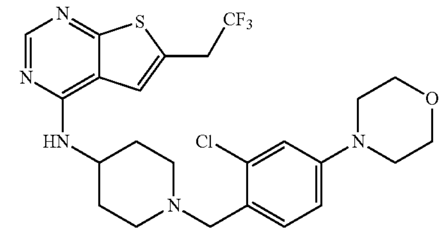 [SMILES: FC(F)(F)Cc1cc2c(NC3CCN(Cc4ccc(N5CCOCC5)cc4Cl)CC3)ncnc2s1] | 526.3 | 1.59 min |
| 116 | 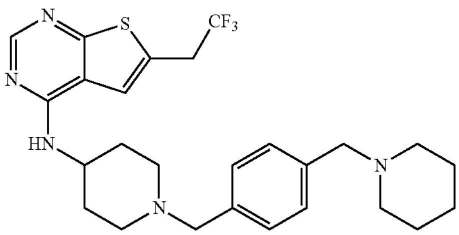 [SMILES: FC(F)(F)Cc1cc2c(NC3CCN(Cc4ccc(CN5CCCCC5)cc4)CC3)ncnc2s1] | 504.1 | 1.47 min |
| 117 | 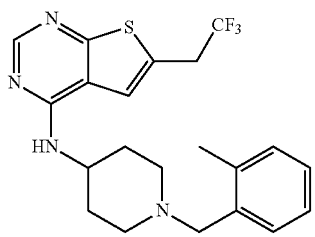 [SMILES: Cc1ccccc1CN1CCC(Nc2ncnc3sc(CC(F)(F)F)cc23)CC1] | 421.0 | 1.55 min |
| 118 | 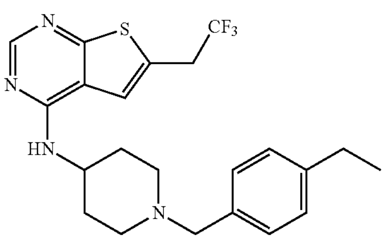 [SMILES: CCc1ccc(CN2CCC(Nc3ncnc4sc(CC(F)(F)F)cc34)CC2)cc1] | 435.4 | 2.06 min |
| 119 | 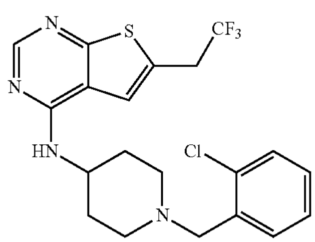 [SMILES: FC(F)(F)Cc1cc2c(NC3CCN(Cc4ccccc4Cl)CC3)ncnc2s1] | 441.1 | 1.76 min |
| 120 | 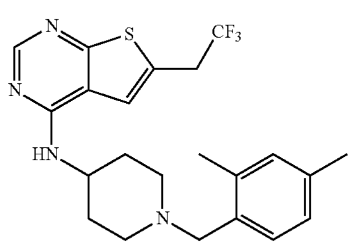 [SMILES: Cc1ccc(CN2CCC(Nc3ncnc4sc(CC(F)(F)F)cc34)CC2)c(C)c1] | 435.5 | 1.59 min |

TABLE 3-continued

Examples of subscaffold 3 inhibitors of menin-MLL.

| Compound# | Structure | [MH]+ | LC-MS RT, min. or TLC $R_f$ |
|---|---|---|---|
| 121 | 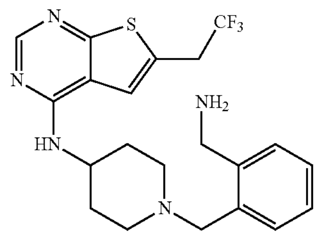 [SMILES: NCc1ccccc1CN1CCC(Nc2ncnc3sc(CC(F)(F)F)cc23)CC1] | 436.3 | 1.12 min |
| 122 | 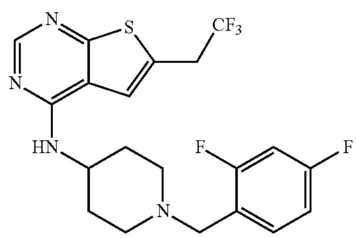 [SMILES: Fc1ccc(CN2CCC(Nc3ncnc4sc(CC(F)(F)F)cc34)CC2)c(F)c1] | 457.3 | 1.65 min |
| 123 | 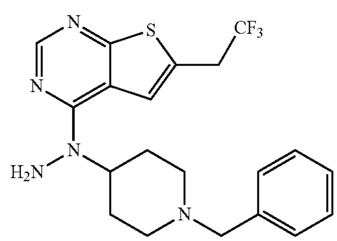 [SMILES: NN(c1ncnc2sc(CC(F)(F)F)cc12)C1CCN(Cc2ccccc2)CC1] | 422.1618 | 0.2 |
| 124 | 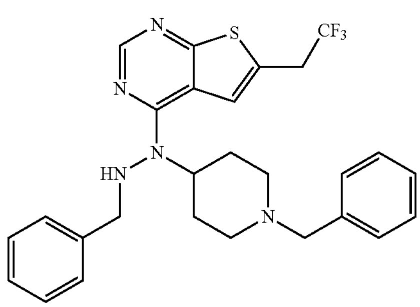 [SMILES: FC(F)(F)Cc1cc2c(N(NCc3ccccc3)C3CCN(Cc4ccccc4)CC3)ncnc2s1] | 512.2093 | 0.4 |
| 125 | 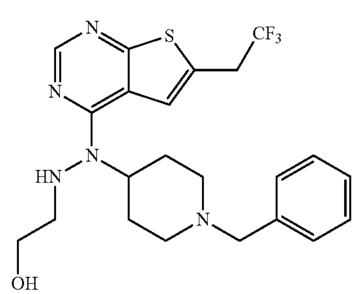 [SMILES: OCCNN(c1ncnc2sc(CC(F)(F)F)cc12)C1CCN(Cc2ccccc2)CC1] | 466.1885 | 0.1 |

TABLE 3-continued
Examples of subscaffold 3 inhibitors of menin-MLL.
| Compound# | Structure | [MH]+ | LC-MS RT, min. or TLC R_f |
|---|---|---|---|
| 126 | 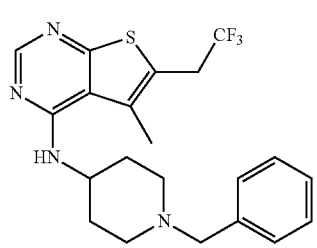 [SMILES: Cc1c(CC(F)(F)F)sc2ncnc(NC3CCN(Cc4ccccc4)CC3)c12] | 420.7 | 1.47 min |
| 127 | 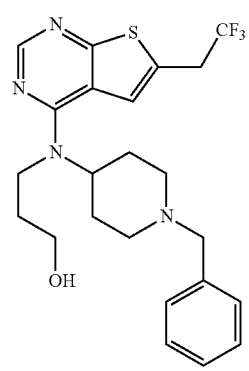 [SMILES: OCCCN(c1ncnc2sc(CC(F)(F)F)cc12)C1CCN(Cc2ccccc2)CC1] | 465.2 | 0.1 |
| 128 | 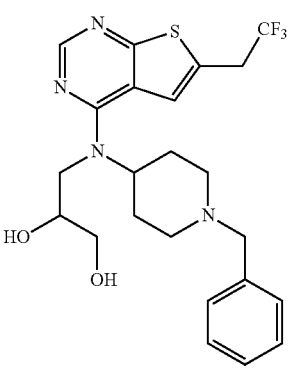 [SMILES: OCC(O)CN(c1ncnc2sc(CC(F)(F)F)cc12)C1CCN(Cc2ccccc2)CC1] | 481.1 | 0.1 |
| 129 | 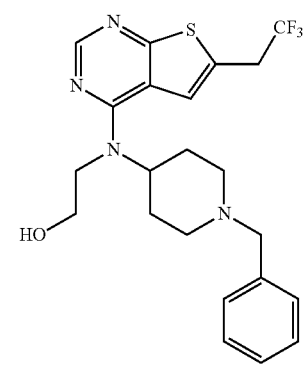 [SMILES: OCCN(c1ncnc2sc(CC(F)(F)F)cc12)C1CCN(Cc2ccccc2)CC1] | 451.1 | 0.3 |

TABLE 3-continued

Examples of subscaffold 3 inhibitors of menin-MLL.

| Compound# | Structure | [MH]+ | LC-MS RT, min. or TLC R$_f$ |
|---|---|---|---|
| 130 | 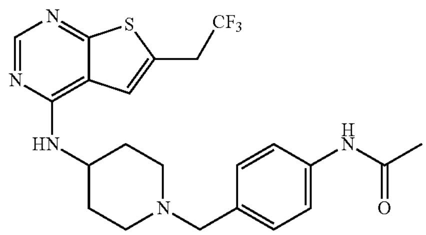 [SMILES: CC(=O)Nc1ccc(CN2CCC(Nc3ncnc4sc(CC(F)(F)F)cc34)CC2)cc1] | 464.2 | 1.32 min |
| 131 | 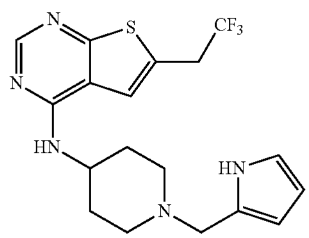 [SMILES: FC(F)(F)Cc1cc2c(NC3CCN(Cc4ccc[nH]4)CC3)ncnc2s1] | 396.1 | 1.25 min |
| 132 | 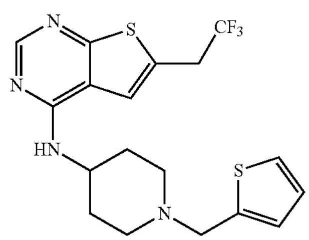 [SMILES: FC(F)(F)Cc1cc2c(NC3CCN(Cc4cccs4)CC3)ncnc2s1] | 413.5 | 1.37 min |
| 133 | 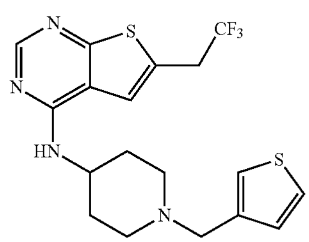 [SMILES: FC(F)(F)Cc1cc2c(NC3CCN(Cc4ccsc4)CC3)ncnc2s1] | 413.5 | 1.37 min |
| 134 | 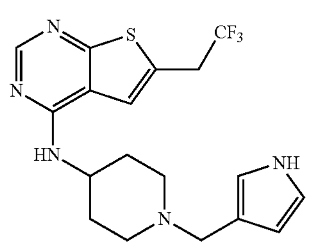 [SMILES: FC(F)(F)Cc1cc2c(NC3CCN(Cc4cc[nH]c4)CC3)ncnc2s1] | 396.1459 | 0.3 |

TABLE 3-continued

Examples of subscaffold 3 inhibitors of menin-MLL.

| Compound# | Structure | [MH]+ | LC-MS RT, min. or TLC R_f |
|---|---|---|---|
| 135 | (structure) | 433.3 | 1.62 min |

Inhibitors with IC50 0.5 μM-2 μM

| | | | |
|---|---|---|---|
| 136 | (structure) | 476.2 | 1.35 min |
| 137 | (structure) | 436.3 | 1.05 min |
| 138 | (structure) | 433.3 | 1.15 min |
| 139 | (structure) | 422.2 | 1.01 min |

TABLE 3-continued

Examples of subscaffold 3 inhibitors of menin-MLL.

| Compound# | Structure | [MH]+ | LC-MS RT, min. or TLC R_f |
|---|---|---|---|
| 140 | 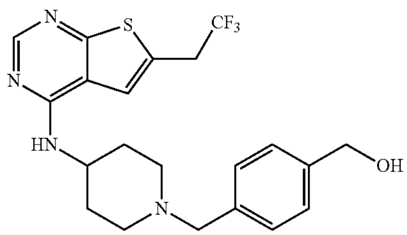 [SMILES: OCc1ccc(CN2CCC(Nc3ncnc4sc(CC(F)(F)F)cc34)CC2)cc1] | 437.2 | 1.16 min |
| 141 | 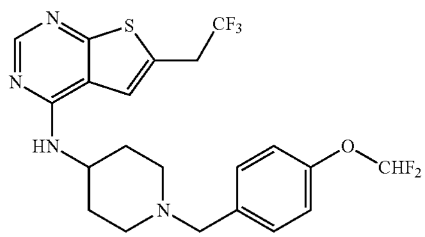 [SMILES: FC(F)Oc1ccc(CN2CCC(Nc3ncnc4sc(CC(F)(F)F)cc34)CC2)cc1] | 473.2 | 1.57 min |
| 142 | 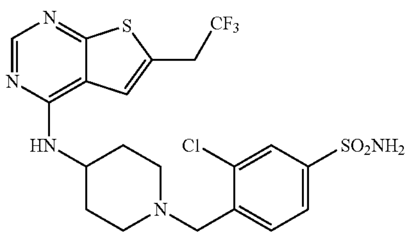 [SMILES: NS(=O)(=O)c1ccc(CN2CCC(Nc3ncnc4sc(CC(F)(F)F)cc34)CC2)c(Cl)c1] | 520.3 | 1.41 min |
| 143 | 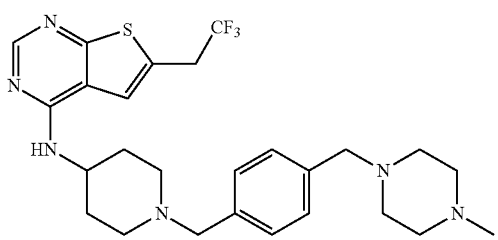 [SMILES: CN1CCN(Cc2ccc(CN3CCC(Nc4ncnc5sc(CC(F)(F)F)cc45)CC3)cc2)CC1] | 519.4 | 1.28 |
| 144 | 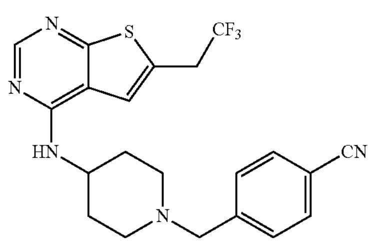 [SMILES: N#Cc1ccc(CN2CCC(Nc3ncnc4sc(CC(F)(F)F)cc34)CC2)cc1] | | |
| 145 | 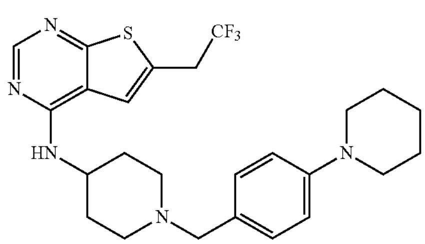 [SMILES: FC(F)(F)Cc1cc2c(NC3CCN(Cc4ccc(N5CCCCC5)cc4)CC3)ncnc2s1] | | |

TABLE 3-continued
Examples of subscaffold 3 inhibitors of menin-MLL.
| Compound# | Structure | [MH]+ | LC-MS RT, min. or TLC R$_f$ |
|---|---|---|---|
| 146 | 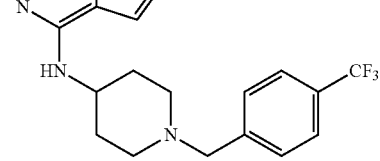 | 475.0 | 1.72 min |
| 147 | 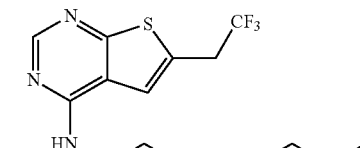 | 421.3 | 1.95 min |
| 148 | 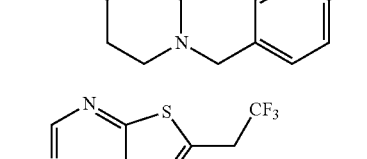 | 475.0 | 1.54 min |
| 149 | 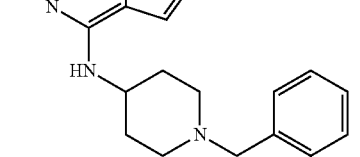 | 367.0 | 1.29 min |
| 150 | 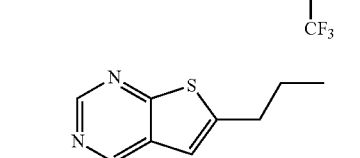 | 381.5 | 1.42 min |

TABLE 3-continued

Examples of subscaffold 3 inhibitors of menin-MLL.

| Compound# | Structure | [MH]+ | LC-MS RT, min. or TLC R_f |
|---|---|---|---|
| 151 | 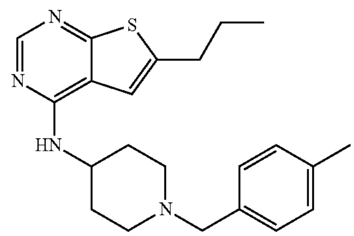 [SMILES: CCCc1cc2c(NC3CCN(Cc4ccc(C)cc4)CC3)ncnc2s1] | 381.5 | 1.46 min |
| 152 | 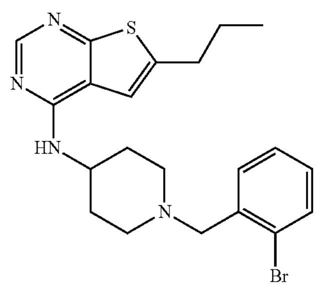 [SMILES: CCCc1cc2c(NC3CCN(Cc4ccccc4Br)CC3)ncnc2s1] | 447.0 | 1.44 min |
| 153 | 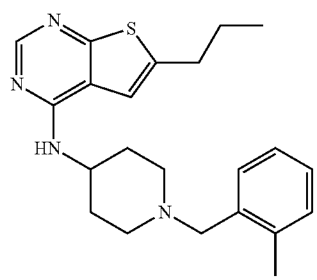 [SMILES: CCCc1cc2c(NC3CCN(Cc4ccccc4C)CC3)ncnc2s1] | 381.5 | 1.42 min |
| 154 | 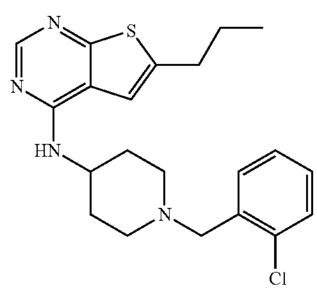 [SMILES: CCCc1cc2c(NC3CCN(Cc4ccccc4Cl)CC3)ncnc2s1] | | |
| 155 | 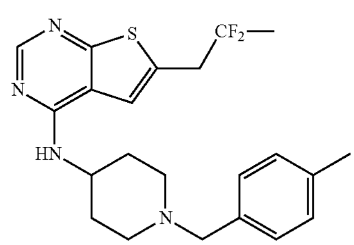 [SMILES: Cc1ccc(CN2CCC(Nc3ncnc4sc(CC(C)(F)F)cc34)CC2)cc1] | 403.6 | 1.35 min |

TABLE 3-continued

Examples of subscaffold 3 inhibitors of menin-MLL.

| Compound# | Structure | [MH]+ | LC-MS RT, min. or TLC R_f |
|---|---|---|---|
| 156 | 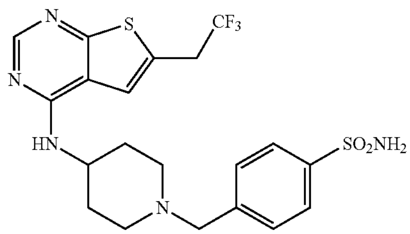 [SMILES: NS(=O)(=O)c1ccc(CN2CCC(Nc3ncnc4sc(CC(F)(F)F)cc34)CC2)cc1] | 486.4 | 1.49 min |
| 157 | 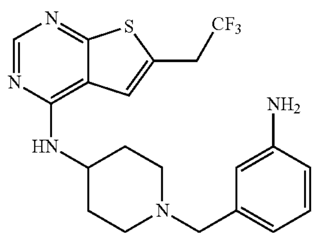 [SMILES: Nc1cccc(CN2CCC(Nc3ncnc4sc(CC(F)(F)F)cc34)CC2)c1] | 422.1629 | 0.3 |
| 158 | 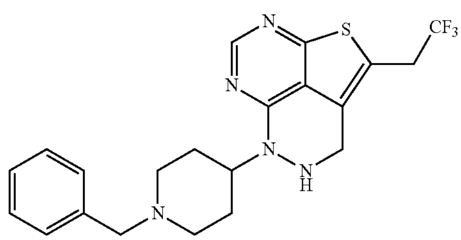 [SMILES: FC(F)(F)Cc1sc2ncnc3c2c1CNN3C1CCN(Cc2ccccc2)CC1] | 434.1630 | 0.2 |
| 159 | 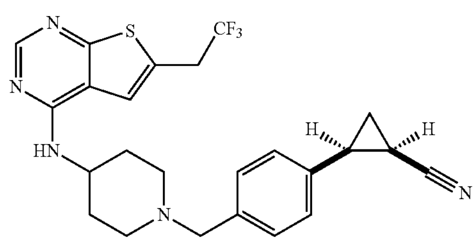 | 472.3 | 1.51 min |

TABLE 4

Examples of subscaffold 3 and 4 inhibitors of menin-MLL.

| Compound# | Structure | [MH]+ | LC-MS RT, min. or TLC R_f |
|---|---|---|---|
| Inhibitors with IC50 0.01 nM-0.1 μM | | | |
| 160 | 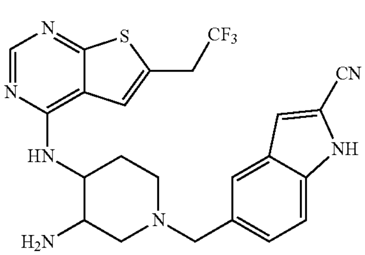 [SMILES: N#Cc1cc2cc(CN3CCC(Nc4ncnc5sc(CC(F)(F)F)cc45)C(N)C3)ccc2[nH]1] | 486.1676 | 0.2 |

TABLE 4-continued
Examples of subscaffold 3 and 4 inhibitors of menin-MLL.
| Compound# | Structure | [MH]+ | LC-MS RT, min. or TLC R_f |
|---|---|---|---|
| 161 | 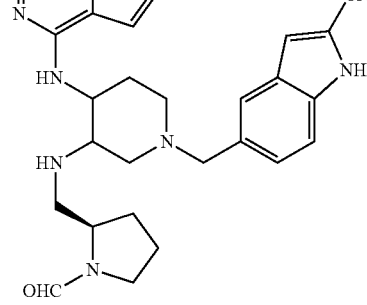 | 597.2367 | 0.2 |
| 162 | 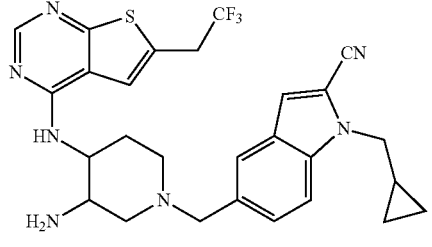 [SMILES: N#Cc1cc2cc(CN3CCC(Nc4ncnc5sc(CC(F)(F)F)cc45)C(N)C3)ccc2n1CC1CC1] | 540.2159 | 0.3 |
| 163 | 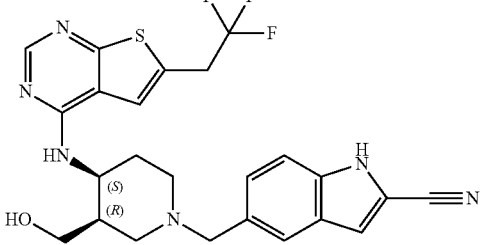 | 501.1 | 1.91 min |
| 164 | 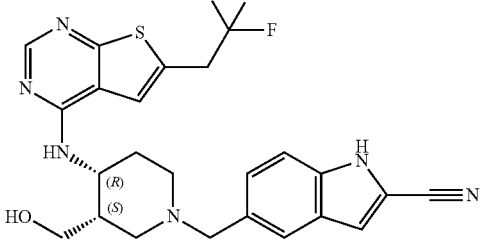 | 501.1 | 1.94 min |
Inhibitors with IC50 0.1 μM-0.5 μM
| 165 | 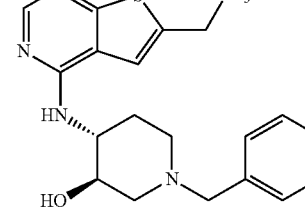 | 423.1458 | 0.2 |

TABLE 4-continued

Examples of subscaffold 3 and 4 inhibitors of menin-MLL.

| Compound# | Structure | [MH]+ | LC-MS RT, min. or TLC R$_f$ |
|---|---|---|---|
| 166 | 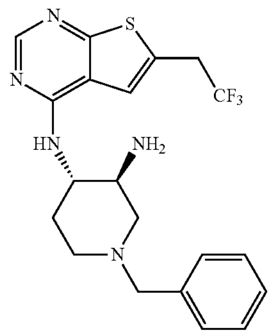 [SMILES: N[C@H]1CN(Cc2ccccc2)CC[C@@H]1Nc1ncnc2sc(CC(F)(F)F)cc12] | 422.1625 | 0.2 |
| 167 | 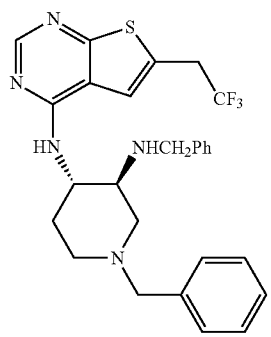 | 512.2095 | 0.3 |
| 168 | 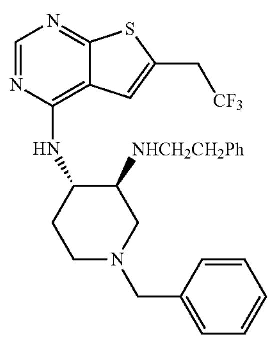 | 526.2243 | 0.3 |
| 169 | 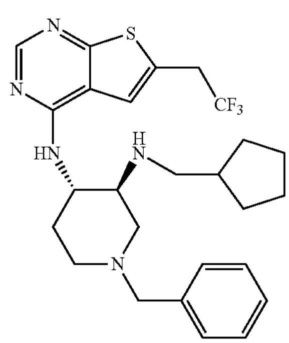 [SMILES: FC(F)(F)Cc1cc2c(N[C@H]3CCN(Cc4ccccc4)C[C@@H]3NCC3CCCC3)ncnc2s1] | 504.2400 | 0.3 |

TABLE 4-continued

Examples of subscaffold 3 and 4 inhibitors of menin-MLL.

| Compound# | Structure | [MH]+ | LC-MS RT, min. or TLC $R_f$ |
|---|---|---|---|
| 170 | 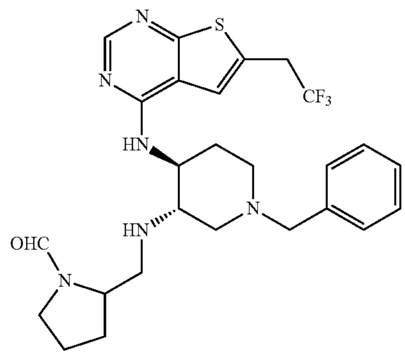 [SMILES: O=CN1CCCC1CN[C@H]1CN(Cc2ccccc2)CC[C@@H]1Nc1ncnc2sc(CC(F)(F)F)cc12] | 533.2310 | 0.3 |
| 171 | 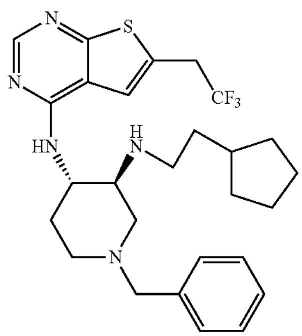 [SMILES: FC(F)(F)Cc1cc2c(N[C@H]3CCN(Cc4ccccc4)C[C@@H]3NCCC3CCCC3)ncnc2s1] | 518.2557 | 0.3 |
| 172 | 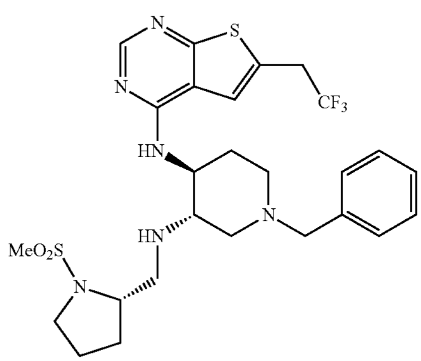 [SMILES: CS(=O)(=O)N1CCC[C@H]1CN[C@H]1CN(Cc2ccccc2)CC[C@@H]1Nc1ncnc2sc(CC(F)(F)F)cc12] | 583.2127 | 0.3 |
| 173 | 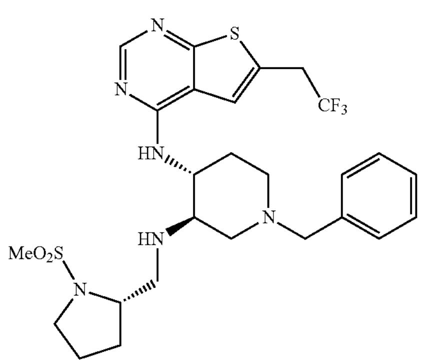 [SMILES: CS(=O)(=O)N1CCC[C@H]1CN[C@@H]1CN(Cc2ccccc2)CC[C@H]1Nc1ncnc2sc(CC(F)(F)F)cc12] | 583.2133 | 0.3 |

TABLE 4-continued

Examples of subscaffold 3 and 4 inhibitors of menin-MLL.

| Compound# | Structure | [MH]+ | LC-MS RT, min. or TLC $R_f$ |
|---|---|---|---|
| 174 | 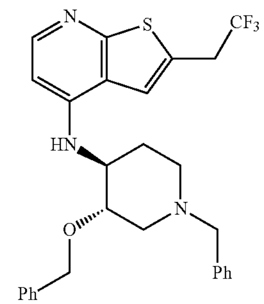 [SMILES: FC(F)(F)Cc1cc2c(N[C@H]3CCN(Cc4ccccc4)C[C@@H]3OCc3ccccc3)ccnc2s1] | 512.1974 | 0.3 |

TABLE 5

Examples of subscaffold 4 inhibitors of menin-MLL.

| Compound# | Structure | [MH]+ | LC-MS RT, min. or TLC $R_f$ |
|---|---|---|---|
| Inhibitors with IC50 0.01 nM-0.1 μM | | | |
| 175 | 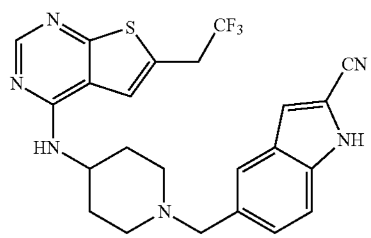 [SMILES: N#Cc1cc2cc(CN3CCC(Nc4ncnc5sc(CC(F)(F)F)cc45)CC3)ccc2[nH]1] | 471.1579 | 0.3 |
| 176 | 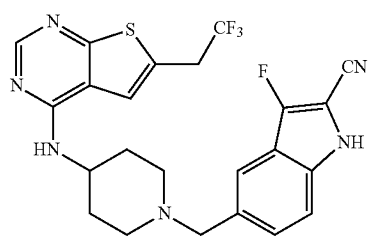 [SMILES: N#Cc1[nH]c2ccc(CN3CCC(Nc4ncnc5sc(CC(F)(F)F)cc45)CC3)cc2c1F] | 489.1485 | 0.3 |
| 177 | 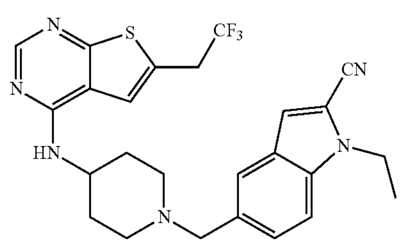 [SMILES: CCn1c(C#N)cc2cc(CN3CCC(Nc4ncnc5sc(CC(F)(F)F)cc45)CC3)ccc21] | 499.1891 | 0.4 |
| 178 | 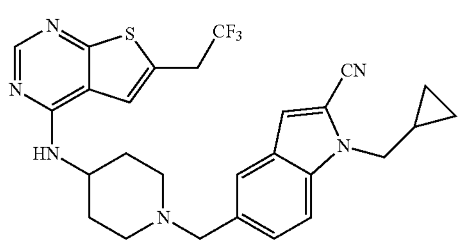 [SMILES: N#Cc1cc2cc(CN3CCC(Nc4ncnc5sc(CC(F)(F)F)cc45)CC3)ccc2n1CC1CC1] | 525.2052 | 0.4 |

TABLE 5-continued
Examples of subscaffold 4 inhibitors of menin-MLL.
| Compound# | Structure | [MH]+ | LC-MS RT, min. or TLC R$_f$ |
|---|---|---|---|
| 179 | 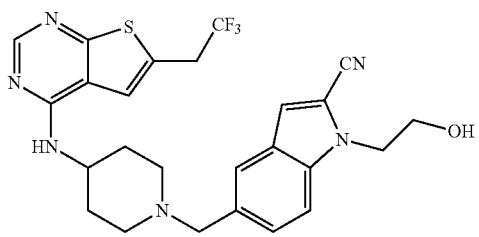 [SMILES: N#Cc1cc2cc(CN3CCC(Nc4ncnc5sc(CC(F)(F)F)cc45)CC3)ccc2n1CCO] | 515.1828 | 0.2 |
| 180 | 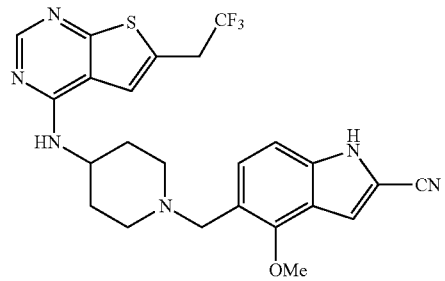 | 501.1684 | 0.3 |
| 181 | 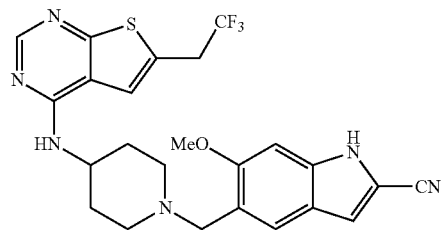 [SMILES: COc1cc2[nH]c(C#N)cc2cc1CN1CCC(Nc2ncnc3sc(CC(F)(F)F)cc23)CC1] | 501.1675 | 0.3 |
| 182 | 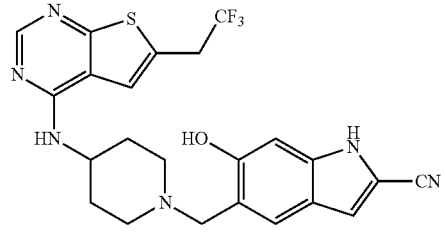 [SMILES: N#Cc1cc2cc(CN3CCC(Nc4ncnc5sc(CC(F)(F)F)cc45)CC3)c(O)cc2[nH]1] | 487.1519 | 0.3 |
| 183 | 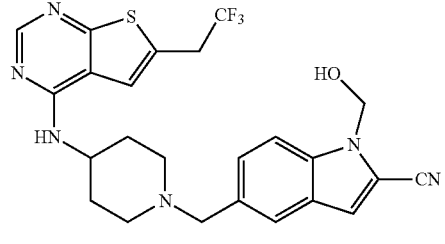 [SMILES: N#Cc1cc2cc(CN3CCC(Nc4ncnc5sc(CC(F)(F)F)cc45)CC3)ccc2n1CO] | 501.1678 | 0.2 |

TABLE 5-continued

Examples of subscaffold 4 inhibitors of menin-MLL.

| Compound# | Structure | [MH]+ | LC-MS RT, min. or TLC R$_f$ |
|---|---|---|---|
| 184 | 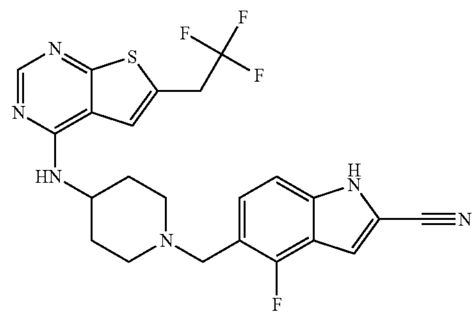 [SMILES: N#Cc1cc2c(F)c(CN3CCC(Nc4ncnc5sc(CC(F)(F)F)cc45)CC3)ccc2[nH]1] | 489.4 | 1.60 min |
| 185 | 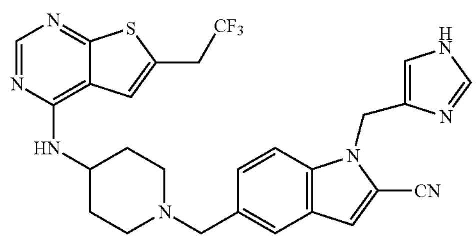 [SMILES: N#Cc1cc2cc(CN3CCC(Nc4ncnc5sc(CC(F)(F)F)cc45)CC3)ccc2n1Cc1c[nH]cn1] | 551.2 | 1.23 min |
| 186 | 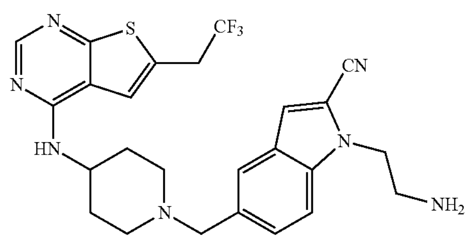 [SMILES: N#Cc1cc2cc(CN3CCC(Nc4ncnc5sc(CC(F)(F)F)cc45)CC3)ccc2n1CCN] | 514.1998 | 0.1 |
| 187 | 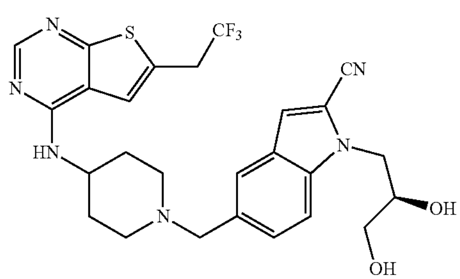 [SMILES: N#Cc1cc2cc(CN3CCC(Nc4ncnc5sc(CC(F)(F)F)cc45)CC3)ccc2n1C[C@@H](O)CO] | 545.1951 | 0.2 |
| 188 | 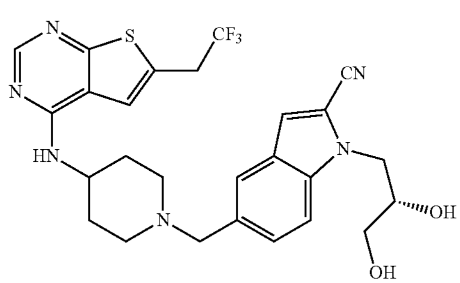 [SMILES: N#Cc1cc2cc(CN3CCC(Nc4ncnc5sc(CC(F)(F)F)cc45)CC3)ccc2n1C[C@H](O)CO] | 545.1941 | 0.2 |

TABLE 5-continued
Examples of subscaffold 4 inhibitors of menin-MLL.
| Compound# | Structure | [MH]+ | LC-MS RT, min. or TLC R_f |
|---|---|---|---|
| 189 | 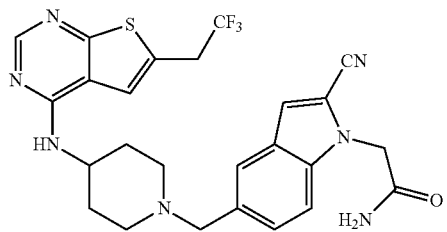 [SMILES: N#Cc1cc2cc(CN3CCC(Nc4ncnc5sc(CC(F)(F)F)cc45)CC3)ccc2n1CC(N)=O] | 528.1783 | 0.2 |
| 190 | 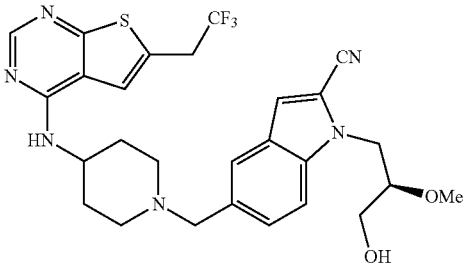 [SMILES: CO[C@@H](CO)Cn1c(C#N)cc2cc(CN3CCC(Nc4ncnc5sc(CC(F)(F)F)cc45)CC3)ccc21] | 559.2098 | 0.2 |
| 191 | 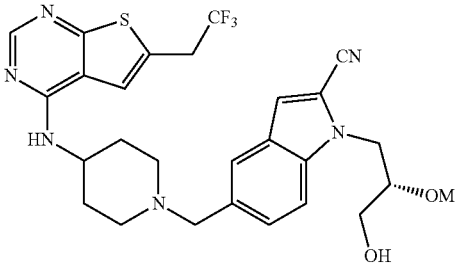 | 559.2096 | 0.2 |
| 192 | 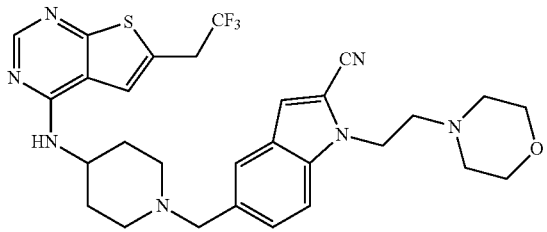 [SMILES: N#Cc1cc2cc(CN3CCC(Nc4ncnc5sc(CC(F)(F)F)cc45)CC3)ccc2n1CCN1CCOCC1] | 584.2415 | 0.15 |
| 193 | 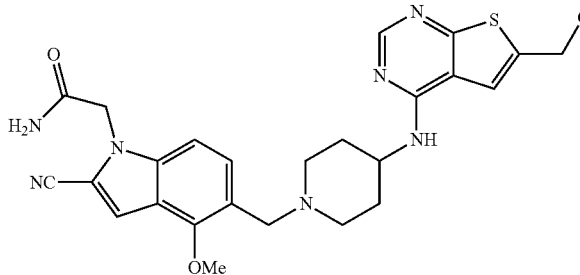 | 558.123 | 0.1 |

TABLE 5-continued
Examples of subscaffold 4 inhibitors of menin-MLL.
| Compound# | Structure | [MH]+ | LC-MS RT, min. or TLC R$_f$ |
|---|---|---|---|
| 194 | 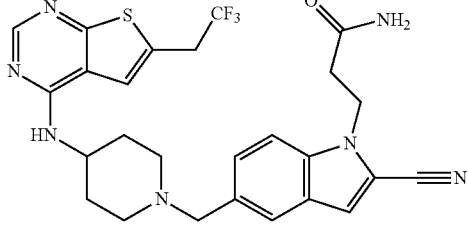 | 542.5 | 1.33 min |
| 195 | 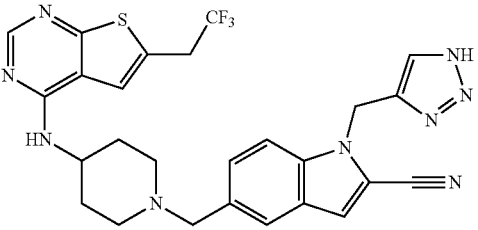 [SMILES: N#Cc1cc2cc(CN3CCC(Nc4ncnc5sc(CC(F)(F)F)cc45)CC3)ccc2n1Cc1c[nH]nn1] | 552.4 | 1.55 min |
| 196 | 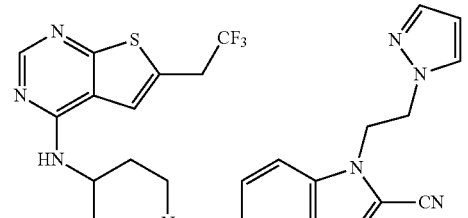 | 565.3 | 1.63 min |
| 197 | 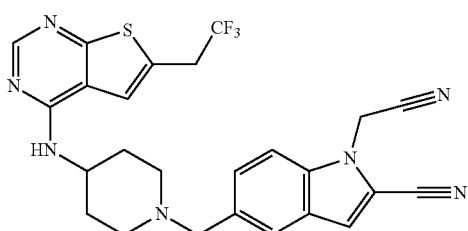 | 510.4 | 1.65 min |
| 198 | 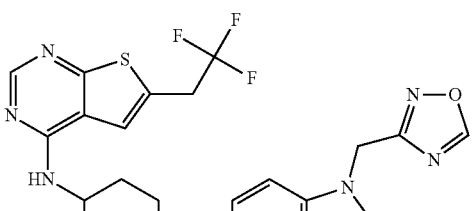 | 553.6 | 1.63 min |
| 199 | 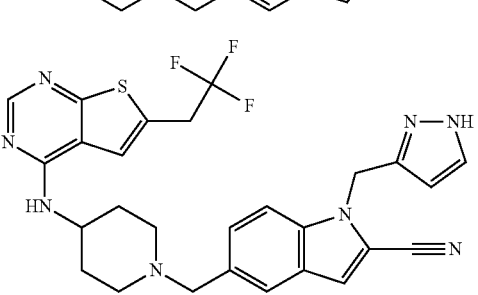 | 551.8 | 1.65 min |

TABLE 5-continued

Examples of subscaffold 4 inhibitors of menin-MLL.

| Compound# | Structure | [MH]+ | LC-MS RT, min. or TLC R_f |
|---|---|---|---|
| 200 | 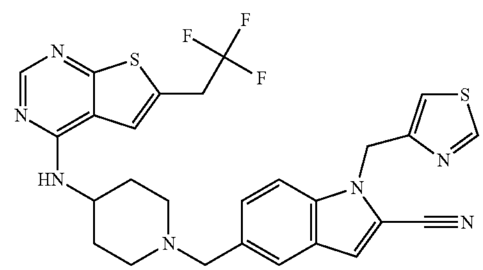 [SMILES: N#Cc1cc2cc(CN3CCC(Nc4ncnc5sc(CC(F)(F)F)cc45)CC3)ccc2n1Cc1cscn1] | 568.3 | 1.73 min |
| 201 | 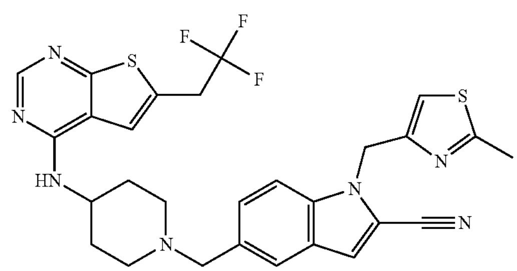 [SMILES: Cc1nc(Cn2c(C#N)cc3cc(CN4CCC(Nc5ncnc6sc(CC(F)(F)F)cc56)CC4)ccc32)cs1] | 582.1 | 1.80 min |
| 202 | 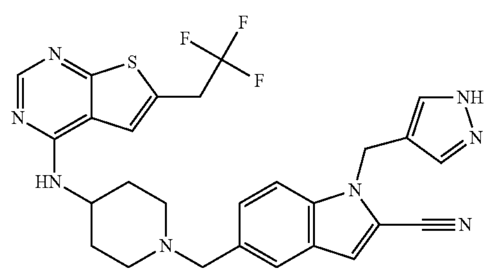 | 551.2 | 1.55 min |
| 203 | 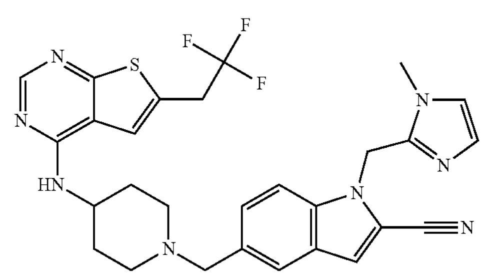 [SMILES: Cn1ccnc1Cn1c(C#N)cc2cc(CN3CCC(Nc4ncnc5sc(CC(F)(F)F)cc45)CC3)ccc21] | 565.3 | 1.31 min |
| 204 | 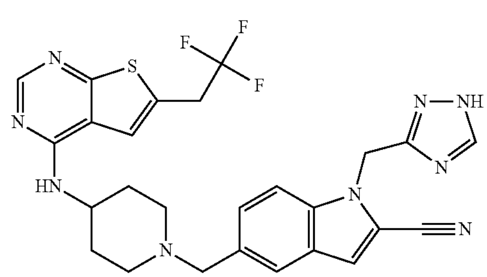 [SMILES: N#Cc1cc2cc(CN3CCC(Nc4ncnc5sc(CC(F)(F)F)cc45)CC3)ccc2n1Cc1nc[nH]n1] | 552.4 | 1.52 min |

TABLE 5-continued

Examples of subscaffold 4 inhibitors of menin-MLL.

| Compound# | Structure | [MH]+ | LC-MS RT, min. or TLC R$_f$ |
|---|---|---|---|
| 205 | 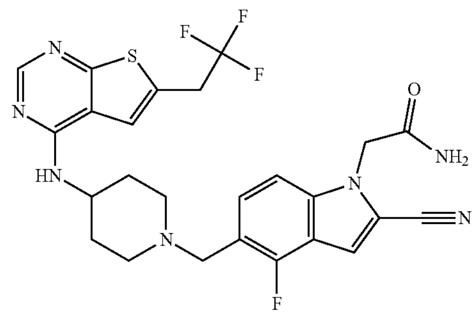 [SMILES: N#Cc1cc2c(F)c(CN3CCC(Nc4ncnc5sc(CC(F)(F)F)cc45)CC3)ccc2n1CC(N)=O] | 546.1 | 1.48 min |
| 206 | 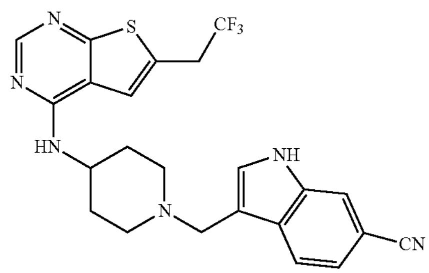 [SMILES: N#Cc1ccc2c(CN3CCC(Nc4ncnc5sc(CC(F)(F)F)cc45)CC3)c[nH]c2c1] | 471.1576 | 0.4 |
| 207 | 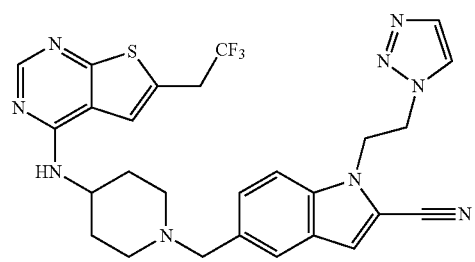 [SMILES: N#Cc1cc2cc(CN3CCC(Nc4ncnc5sc(CC(F)(F)F)cc45)CC3)ccc2n1CCn1ccnn1] | 566.5 | 1.53 min |
| 208 | 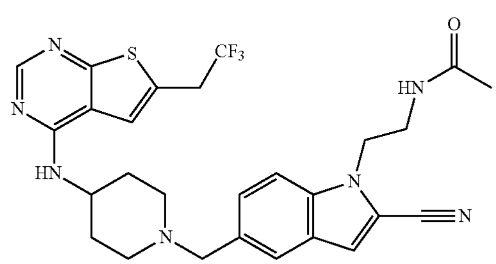 [SMILES: CC(=O)NCCn1c(C#N)cc2cc(CN3CCC(Nc4ncnc5sc(CC(F)(F)F)cc45)CC3)ccc21] | 556.0 | 1.46 min |
| 209 | 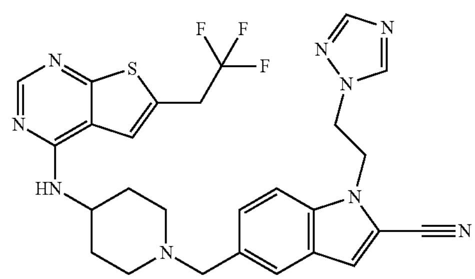 [SMILES: N#Cc1cc2cc(CN3CCC(Nc4ncnc5sc(CC(F)(F)F)cc45)CC3)ccc2n1CCn1cncn1] | 566.2 | 1.52 min |

TABLE 5-continued

Examples of subscaffold 4 inhibitors of menin-MLL.

| Compound# | Structure | [MH]+ | LC-MS RT, min. or TLC R_f |
|---|---|---|---|
| 210 | 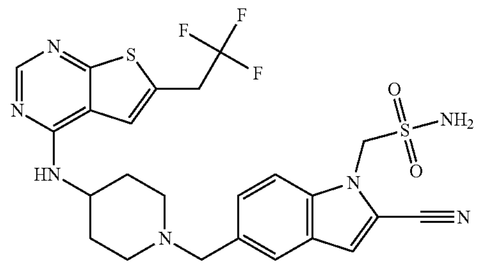 [SMILES: N#Cc1cc2cc(CN3CCC(Nc4ncnc5sc(CC(F)(F)F)cc45)CC3)ccc2n1CS(N)(=O)=O] | 564.4 | 1.43 min |
| 211 | 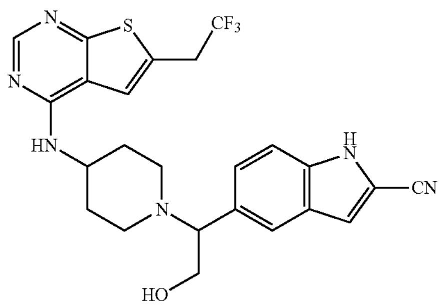 [SMILES: N#Cc1cc2cc(C(CO)N3CCC(Nc4ncnc5sc(CC(F)(F)F)cc45)CC3)ccc2[nH]1] | 501.1 | 1.77 min |
| 212 | 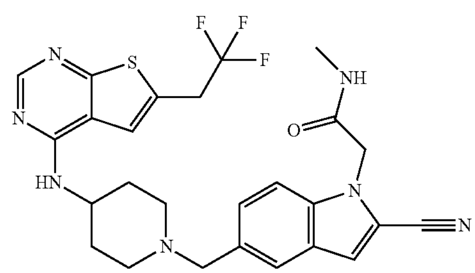 [SMILES: CNC(=O)Cn1c(C#N)cc2cc(CN3CCC(Nc4ncnc5sc(CC(F)(F)F)cc45)CC3)ccc21] | 541.9 | 1.82 min |
| 213 | 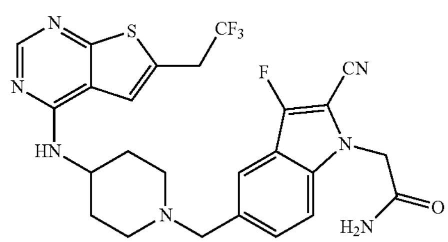 [SMILES: N#Cc1c(F)c2cc(CN3CCC(Nc4ncnc5sc(CC(F)(F)F)cc45)CC3)ccc2n1CC(N)=O] | 546.1690 | 0.1 |
| 214 | 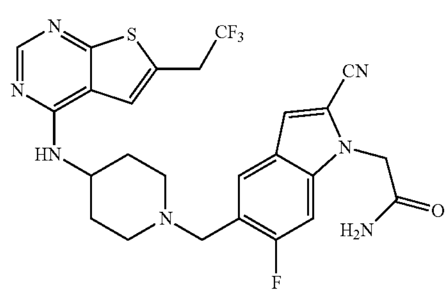 [SMILES: N#Cc1cc2cc(CN3CCC(Nc4ncnc5sc(CC(F)(F)F)cc45)CC3)c(F)cc2n1CC(N)=O] | 546.1693 | 0.1 |

TABLE 5-continued
Examples of subscaffold 4 inhibitors of menin-MLL.
| Compound# | Structure | [MH]+ | LC-MS RT, min. or TLC R$_f$ |
|---|---|---|---|
| 215 | 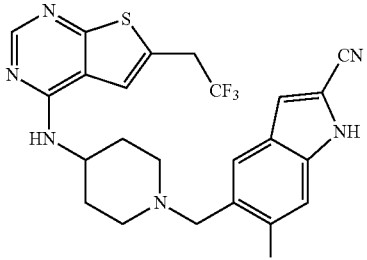 | 515.1835 | 0.2 |
| 216 | 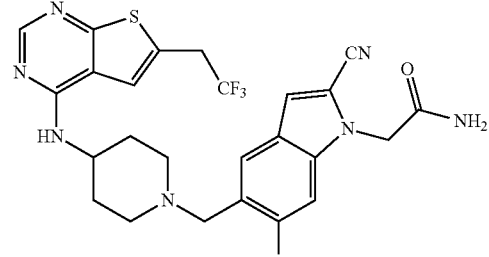 | 572.2050 | 0.1 |
| 217 | 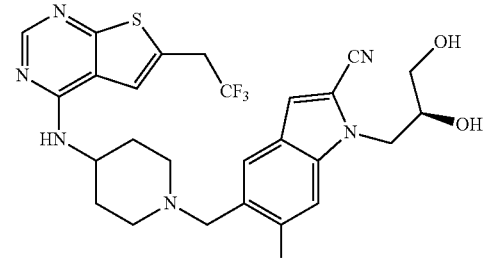 | 589.2204 | 0.1 |
| 218 | 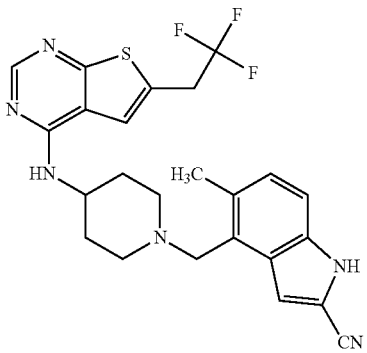 [SMILES: Cc1ccc2[nH]c(C#N)cc2c1CN1CCC(Nc2ncnc3sc(CC(F)(F)F)cc23)CC1] | 485.2 | 2.10 min |
| 219 | 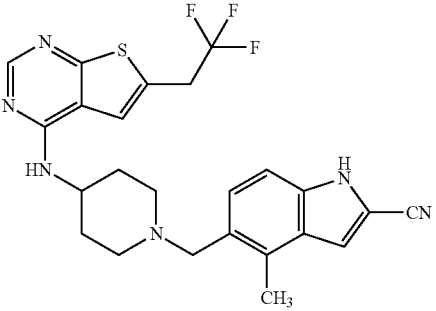 [SMILES: Cc1c(CN2CCC(Nc3ncnc4sc(CC(F)(F)F)cc34)CC2)ccc2[nH]c(C#N)cc12] | 485.2 | 2.02 min |

TABLE 5-continued

Examples of subscaffold 4 inhibitors of menin-MLL.

| Compound# | Structure | [MH]+ | LC-MS RT, min. or TLC R$_f$ |
|---|---|---|---|
| 220 | 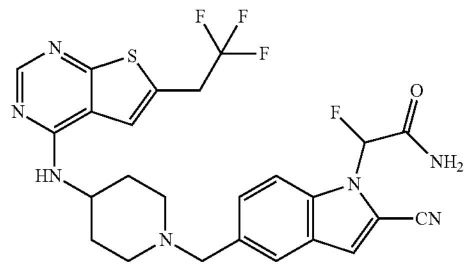 [SMILES: N#Cc1cc2cc(CN3CCC(Nc4ncnc5sc(CC(F)(F)F)cc45)CC3)ccc2n1C(F)C(N)=O] | 546.4 | 1.86 min |
| 221 | 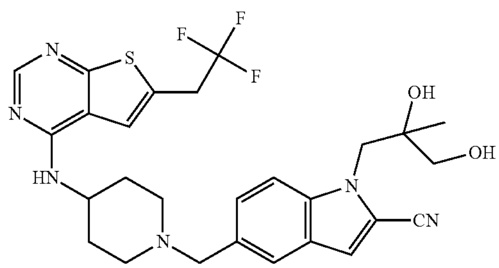 [SMILES: CC(O)(CO)Cn1c(C#N)cc2cc(CN3CCC(Nc4ncnc5sc(CC(F)(F)F)cc45)CC3)ccc21] | 559.0 | 1.82 min |
| 222 | 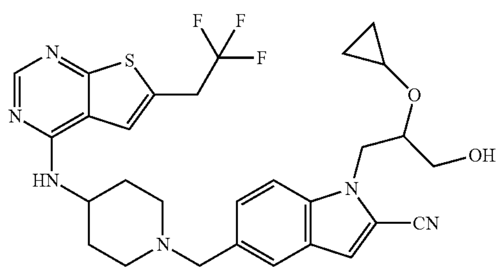 [SMILES: N#Cc1cc2cc(CN3CCC(Nc4ncnc5sc(CC(F)(F)F)cc45)CC3)ccc2n1CC(CO)OC1CC1] | 585.1 | 1.72 min |
| 223 | 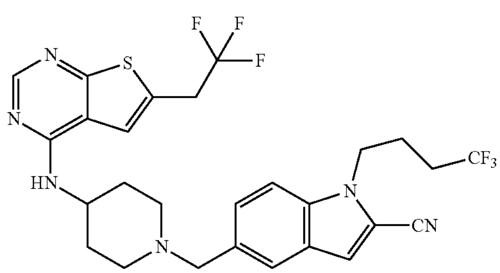 [SMILES: N#Cc1cc2cc(CN3CCC(Nc4ncnc5sc(CC(F)(F)F)cc45)CC3)ccc2n1CCCC(F)(F)F] | 581.2 | 2.12 min |
| 224 | 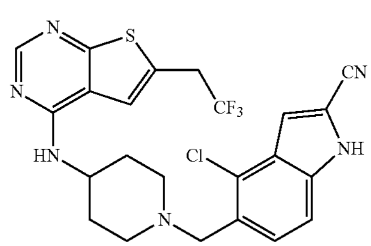 [SMILES: N#Cc1cc2c(Cl)c(CN3CCC(Nc4ncnc5sc(CC(F)(F)F)cc45)CC3)ccc2[nH]1] | 505.1181 | 0.3 |

TABLE 5-continued

Examples of subscaffold 4 inhibitors of menin-MLL.

| Compound# | Structure | [MH]+ | LC-MS RT, min. or TLC R$_f$ |
|---|---|---|---|
| 225 | 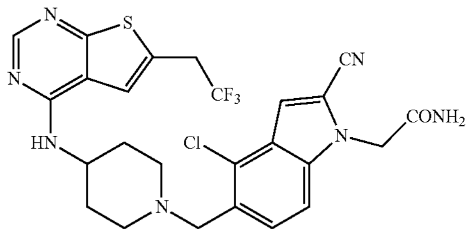 [SMILES: N#Cc1cc2c(Cl)c(CN3CCC(Nc4ncnc5sc(CC(F)(F)F)cc45)CC3)ccc2n1CC(N)=O] | 562.1400 | 0.1 |
| 226 | 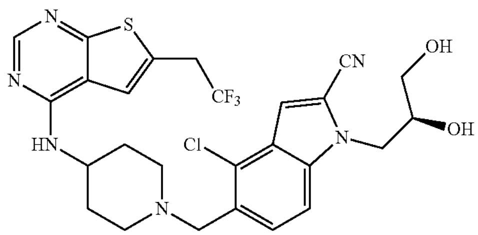 [SMILES: N#Cc1cc2c(Cl)c(CN3CCC(Nc4ncnc5sc(CC(F)(F)F)cc45)CC3)ccc2n1C[C@H](O)CO] | 579.1552 | 0.1 |
| Inhibitors with IC50 0.1 µM-0.5 µM | | | |
| 227 | 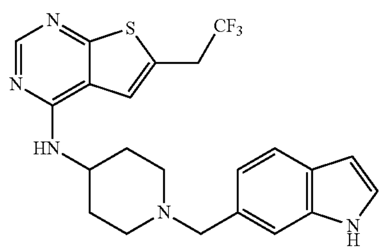 [SMILES: FC(F)(F)Cc1cc2c(NC3CCN(Cc4ccc5cc[nH]c5c4)CC3)ncnc2s1] | 446.2 | 1.53 min |
| 228 | 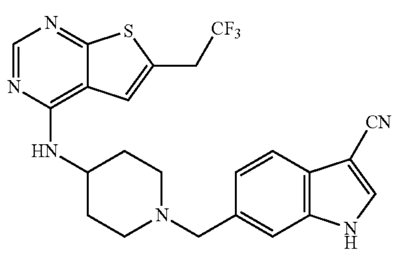 [SMILES: N#Cc1c[nH]c2cc(CN3CCC(Nc4ncnc5sc(CC(F)(F)F)cc45)CC3)ccc12] | 471.1584 | 0.3 |
| 229 | 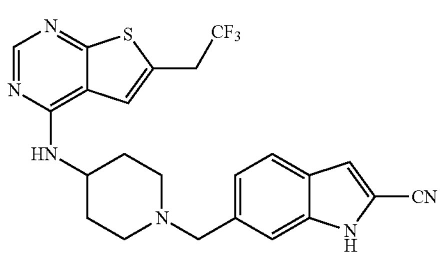 [SMILES: N#Cc1cc2ccc(CN3CCC(Nc4ncnc5sc(CC(F)(F)F)cc45)CC3)cc2[nH]1] | 471.1579 | 0.3 |
| 230 | 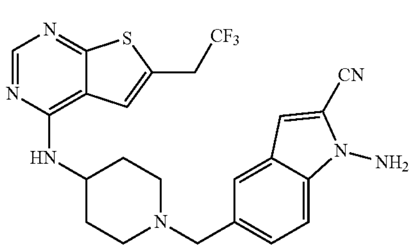 [SMILES: N#Cc1cc2cc(CN3CCC(Nc4ncnc5sc(CC(F)(F)F)cc45)CC3)ccc2n1N] | 486.1675 | 0.2 |

TABLE 5-continued

Examples of subscaffold 4 inhibitors of menin-MLL.

| Compound# | Structure | [MH]+ | LC-MS RT, min. or TLC R$_f$ |
|---|---|---|---|
| 231 | 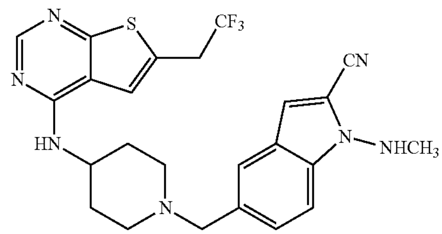 [SMILES: CNn1c(C#N)cc2cc(CN3CCC(Nc4ncnc5sc(CC(F)(F)F)cc45)CC3)ccc21] | 500.1844 | 0.3 |
| 232 | 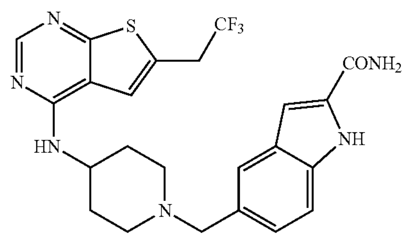 [SMILES: NC(=O)c1cc2cc(CN3CCC(Nc4ncnc5sc(CC(F)(F)F)cc45)CC3)ccc2[nH]1] | 489.1685 | 0.2 |
| 233 | 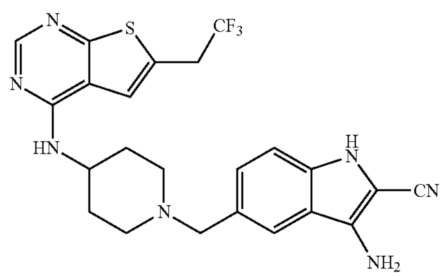 [SMILES: N#Cc1[nH]c2ccc(CN3CCC(Nc4ncnc5sc(CC(F)(F)F)cc45)CC3)cc2c1N] | 486.1679 | 0.3 |
| 234 | 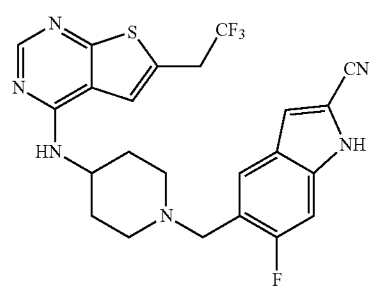 [SMILES: N#Cc1cc2cc(CN3CCC(Nc4ncnc5sc(CC(F)(F)F)cc45)CC3)c(F)cc2[nH]1] | 489.1483 | 0.3 |
| 235 | 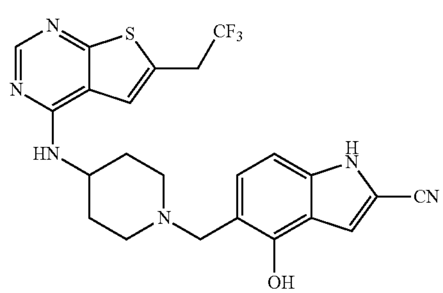 [SMILES: N#Cc1cc2c(O)c(CN3CCC(Nc4ncnc5sc(CC(F)(F)F)cc45)CC3)ccc2[nH]1] | 487.1517 | 0.3 |

TABLE 5-continued

Examples of subscaffold 4 inhibitors of menin-MLL.

| Compound# | Structure | [MH]+ | LC-MS RT, min. or TLC R$_f$ |
|---|---|---|---|
| 236 | 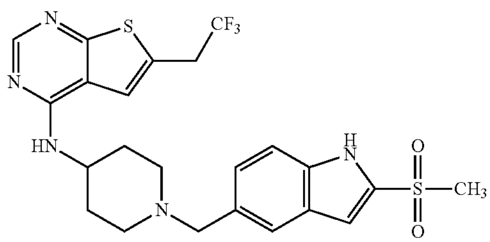 [SMILES: CS(=O)(=O)c1cc2cc(CN3CCC(Nc4ncnc5sc(CC(F)(F)F)cc45)CC3)ccc2[nH]1] | 524.8 | 1.45 min |
| 237 | 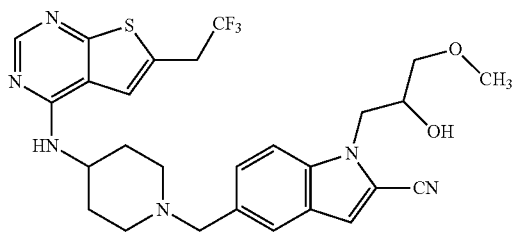 [SMILES: COCC(O)Cn1c(C#N)cc2cc(CN3CCC(Nc4ncnc5sc(CC(F)(F)F)cc45)CC3)ccc21] | 559.3 | 1.57 min |
| 238 | 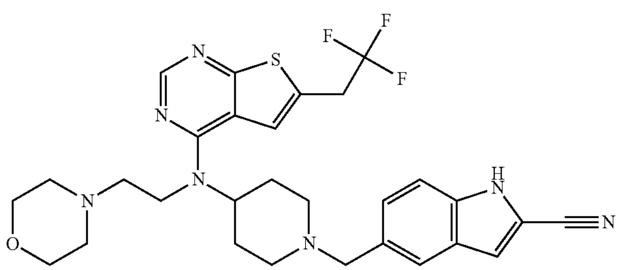 [SMILES: N#Cc1cc2cc(CN3CCC(N(CCN4CCOCC4)c4ncnc5sc(CC(F)(F)F)cc45)CC3)ccc2[nH]1] | 584.2 | 1.52 min |
| 239 | 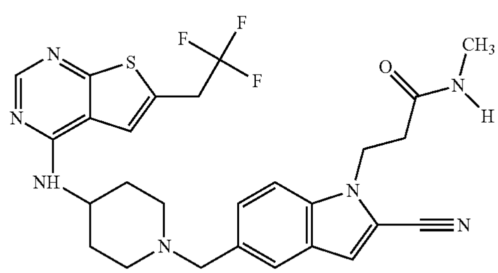 [SMILES: CNC(=O)CCn1c(C#N)cc2cc(CN3CCC(Nc4ncnc5sc(CC(F)(F)F)cc45)CC3)ccc21] | 556.3 | 1.52 min |
| 240 | 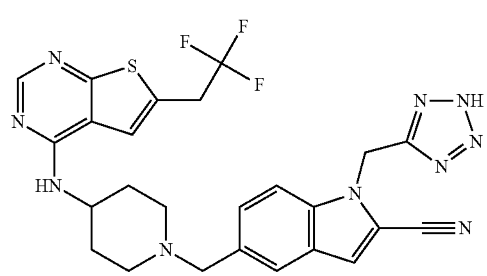 [SMILES: N#Cc1cc2cc(CN3CCC(Nc4ncnc5sc(CC(F)(F)F)cc45)CC3)ccc2n1Cc1nn[nH]n1] | 556.3 | 1.52 min |

TABLE 5-continued

Examples of subscaffold 4 inhibitors of menin-MLL.

| Compound# | Structure | [MH]+ | LC-MS RT, min. or TLC R_f |
|---|---|---|---|
| 241 | 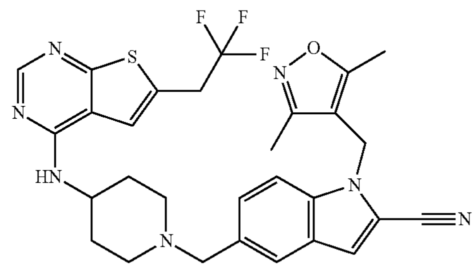 [SMILES: Cc1noc(C)c1Cn1c(C#N)cc2cc(CN3CCC(Nc4ncnc5sc(CC(F)(F)F)cc45)CC3)ccc21] | 580.3 | 1.81 min |
| 242 | 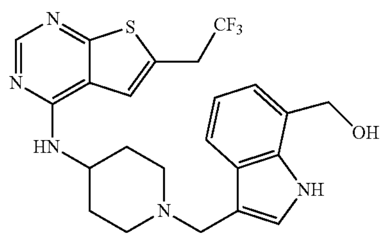 [SMILES: OCc1cccc2c(CN3CCC(Nc4ncnc5sc(CC(F)(F)F)cc45)CC3)c[nH]c12] | 476.1729 | 0.2 |
| 243 | 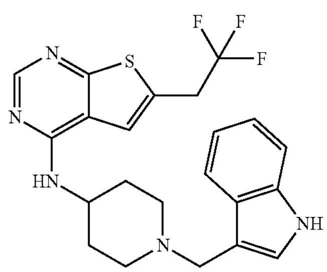 [SMILES: FC(F)(F)Cc1cc2c(NC3CCN(Cc4c[nH]c5ccccc45)CC3)ncnc2s1] | 446.2 | 1.52 min |
| 244 | 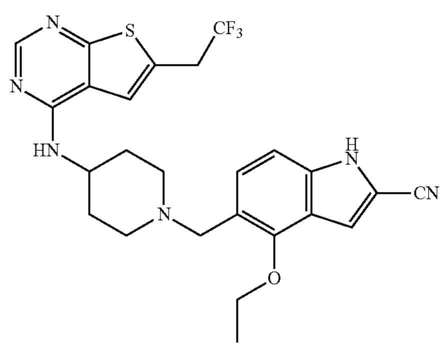 [SMILES: CCOc1c(CN2CCC(Nc3ncnc4sc(CC(F)(F)F)cc34)CC2)ccc2[nH]c(C#N)cc12] | 515.2 | 1.98 min |
| 245 | 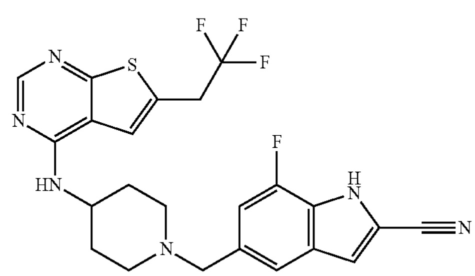 [SMILES: N#Cc1cc2cc(CN3CCC(Nc4ncnc5sc(CC(F)(F)F)cc45)CC3)cc(F)c2[nH]1] | 489.1 | 1.96 min |

TABLE 5-continued

Examples of subscaffold 4 inhibitors of menin-MLL.

| Compound# | Structure | [MH]+ | LC-MS RT, min. or TLC R$_f$ |
|---|---|---|---|
| 246 | 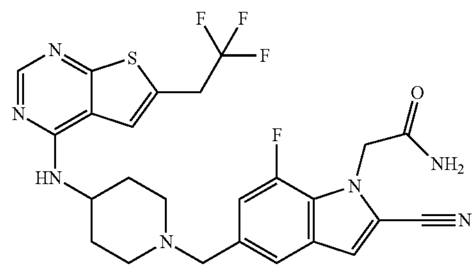 [SMILES: N#Cc1cc2cc(CN3CCC(Nc4ncnc5sc(CC(F)(F)F)cc45)CC3)cc(F)c2n1CC(N)=O] | 546.1 | 1.77 min |
| 247 | 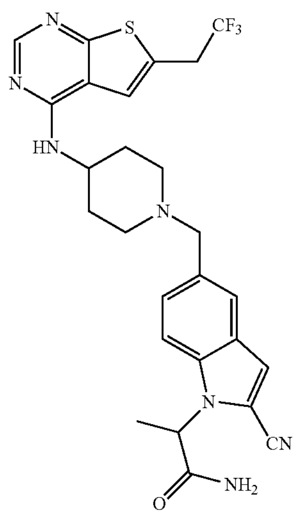 [SMILES: CC(C(N)=O)n1c(C#N)cc2cc(CN3CCC(Nc4ncnc5sc(CC(F)(F)F)cc45)CC3)ccc21] | 542.1945 | 0.1 |

Inhibitors with IC50 0.5 μM-2 μM

| | | | |
|---|---|---|---|
| 248 | | 473.2 | 1.47 min |
| 249 | | 472.3 | 1.39 min |

TABLE 5-continued
Examples of subscaffold 4 inhibitors of menin-MLL.
| Compound# | Structure | [MH]+ | LC-MS RT, min. or TLC R_f |
|---|---|---|---|
| 250 | 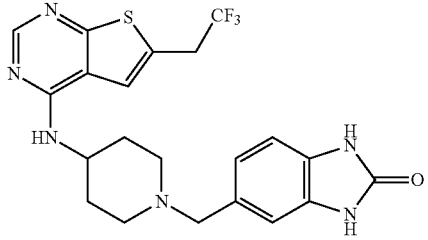 [SMILES: O=c1[nH]c2ccc(CN3CCC(Nc4ncnc5sc(CC(F)(F)F)cc45)CC3)cc2[nH]1] | 463.3 | 1.14 |
| 251 | 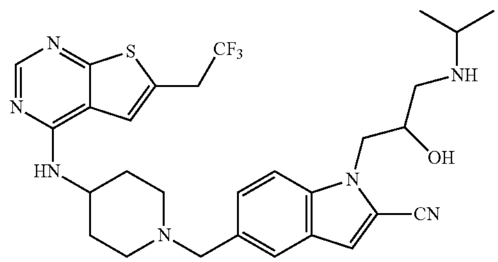 [SMILES: CC(C)NCC(O)Cn1c(C#N)cc2cc(CN3CCC(Nc4ncnc5sc(CC(F)(F)F)cc45)CC3)ccc21] | 586.4 | 1.27 min |
| 252 | 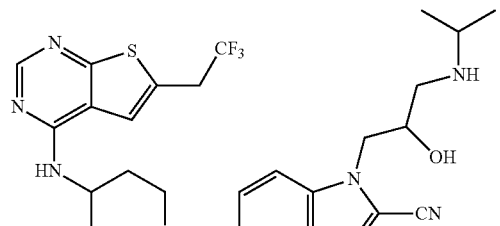 | 485.1735 | 0.3 |
TABLE 6
Examples of subscaffold 5 inhibitors of menin-MLL.
| Compound# | Structure | [MH]+ | LC-MS RT, min. or R_f |
|---|---|---|---|
| Inhibitors with IC50 0.1 μM-0.5 μM | | | |
| 253 | 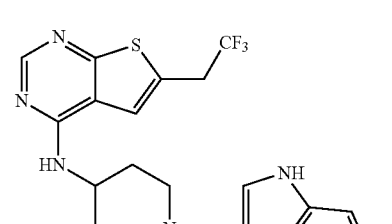 | 534.1 | 1.20 min |

TABLE 6-continued

Examples of subscaffold 5 inhibitors of menin-MLL.

| Compound# | Structure | [MH]+ | LC-MS RT, min. or R$_f$ |
|---|---|---|---|
| 254 | 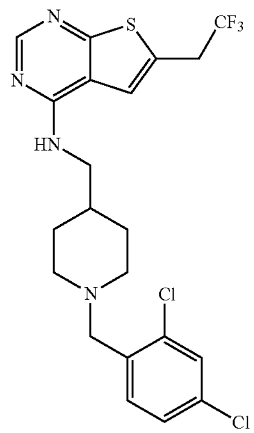 [SMILES: FC(F)(F)Cc1cc2c(NCC3CCN(Cc4ccc(Cl)cc4Cl)CC3)ncnc2s1] | 489.1 | 1.63 min |
| 255 | 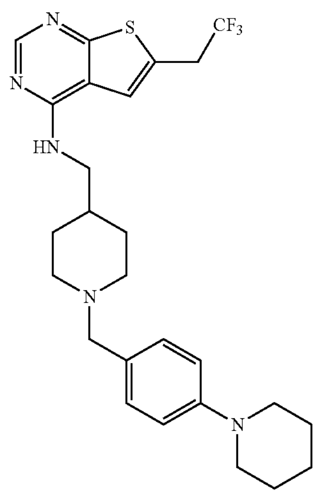 [SMILES: FC(F)(F)Cc1cc2c(NCC3CCN(Cc4ccc(N5CCCCC5)cc4)CC3)ncnc2s1] | 504.4 | 1.52 min |
| 256 | 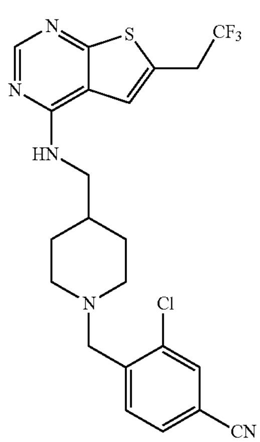 [SMILES: N#Cc1ccc(CN2CCC(CNc3ncnc4sc(CC(F)(F)F)cc34)CC2)c(Cl)c1] | 480.1 | 1.65 min |

TABLE 6-continued

Examples of subscaffold 5 inhibitors of menin-MLL.

| Compound# | Structure | [MH]+ | LC-MS RT, min. or R$_f$ |
|---|---|---|---|
| 257 | 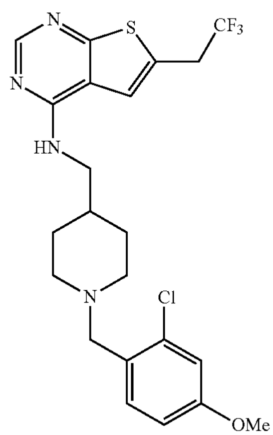 [SMILES: COc1ccc(CN2CCC(CNc3ncnc4sc(CC(F)(F)F)cc34)CC2)c(Cl)c1] | 485.2 | 1.67 min |
| 258 | 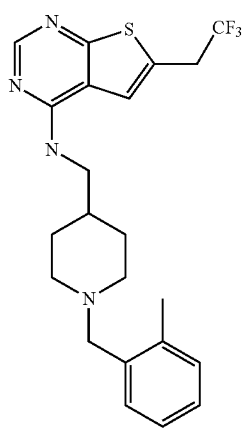 [SMILES: Cc1ccccc1CN1CCC(CNc2ncnc3sc(CC(F)(F)F)cc23)CC1] | 435.4 | 1.49 min |
| 259 | 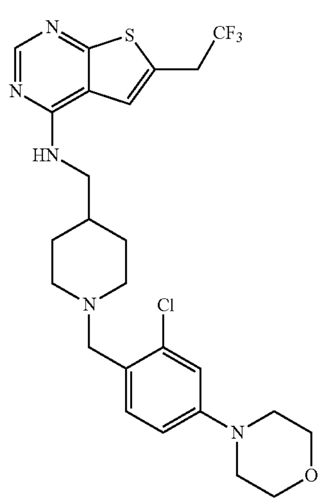 [SMILES: FC(F)(F)Cc1cc2c(NCC3CCN(Cc4ccc(N5CCOCC5)cc4Cl)CC3)ncnc2s1] | 540.4 | 1.57 min |

TABLE 6-continued

Examples of subscaffold 5 inhibitors of menin-MLL.

| Compound# | Structure | [MH]+ | LC-MS RT, min. or R_f |
|---|---|---|---|
| 260 | 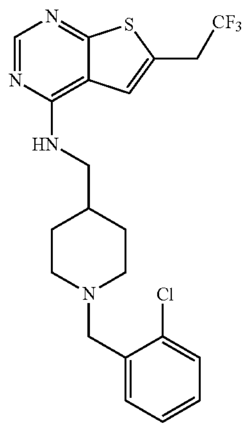 [SMILES: FC(F)(F)Cc1cc2c(NCC3CCN(Cc4ccccc4Cl)CC3)ncnc2s1] | 455.2 | 1.54 min |
| 261 | 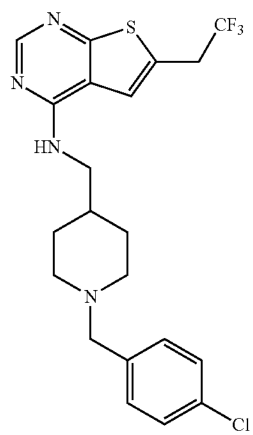 [SMILES: FC(F)(F)Cc1cc2c(NCC3CCN(Cc4ccc(Cl)cc4)CC3)ncnc2s1] | 455.2 | 1.59 min |
| 262 | 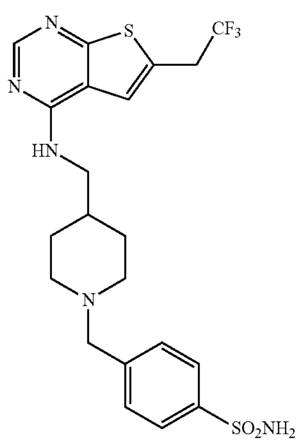 [SMILES: NS(=O)(=O)c1ccc(CN2CCC(CNc3ncnc4sc(CC(F)(F)F)cc34)CC2)cc1] | 500.2 | 1.45 min |

TABLE 6-continued

Examples of subscaffold 5 inhibitors of menin-MLL.

| Compound# | Structure | [MH]+ | LC-MS RT, min. or R$_f$ |
|---|---|---|---|
| 263 | 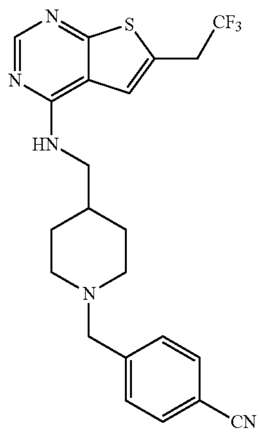 [SMILES: N#Cc1ccc(CN2CCC(CNc3ncnc4sc(CC(F)(F)F)cc34)CC2)cc1] | 446.2 | 1.62 min |
| Inhibitors with IC50 0.5 μM-2 μM | | | |
| 264 | 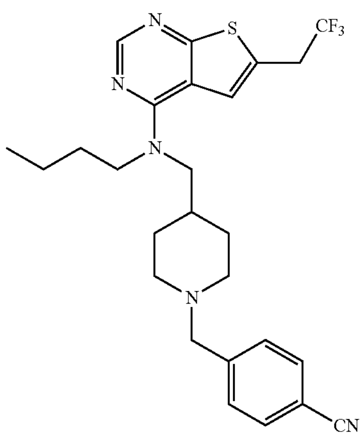 [SMILES: CCCCN(CC1CCN(Cc2ccc(C#N)cc2)CC1)c1ncnc2sc(CC(F)(F)F)cc12] | 502.3 | 1.77 min |
| 265 | 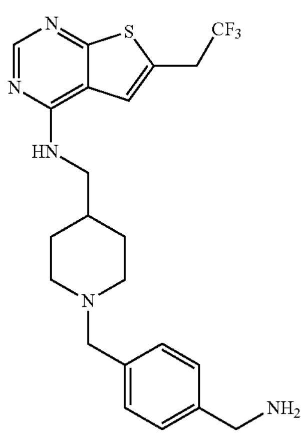 [SMILES: NCc1ccc(CN2CCC(CNc3ncnc4sc(CC(F)(F)F)cc34)CC2)cc1] | 450.4 | 1.09 min |

TABLE 6-continued

Examples of subscaffold 5 inhibitors of menin-MLL.

| Compound# | Structure | [MH]+ | LC-MS RT, min. or R$_f$ |
|---|---|---|---|
| 266 | 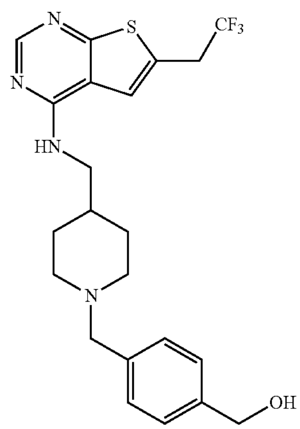 [SMILES: OCc1ccc(CN2CCC(CNc3ncnc4sc(CC(F)(F)F)cc34)CC2)cc1] | 451.3 | 1.15 min |
| 267 | 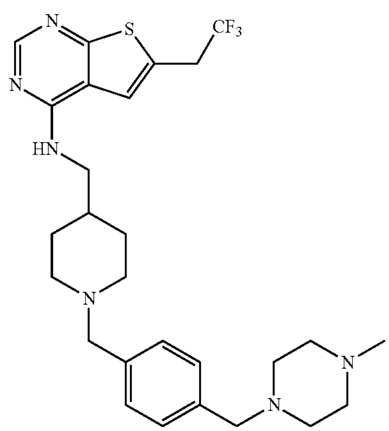 [SMILES: CN1CCN(Cc2ccc(CN3CCC(CNc4ncnc5sc(CC(F)(F)F)cc45)CC3)cc2)CC1] | 533.5 | 1.26 min |
| 268 | 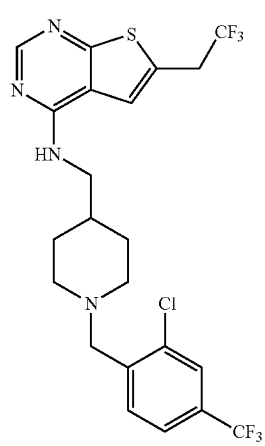 [SMILES: FC(F)(F)Cc1cc2c(NCC3CCN(Cc4ccc(C(F)(F)F)cc4Cl)CC3)ncnc2s1] | 523.6 | 1.68 min |

TABLE 6-continued

Examples of subscaffold 5 inhibitors of menin-MLL.

| Compound# | Structure | [MH]+ | LC-MS RT, min. or R_f |
|---|---|---|---|
| 269 | 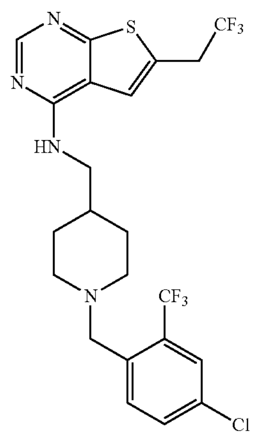 [SMILES: FC(F)(F)Cc1cc2c(NCC3CCN(Cc4ccc(Cl)cc4C(F)(F)F)CC3)ncnc2s1] | 523.3 | 2.00 min |
| 270 | 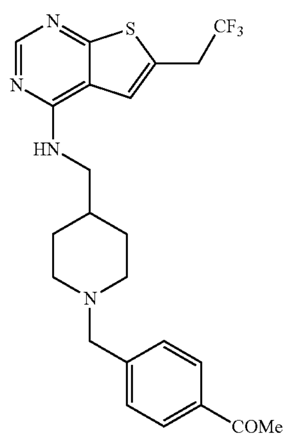 | 463.0 | 1.76 min |
| 271 | 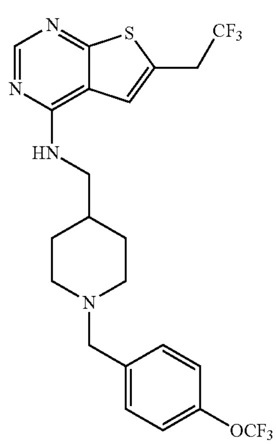 [SMILES: FC(F)(F)Cc1cc2c(NCC3CCN(Cc4ccc(OC(F)(F)F)cc4)CC3)ncnc2s1] | 505.3 | 1.70 min |

TABLE 6-continued

Examples of subscaffold 5 inhibitors of menin-MLL.

| Compound# | Structure | [MH]+ | LC-MS RT, min. or R_f |
|---|---|---|---|
| 272 | 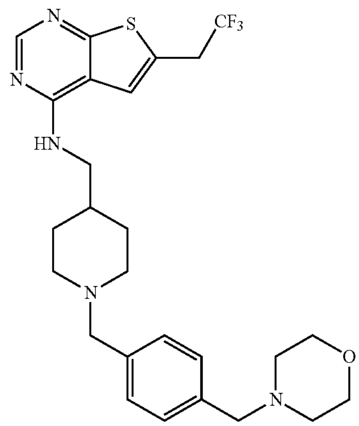 [SMILES: FC(F)(F)Cc1cc2c(NCC3CCN(Cc4ccc(CN5CCOCC5)cc4)CC3)ncnc2s1] | 520.3 | 1.19 min |
| 273 | 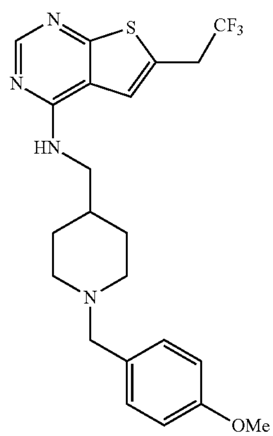 [SMILES: COc1ccc(CN2CCC(CNc3ncnc4sc(CC(F)(F)F)cc34)CC2)cc1] | 451.3 | 1.50 min |
| 274 | 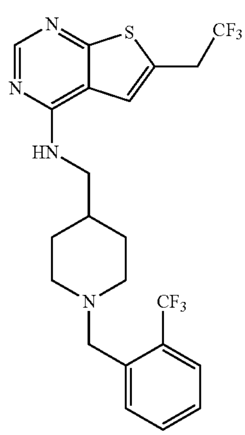 [SMILES: FC(F)(F)Cc1cc2c(NCC3CCN(Cc4ccccc4C(F)(F)F)CC3)ncnc2s1] | 489.5 | 1.49 min |

TABLE 6-continued

Examples of subscaffold 5 inhibitors of menin-MLL.

| Compound# | Structure | [MH]+ | LC-MS RT, min. or R$_f$ |
|---|---|---|---|
| 275 | 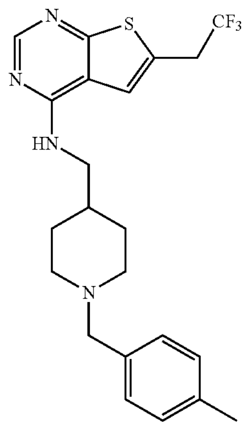 [SMILES: Cc1ccc(CN2CCC(CNc3ncnc4sc(CC(F)(F)F)cc34)CC2)cc1] | 435.4 | 1.79 min |
| 276 | 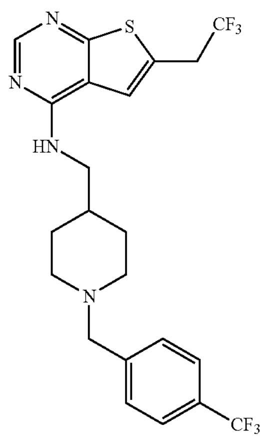 [SMILES: FC(F)(F)Cc1cc2c(NCC3CCN(Cc4ccc(C(F)(F)F)cc4)CC3)ncnc2s1] | 489.5 | 1.58 min |
| 277 | 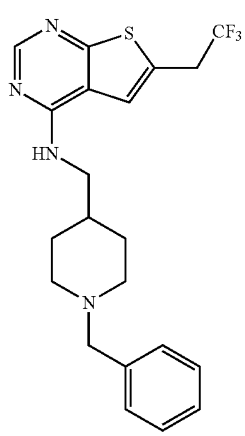 [SMILES: FC(F)(F)Cc1cc2c(NCC3CCN(Cc4ccccc4)CC3)ncnc2s1] | 421.0 | 1.27 min |

TABLE 7

Examples of subscaffold 3 and 4 inhibitors of menin-MLL.

| Compound# | Structure | [MH]+ | LC-MS RT, min. or TLC $R_f$ |
|---|---|---|---|
| Inhibitors with IC50 0.01 nM-0.1 µM | | | |
| 278 | 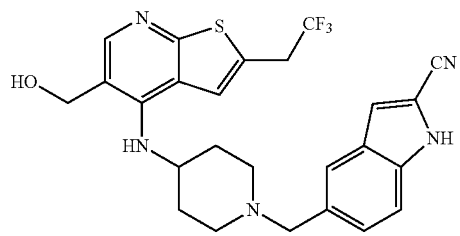 [SMILES: N#Cc1cc2cc(CN3CCC(Nc4c(CO)cnc5sc(CC(F)(F)F)cc45)CC3)ccc2[nH]1] | 500.2 | 1.45 min |
| 279 | 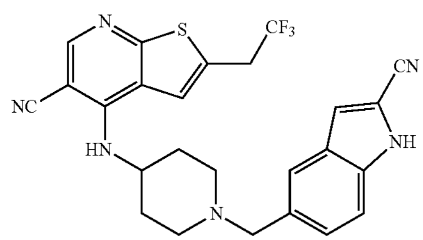 [SMILES: N#Cc1cc2cc(CN3CCC(Nc4c(C#N)cnc5sc(CC(F)(F)F)cc45)CC3)ccc2[nH]1] | 431.2 | 1.78 min |
| 280 | 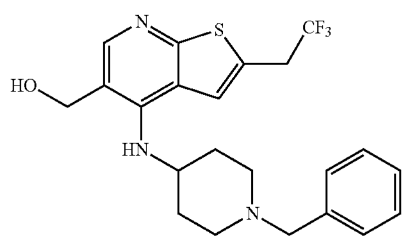 [SMILES: OCc1cnc2sc(CC(F)(F)F)cc2c1NC1CCN(Cc2ccccc2)CC1] | 436.0 | 1.19 min |
| Inhibitors with IC50 0.1 µM-0.5 µM | | | |
| 281 | 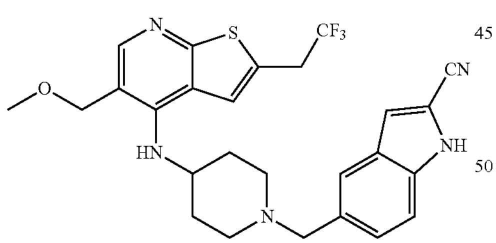 | 450.1 | 1.30 min |
| Inhibitors with IC50 0.5 µM-2 µM | | | |
| 282 | 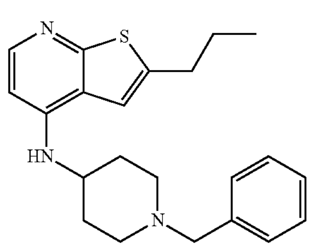 [SMILES: CCCc1cc2c(NC3CCN(Cc4ccccc4)CC3)ccnc2s1] | 366.3 | 1.35 min |

TABLE 8

Examples of subscaffold 6 inhibitors of menin-MLL.

| Compound# | Structure | [MH]+ | LC-MS RT, min. or TLC $R_f$ |
|---|---|---|---|
| Inhibitors with $IC_{50}$ 0.01 nM-0.1 μM | | | |
| 283 | 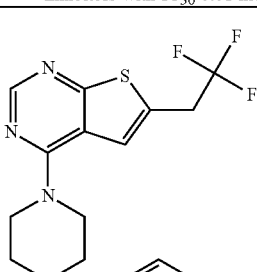 | 407.2 | 1.51 min |

In other embodiments, additional substituents, not depicted in Tables 1-8 or described herein by name or formula, are formed by combination of the above functional groups; such substituents are within the scope of the present invention, and may be appended to one or more of subscaffolds 1-6 to yield compositions within the scope of the present invention.

Subscaffolds 1-6 are provided herein as exemplary subscaffolds of the general thienopyrimidine and thienopyridine class of compounds. While these subscaffolds, with any combination of the substituents depicted or described herein (e.g., explicitly or through combination of functional groups), are within the scope of embodiments of the invention, the present invention is not limited to such subscaffolds. Thienopyrimidine and thienopyridine derivatives of subscaffolds 1-6 are also within the scope of embodiments of the present invention. Substitutions and/or addition/deletion of substituents of subscaffolds 1-6 that produce functional equivalents and/or improved functionality (e.g., enhanced therapeutic effect, enhanced bioavailability, improved human tolerance, reduced side effects, etc.) are also within the scope of embodiments of the present invention.

In some embodiments, the present invention provides compositions and methods for prevention and/or treatment of leukemia (e.g. MLL-related leukemia and other acute leukemias). In some embodiments, the present invention provides compositions and method for the inhibition of the protein-protein interaction between menin and MLL fusion proteins and/or menin and MLL wild type proteins (both MLL1 and MLL2). In some embodiments, compositions and methods inhibit the interaction that is important for the oncogenic (e.g. leukemogenic) potential of MLL fusions. In some embodiments, the present invention provides small molecule inhibitors of interactions between menin and MLL fusion proteins and/or menin and MLL wild type proteins (both MLL1 and MLL2). In some embodiments, compositions and methods reverse (e.g. inhibit, decrease, abolish, etc.) the oncogenic (e.g. leukemogenic) potential of MLL fusion proteins. In some embodiments, compositions find utility in targeted therapies (e.g. anti-leukemia agents). In some embodiments, compounds block menin-MLL interactions.

In some embodiments, the present invention provides compositions which inhibit the interaction between MLL (e.g. MLL fusion proteins and MLL wild type) and menin. In some embodiments, any compounds, small molecules (e.g. pharmaceuticals, drugs, drug-like molecules, etc.), macromolecules (e.g. peptides, nucleic acids, etc.) and/or macromolecular complexes which inhibit the MLL-menin interaction find utility in the present invention. In some embodiments, the present invention provides small molecule compounds which inhibit MLL-menin interactions. In some embodiments, compositions of the present invention decrease the affinity of menin for MLL (e.g. MLL fusion proteins) and/or MLL (e.g. MLL wild type protein) for menin. In some embodiments, compositions of the present invention disrupt bonding (e.g. hydrogen bonding, ionic bonding, covalent bonding, etc.), molecular interactions (e.g. hydrophobic interactions, electrostatic interactions, van der Waals interactions, etc.), shape recognition, and/or molecular recognition between MLL (e.g. MLL fusion proteins or MLL wild type protein) and menin. However, an understanding of the mechanisms of action is not required to practice the invention and the invention is not limited to any particular mechanism of action.

The present invention provides any small molecules or classes of small molecules which disrupt, target, or inhibit MLL/menin interactions; and/or treat/prevent leukemia. In some embodiments, small molecules are effective in inhibiting the interaction of MLL-fusion proteins with menin or MLL wild type protein with menin. In particular embodiments, the present invention provides thienopyrimidine and thienopyridine classes of small molecules. In some embodiments, thienopyrimidine small molecules of the present invention inhibit the interaction of MLL (e.g. MLL-fusion proteins or MLL wild type, both MLL1 and MLL2) with menin. In some embodiments, thienopyrimidine and thienopyridine small molecules of the present invention inhibit the oncogenic (e.g. leukemogenic) effects of MLL-fusion proteins, and/or MLL-menin and MLL fusion protein-menin interactions. In some embodiments, thienopyrimidine and thienopyridine small molecules of the present invention treat and/or prevent leukemia (e.g. MLL-dependant leukemias, MLL-related leukemias, or other leukemias with and without high level of HOX genes expression etc.).

In some embodiments, the present invention provides administration of compositions of the present invention to subjects (e.g. leukemia patients) to treat or prevent disease (e.g. cancer, leukemia, MLL-related leukemia, etc.). In some embodiments, the present invention provides administration of compositions for the treatment or prevention of leukemia (e.g. acute leukemias, chronic leukemias, lymphoblastic leukemias, lymphocytic leukemias, myeloid leukemias, myelogenous leukemias, Acute lymphoblastic leukemia (ALL), Chronic lymphocytic leukemia (CLL), Acute myelogenous leukemia (AML), Chronic myelogenous leukemia (CML), Hairy cell leukemia (HCL), T-cell prolymphocytic leukemia (T-PLL), Large granular lymphocytic leukemia, MLL-positive leukemias, MLL-induced lukemias, etc.).

In some embodiments, any of the above compounds is co-administered or used in combination with a known therapeutic agent (e.g., methotrexate, 6-mercaptopurine, antibody therapies, etc.). In some embodiments, a compound of the present invention is co-administered with another therapeutic agent effective in treating one or more leukemias.

In some embodiments, a compound of the present invention is co-administered with one or more therapeutic agents approved for the treatment of Acute Lymphoblastic Leukemia (ALL), for example: ABITREXATE (Methotrexate), ADRIAMYCIN PFS (Doxorubicin Hydrochloride), ADRIAMYCIN RDF (Doxorubicin Hydrochloride), ARRANON (Nelarabine), Asparaginase *Erwinia chrysanthemi*, CERUBIDINE (Daunorubicin Hydrochloride), CLAFEN (Cyclophosphamide), CLOFARABINE, CLOFAREX (Clofarabine), CLOLAR (Clofarabine), Cyclophosphamide, Cytarabine, CYTOSAR-U (Cytarabine), CYTOXAN (Cyclophosphamide), Dasatinib, Daunorubicin Hydrochloride, Doxorubicin Hydrochloride, Erwinaze (Asparaginase *Erwinia Chrysanthemi*), FOLEX (Methotrexate), FOLEX PFS (Methotrexate), GLEEVEC (Imatinib Mesylate), ICLUSIG (Ponatinib Hydrochloride), Imatinib Mesylate, MARQIBO (Vincristine Sulfate Liposome), Methotrexate, METHOTREXATE LPF (Methorexate), MEXATE (Methotrexate), MEXATE-AQ (Methotrexate), Nelarabine, NEOSAR (Cyclophosphamide), ONCASPAR (Pegaspargase), Pegaspargase, Ponatinib Hydrochloride, RUBIDOMYCIN (Daunorubicin Hydrochloride), SPRYCEL (Dasatinib), TARABINE PFS (Cytarabine), VINCASAR PFS (Vincristine Sulfate), Vincristine Sulfate, etc.

In some embodiments, a compound of the present invention is co-administered with one or more therapeutic agents approved for the treatment of Acute Myeloid Leukemia (AML), for example: ADRIAMYCIN PFS (Doxorubicin Hydrochloride), ADRIAMYCIN RDF (Doxorubicin Hydrochloride), Arsenic Trioxide, CERUBIDINE (Daunorubicin Hydrochloride), CLAFEN (Cyclophosphamide), Cyclophosphamide, Cytarabine, CYTOSAR-U (Cytarabine), CYTOXAN (Cyclophosphamide), Daunorubicin Hydrochloride, Doxorubicin Hydrochloride, NEOSAR (Cyclophosphamide), RUBIDOMYCIN (Daunorubicin Hydrochloride), TARABINE PFS (Cytarabine), TRISENOX (Arsenic Trioxide), VINCASAR PFS (Vincristine Sulfate), Vincristine Sulfate, etc.

In some embodiments, a compound of the present invention is co-administered with one or more therapeutic agents approved for the treatment of Chronic Lymphocytic Leukemia (CLL), for example: Alemtuzumab, AMBOCHLORIN (Chlorambucil), AMBOCLORIN (Chlorambucil), ARZERRA (Ofatumumab), Bendamustine Hydrochloride, CAMPATH (Alemtuzumab), CHLORAMBUCILCLAFEN (Cyclophosphamide), Cyclophosphamide, CYTOXAN (Cyclophosphamide), FLUDARA (Fludarabine Phosphate), Fludarabine Phosphate, LEUKERAN (Chlorambucil), LINFOLIZIN (Chlorambucil), NEOSAR (Cyclophosphamide), Ofatumumab, TREANDA (Bendamustine Hydrochloride), etc.

In some embodiments, a compound of the present invention is co-administered with one or more therapeutic agents approved for the treatment of Chronic Myelogenous Leukemia (CML), for example: BOSULIF (Bosutinib), Bosutinib, CLAFEN (Cyclophosphamide), Cyclophosphamide, Cytarabine, CYTOSAR-U (Cytarabine), CYTOXAN (Cyclophosphamide), Dasatinib, GLEEVEC (Imatinib Mesylate), ICLUSIG (Ponatinib Hydrochloride), Imatinib Mesylate, NEOSAR (Cyclophosphamide), Nilotinib, Omacetaxine Mepesuccinate, Ponatinib Hydrochloride, SPRYCEL (Dasatinib), SYNRIBO (Omacetaxine Mepesuccinate), TARABINE PFS (Cytarabine), TASIGNA (Nilotinib), etc.

In some embodiments, a compound of the present invention is co-administered with one or more therapeutic agents approved for the treatment of Meningeal Leukemia, for example: CYTARABINE, CYTOSAR-U (Cytarabine), TARABINE PFS (Cytarabine), etc.

In some embodiments, the compositions of the present invention are provided as pharmaceutical and/or therapeutic compositions. The pharmaceutical and/or therapeutic compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for topical administration can include transdermal patches, ointments, lotions, creams, gels, drops, suppositories, sprays, liquids and powders. Conventional carriers; aqueous, powder, or oily bases; thickeners; and the like can be necessary or desirable. Compositions and formulations for oral administration include powders or granules, suspensions or solutions in water or non aqueous media, capsules, sachets or tablets. Thickeners, flavoring agents, diluents, emulsifiers, dispersing aids or binders can be desirable. Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Pharmaceutical and/or therapeutic compositions of the present invention include, but are not limited to, solutions, emulsions, and liposome containing formulations. These compositions can be generated from a variety of components that include, but are not limited to, preformed liquids, self emulsifying solids and self emulsifying semi-solids.

The pharmaceutical and/or therapeutic formulations of the present invention, which can conveniently be presented in unit dosage form, can be prepared according to conventional techniques well known in the pharmaceutical/nutriceutical industries. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

Dosing and administration regimes are tailored by the clinician, or others skilled in the pharmacological arts, based upon well known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg.

When the compounds described herein are co-administered with another agent (e.g., as sensitizing agents), the effective amount may be less than when the agent is used alone. Dosing may be once per day or multiple times per day for one or more consecutive days.

EXPERIMENTAL

Example 1

General Methods of Compounds Synthesis

Compounds of Subscaffold 1 can be prepared according to the following general methods (Scheme 1 and 2).

Scheme 1.

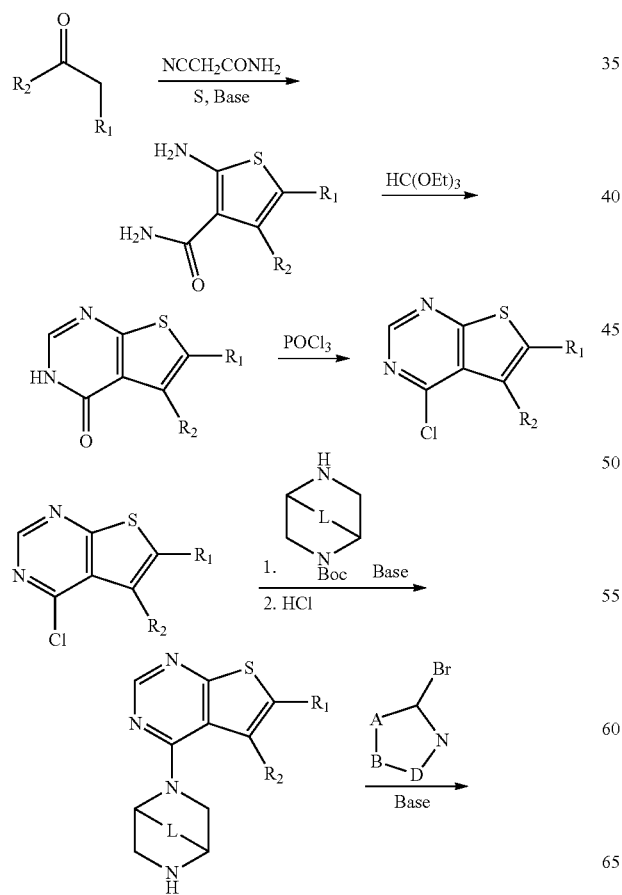

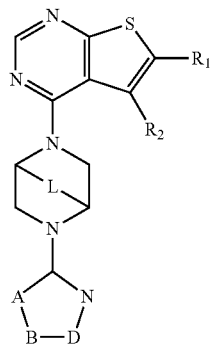

Scheme 2.

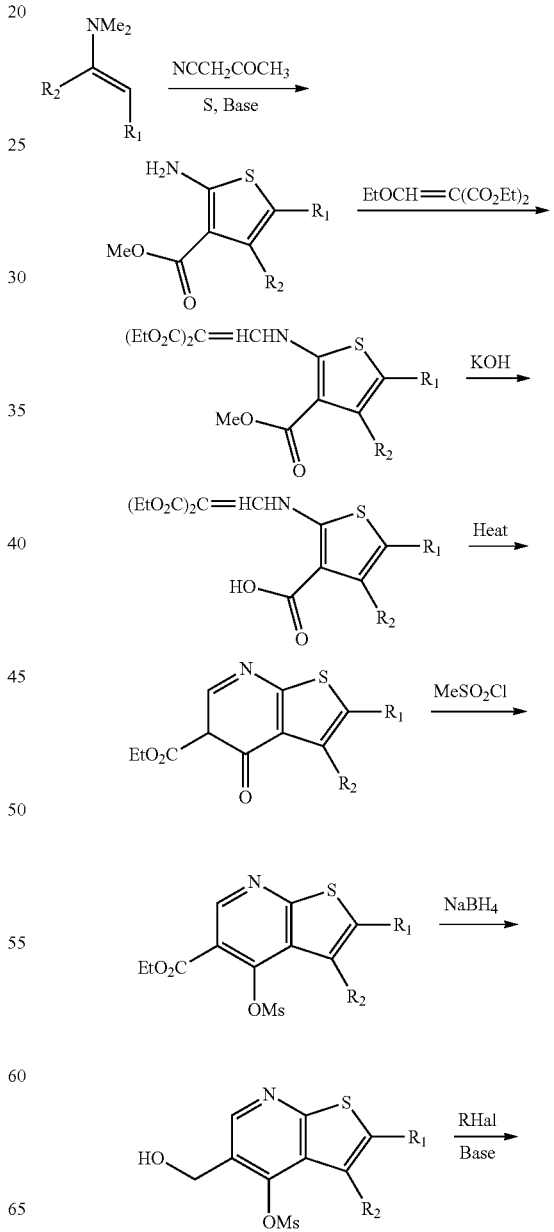

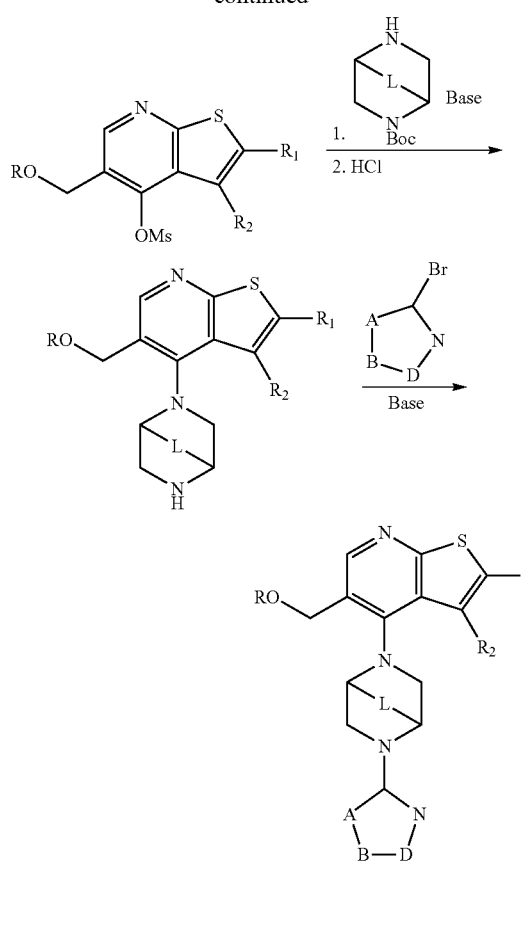
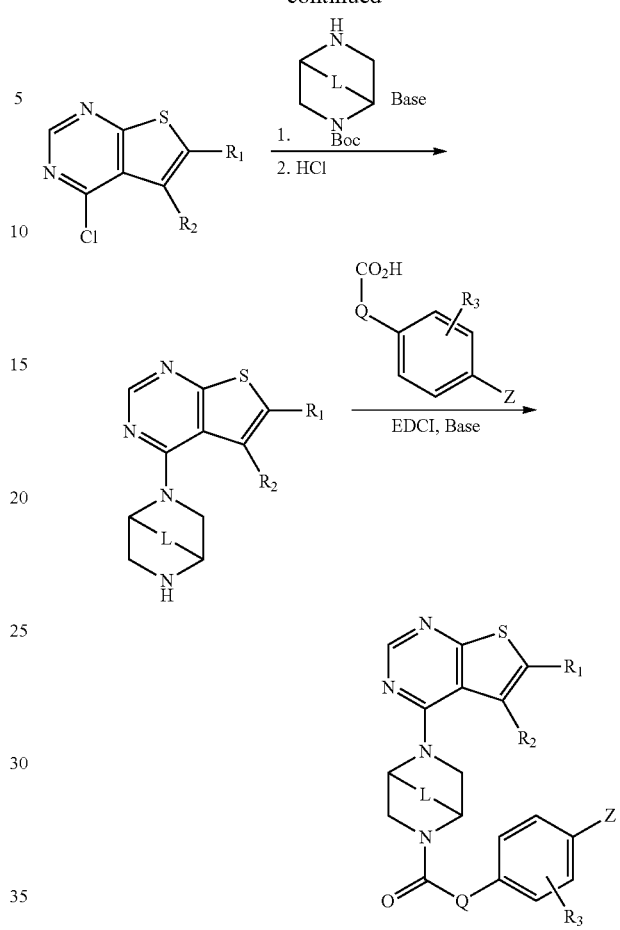
Compounds of Subscaffold 2 can be prepared according to the following general methods (Scheme 3 and 4).
Scheme 3.
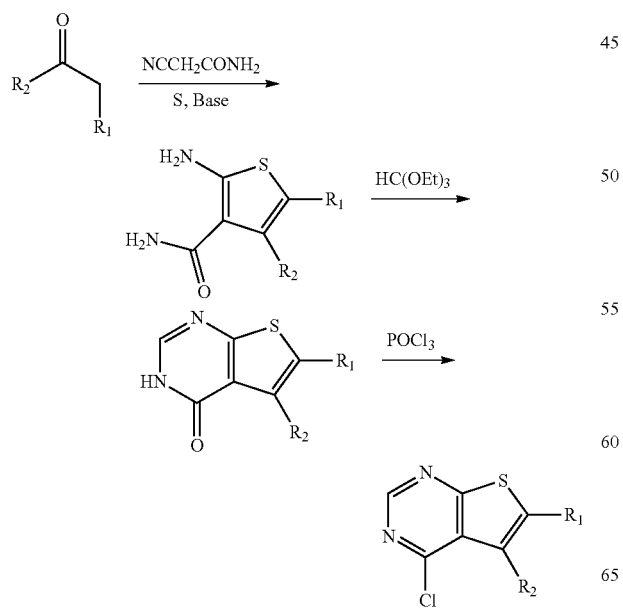
Scheme 4.
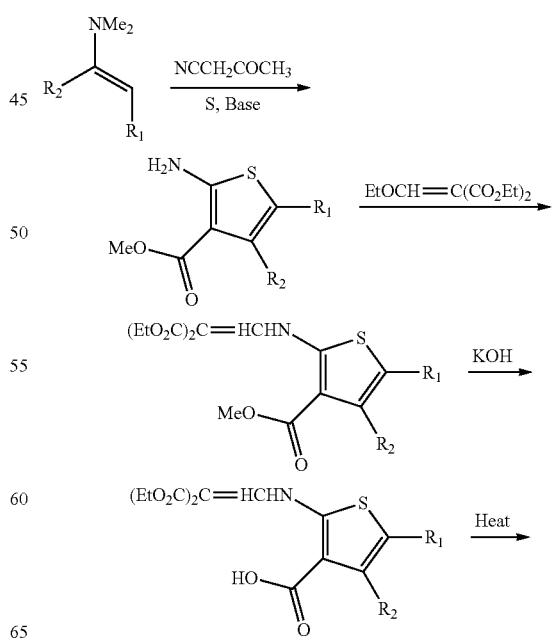

181
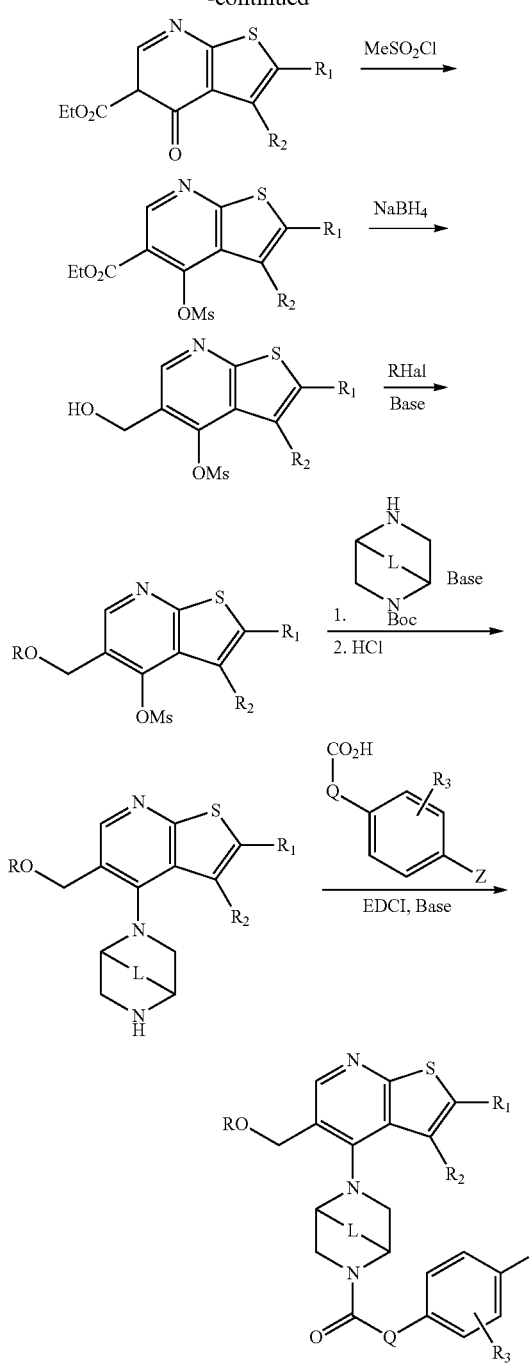
182
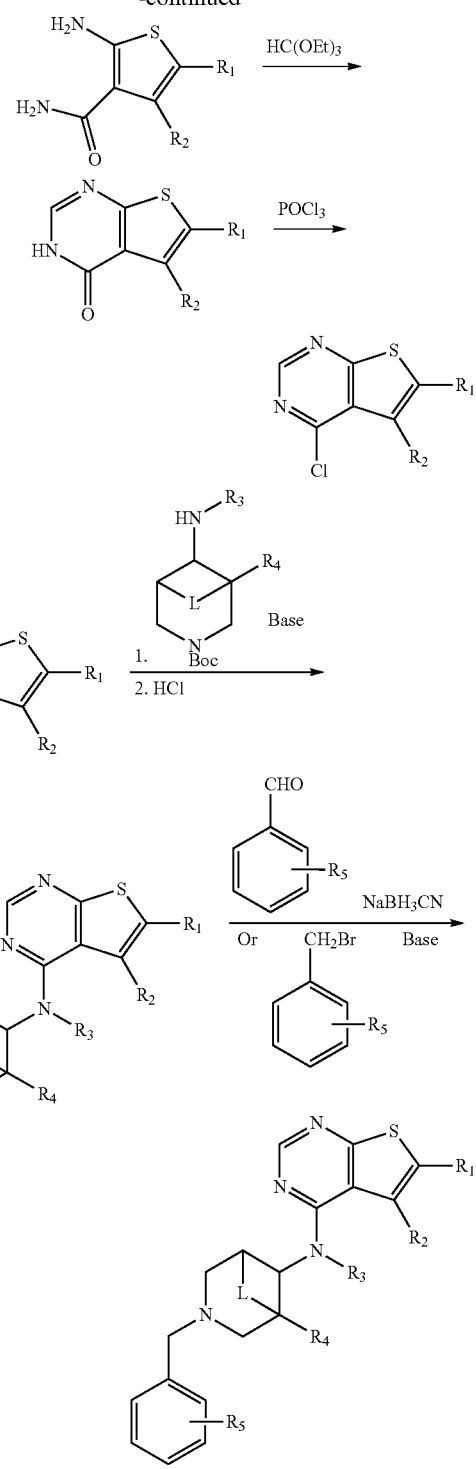
Compounds of Subscaffold 3 can be prepared according to the following general methods (Scheme 5 and 6).
Scheme 5.
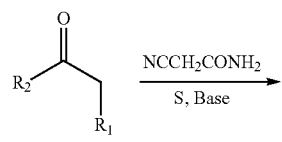
Scheme 6.
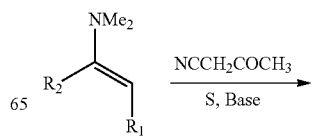

183
-continued
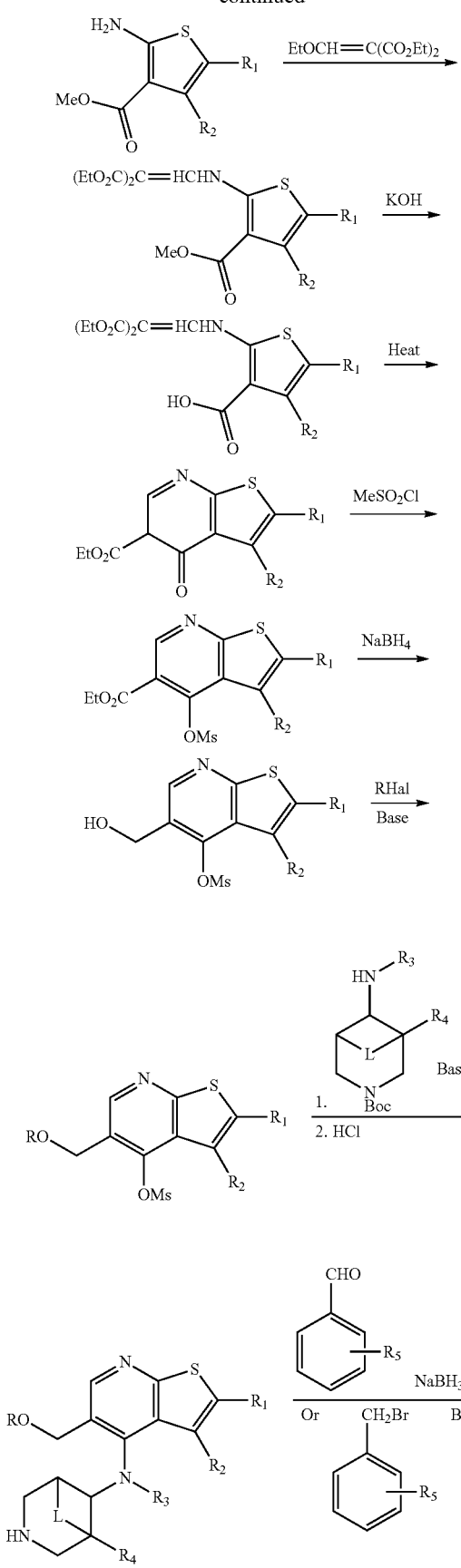
184
-continued
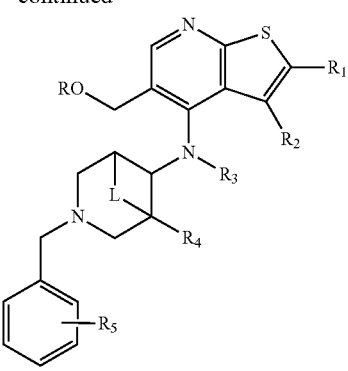
Compounds of Subscaffold 4 can be prepared according to the following general methods (Scheme 7 and 8).
Scheme 7.
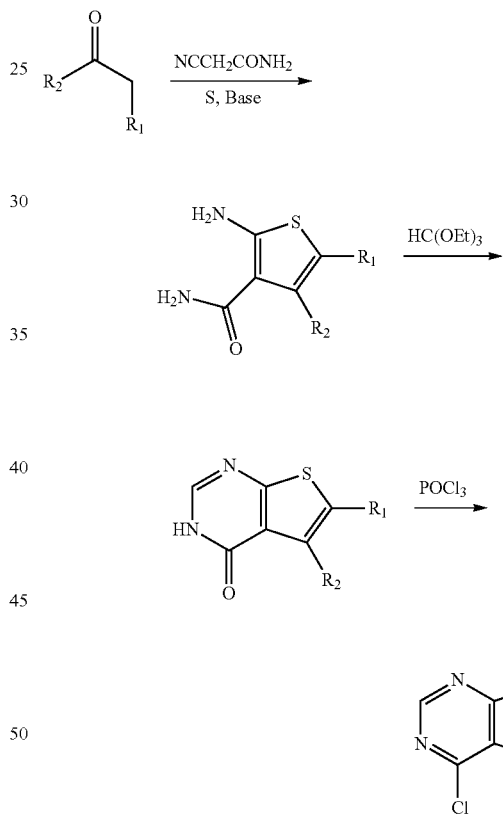
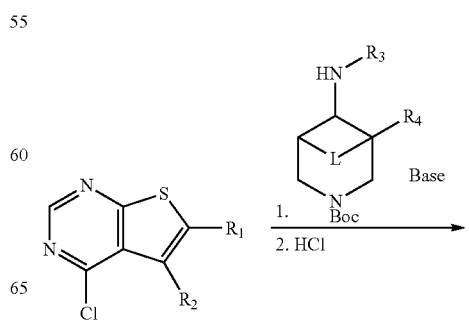

185
-continued
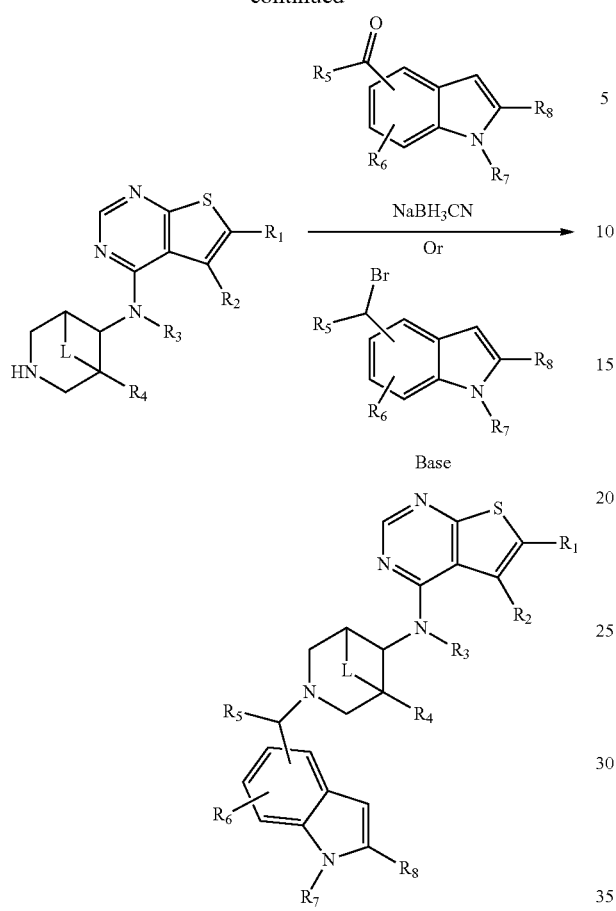
186
-continued
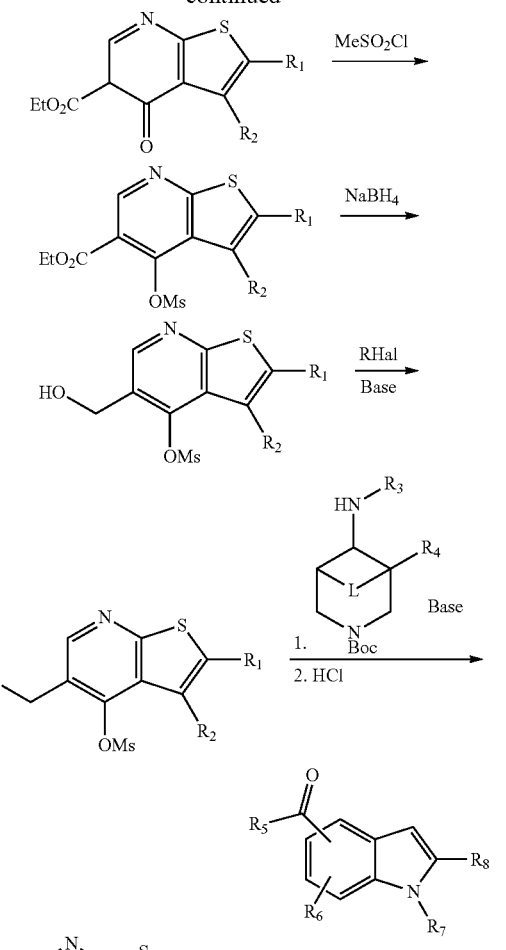
Compounds of Subscaffold 5 can be prepared according to the following general methods (Scheme 9 and 10).
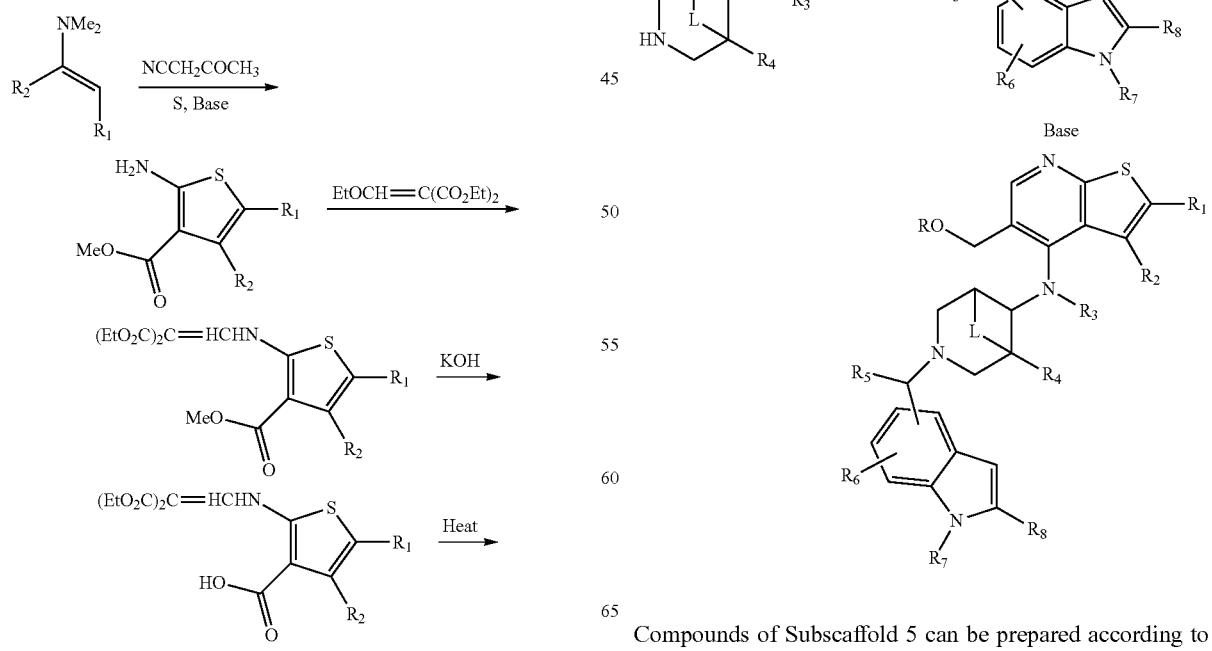
Scheme 8.

Scheme 9.
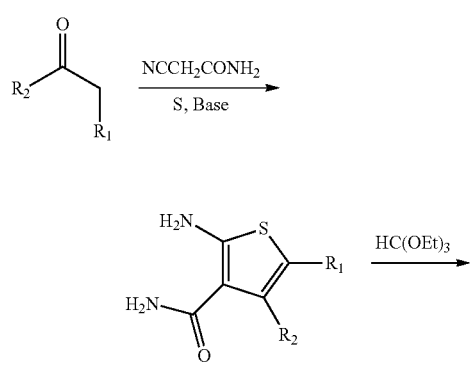
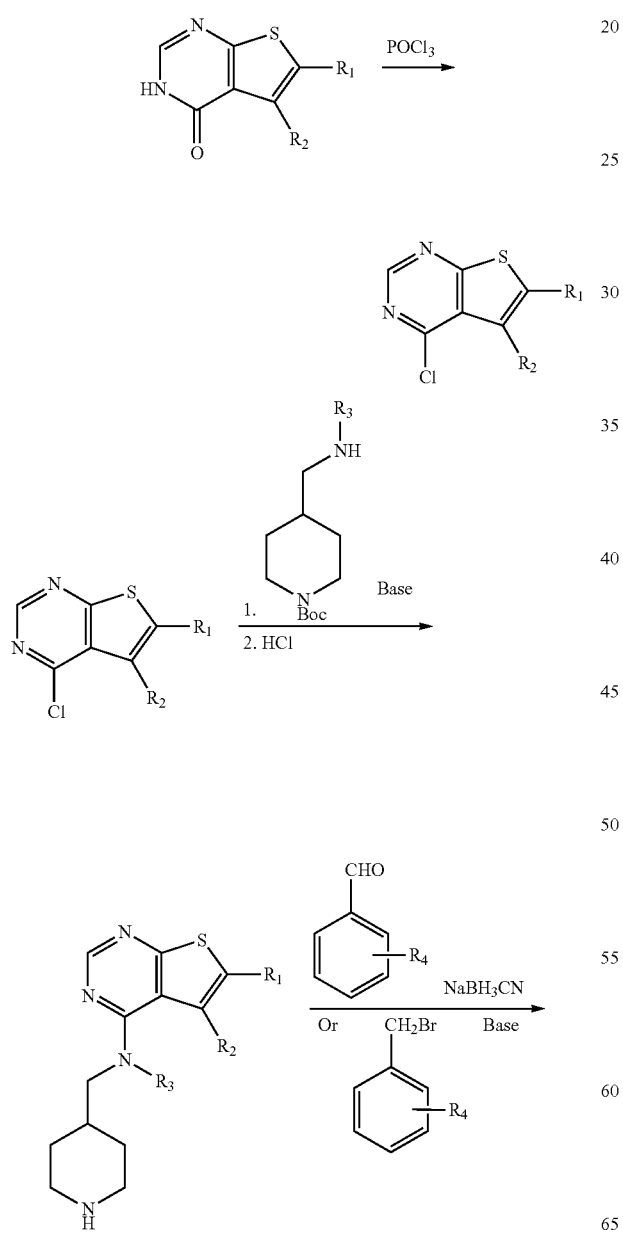
Scheme 10.
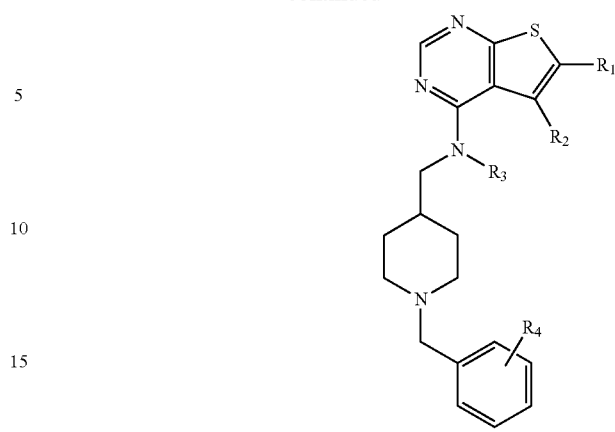

189
-continued
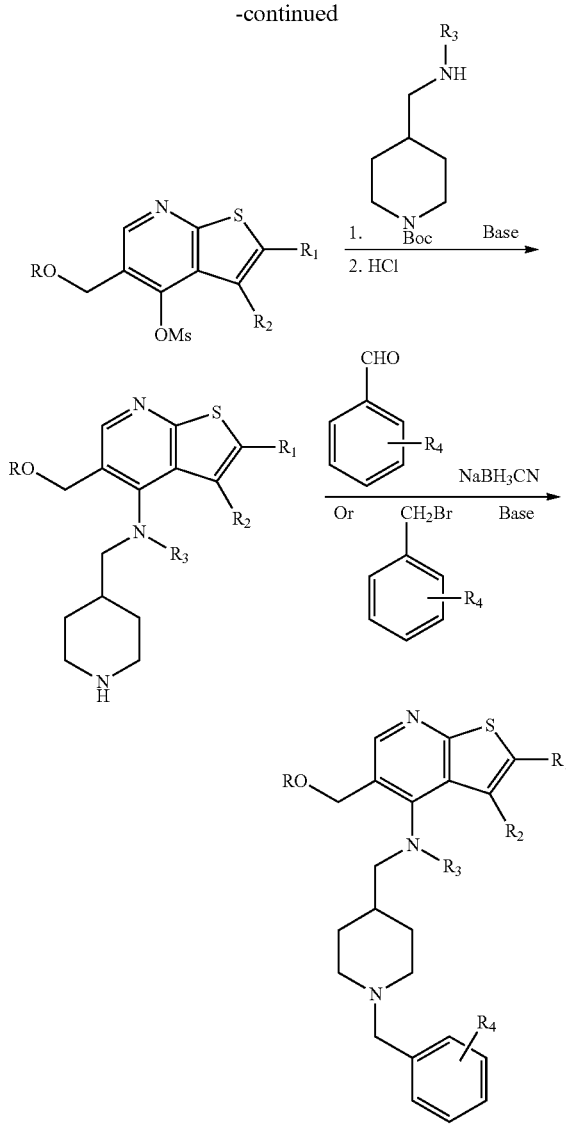
190
-continued
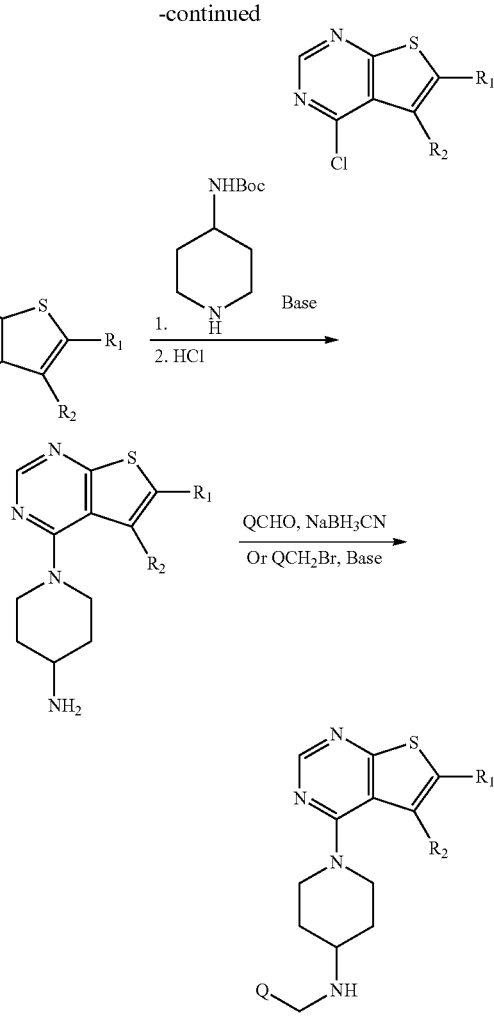
Compounds of Subscaffold 6 can be prepared according to the following general methods (Scheme 11 and 12).
Scheme 11.
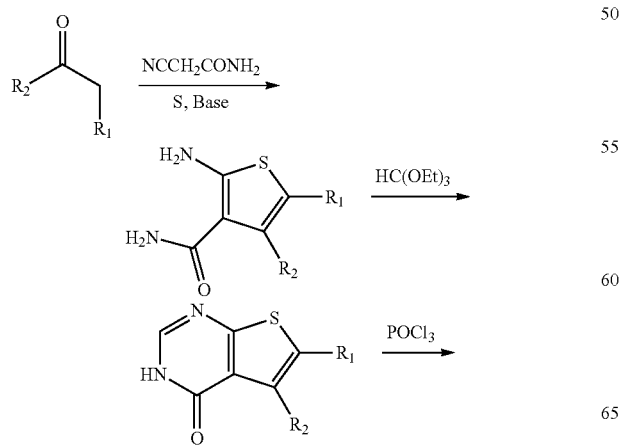
Scheme 12.
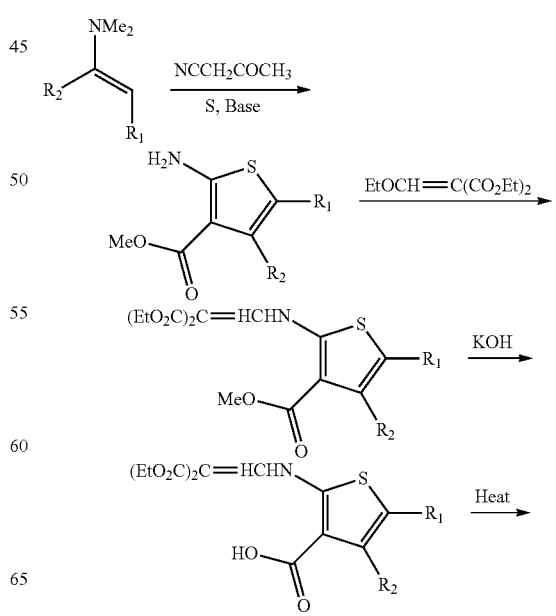

-continued

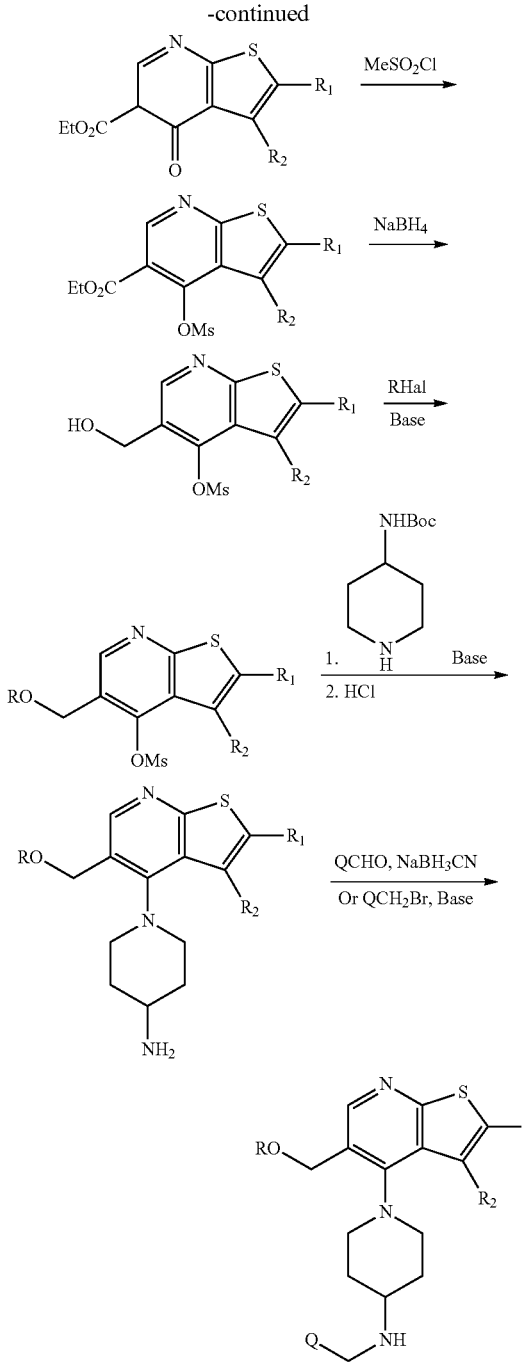

Example 2

Representative Procedure for the Synthesis of Compounds from Subscaffold 1

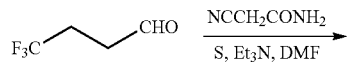

-continued

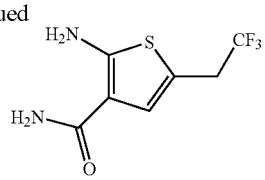

4,4,4-trifluorobuteraldehyde 5 g (39.6 mmol), cyanoacetamide 3.36 g (39.6 mmol) and sulfur 1.28 g (39.6 mmol) was stirred in 40 mL of DMF in the presence of 6.7 mL of triethylamine for 24 hs. Solvent was evaporated under reduced pressure and the residue was loaded on silica gel column and eluted with pure ethyl acetate to afford 8.4 g of 2-amino-5-(2,2,2-trifluoroethyl)thiophene-3-carboxamide. $^1$H NMR CDCl$_3$ (300 MHz): 7.97 (s, 1H), 6.76 (s, 1H), 3.59 (br, 2H), 3.35 (q, 2H, J 10.3 Hz), 2.98 (s, 1H), 2.88 (s, 1H). $^{13}$C NMR CDCl$_3$ (75 MHz): 168.6, 125.6, 124.3, 111.7, 107.3, 36.8, 34.7 (q, J31.4 Hz).

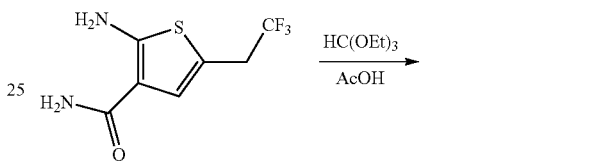

8.4 g of 2-amino-5-(2,2,2-trifluoroethyl)thiophene-3-carboxamide was refluxed in a mixture of 28 mL of triethylorthoformate and 20 mL of acetic acid for 4 hs. Solvents were removed under reduced pressure and the residue was triturated hexane-ethyl acetate mixture (1:1). The solid was filtered off to afford 5.7 g of 6-(2,2,2-trifluoroethyl)thieno[2,3-d]pyrimidin-4(3H)-one. $^1$H NMR MeOH-d4 (300 MHz): 12.6 (br, 1H), 8.14 (s, 1H), 7.42 (s, 1H), 4.07 (q, 2H, J 11.0 Hz). $^{13}$C NMR MeOH-d4 (75 MHz): 164.5, 157.01, 146.1, 128.4, 124.6, 123.5, 33.6 (q, J31.5 Hz).

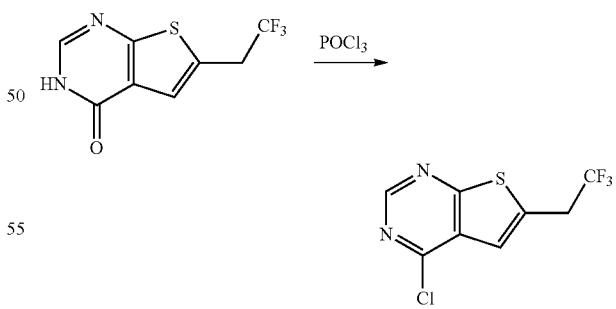

5.7 g of 6-(2,2,2-trifluoroethyl)thieno[2,3-d]pyrimidin-4 (3H)-one was added to 16 mL of POCl$_3$ with one drop of DMF. The heterogeneous mixture was refluxed for 3 hs and then evaporated. The residue was quenched with ice and saturated ammonia solution and extracted with chloroform. Combined extracts were evaporated with silica gel and loaded on a short silica gel column. The column was eluted with hexane-ethyl acetate (5:1) to afford 5.9 g of 4-chloro- 6-(2,2,2-trifluoroethyl)thieno[2,3-d]pyrimidine. $^1$H NMR CDCl$_3$ (300 MHz): 8.86 (s, 1H), 7.39 (s, 1H), 3.76 (q, 2H, J9.9 Hz). $^{13}$C NMR CDCl$_3$ (75 MHz): 169.0, 154.7, 153.2, 129.9, 125.3, 123.5, 121.3, 35.9 (q, J33.0 Hz).

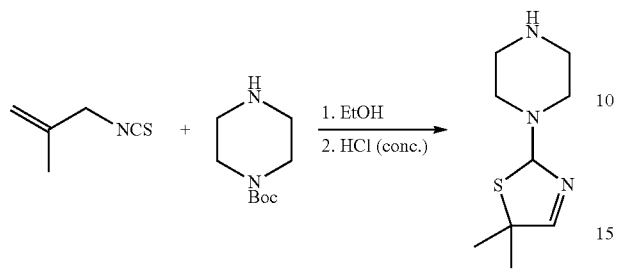

0.5 g of 3-isothiocyanato-2-methylprop-1-ene was added to dropwise via syringe to a solution of 1-Bocpiperazine in 5 mL of ethanol. The mixture was stirred for 1.5 hs at RT and then evaporated. The residue was washed several times with diethyl ether to produce 1. g of white solid intermediate, which was dissolved in 3 mL of conc. HCl and heated in the pressure tube at 100 degrees for 1.5 hours. Cooled solution was quenched with ammonia solution and extracted with ethyl acetate. Combined organic layers were washed with brine, dried over MgSO$_4$ and evaporated to afford pure 382 mg of 5,5-dimethyl-2-(piperazin-1-yl)-2,5-dihydrothiazole, which was use as is in the next step. $^1$H NMR (400 MHz, CDCl3): δ 1.53 (6H, s), 2.96 (4H, t, J=5 Hz), 3.49 (4H, t, J=5 Hz), 3.73 (2H, s). $^{13}$C NMR (100 MHz, CDCl3): δC 28.83 (2C), 45.76 (2C), 49.34 (2C), 59.52, 73.30, 164.16; mp 67° C.-70° C.; Mass spec (ES+): m/z 199.2 (M$^+$+1).

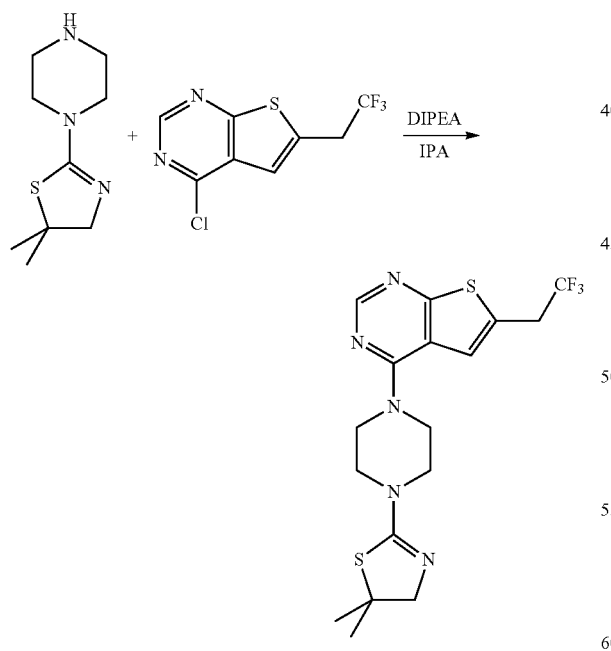

A solution of 0.5 g of 4-chloro-6-(2,2,2-trifluoroethyl)thieno[2,3-d]pyrimidine (2.4 mmol), 0.56 g of 5,5-dimethyl-2-(piperazin-1-yl)-2,5-dihydrothiazole (2.8 mmol), and 0.91 g of N,N-diisopropylethylamine (7.1 mmol) in 20 mL of THF was refluxed for 6 h. After cooling, the mixture was partitioned between ethyl acetate and H$_2$O. The combined organic extracts were washed with brine, dried over MgSO$_4$ and concentrated to a pale yellow solid. Purification by silica gel column chromatography using dichloromethane/methanol (97:3) as eluent gave 0.82 g of 4-(4-(5,5-dimethyl-4,5-dihydrothiazol-2-yl)piperazin-1-yl)-6-(2,2,2-trifluoroethyl)thieno[2,3-d]pyrimidine (compound 1) as a pale yellow solid. Its monohydrochloride salt was obtained by adding 1 equivalent of 1N HCl solution in diethyl ether to a solution of compound in ethanol. $^1$H NMR (400 MHz DMSO-d6): δ 8.46 (s, 1H), 7.70 (s, 1H), 4.37 (s, 1H), 4.09 (m, 4H), 3.81, (m, 4H), 3.45 (q, 2H, J=10.1 Hz), 1.61 (s, 6H). ESI MS [MH$^+$]: 416.1.

Example 3

Representative Procedure for the Synthesis of Compounds from Subscaffold 2

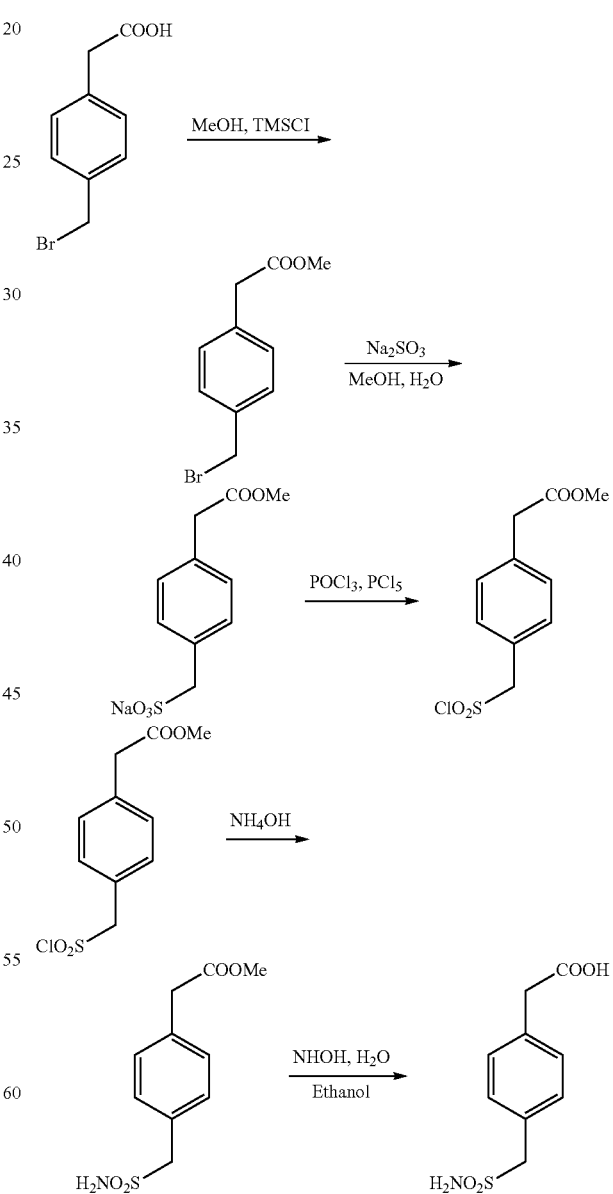

To a solution of 2 g of 4-(bromomethyl)phenyl acetic acid in 20 mL of methanol was added 0.2 mL of TMSCl and mixture was stirred for 2 hrs. The solvent was removed in vacuo and residue was twice redissolved in MeOH and reconcentrated to give desired product, which was used in the xet step without purification. Bromoester was refluxed in 50 mL of water in the presence of 2.5 g of sodium bisulfilte for 3 hs. After cooling down the precipitate was filtered off and dried on the funnel overnight. The solid was suspended in 15 mL of $POCl_3$ and 1 g of $PCl_5$ was slowly added to a suspension. The mixture stirred for 3 hs at RT. A mixture was concentrated and 10 mL of conc. ammonia in water was slowly added to 0° C., redissolved compound in 30 mL of acetonitrile. After stirring for 12 hs at RT, a mixture was concentrated, partitioned between ethyl acetate and saturated sodium carbonate solution. Organic layer was washed with brine, dried over $MgSO_4$ and evaporated.

The intermediate ester was dissolved in 5 mL of EtOH and 10 ml of 10M NaOH was added. The mixture was stirred for 24 hs and then concentrated. Acidification with 12M HCl resulted in precipitate. 2-(4-(sulfamoylmethyl)phenyl)acetic acid was filtered off and dried overnight. Used without purification in the next step.

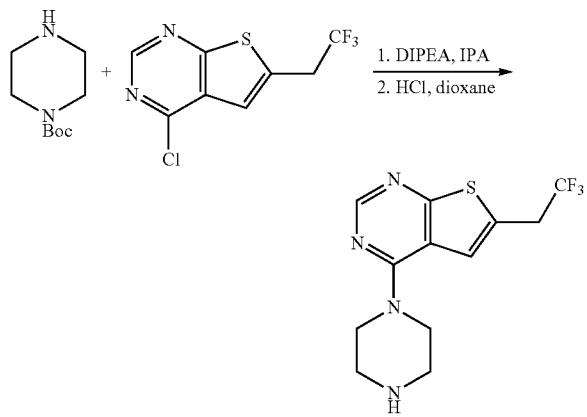

190 mg of 4-chloro-6-(2,2,2-trifluoroethyl)thieno[2,3-d]pyrimidine (0.75 mmol) was added to a stirred solution of 290 mg of N,N-diisopropylethylamine (2.25 mmol) and 168 mg of 1-Boc-piperazine (0.9 mmol) in 20 mL and was heated at reflux overnight. Solvent was removed under reduced pressure and the residue was loaded on silica gel column. Elution with DCM:MeOH produced 215 mg of Boc-intermediate as a pale yellow solid. Later it was dissolved in 20 mL of 4M HCl in dioxane and stirred for 2 hs. Solvent was evaporated under reduced pressure and the residue was partitioned between ethyl acetate and saturated sodium carbonate solution. Organic layer was washed with brine, dried over $MgSO_4$ and evaporated to afford 150 mg of 4-(piperazin-1-yl)-6-(2,2,2-trifluoroethyl)thieno[2,3-d]pyrimidine, which was used in the next step without purification.

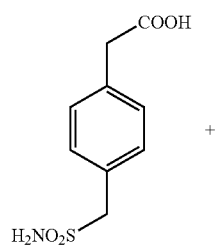

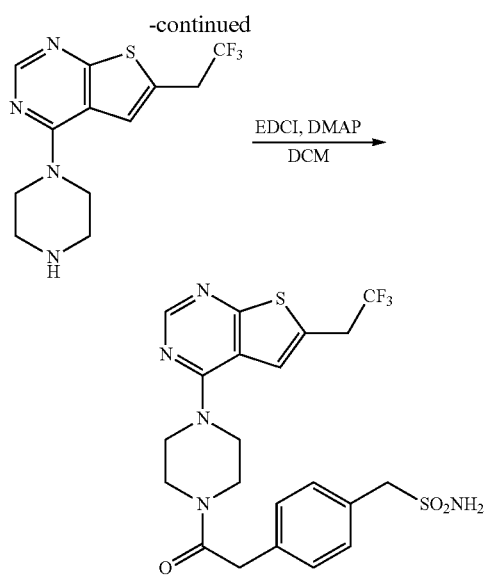

23 mg of 2-(4-(sulfamoylmethyl)phenyl)acetic acid (0.1 mmol), 20 mg of 4-(piperazin-1-yl)-6-(2,2,2-trifluoroethyl)thieno[2,3-d]pyrimidine (0.067 mmol), 20 mg of EDCI (0.1 mmol) and 4 mg of DMAP (0.033 mmol) was stirred in 2 mL of DCM. After 2 hs reaction mixture was concentrated and residue was loaded on silica gel column. Elution with DCM-MeOH 9:1 and evaporation of fraction produced 38 mg of (4-(2-oxo-2-(4-(6-(2,2,2-trifluoroethyl)thieno[2,3-d]pyrimidin-4-yl)piperazin-1-yl)ethyl)phenyl)methanesulfonamide (compound 44). $^1H$ NMR (400 MHz, CDCl3): δ 8.44 (s, 1H), 7.36 (d, 2H, J=8 Hz), 7.25 (d, 2H, J=8 Hz), 7.20 (s, 1H), 4.88 (s, 2H), 4.26 (s, 1H), 3.5-4.0 (m, 10H). ESI MS [MH$^+$]: 514.1. Its monohydrochloride salt was obtained by adding 1 equivalent of 1N HCl solution in diethyl ether to a solution of compound in ethanol.

Example 4

Representative Procedure for the Synthesis of Compounds from Subscaffold 3

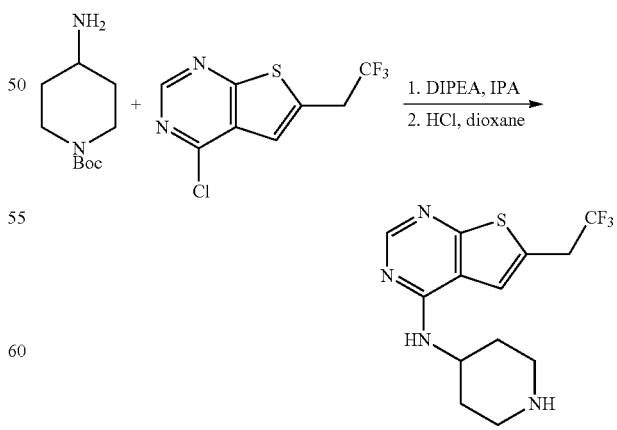

4.8 g of 4-chloro-6-(2,2,2-trifluoroethyl)thieno[2,3-d]pyrimidine (19 mmol) was added to a stirred solution of 7.4 g of N,N-diisopropylethylamine (57 mmol) and 168 mg of 1-Boc-piperazine (0.9 mmol) in 95 mL and was heated at reflux overnight. On the morning reaction mixture was evaporated with silica gel and loaded on the column. The product was eluted with hexane-ethyl acetate from 1:1 to 1:5 yielding 7.42 g of boc-derivative. Boc-intermediate was dissolved in 40 mL of 4M HCl in dioxane and stirred for 2 hs. Solvent was evaporated under reduced pressure and the residue was partitioned between ethyl acetate and saturated sodium carbonate solution. Organic layer was washed with brine, dried over MgSO$_4$ and evaporated to afford 5.3 g of N-(piperidin-4-yl)-6-(2,2,2-trifluoroethyl)thieno[2,3-d]pyrimidin-4-amine, which was used in later steps without purification. $^1$H NMR (600 MHz, CDCl3): δ 8.47 (s, 1H), 7.13 (s, 1H), 5.32 (d, 1H, J=7.7 Hz), 4.32 (m, 1H), 3.64 (q, 2H, 10 Hz), 3.19 (m, 2H), 2.83 (m, 2H), 2.57 (br, 1H), 2.14 (m, 2H), 1.55 (m, 2H). $^{13}$C NMR (150 MHz, CDCl3): δC 166.85, 155.96, 154.33, 128.12, 126.62, 118.66, 116.48, 47.98, 45.32, 35.56 (q, J=31.5 Hz), 33.10. ESI MS [MH$^+$]: 317.2.

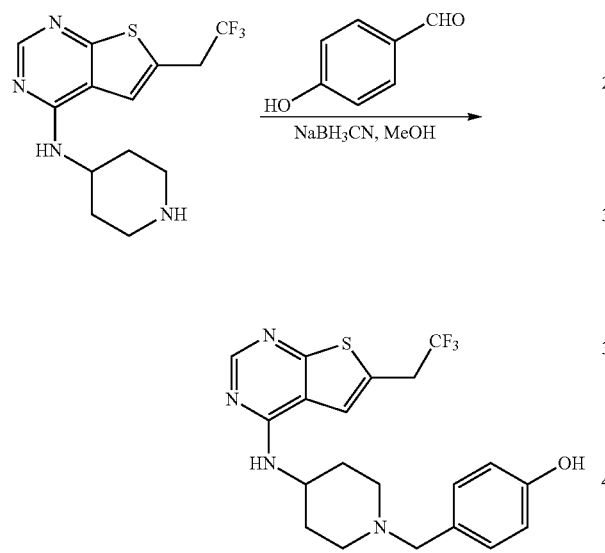

59 mg of N-(piperidin-4-yl)-6-(2,2,2-trifluoroethyl)thieno[2,3-d]pyrimidin-4-amine (0.19 mmol) and 21 mg of p-hydroxybenzaldehyde (0.19 mmol) were dissolved in 0.5 mL of MeOH in the presence of 10 uL of acetic acid. 19 mg of NaBH$_3$CN (0.3 mmol) was slowly added to that mixture and solution was stirred for 24 hs. All volatiles were removed under reduced pressure and residue was partitioned between water and ethyl acetate. Organic layer was washed with brine, dried over magnesium sulfate and evaporated. The residue was purified on silica gel column with DCM:MeOH:Et3N as eluent resulting in 62 mg of 4-((4-((6-(2,2,2-trifluoroethyl)thieno[2,3-d]pyrimidin-4-yl)amino)piperidin-1-yl)methyl)phenol (compound 105). $^1$H NMR (600 MHz, CDCl3): δ 8.46 (s, 1H), 7.09 (d, 2H, J=8.4 Hz), 7.07 (s, 1H), 6.68 (d, 2H, J=8.4 Hz), 5.28 (d, 1H, J=7.7 Hz), 4.21 (m, 1H), 3.59 (q, 2H, 9.9 Hz), 3.46 (s, 2H), 2.96 (m, 2H), 2.21 (m, 2H), 2.09 (m, 2H), 1.62 (m, 2H). $^{13}$C NMR (150 MHz, CDCl3): δC 166.45, 156.08, 155.98, 154.14, 131.01, 128.23, 125.57, 118.65, 116.52, 115.62, 62.48, 52.10, 47.96, 35.50 (q, J=31.5 Hz), 31.89. ESI MS [MH$^+$]: 423.1458. Its monohydrochloride salt was obtained by adding 1 equivalent of 1N HCl solution in diethyl ether to a solution of compound in ethanol.

Example 5

Analytical Data for Selected Compounds from Subscaffold 3 and 4 and Representative Procedures for their Synthesis Compound 160

Synthesized according to this synthetic route:

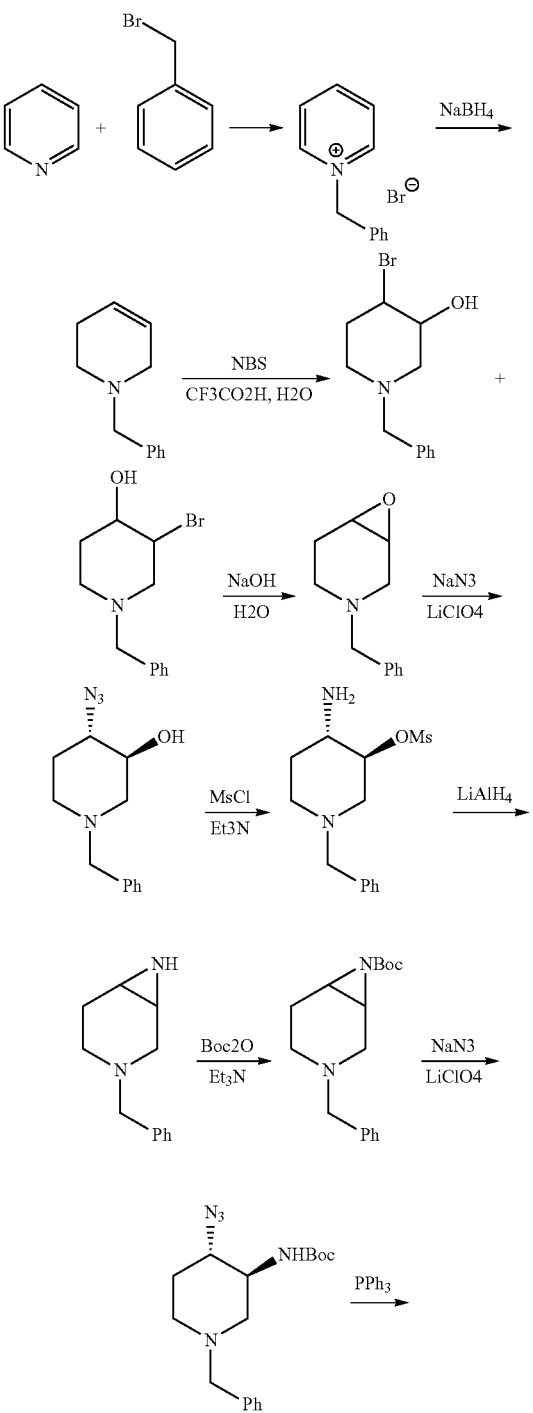

-continued

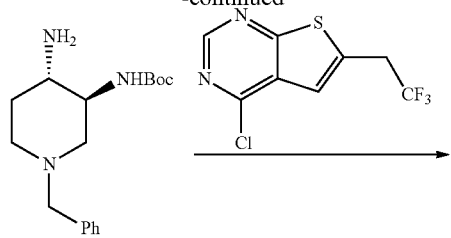

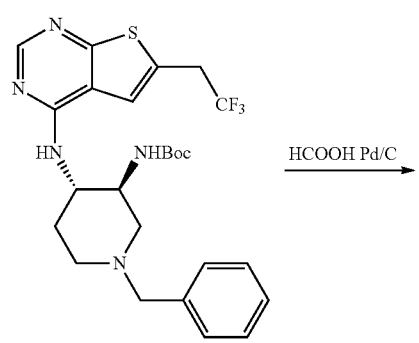

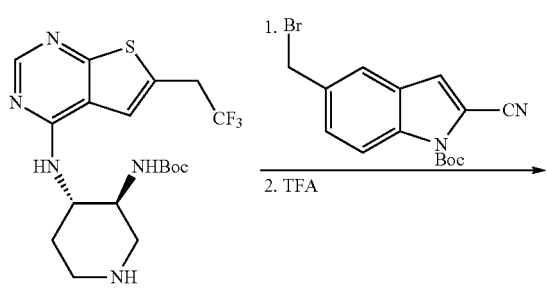

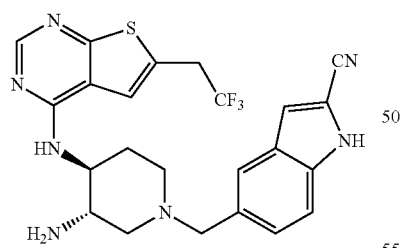

Monohydrochloride salt exists as a mixture of rotomers in approximate ratio 10:1, NMR is described for the major one:
¹H NMR (600 MHz, CD₃OD): δ 8.41 (s, 1H), 7.76 (s, 1H), 7.62 (m, 2H), 7.57 (d, 1H, J=8.3 Hz), 7.33 (s, 1H), 4.57 (m, 1H), 4.05 (m, 1H), 3.96 (m, 1H), 3.91 (q, 2H, J=10.3 Hz), 3.53 (m, 1H), 3.42 (m, 1H), 3.22 (m, 1H), 2.60 (m, 2H), 2.16 (m, 1H), 2.04 (m, 1H). ¹³C NMR (150 MHz, CD₃OD): δC 167.34, 158.35, 154.49, 138.61, 130.12, 128.67, 127.53, 127.29, 125.19, 121.45, 118.12, 114.51, 113.72, 112.03, 111.14, 53.12, 52.61, 51.47, 51.22, 50.34, 49.41, 35.46 (q, J=33 Hz), 30.32. ESI MS [MH⁺]: 486.1676.

Compound 161

Synthesized according to this synthetic route:

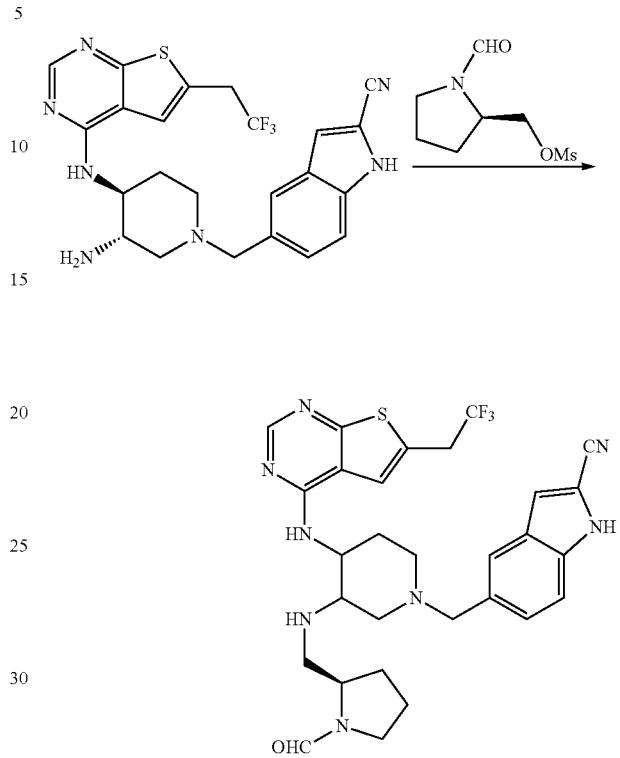

Monohydrochloride salt exists as a mixture of rotomers in approximate ratio 10:1, NMR is described for the major one:
¹H NMR (600 MHz, CD₃OD): δ 9.34 (s, 1H), 8.39 (s, 1H), 7.72 (s, 1H), 7.59 (m, 2H), 7.53 (d, 1H, J=8.3 Hz), 7.29 (s, 1H), 4.51 (m, 1H), 4.02 (m, 1H), 3.91 (m, 1H), 3.88 (q, 2H, J=10.3 Hz), 3.54 (m, 2H), 3.51 (m, 1H), 3.41 (m, 2H), 3.19 (m, 1H), 2.98 (m, 2H), 2.59 (m, 2H), 2.12 (m, 1H), 2.03 (m, 1H), 1.97 (m, 2H), 1.85 (m, 1H), 1.83 (m, 1H). ¹³C NMR (150 MHz, CD₃OD): δC 168.29, 164.2, 157.42, 154.41, 139.41, 131.32, 128.62, 127.41, 127.05, 124.49, 121.42, 117.12, 113.94, 113.45, 111.97, 111.21, 63.11, 53.31, 52.59, 51.42, 51.13, 50.48, 48.31, 48.21, 47.97, 35.48 (q, J=33 Hz), 30.21, 28.71, 26.33. ESI MS [MH⁺]: 597.2367.

Compound 162

Synthesized according to this synthetic route:

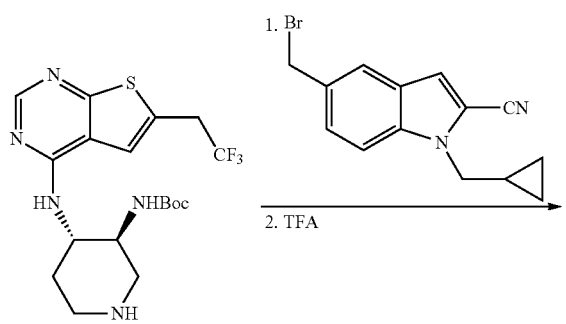

-continued

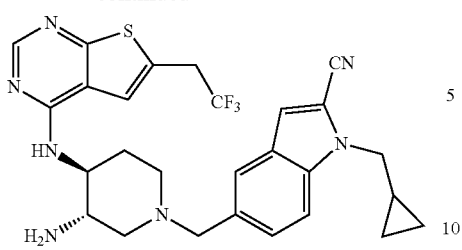

Monohydrochloride salt exists as a mixture of rotomers in approximate ratio 10:1, NMR is described for the major one: $^1$H NMR (600 MHz, CD$_3$OD): δ 8.39 (s, 1H), 7.74 (s, 1H), 7.61 (m, 2H), 7.52 (d, 1H, J=8.3 Hz), 7.27 (s, 1H), 4.54 (m, 1H), 4.24 (m, 2H), 4.03 (m, 1H), 3.94 (m, 1H), 3.88 (q, 2H, J=10.3 Hz), 3.51 (m, 1H), 3.37 (m, 1H), 3.21 (m, 1H), 2.58 (m, 2H), 2.16 (m, 1H), 2.03 (m, 1H), 1.28 (m, 1H), 0.59 (m, 2H), 0.48 (m, 2H). $^{13}$C NMR (150 MHz, CD$_3$OD): δC 167.24, 158.39, 154.62, 138.67, 130.19, 128.64, 127.62, 127.38, 125.55, 121.75, 118.37, 114.53, 113.85, 112.07, 111.07, 62.75, 53.33, 52.73, 51.39, 51.25, 50.52, 49.43, 35.52 (q, J=33 Hz), 31.23, 12.50, 4.18. ESI MS [MH$^+$]: 540.2159.

Compound 165

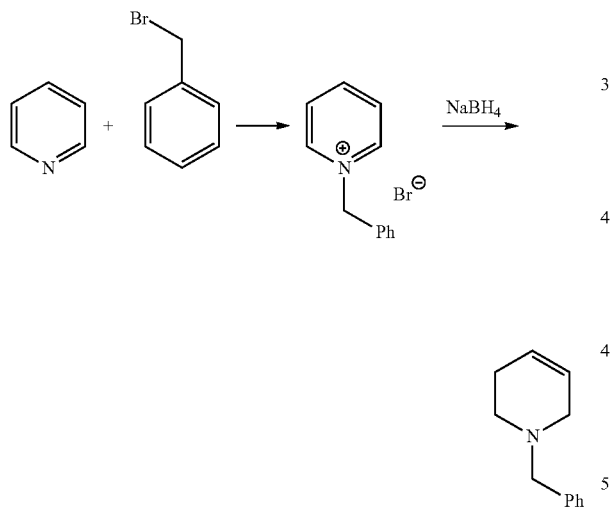

2.4 mL of benzyl bromide (20 mmol) was added dropwise over an hour to a solution of 1.6 mL of pyridine in 5 mL of acetonitrile. Then reaction mixture was heated at 70 to 72° C. for 3 hours. Solvent was removed under reduced pressure and the residue was dissolved in 16 mL of ethanol. 1.1 g of sodium borohydride (30 mmol) was added in small portions over 30 minutes. After stirring for 24 hs reaction mixture was carefully quenched with 50 mL of water and solvents were removed in vacuo. The residue was portioned between ethyl acetate and 2M NaOH solution. Organic extracts were washed with brine, dried over MgSO$_4$ and evaporated to afford crude 3.36 g of crude 1-benzyl-1,2,3,6-tetrahydropyridine which was used in the next step without purification.

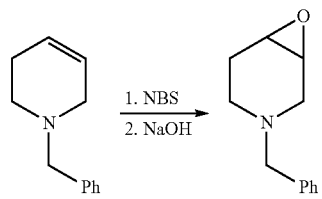

3.36 g of 1-benzyl-1,2,3,6-tetrahydropyridine (0.19 mmol) was dissolved in 35 mL of water containing 1.5 mL of trifluoroacetic acid (0.2 mmol). To that solution 5.87 g of NBS was added in small portions. After 4 hs reaction mixture was transferred to 50 mL of 20% NaOH solution and stirred overnight. On the morning reaction mixture was extracted with dichloromethane and combined organic fractions were dried over sodium sulfate and concentrated. The residue was purified on silica gel column using hexane-ethyl acetate 3:1 as eluent. Evaporation of solvent produced 1.2 g of 3-benzyl-7-oxa-3-azabicyclo[4.1.0]heptane as colorless oil.

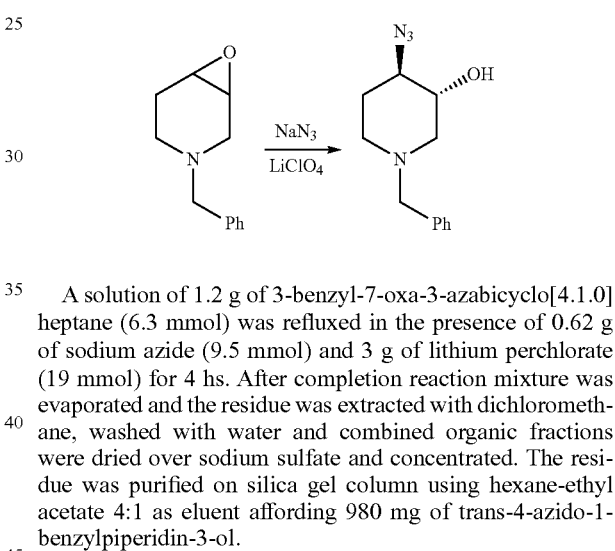

A solution of 1.2 g of 3-benzyl-7-oxa-3-azabicyclo[4.1.0]heptane (6.3 mmol) was refluxed in the presence of 0.62 g of sodium azide (9.5 mmol) and 3 g of lithium perchlorate (19 mmol) for 4 hs. After completion reaction mixture was evaporated and the residue was extracted with dichloromethane, washed with water and combined organic fractions were dried over sodium sulfate and concentrated. The residue was purified on silica gel column using hexane-ethyl acetate 4:1 as eluent affording 980 mg of trans-4-azido-1-benzylpiperidin-3-ol.

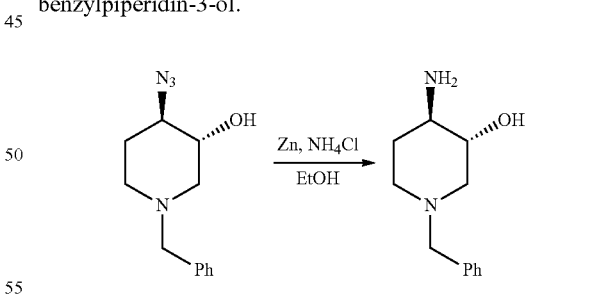

201 mg of trans-4-azido-1-benzylpiperidin-3-ol (0.87 mmol) was dissolved in 3 ml of EtOH-water 3:1. To that solution 77 mg of zinc (12 mmol), 112 mg of ammonium chloride (2.1 mmol) were added and heterogeneous mixture was refluxed for 10 minutes. After cooling down reaction mixture was diluted with 8 mL of ethyl acetate and 0.5 mL of conc. ammonia in water, filtered off. Organic layer washed with brine, dried over sodium sulfate and evaporated. The residue was purified on silica gel column using DCM:MeOH 10:1 as eluent affording 120 mg of trans-4-amino-1-benzylpiperidin-3-ol.

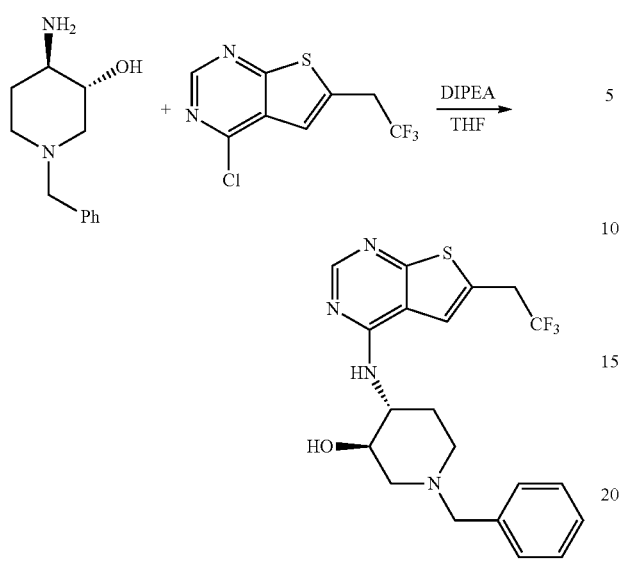

The mixture of 36.7 mg of trans-4-amino-1-benzylpiperidin-3-ol (0.18 mmol), 30 mg of 4-chloro-6-(2,2,2-trifluoroethyl)thieno[2,3-d]pyrimidine (0.12 mmol) and 46 mg of N,N-diisopropylethylamine (0.36 mmol) was refluxed in 0.75 mL of isopropanol for 18 hs. Then reaction mixture was concentrated and purified on silica gel column eluting with DCM:MeOH 20:1 to afford 45 mf of trans-1-benzyl-4-((6-(2,2,2-trifluoroethyl)thieno[2,3-d]pyrimidin-4-yl)amino)piperidin-3-ol (Compound 165). Its monohydrochloride salt was obtained by adding 1 equivalent of 1N HCl solution in diethyl ether to a solution of compound in ethanol. $^1$H NMR (600 MHz, CD$_3$OD) of HCl salt, signals are all broadened because of intramolecular H-bond: δ 8.37 (1H), 7.51-7.60 (6H), 4.43 (4H), 4.12 (1H), 3.85 (2H), 3.55 (2H), 3.21 (1H), 2.99 (1H), 2.06 (1H). $^{13}$C NMR (150 MHz, CD$_3$OD): δC 165.78, 158.45, 153.97, 132.59, 131.46, 130.51, 130.18, 127.45, 125.62, 122.09, 118.50, 68.02, 61.86, 56.88, 54.15, 52.38, 35.81 (q, J=31.5 Hz), 28.14. ESI MS [MH$^+$]: 423.1458.

Compound 167

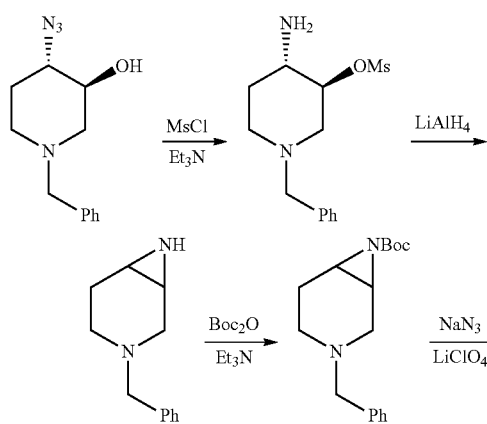

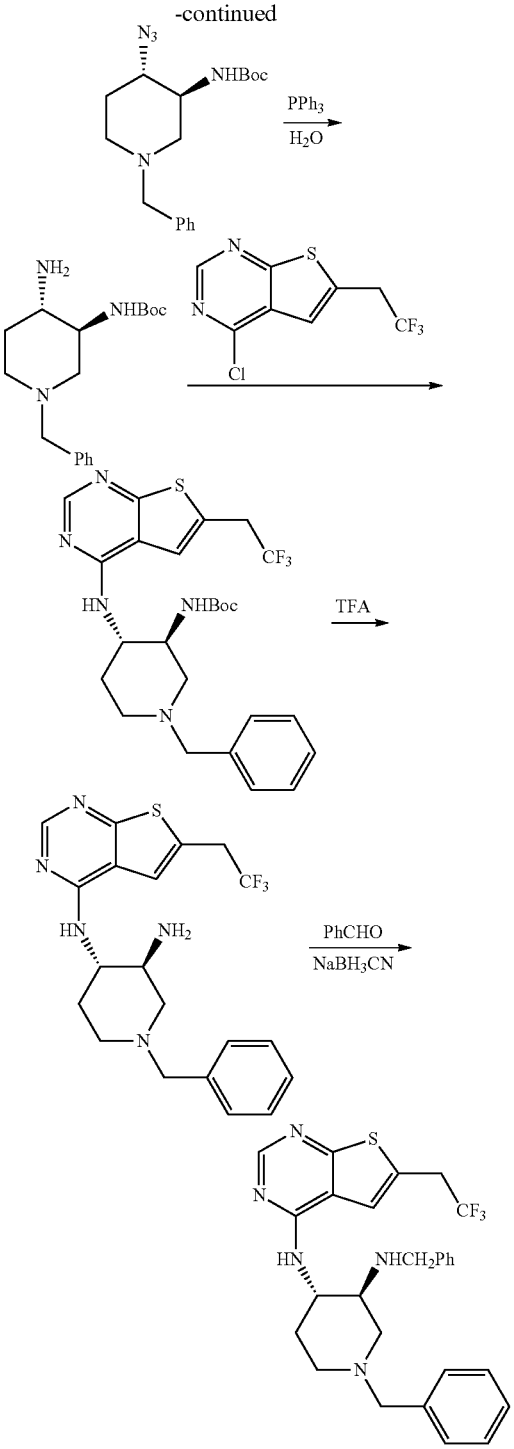

Monohydrochloride salt exists as a mixture of rotomers in approximate ratio 10:1, NMR is described for the major one: $^1$H NMR (600 MHz, CD$_3$OD): δ 8.69 (s, 1H), 7.87 (s, 1H), 7.66 (m, 2H), 7.55 (m, 3H), 7.44 (m, 2H)m 7.34 (m, 2H), 5.13 (m, 1H), 4.53 (m, 3H), 4.35 (m, 2H), 4.07 (m, 1H), 3.99 (q, 2H, J=10.3 Hz), 3.75 (m, 1H), 3.63 (m, 1H), 3.42 (m, 1H), 2.41 (m, 2H). $^{13}$C NMR (150 MHz, CD$_3$OD): δC 159.23, 158.93, 151.86, 132.75, 132.67, 132.65, 131.70, 130.59, 129.75, 129.20, 127.37, 125.54, 122.78, 119.37, 4095, 38.63, 35.33 (q, J=33 Hz), 33.39, 33.25, 33.15, 25.98, 25.97. ESI MS [MH$^+$]: 512.2095.

Example 6

Analytical Data for Selected Compounds from Subscaffold 4 and Representative Procedures for their Synthesis

Compound 175

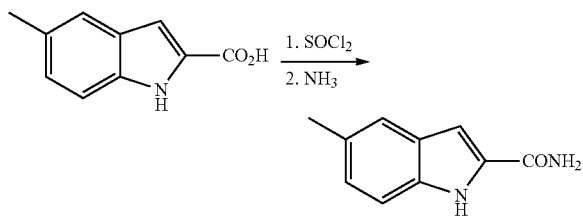

A mixture of 0.5 g of 5-methylindole-2-carboxylic acid, 0.25 mL of thionyl chloride, 5 mL of chloroform and small drop of DMF was refluxed for 2 hs. The reaction mixture was cooled to RT, poured into a mixture of 5 g of ice and 5 mL of 25% ammonia solution, and then stirred for 2 hs. The precipitated product was filtered off, washed with water and dried to yield 350 mg of 5-methylindole-2-carboxamide. $^1$H NMR (600 MHz, DMSO-d6): δ 11.37 (s, 1H), 7.89 (br, 1H), 7.36 (s, 1H), 7.30 (d, 1H, J=8.4 Hz), 7.28 (br, 1H), 7.02 (s, 1H), 6.99, (d, 1H, J=8.4 Hz), 2.36 (s, 3H). $^{13}$C NMR (150 MHz, CDCl3): δC 160.95, 132.95, 129.77, 126.15, 125.44, 123.10, 118.77, 110.02, 100.65, 19.20.

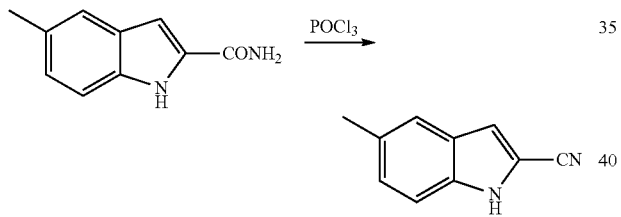

A mixture of 340 mg of 5-methylindole-2-carboxamide (1.95 mmol), 1.5 g of phosphorus oxychloride (9.75) and 8 mL of chloroform was refluxed for 2 hs. Then cooled solution was poured into 20 mL of water and stirred for 1 hr. After separation the organic layer was dried over sodium sulfate and concentrated. The residue was purified on silica gel column using hexane-ethyl acetate 5:1 to afford 245 mg of 5-methyl-1H-indole-2-carbonitrile. $^1$H NMR (600 MHz, CDCl3): δ 8.61 (br, 1H), 7.44 (s, 1H), 7.30 (d, 1H, J=8.4 Hz), 7.21 (d, 1H, J=8.4 Hz), 7.11 (s, 1H), 2.44 (s, 3H). $^{13}$C NMR (150 MHz, CDCl3): δC 135.34, 131.25, 128.28, 126.53, 121.33, 114.41, 113.95, 111.39, 106.11, 21.36.

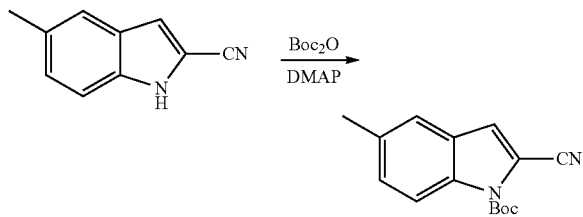

To a solution of 245 mg of 5-methyl-1H-indole-2-carbonitrile (1.6 mmol) in 5 mL of acetonitrile 0.434 mL of di-tert-butyl dicarbonate (1.9 mmol) and 29 mg of DMAP (0.24 mmol) were added and stirred at room temperature for 30 min. The solvent was removed in vacuo, and the resultant crude product was purified by column chromatography (silica gel) using pure hexane-ethyl acetate 10:1 as an eluant to afford 334 mg of tert-butyl 2-cyano-5-methyl-1H-indole-1-carboxylate. $^1$H NMR (600 MHz, CDCl3): δ 8.10 (d, 1H, J=8.8 Hz), 7.39 (s, 1H), 7.31 (d, 1H, J=8.8 Hz), 7.26 (s, 1H), 2.45 (s, 3H), 1.72, (s, 9H). $^{13}$C NMR (150 MHz, CDCl3): δC 148.22, 134.94, 133.78, 129.85, 121.61, 121.24, 115.53, 113.46, 108.76, 85.54, 28.05, 21.21.

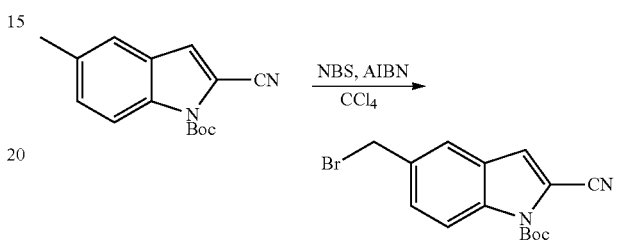

To a stirred solution of 334 mg of tert-butyl 2-cyano-5-methyl-1H-indole-1-carboxylate (1.3 mmol) in carbon tetrachloride (5 mL) was added 232 mg of N-bromosuccinimide (1.3 mmol) and 11 mg of AIBN (0.065 mmol). The mixture was refluxed for 1 h, then cooled and concentrated, and the residues were purified by chromatography on silica gel using hexane-ethyl acetate 20:1 to give 340 mg of tert-butyl 2-cyano-5-bromomethyl-1H-indole-1-carboxylate. $^1$H NMR (600 MHz, CDCl3): δ 8.22 (d, 1H, J=8.8 Hz), 7.64 (s, 1H), 7.53 (d, 1H, J=8.8 Hz), 7.31 (s, 1H), 4.60 (s, 2H), 1.73, (s, 9H). $^{13}$C NMR (150 MHz, CDCl3): δC 147.64, 136.27, 133.92, 129.34, 127.45, 122.33, 121.15, 116.46, 113.02, 109.75, 87.14, 33.23, 28.01.

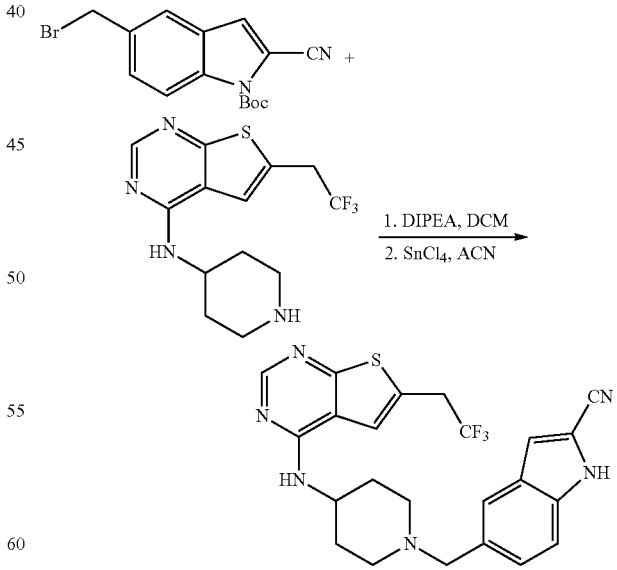

16.7 mg of tert-butyl 2-cyano-5-bromomethyl-1H-indole-1-carboxylate (0.05 mmol) and 15.8 mg of N-(piperidin-4-yl)-6-(2,2,2-trifluoroethyl)thieno[2,3-d]pyrimidin-4-amine (0.05 mmol) were dissolved in 0.6 mL of DCM. 12.9 mg of DIPEA (0.1 mmol) was added to that solution and reaction mixture was stirred for 18 hs. Then reaction mixture was directly loaded on silica gel column and the product was eluted with DCM-MeOH 30:1. After evaporation of solvent boc-protected intermediate was dissolved in 0.5 mL of ACN and 0.06 mL of SnCl₄ (0.5 mmol) was added. The homogenous reaction mixture was stirred for 1 h and then all volatiles were removed in vacuo. The residue was quenched ammonia and extracted with ethyl acetate. Combined organic fractions were dried over MgSO₄ and concentrated. The residue was purified on silica gel column using hexane-ethyl acetate-MeOH 1:1:0.1 to produce 16 mg of 5-((4-((6-(2,2,2-trifluoroethyl)thieno[2,3-d]pyrimidin-4-yl)amino)piperidin-1-yl)methyl)-1H-indole-2-carbonitrile (Compound 175). Its monohydrochloride salt was obtained by adding 1 equivalent of 1N HCl solution in diethyl ether to a solution of compound in ethanol. The hydrochloride salt was recrystallized from methanol. $^1$H NMR (600 MHz, DMSO-d6): δ 12.62 (s, 1H), 10.74 (br, 1H), 8.33 (s, 1H), 8.07 (d, 1H, J=7 Hz), 7.93, s, 1H), 7.70 (s, 1H), 7.62 (d, 1H, J=12 Hz), 7.56 (d, 1H, J=12 Hz), 7.45 (s, 1H), 4.36 (s, 1H), 4.30 (m, 1H), 4.03 (q, 2H, J=11 Hz), 3.41 (m, 2H), 3.11 (m, 2H), 2.12 (m, 2H), 1.98 (m, 2H). $^{13}$C NMR (150 MHz, DMSO-d6): δC 165.88, 155.72, 153.78, 137.18, 128.42, 126.97, 125.78, 125.37, 124.52, 122.22, 121.31, 116.12, 114.22, 113.36, 112.54, 106.84, 59.27, 50.36, 45.46, 33.73 (q, J=33 Hz), 28.23. ESI MS [MH⁺]: 471.1579.

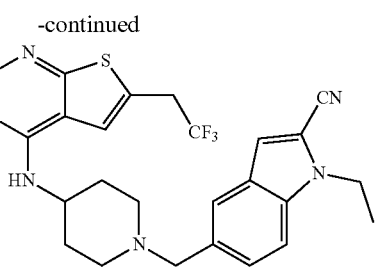

Monohydrochloride salt exists as a mixture of rotomers in approximate ratio 10:1, NMR is described for the major one:
$^1$H NMR (600 MHz, MeOD-d4): 8.68 (s, 1H), 7.94 (s, 1H), 7.82 (s, 1H), 7.69 (d, 1H, J=8.4 Hz), 7.62 (d, 1H, J=8.4 Hz), 7.35 (s, 1H), 4.63 (m, 1H), 4.48 (s, 2H), 4.45 (q, 2H, J=7.2 Hz), 3.99 (q, 2H, J=10.3 Hz), 3.63 (m, 2H), 3.26 (m, 2H), 2.34 (m, 2H), 2.14 (m, 2H), 1.45 (t, 3H, 7.2 Hz). $^{13}$C NMR (150 MHz, MeOD-d4): δC 149.93, 138.83, 132.93, 129.40, 127.94, 127.30, 127.26, 125.43, 123.06, 122.70, 118.69, 114.30, 113.86, 112.75, 112.60, 111.75, 62.02, 52.39, 48.39, 41.53, 35.22 (q, J=33 Hz), 29.53, 15.76. ESI MS [MH⁺]: 499.1891.

Compound 178

Compound 177

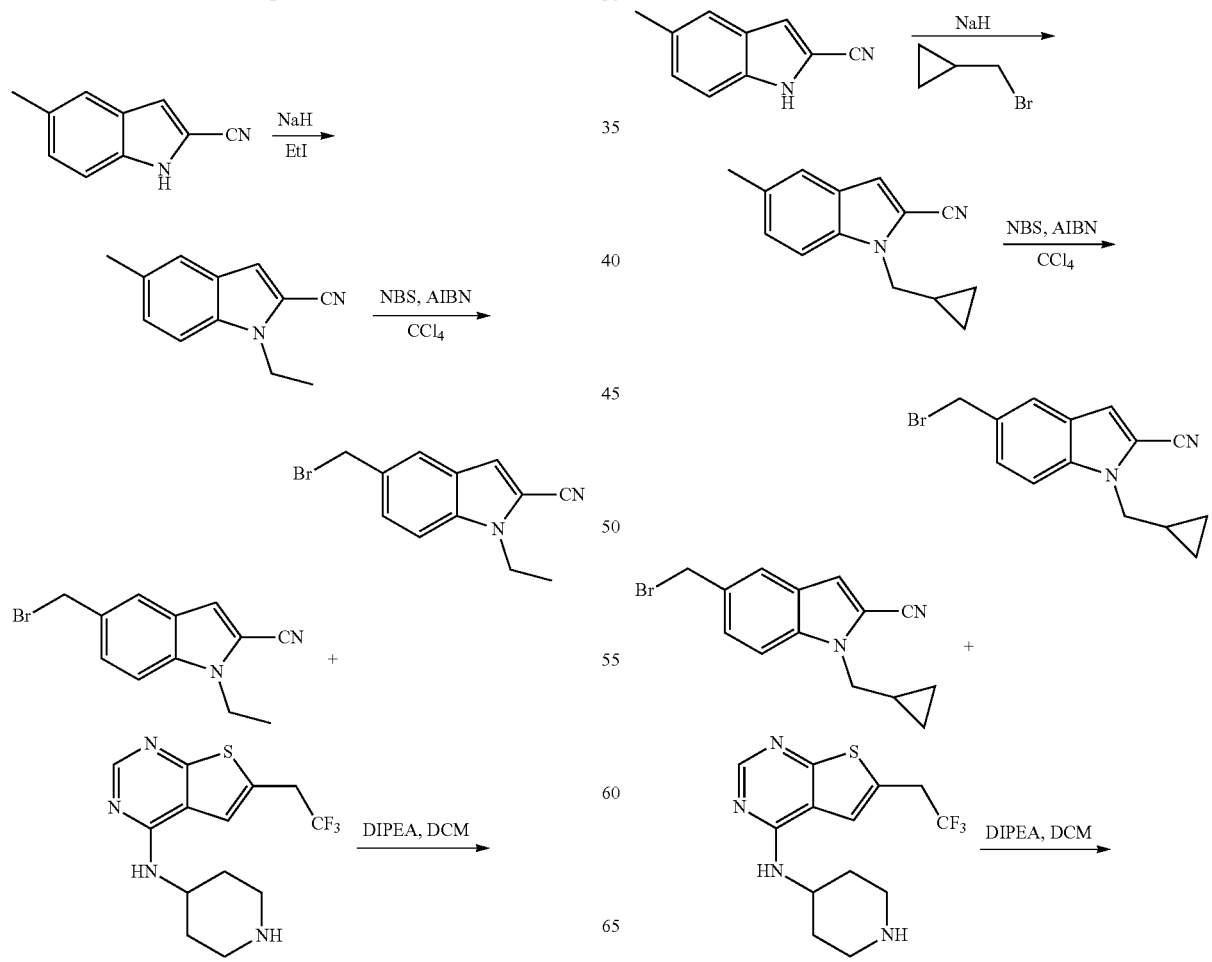

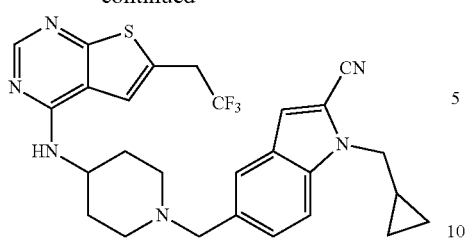
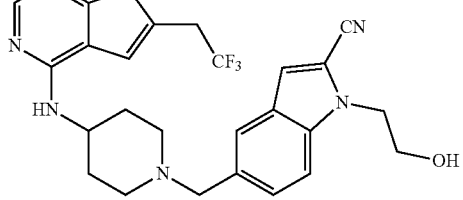

Monohydrochloride salt exists as a mixture of rotomers in approximate ratio 10:1, NMR is described for the major one: $^{1}$H NMR (600 MHz, MeOD-d4): 8.40 (s, 1H), 7.94 (s, 1H), 7.72 (d, 1H, J=8.8 Hz), 7.61 (d, 1H, J=8.8 Hz), 7.59 (s, 1H), 7.35 (s, 1H), 4.48 (m, 3H), 4.27 (m, 2H), 4.88 (q, 2H, J=10.6 Hz), 3.61 (m, 2H), 3.25 (m, 2H), 2.34 (m, 2H), 2.02 (m, 2H), 1.30 (m, 1H), 0.58 (m, 2H), 0.50 (m, 2H). $^{13}$C NMR (150 MHz, MeOD-d4): δC 164.91, 157.63, 153.86, 139.38, 130.60, 129.39, 127.91, 127.49, 127.17, 125.66, 123.22, 121.97, 118.29, 114.36, 112.89, 112.18, 61.96, 52.69, 50.85, 47.34, 35.54 (q, J=33 Hz), 29.95, 12.65, 4.38. ESI MS [MH$^{+}$]: 525.2052.

Compound 179

Monohydrochloride salt exists as a mixture of rotomers in approximate ratio 10:1, NMR is described for the major one: $^{1}$H NMR (600 MHz, MeOD-d4): 8.75 (s, 1H), 7.96 (s, 1H), 7.88 (d, 1H, J=8.8 Hz), 7.74 (d, 1H, J=8.8 Hz), 7.64 (s, 1H), 7.37 (s, 1H), 4.67 (m, 1H), 4.51 (m, 3H), 4.03 (q, 2H, J=10.6 Hz), 3.93 (m, 2H), 3.65 (m, 2H), 3.30 (m, 2H), 2.36 (m, 2H), 2.18 (m, 2H). $^{13}$C NMR (150 MHz, MeOD-d4): δC 164.91, 139.70, 133.26, 129.21, 127.95, 127.11, 127.10, 125.48, 123.11, 122.84, 122.79, 118.74, 114.21, 113.09, 112.99, 61.95, 61.79, 52.29, 49.60, 48.54, 35.12 (q, J=33 Hz), 29.45. ESI MS [MH$^{+}$]: 515.1828.

Compound 180

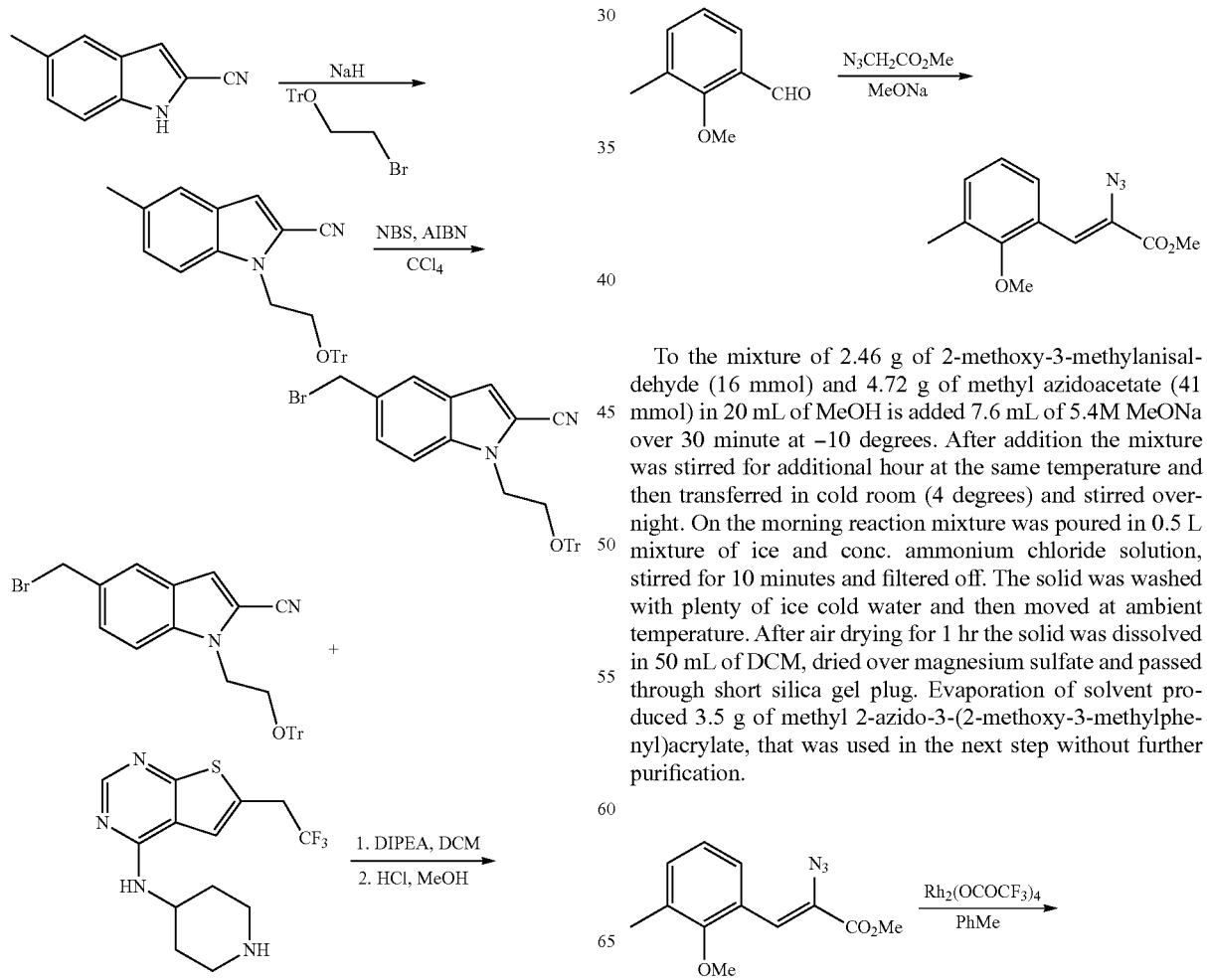

To the mixture of 2.46 g of 2-methoxy-3-methylanisaldehyde (16 mmol) and 4.72 g of methyl azidoacetate (41 mmol) in 20 mL of MeOH is added 7.6 mL of 5.4M MeONa over 30 minute at −10 degrees. After addition the mixture was stirred for additional hour at the same temperature and then transferred in cold room (4 degrees) and stirred overnight. On the morning reaction mixture was poured in 0.5 L mixture of ice and conc. ammonium chloride solution, stirred for 10 minutes and filtered off. The solid was washed with plenty of ice cold water and then moved at ambient temperature. After air drying for 1 hr the solid was dissolved in 50 mL of DCM, dried over magnesium sulfate and passed through short silica gel plug. Evaporation of solvent produced 3.5 g of methyl 2-azido-3-(2-methoxy-3-methylphenyl)acrylate, that was used in the next step without further purification.

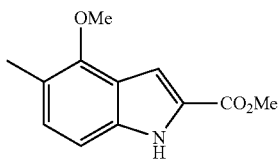

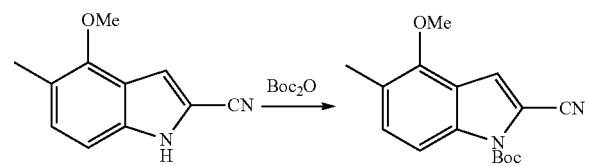 [SMILES: "Boc2O" ; COc1c(C)ccc2[nH]c(C#N)cc12 ; COc1c(C)ccc2c1cc(C#N)n2C(=O)OC(C)(C)C]

4.16 g of methyl 2-azido-3-(2-methoxy-3-methylphenyl) acrylate (16.8 mmol) was dissolved in 20 mL of toluene. 560 mg of rhodium (II) trifluoroacetate dimer (0.84 mmol) was added and the reaction mixture was heated at 50 degrees for 24 hs. Then solvent was evaporated and residue was loaded on silica gel column and eluted with hexane-ethyl acetate 10:1 to produce after evaporation 1.3 g of methyl 4-methoxy-5-methyl-1H-indole-2-carboxylate. $^1$H NMR (600 MHz, CDCl$_3$): δ 9.05 (br, 1H), 7.32 (s, 1H), 7.11 (d, 1H, J=8 Hz), 7.04 (d, 1H, J=8 Hz), 4.03 (s, 3H), 3.94 (s, 1H), 2.33 (s, 1H).

To a solution of 390 mg of 4-methoxy-5-methyl-1H-indole-2-carbonitrile (2.1 mmol) in 7 mL of acetonitrile 0.574 mL of di-tert-butyl dicarbonate (0.74 mmol) and 25 mg of DMAP (0.21 mmol) were added and stirred at room temperature for 30 min. The solvent was removed in vacuo, and the resultant crude product was purified by column chromatography (silica gel) using hexane-ethyl acetate 10:1 as an eluent to afford 561 mg of tert-butyl 2-cyano-4-methoxy-5-methyl-1H-indole-1-carboxylate.

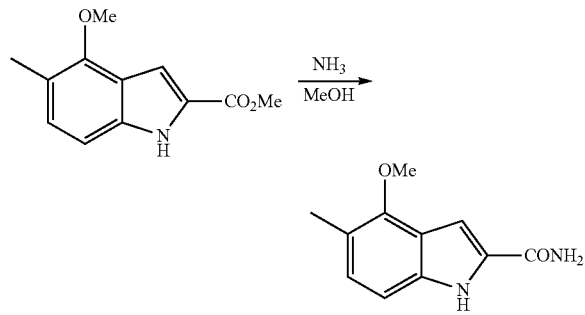

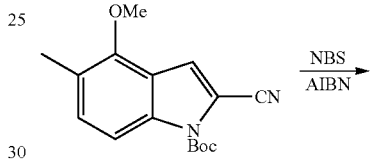

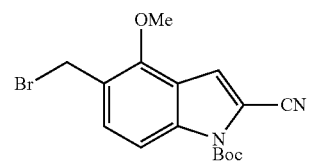

80 mg of methyl 4-methoxy-5-methyl-1H-indole-2-carboxylate (0.39 mmol) was heated at 80 degrees in a sealed tube with 1 mL of 7M ammonia in methanol. After one week reaction the solvent evaporated to produce 79 mg of 4-methoxy-5-methyl-1H-indole-2-carboxamide that was used without purification in the next step.

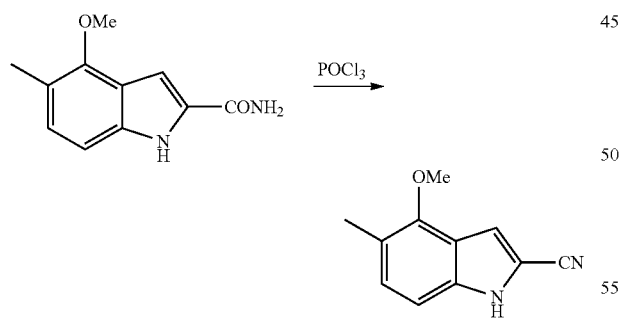

To a stirred solution of 561 mg of tert-butyl 2-cyano-4-methoxy-5-methyl-1H-indole-1-carboxylate (1.96 mmol) in carbon tetrachloride (9 mL) was added 349 mg of N-bromosuccinimide (1.96 mmol) and 64 mg of AIBN (0.39 mmol). The mixture was refluxed for 1 h, then cooled and concentrated and filtered through short silica gel plug using hexane-ethyl acetate 10:1 to give 852 mg of crude tert-butyl 5-(bromomethyl)-2-cyano-4-methoxy-1H-indole-1-carboxylate that was used in the next step without further purification.

A mixture of 79 mg of 4-methoxy-5-methyl-1H-indole-2-carboxamide (0.39 mmol), 0.19 mL of phosphorus oxychloride (2 mmol) and 1.5 mL of chloroform was refluxed for 2 hs. Then cooled solution was poured into 10 mL of water and stirred for 1 hr. After separation the organic layer was dried over sodium sulfate and concentrated. The residue was purified on silica gel column using hexane-ethyl acetate 5:1 to afford 51 mg of 4-methoxy-5-methyl-1H-indole-2-carbonitrile.

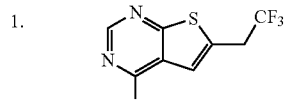

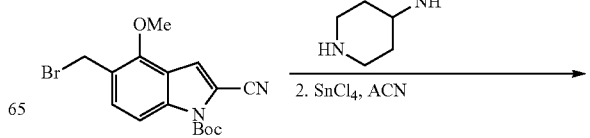

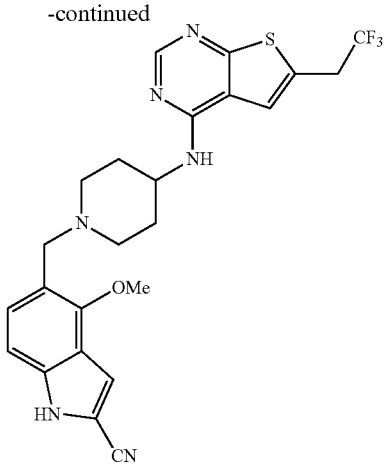

852 mg of crude tert-butyl 2-cyano-5-bromomethyl-1H-indole-1-carboxylate (1.96 mmol) and 829 mg of N-(piperidin-4-yl)-6-(2,2,2-trifluoroethyl)thieno[2,3-d]pyrimidin-4-amine (2.62 mmol) were dissolved in 5 mL of DCM. 1.3 mL of DIPEA (7.5 mmol) was added to that solution and reaction mixture was stirred for 18 hs. Then reaction mixture was directly loaded on silica gel column and the product was eluted with Hexane-Ethyl acetate-MeOH 2:1:0.1. After evaporation of solvent boc-protected intermediate was dissolved in 14 mL of ACN and 1.7 mL of SnCl$_4$ (0.5 mmol) was added. The homogenous reaction mixture was stirred for 1 h and then all volatiles were removed in vacuo. The residue was quenched ammonia and extracted with ethyl acetate. Combined organic fractions were dried over MgSO$_4$ and concentrated. The residue was purified on silica gel column using hexane-ethyl acetate-MeOH 1:1:0.2 to produce 494 mg of 4-methoxy-5-((4-((6-(2,2,2-trifluoroethyl)thieno[2,3-d]pyrimidin-4-yl)amino)piperidin-1-yl)methyl)-1H-indole-2-carbonitrile (Compound 180). Its monohydrochloride salt was obtained by adding 1 equivalent of 1N HCl solution in diethyl ether to a solution of compound in ethanol. Monohydrochloride salt exists as a mixture of rotomers in approximate ratio 10:1, NMR is described for the major one: $^1$H NMR (600 MHz, MeOD-d4): δ 8.71 (s, 1H), 7.85 (s, 1H), 7.60 (s, 1H), 7.45 (d, 1H, J=8 Hz), 7.23 (d, 1H, J=8 Hz), 4.63 (m, 1H), 4.46 (s, 2H), 4.29 (s, 3H), 4.01 (q, 2H, J=10.5 Hz), 3.64 (m, 2H), 3.29 (m, 2H), 2.33 (m, 2H), 2.13 (m, 2H). $^{13}$C NMR (150 MHz, MeOD-d4): δC 155.08, 149.56, 142.48, 133.14, 130.79, 130.44, 127.31, 123.36, 122.79, 118.72, 118.60, 114.63, 113.09, 110.78, 107.95, 108.25, 61.21, 56.92, 52.45, 35.11 (q, J=33 Hz), 29.50. ESI MS [MH$^+$]: 501.1684.

Compounds 181 and 182

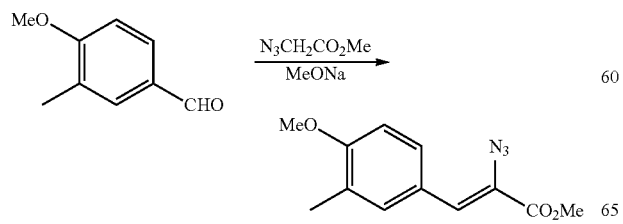

To the mixture of 6.59 g of 3-methylanisaldehyde (44 mmol) and 12.65 g of methyl azidoacetate (110 mmol) in 60 mL of MeOH is added 20 mL of 5.4M MeONa over 30 minute at −10 degrees. After addition the mixture was stirred for additional hour at the same temperature and then transferred in cold room (4 degrees) and stirred overnight. On the morning reaction mixture was poured in 1 L mixture of ice and conc. ammonium chloride solution, stirred for 10 minutes and filtered off. The solid was washed with plenty of ice cold water and then moved at ambient temperature. After air drying for 1 hr the solid was dissolved in 50 mL of DCM, dried over magnesium sulfate and passed through short silica gel plug. Evaporation of solvent produced 9.8 g of methyl 2-azido-3-(4-methoxy-3-methylphenyl)acrylate, that was used in the next step without further purification.

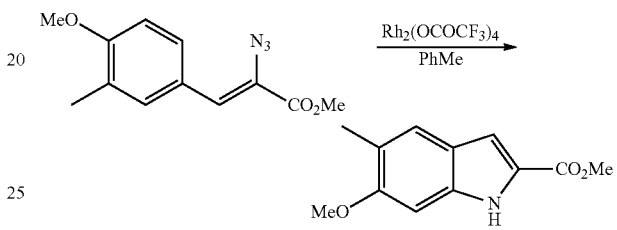

250 mg of 2-azido-3-(4-methoxy-3-methylphenyl)acrylate (1 mmol) was dissolved in 1 mL of toluene. 30 mg of rhodium (II) trifluoroacetate dimer (0.045 mmol) was added and the reaction mixture was heated at 50 degrees for 24 hs. Then solvent was evaporated and residue was loaded on silica gel column and eluted with hexane-ethyl acetate 10:1 to produce after evaporation 125 mg of methyl 6-methoxy-5-methyl-1H-indole-2-carboxylate. $^1$H NMR (600 MHz, CDCl$_3$): δ 8.73 (br, 1H), 7.39 (s, 1H), 7.10 (s, 1H), 6.77 (s, 1H), 3.92 (s, 3H), 3.88 (s, 1H), 2.28 (s, 1H).

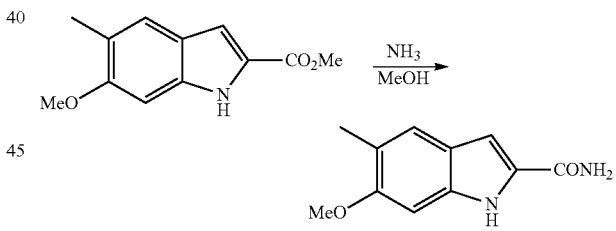

200 mg of methyl 6-methoxy-5-methyl-1H-indole-2-carboxylate (1 mmol) was heated at 80 degrees in a sealed tube with 2 mL of 7M ammonia in methanol. After one week reaction the solvent evaporated to produce 202 mg of 6-methoxy-5-methyl-1H-indole-2-carboxamide that was used without purification in the next step.

A mixture of 202 mg of 6-methoxy-5-methyl-1H-indole-2-carboxamide (1 mmol), 0.47 mL of phosphorus oxychloride (5 mmol) and 3 mL of chloroform was refluxed for 2 hs. Then cooled solution was poured into 10 mL of water and stirred for 1 hr. After separation the organic layer was dried over sodium sulfate and concentrated. The residue was purified on silica gel column using hexane-ethyl acetate 5:1 to afford 116 mg of 6-methoxy-5-methyl-1H-indole-2-carbonitrile. $^1$H NMR (600 MHz, CDCl$_3$): δ 8.26 (br, 1H), 7.37 (s, 1H), 7.06 (s, 1H), 6.76 (s, 1H), 3.88 (s, 1H), 2.28 (s, 3H).

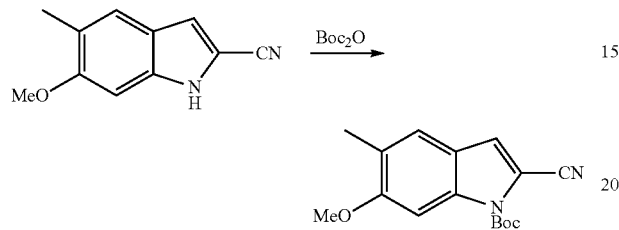

To a solution of 116 mg of 6-methoxy-5-methyl-1H-indole-2-carbonitrile (0.62 mmol) in 2 mL of acetonitrile 0.171 mL of di-tert-butyl dicarbonate (0.74 mmol) and 20 mg of DMAP (0.24 mmol) were added and stirred at room temperature for 30 min. The solvent was removed in vacuo, and the resultant crude product was purified by column chromatography (silica gel) using hexane-ethyl acetate 10:1 as an eluent to afford 174 mg of tert-butyl 2-cyano-6-methoxy-5-methyl-1H-indole-1-carboxylate.

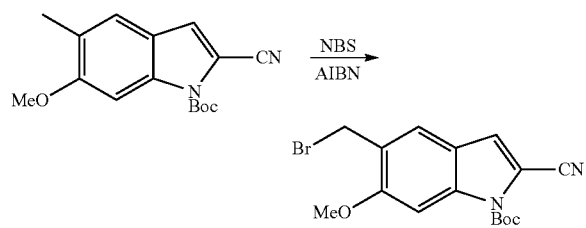

To a stirred solution of 174 mg of tert-butyl 2-cyano-6-methoxy-5-methyl-1H-indole-1-carboxylate (0.61 mmol) in carbon tetrachloride (2.5 mL) was added 108 mg of N-bromosuccinimide (0.61 mmol) and 11 mg of AIBN (0.065 mmol). The mixture was refluxed for 1 h, then cooled and concentrated and filtered through short silica gel plug using hexane-ethyl acetate 10:1 to give 223 mg of crude tert-butyl 5-(bromomethyl)-2-cyano-6-methoxy-1H-indole-1-carboxylate that was used in the next step without further purification.

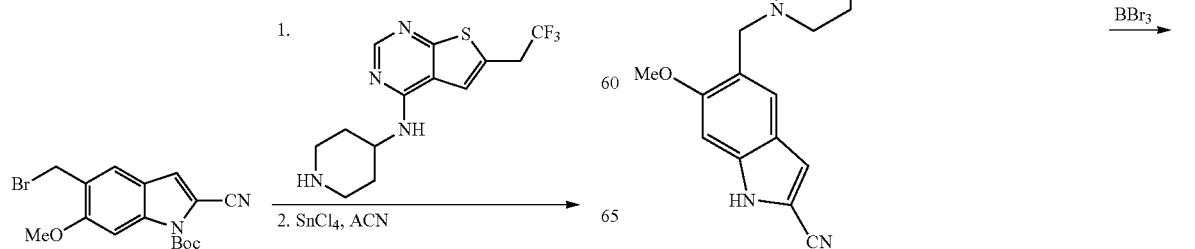

223 mg of tert-butyl 2-cyano-5-bromomethyl-1H-indole-1-carboxylate (0.61 mmol) and 193 mg of N-(piperidin-4-yl)-6-(2,2,2-trifluoroethyl)thieno[2,3-d]pyrimidin-4-amine (0.61 mmol) were dissolved in 2 mL of DCM. 0.22 mL of DIPEA (0.2 mmol) was added to that solution and reaction mixture was stirred for 18 hs. Then reaction mixture was directly loaded on silica gel column and the product was eluted with DCM-MeOH 30:1. After evaporation of solvent boc-protected intermediate was dissolved in 0.5 mL of ACN and 0.06 mL of SnCl$_4$ (0.5 mmol) was added. The homogenous reaction mixture was stirred for 1 h and then all volatiles were removed in vacuo. The residue was quenched ammonia and extracted with ethyl acetate. Combined organic fractions were dried over MgSO$_4$ and concentrated. The residue was purified on silica gel column using hexane-ethyl acetate-MeOH 1:1:0.1 to produce 210 mg of 6-methoxy-5-((4-((6-(2,2,2-trifluoroethyl)thieno[2,3-d]pyrimidin-4-yl)amino)piperidin-1-yl)methyl)-1H-indole-2-carbonitrile (Compound 181). Its monohydrochloride salt was obtained by adding 1 equivalent of 1N HCl solution in diethyl ether to a solution of compound in ethanol. Monohydrochloride salt exists as a mixture of rotamers in approximate ratio 10:1, NMR is described for the major one: $^1$H NMR (600 MHz, MeOD-d4): δ 8.71 (s, 1H), 7.87 (s, 1H), 7.86 (s, 1H), 7.24 (s, 1H), 7.12 (s, 1H), 4.66 (m, 1H), 4.49 (s, 2H), 4.03 (m, 5H), 3.69 (m, 2H), 3.34 (m, 2H), 2.36 (m, 2H), 2.18 (m, 2H). $^{13}$C NMR (150 MHz, MeOD-d4): δC 158.72, 149.70, 140.86, 133.08, 128.17, 127.75, 127.31, 12, 3.36, 122.81, 121.69, 118.72, 115.07, 114.82, 114.60, 107.47, 94.60, 57.67, 56.62, 52.72, 35.22 (q, J=33 Hz), 29.53. ESI MS [MH$^+$]: 501.1675.

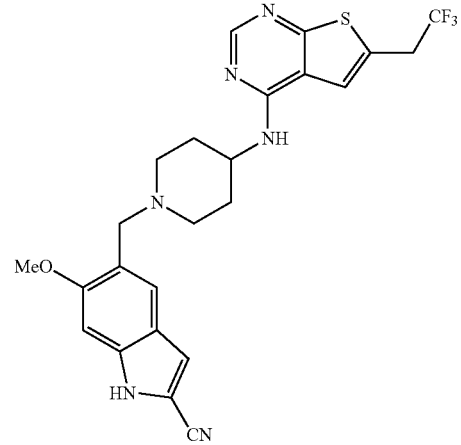

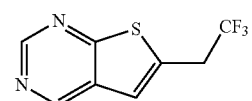

-continued

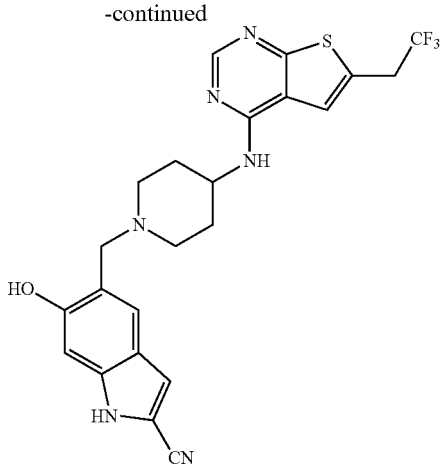

500 mg of 6-methoxy-5-((4-((6-(2,2,2-trifluoroethyl)thieno[2,3-d]pyrimidin-4-yl)amino)piperidin-1-yl)methyl)-1H-indole-2-carbonitrile (1 mmol) was slowly added to 5 mL of 1M BBr$_3$ in DCM at 0 degrees and reaction mixture was brought to RT. After 4 days ice was added to reaction mixture in the presence of sodium bicarbonate. Volatile organic was evaporated and the residue was partitioned between water and ethyl acetate-methanol 10:1. Organic layer was evaporated with silica gel and loaded on the column. The product was eluted with hexane-ethyl acetate-methanol 1:1:0.1, evaporation of fractions produced 300 mg of 6-hydroxy-5-((4-((6-(2,2,2-trifluoroethyl)thieno[2,3-d]pyrimidin-4-yl)amino)piperidin-1-yl)methyl)-1H-indole-2-carbonitrile (Compound 182). Its monohydrochloride salt was obtained by adding 1 equivalent of 1N HCl solution in diethyl ether to a solution of compound in ethanol. Monohydrochloride salt exists as a mixture of rotomers in approximate ratio 10:1, NMR is described for the major one: $^1$H NMR (600 MHz, MeOD-d4): 8.70 (s, 1H), 7.81 (s, 1H), 7.77 (s, 1H), 7.21 (s, 1H), 6.98 (s, 1H), 4.64 (m, 1H), 4.48 (s, 1H), 4.01 (q, 2H, J=10.3 Hz), 3.66 (m, 2H), 3.35 (m, 2H), 2.37 (m, 2H), 2.12 (m, 2H). $^{13}$C NMR (150 MHz, MeOD-d4): δC 157.64, 156.62, 153.92, 141.09, 130.54, 127.75, 127.48, 125.65, 121.96, 121.59, 118.27, 115.23, 114.85, 113.98, 107.11, 97.45, 57.78, 52.88, 47.29, 35.54 (q, J=33 Hz), 29.95. ESI MS [MH$^+$]: 487.1519.

Compound 186

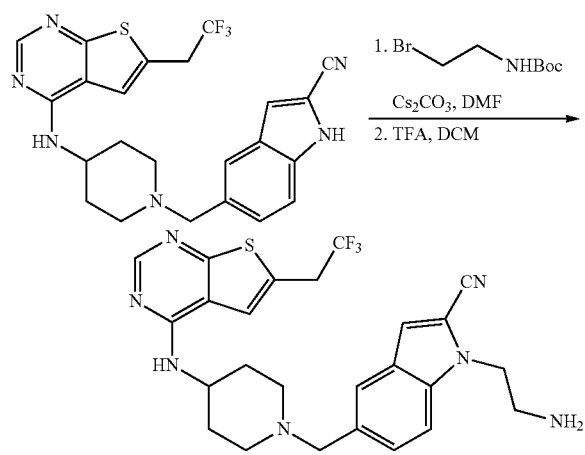

Monohydrochloride salt exists as a mixture of rotomers in approximate ratio 10:1, NMR is described for the major one: $^1$H NMR (600 MHz, MeOD-d4): 8.37 (s, 1H), 8.08 (s, 1H), 7.74 (d, 1H, J=8.8 Hz), 7.69 (s, 1H), 7.64 (d, 1H, J=8.8 Hz), 7.54 (s, 1H), 4.74 (m, 1H), 4.48 (m, 3H), 3.88 (q, 2H, J=10.6 Hz), 3.60 (m, 2H), 3.21 (m, 2H), 2.34 (m, 2H), 2.05 (m, 2H). ESI MS [MH$^+$]: 514.1998.

Compound 188

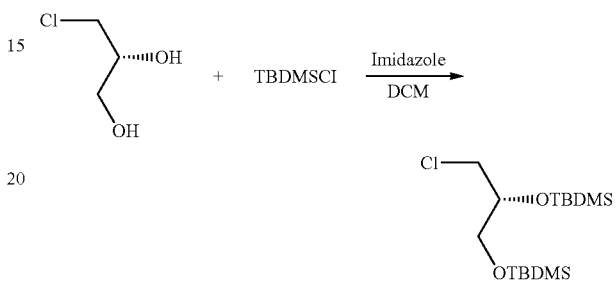

331 mg of (R)-3-chloropropane-1,2-diol (3 mmol) and 530 mg of imidazole (7.8 mmol) were dissolved in 5 mL of dry dichloromethane. Then 7.2 mL of 1M TBDMSCl in dichloromethane was added. Reaction mixture was stirred overnight and then diluted with 20 mL of water. After separation the organic layer was dried over sodium sulfate and concentrated to produce 850 mg of (R)-5-(chloromethyl)-2,2,3,3,8,8,9,9-octamethyl-4,7-dioxa-3,8-disiladecane. The material was used as is in the next step.

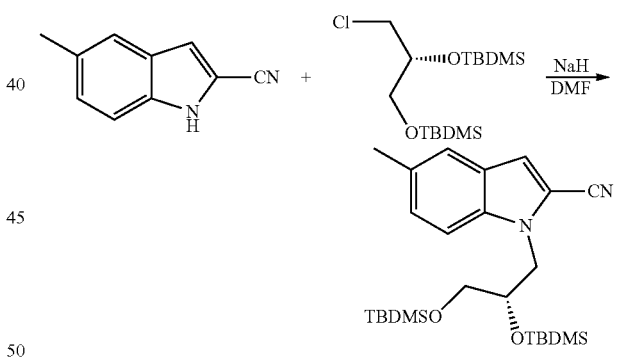

To a solution of 39 mg of 5-methyl-1H-indole-2-carbonitrile (0.25 mmol) in 0.5 mL of DMF 15 mg of NaH (60% in oil, 0.375 mmol) was added and mixture was stirred for 30 min. Then 170 mg of (R)-5-(chloromethyl)-2,2,3,3,8,8,9,9-octamethyl-4,7-dioxa-3,8-disiladecane (0.5 mmol) was added and stirring continued for 24 hs. The reaction mixture was diluted with 10 mL of water and extracted with DCM. Combined organic extracts dried over sodium sulfate, concentrated and purified using silica gel column eluting with hexane-ethyl acetate 50:1 to afford 56 mg of (S)-1-(2,3-bis((tert-butyldimethylsilyl)oxy)propyl)-5-methyl-1H-indole-2-carbonitrile. $^1$H NMR (600 MHz, CDCl3): δ 8.09 (d, 1H, J=8.8 Hz), 7.35 (s, 1H), 7.24 (d, 1H, J=8.8 Hz), 7.18 (s, 1H), 4.04 (m, 1H), 3.82 (m, 1H), 3.77 (m, 2H), 3.68 (m, 1H), 2.43 (s, 3H), 1.08 (m, 18H), 0.26 (m, 12H).

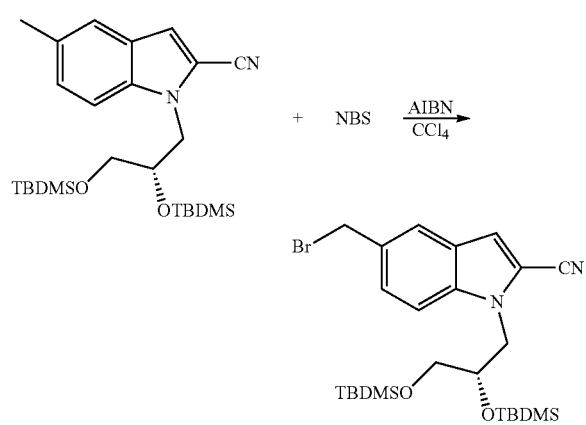

To a stirred solution of 55 mg of (S)-1-(2,3-bis((tert-butyldimethylsilyl)oxy)propyl)-5-methyl-1H-indole-2-carbonitrile (0.12 mmol) in carbon tetrachloride (0.5 mL) was added 21.3 mg of N-bromosuccinimide (0.12 mmol) and 1.1 mg of AIBN (0.0065 mmol). The mixture was refluxed for 1 h, then cooled, concentrated and filtered through short silica gel plug using hexane-ethyl acetate 10:1 to give 58 mg of crude (S)-1-(2,3-bis((tert-butyldimethylsilyl)oxy)propyl)-5-(bromomethyl)-1H-indole-2-carbonitrile that was used in the next step without further purification.

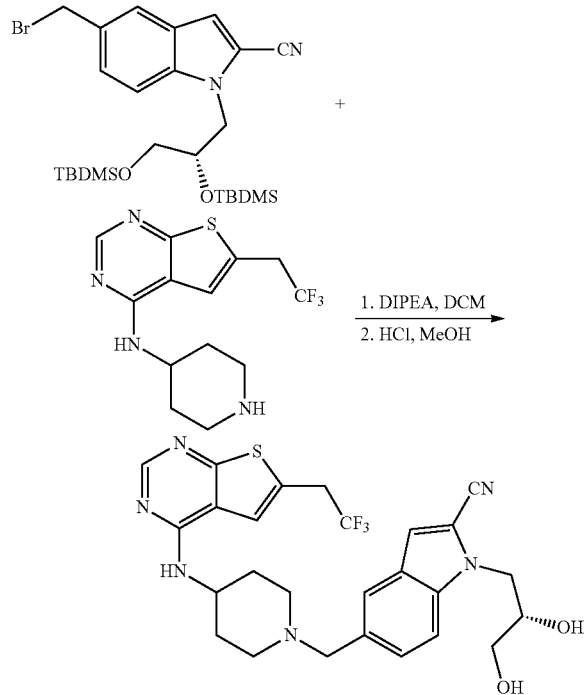

58 mg of (S)-1-(2,3-bis((tert-butyldimethylsilyl)oxy)propyl)-5-(bromomethyl)-1H-indole-2-carbonitrile (0.1 mmol) and 31 mg of N-(piperidin-4-yl)-6-(2,2,2-trifluoroethyl)thieno[2,3-d]pyrimidin-4-amine (0.12 mmol) were dissolved in 0.2 mL of DCM. 26 mg of DIPEA (0.2 mmol) was added to that solution and reaction mixture was stirred for 18 hs. Then reaction mixture was directly loaded on silica gel column and the product was eluted with DCM-MeOH 30:1. After evaporation of solvent TBDMS-protected intermediate was dissolved in 0.2 mL of MeOH and 0.02 mL of 12M HCl was added. The homogenous reaction mixture was stirred overnight and then all volatiles were removed in vacuo. The residue was quenched ammonia and extracted with ethyl acetate. Combined organic fractions were dried over MgSO$_4$ and concentrated. The residue was purified on silica gel column using DCM-MeOH 20:1 to afford 15.9 mg of 5-((4-((6-(2,2,2-trifluoroethyl)thieno[2,3-d]pyrimidin-4-yl)amino)piperidin-1-yl)methyl)-1H-indole-2-carbonitrile (Compound 188). Its monohydrochloride salt was obtained by adding 1 equivalent of 1N HCl solution in diethyl ether to a solution of compound in ethanol. Monohydrochloride salt exists as a mixture of rotomers in approximate ratio 10:1, NMR is described for the major one: $^1$H NMR (600 MHz, MeOD-d4): 8.63 (s, 1H), 7.95 (s, 1H), 7.78 (s, 1H), 7.77 (d, 1H, J=8.6 Hz), 7.63 (d, 1H, J=8.6 Hz), 7.37 (s, 1H), 4.57 (m, 1H), 4.56 (m, 1H), 4.50 (s, 2H) 4.37 (m, 1H), 4.04 (m, 1H), 3.99 (q, 2H, J=10.3 Hz), 3.65 (m, 2H), 3.60 (d, 2H, J=5.5 Hz), 3.29 (m, 2H), 2.37 (m, 2H), 2.12 (m, 2H). $^{13}$C NMR (150 MHz, MeOD-d4): δC 157.45, 150.99, 139.90, 132.27, 129.16 127.89, 127.37, 127.00, 125.54, 123.11, 122.50, 118.58, 114.32, 114.25, 113.35, 113.31, 72.35, 64.85, 61.99, 52.44, 49.82, 48.12, 35.32 (q, J=33 Hz), 29.64. ESI MS [MH$^+$]: 545.1941.

Compound 189

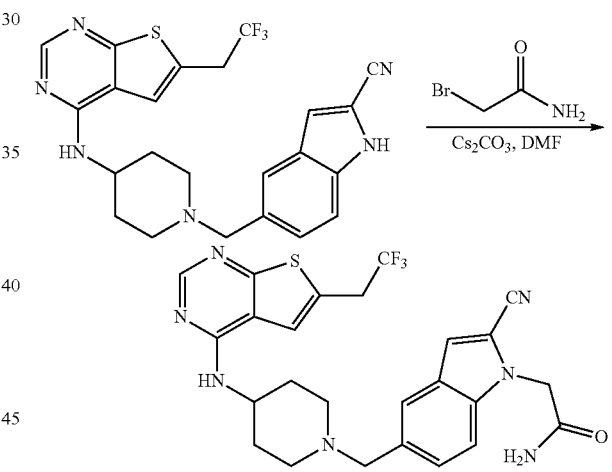

760 mg of 5-((4-((6-(2,2,2-trifluoroethyl)thieno[2,3-d]pyrimidin-4-yl)amino)piperidin-1-yl)methyl)-1H-indole-2-carbonitrile hydrochloride (1.5 mmol) and 207 mg of bromoacetamide (1.5 mmol) were dissolved in 3.6 mL of dry DMF. 1.96 g of cesium carbonate (6 mmol) was added and reaction mixture was stirred for 4 hs. Then it was quenched with 50 mL of water and extracted with DCM-MeOH 10:1. Combined organic extracts were evaporated with silica gel and loaded on column. The product was eluted with DCM-MeOH 10:1 mixture. After evaporation of product containing fractions it was recrystallized from MeOH to produce 319 mg of 2-(2-cyano-5-((4-((6-(2,2,2-trifluoroethyl)thieno[2,3-d]pyrimidin-4-yl)amino)piperidin-1-yl)methyl)-1H-indol-1-yl)acetamide, which was converted to hydrochloride salt by dissolving in 5 mL of MeOH, adding of 1 eq of 1M HCl in water. Hydrochloride salt can be recrystallized further from MeOH. Monohydrochloride salt exists as a mixture of rotomers in approximate ratio 10:1, NMR is described for the major one: $^1$H NMR (600 MHz, MeOD-d4): 8.44 (s, 1H), 7.91 (s, 1H), 7.57 (m, 2H), 7.41 (s, 1H), 5.10 (s, 2H), 4.53 (m, 1H), 4.47 (s, 1H), 3.89 (q, 2H, J=10.3 Hz), 3.62 (m, 2H), 3.24 (m, 2H), 2.35 (m, 2H), 1.93 (m, 2H). $^{13}$C NMR (150 MHz, MeOD-d4): δC 171.07, 157.66, 153.62, 140.17, 130.77, 129.55, 127.95, 127.10, 125.64, 123.46, 121.90, 118.31, 114.76, 113.69, 113.52, 112.60, 61.96, 52.67, 49.60, 47.98, 47.40, 35.52 (q, J=33 Hz), 29.96. ESI MS [MH$^+$]: 528.1783.

Compound 206

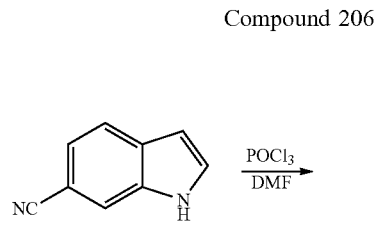

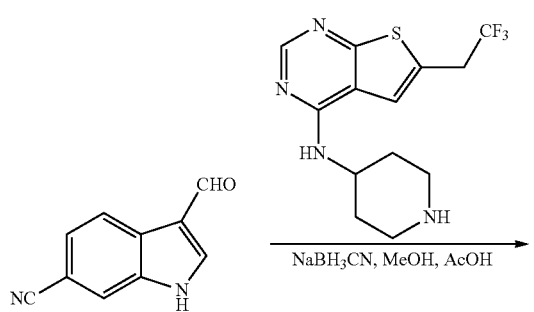

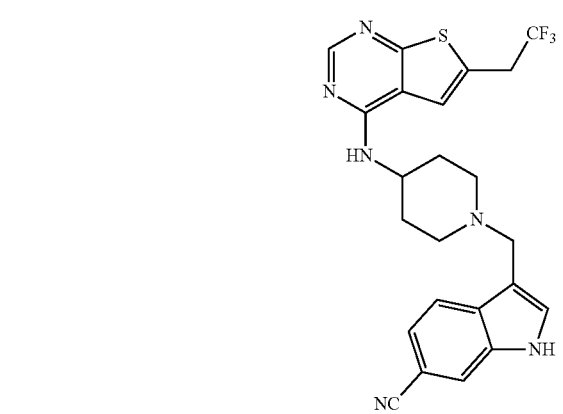

Monohydrochloride salt exists as a mixture of rotamers in approximate ratio 10:1, NMR is described for the major one: $^1$H NMR (600 MHz, MeOD-d4): 8.56 (s, 1H), 7.94 (d, 1H, J=8.4 Hz), 7.89 (m, 2H), 7.70, (s, 1H), 7.46 (d, 1H, J=8.4 Hz), 4.60 (s, 2H), 4.54 (m, 1H), 3.93 (q, 2H, J=10.6 Hz), 3.67 (m, 2H), 3.28 (m, 2H), 2.35 (m, 2H), 2.04 (m, 2H). $^{13}$C NMR (150 MHz, MeOD-d4): δC 157.52, 151.57, 136.80, 134.03, 131.92, 127.24, 125.41, 124.16, 124.12, 122.23, 121.02, 120.49, 118.48, 118.12, 105.91, 104.66, 52.19, 52.06, 47.81, 35.43 (q, J=33 Hz), 29.73. ESI MS [MH$^+$]: 471.1576.

Example 7

Representative Procedure for the Synthesis of Compounds from Subscaffold 5

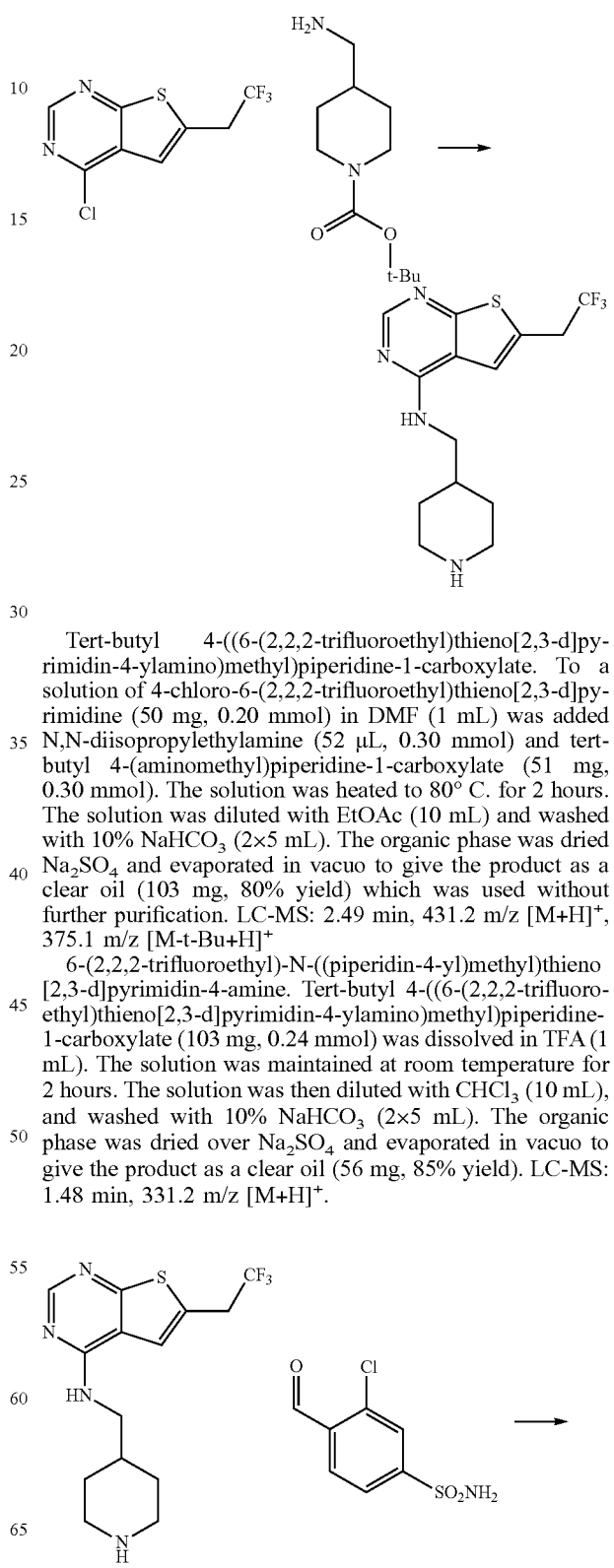

Tert-butyl 4-((6-(2,2,2-trifluoroethyl)thieno[2,3-d]pyrimidin-4-ylamino)methyl)piperidine-1-carboxylate. To a solution of 4-chloro-6-(2,2,2-trifluoroethyl)thieno[2,3-d]pyrimidine (50 mg, 0.20 mmol) in DMF (1 mL) was added N,N-diisopropylethylamine (52 µL, 0.30 mmol) and tert-butyl 4-(aminomethyl)piperidine-1-carboxylate (51 mg, 0.30 mmol). The solution was heated to 80° C. for 2 hours. The solution was diluted with EtOAc (10 mL) and washed with 10% NaHCO$_3$ (2×5 mL). The organic phase was dried Na$_2$SO$_4$ and evaporated in vacuo to give the product as a clear oil (103 mg, 80% yield) which was used without further purification. LC-MS: 2.49 min, 431.2 m/z [M+H]$^+$, 375.1 m/z [M-t-Bu+H]$^+$ 6-(2,2,2-trifluoroethyl)-N-((piperidin-4-yl)methyl)thieno[2,3-d]pyrimidin-4-amine. Tert-butyl 4-((6-(2,2,2-trifluoroethyl)thieno[2,3-d]pyrimidin-4-ylamino)methyl)piperidine-1-carboxylate (103 mg, 0.24 mmol) was dissolved in TFA (1 mL). The solution was maintained at room temperature for 2 hours. The solution was then diluted with CHCl$_3$ (10 mL), and washed with 10% NaHCO$_3$ (2×5 mL). The organic phase was dried over Na$_2$SO$_4$ and evaporated in vacuo to give the product as a clear oil (56 mg, 85% yield). LC-MS: 1.48 min, 331.2 m/z [M+H]$^+$.

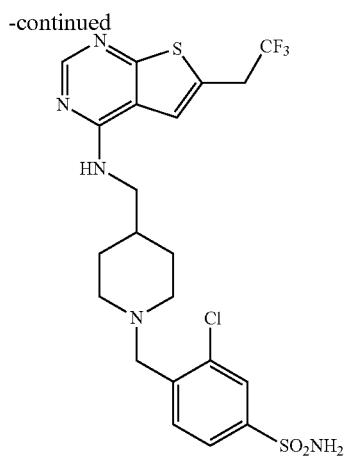

To a vial containing 6-(2,2,2-trifluoroethyl)-N-((piperidin-4-yl)methyl)thieno[2,3-d]pyrimidin-4-amine (20 mg, 0.061 mmol) was added 1,2-dichloroethane (300 uL), 3-chloro-4-formylbenzene-1-sulfonamide (17 mg, 0.077 mmol), and sodium tri(acetoxy)borohydride (20 mg, 0.094 mmol). The mixture was stirred at room temperature for 4 hours. The mixture was diluted with EtOAc (5 mL), and washed with 0.1 N NaOH (2×1 mL). The volatiles were removed in vacuo. The resulting residue was purified by reversed-phase preparative HPLC (95:5-5:95 MeCN/H$_2$O with 0.1% TFA buffer). The product containing fractions were evaporated in vacuo to afford the product as a white solid (2.7 mg, 8.4% yield), Compound 253. LC-MS: 1.20 min, 534.1 m/z [M+H]$^+$ Example 8

Representative Procedure for the Synthesis of Compounds from Subscaffold 3 and 4

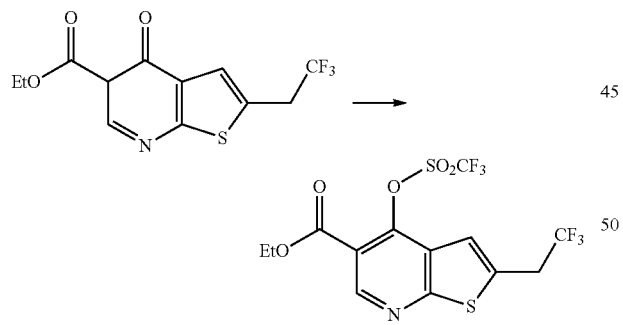

5-(ethoxycarbonyl)-2-(2,2,2-trifluoroethyl)thieno[2,3-b]pyridin-4-yl trifluoromethanesulfonate. Ethyl 2-(2,2,2-trifluoroethyl)-4,5-dihydro-4-oxothieno[2,3-b]pyridine-5-carboxylate (91 mg, 0.30 mmol) (synthesized using similar procedure described in literature procedure *J Het. Chem.* 1991, 28(8), 1953-5) was dissolved in dichloromethane (5 mL). N,N-diisopropylethylamine (157 uL, 0.90 mmol) was added. Solid N-phenyl-bis(trifluoromethanesulfonamide) (214 mg, 0.60 mmol) was added, and the mixture stirred for 10 minutes. The solution was washed with water (5 mL), dried over Na$_2$SO$_4$, and concentrated in vacuo to give an orange residue. Purification of the residue by silica gel chromatography (98:2 hexanes/EtOAc) afforded the product as a yellow solid (108 mg, 82% yield). LC-MS 3.22 min 438.2 m/z [M+H]$^+$

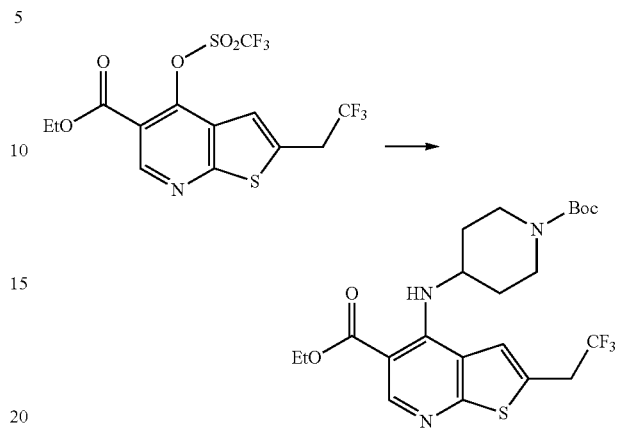

Ethyl 4-(1-(tert-butoxycarbonyl)piperidin-4-ylamino)-2-(2,2,2-trifluoroethyl)thieno[2,3-b]pyridine-5-carboxylate.
To a solution of 5-(ethoxycarbonyl)-2-(2,2,2-trifluoroethyl)thieno[2,3-b]pyridin-4-yl trifluoromethanesulfonate (108 mg, 0.25 mmol) in THF (2.5 mL) was added N,N-diisopropylethylamine (69 uL, 0.40 mmol) and tert-butyl 4-aminopiperidine-1-carboxylate (55 mg, 0.27 mmol). The solution was heated to 60° C. for 2 hours. The volatiles were removed in vacuo. The residue was dissolved in EtOAc (10 mL), washed subsequently with 0.1 N NaHSO$_4$ (2×5 mL) and saturated aq. NaHCO$_3$ (1×5 mL). The organic phase was dried over Na$_2$SO$_4$ and evaporated in vacuo to give the product as a white foam (122 mg), which was used without further purification. LC-MS: 2.73 min, 488.2 m/z [M+H]$^+$, 432.1 m/z [M-t-Bu+H]$^+$

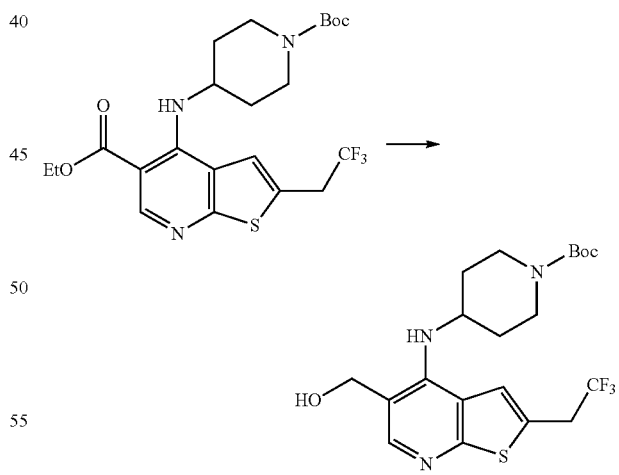

Tert-butyl 4-(2-(2,2,2-trifluoroethyl)-5-(hydroxymethyl)thieno[2,3-b]pyridin-4-ylamino)piperidine-1-carboxylate.
Ethyl 4-(1-(tert-butoxycarbonyl)piperidin-4-ylamino)-2-(2,2,2-trifluoroethyl)thieno[2,3-b]pyridine-5-carboxylate (122 mg, 0.25 mmol) was dissolved in THF (2.0 mL). Lithium borohydride (0.5 mL, 2.0 M solution in THF, 1.0 mmol) was added. The solution was heated to reflux under nitrogen for 1 hour. After cooling to room temperature, water (1 mL) was carefully added to the mixture. The mixture was concentrated in vacuo. Methanol (10 mL) was added and the solution concentrated to dryness on a rotary evaporator. The addition of methanol and evaporation was repeated three additional times. Purification of the resultant residue by silica gel chromatography (10:1 to 1:1 gradient of hexanes/ EtOAc) afforded the product as a yellow solid (45 mg, 40% yield). LC-MS: 2.35 min, 446.3 m/z [M+H]⁺, 390.3 m/z [M-t-Bu+H]⁺

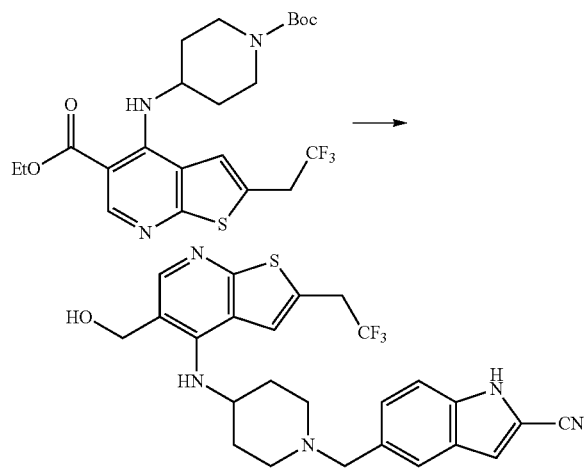

Ethyl 4-(1-(tert-butoxycarbonyl)piperidin-4-ylamino)-2-(2,2,2-trifluoroethyl)thieno[2,3-b]pyridine-5-carboxylate (45 mg, 0.1 mmol) was dissolved in CH₂Cl₂ (3 mL). Trifluoroacetic acid (2 mL) was added to the solution. After 2 hours, the solution was concentrated in vacuo. The residue was dissolved in CH₂Cl₂ (10 mL), and washed with a 10% solution of K₂CO₃ (2×1 mL), and dried over anhydrous K₂CO₃. The organic phase was concentrated to give tan residue, which was used in the next step without further purification. This residue was dissolved in 1,2-dichloroethane (1 mL). 5-formyl-1H-indole-2-carbonitrile (23 mg, 0.14 mmol) and sodium tri(acetoxy)borohydride (32 mg, 0.15 mmol) were added. The mixture was stirred at room temperature for 2 hours. The solution was diluted with EtOAc (10 mL) and washed with 0.1 N NaOH (1×5 mL). The organic phase was dried over Na₂SO₄ and concentrated in vacuo. The resulting residue was purified by reversed-phase preparative HPLC (95:5-5:95 MeCN/H₂O with 0.1% HCl buffer). The product containing fractions were lyophilized to afford the product as a white solid (1.4 mg, 2.5% yield), Compound 278. LC-MS: 1.45 min, 500.2 m/z [M+H]⁺.

Example 9

Fluorescence Polarization (FP) Assay

Fluorescence Polarization Assay.

Assays effective in monitoring the inhibition of the MLL binding to menin were developed during experiments performed during the development of embodiments of the present invention. A fluorescein-labeled 12-amino acid peptide derived from MLL containing the high affinity menin binding motif was produced (Yokoyama et al., Cell., 2005.123(2): p. 207-18., herein incorporated by reference in its entirety). Upon binding of the peptide (1.7 kDa) to the much larger menin (~67 kDa), the rotational correlation time of the fluorophore (peptide labeled with fluorescein at N-terminus) changes significantly, resulting in a substantial increase in the measured fluorescence polarization and fluorescence anisotropy (excitation at 500 nm, emission at 525 nm). The fluorescence polarization (FP) assay was utilized to determine the $K_d$ for the binding of menin and the MLL peptide using a serial dilution of menin and 50 nM fluorescein-labeled MLL peptide. The titration curve demonstrates nanomolar affinity ($K_d$=56 nM) for the menin-MLL interaction.

The effectiveness of compounds ($IC_{50}$ values) in inhibiting the menin-MLL interaction was determined in the FP competition experiments. Compounds that inhibit the interaction decrease the fluorescence anisotropy which is being used as a read-out for compound screening and for $IC_{50}$ determination. For validation of the FP assay, a control competition experiment with unlabeled MLL peptide (no fluorescein attached) was performed. The competitive displacement of the fluorescein-labeled MLL peptide from menin by unlabeled MLL peptide was monitored. Using this assay, the $IC_{50}$ value for the MLL peptide with menin: $IC_{50}$=0.23 μM. In some embodiments of the present invention, the same competition FP assay is used for screening compounds targeting menin and inhibiting the menin-MLL interaction.

Figure 2:
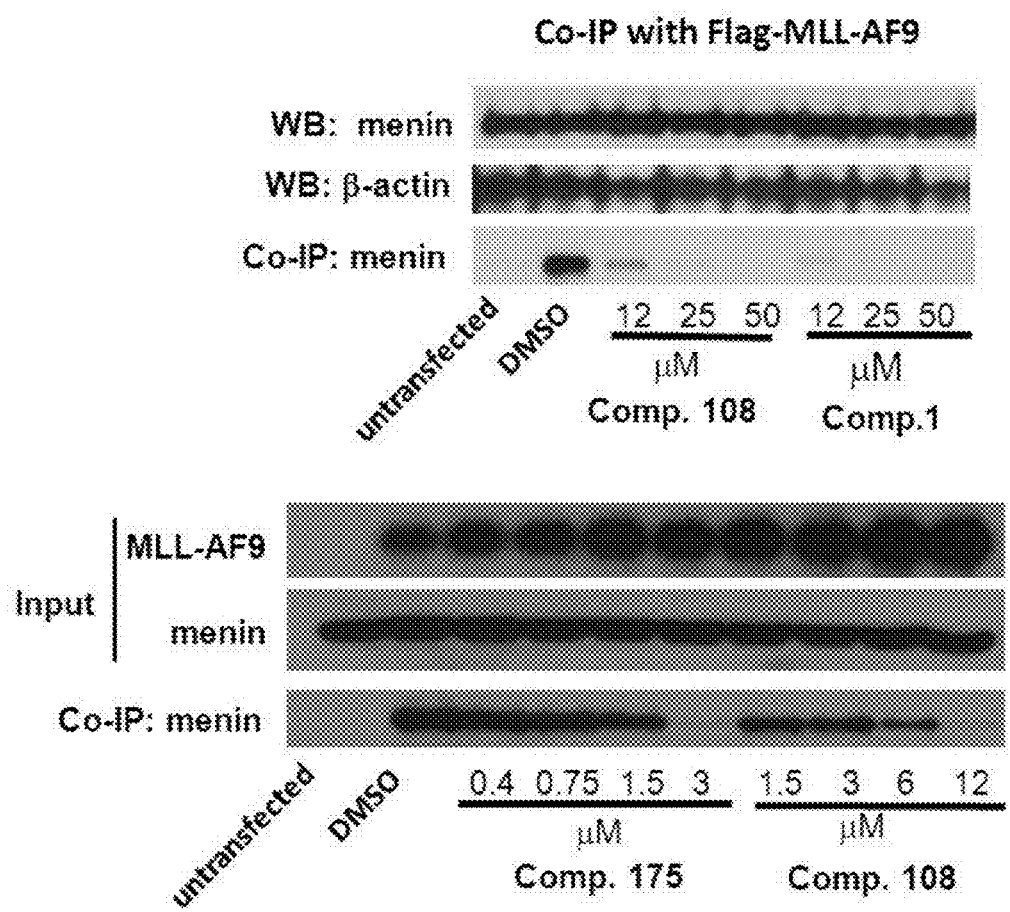
FIG. 2. Co-Immunoprecipitation (co-IP) experiment performed in HEK293 cells transfected with MLL-AF9 demonstrating inhibition of the menin-MLL-AF9 interaction in human cells by thienopyrimidine compounds: 1, 108, 175.
Figure 3:
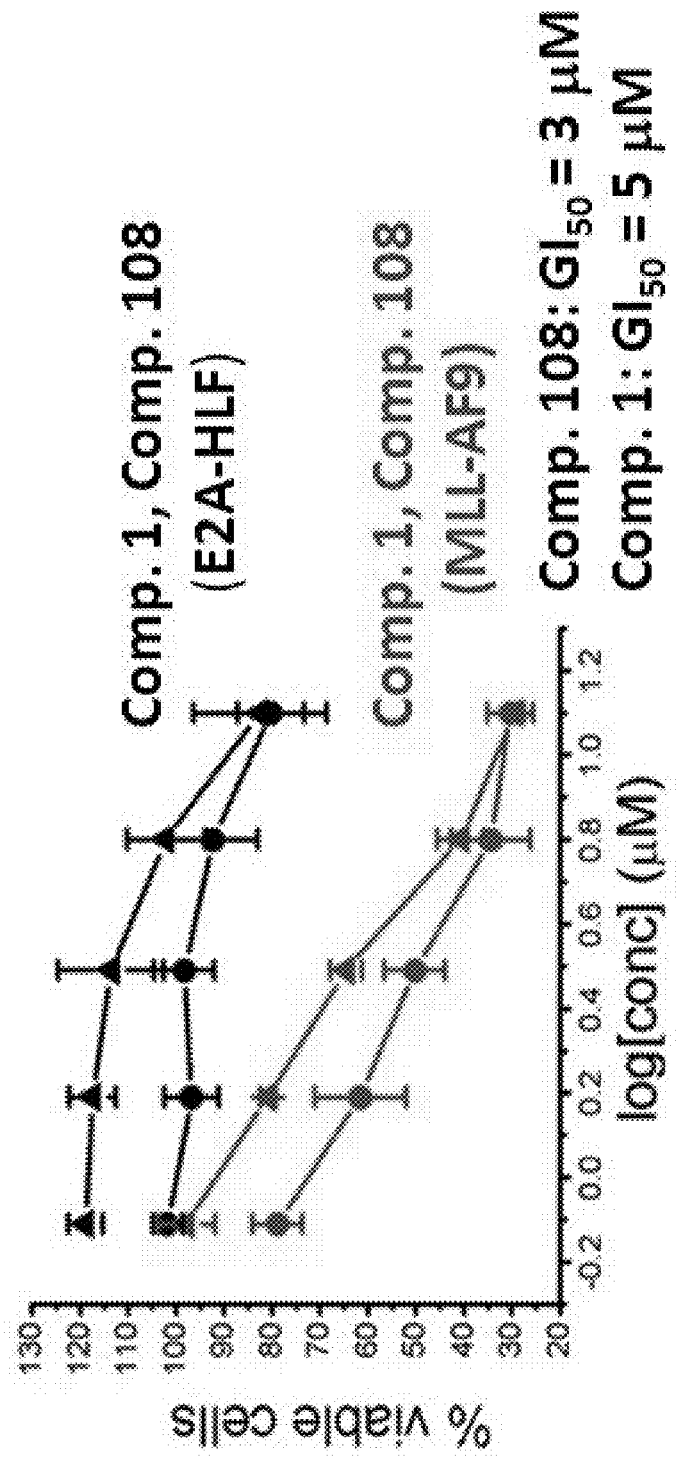
FIG. 3. Thienopyrimidine compounds selectively inhibit proliferation of MLL leukemia cells as shown in MTT cell viability assay performed for compounds 1 and 108 (72 h incubation time) in MLL-AF9 transformed mouse bone marrow cells (BMC) and in E2H-HLF transformed BMC, which were used as a negative control cell line.
Figure 4:
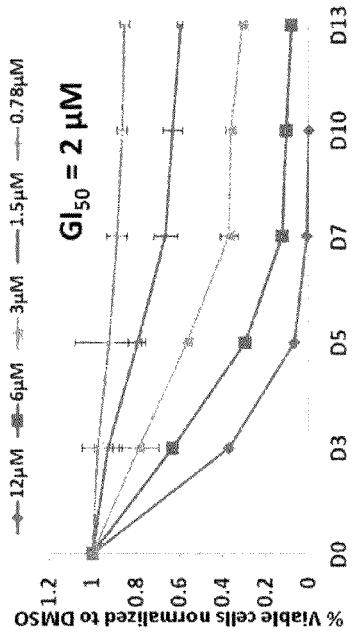
FIG. 4. Thienopyrimidine compounds inhibit growth of MLL-AF9 transformed BMC as demonstrated in the growth curves experiments.
Figure 4:
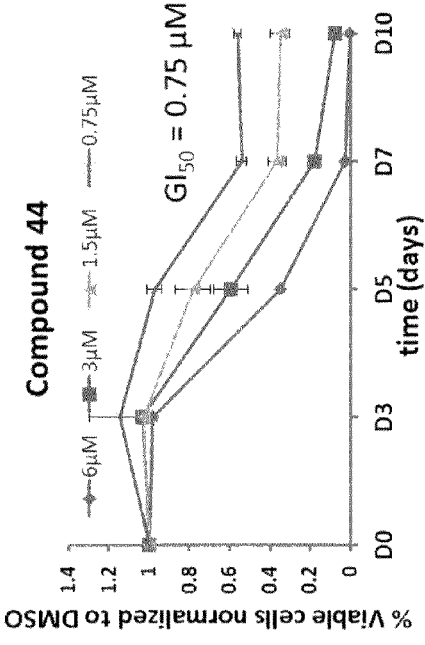
Figure 4:
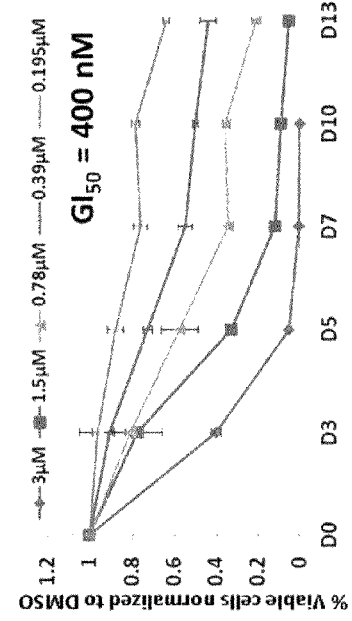
Figure 4:
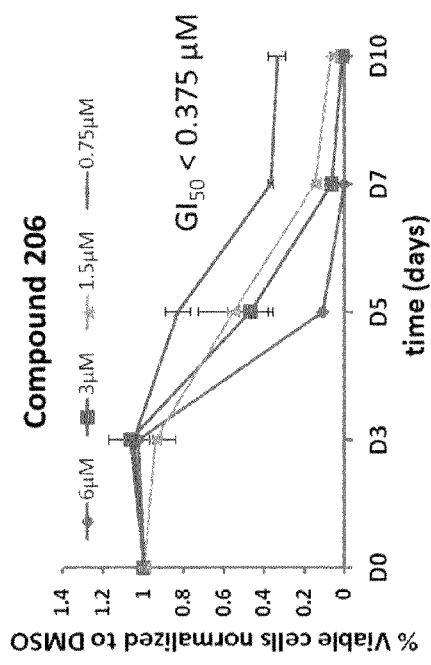
Figure 5:
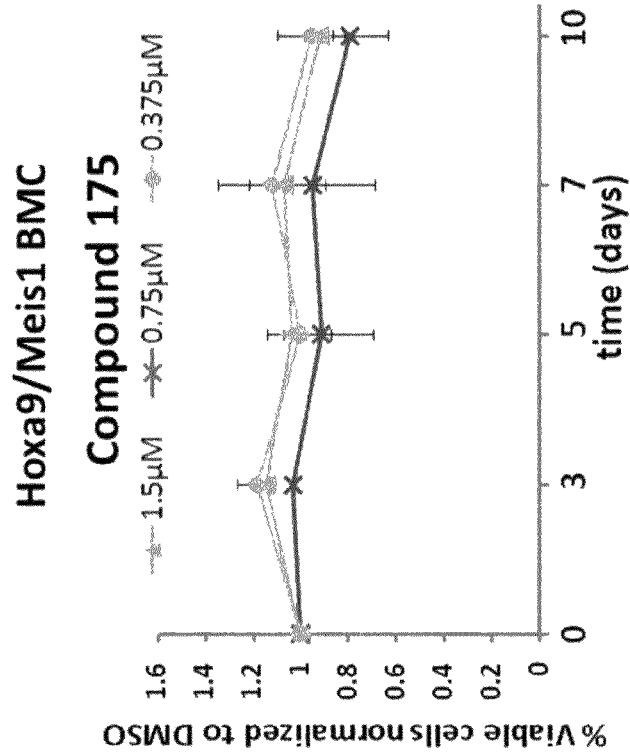
FIG. 5. Growth curves experiments performed for compound 175 in MLL-AF9 transformed BMC and Hoxa9/Meis1 transformed BMC (negative control cell line), showing great selectivity of the compound towards MLL fusion protein transformed cells.
Figure 5:
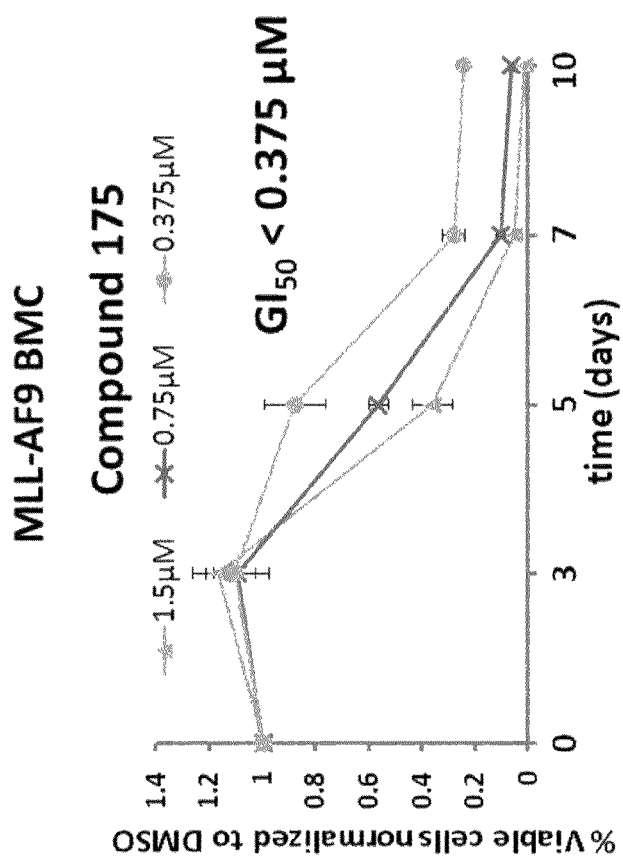
Figure 6:
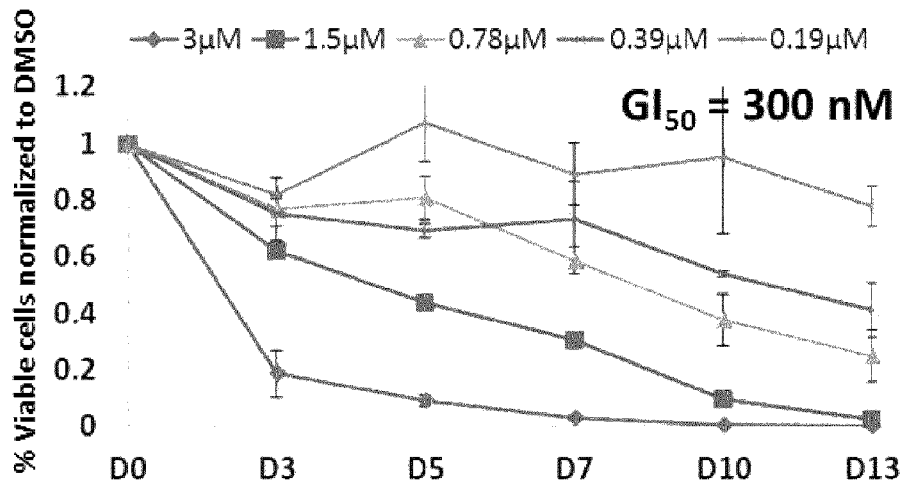
FIG. 6. Growth curves experiments performed for compound 175 in MLL-AF6 and MLL-GAS7 transformed BMC.
Figure 6:
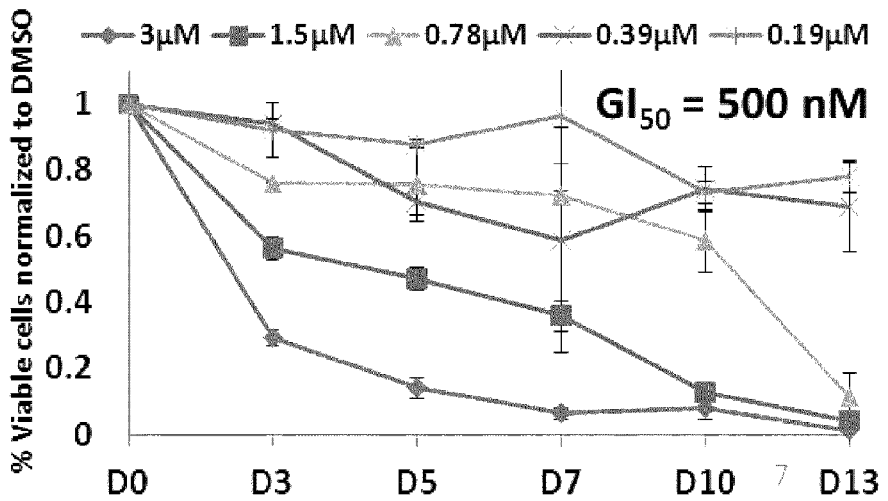
Figure 7:
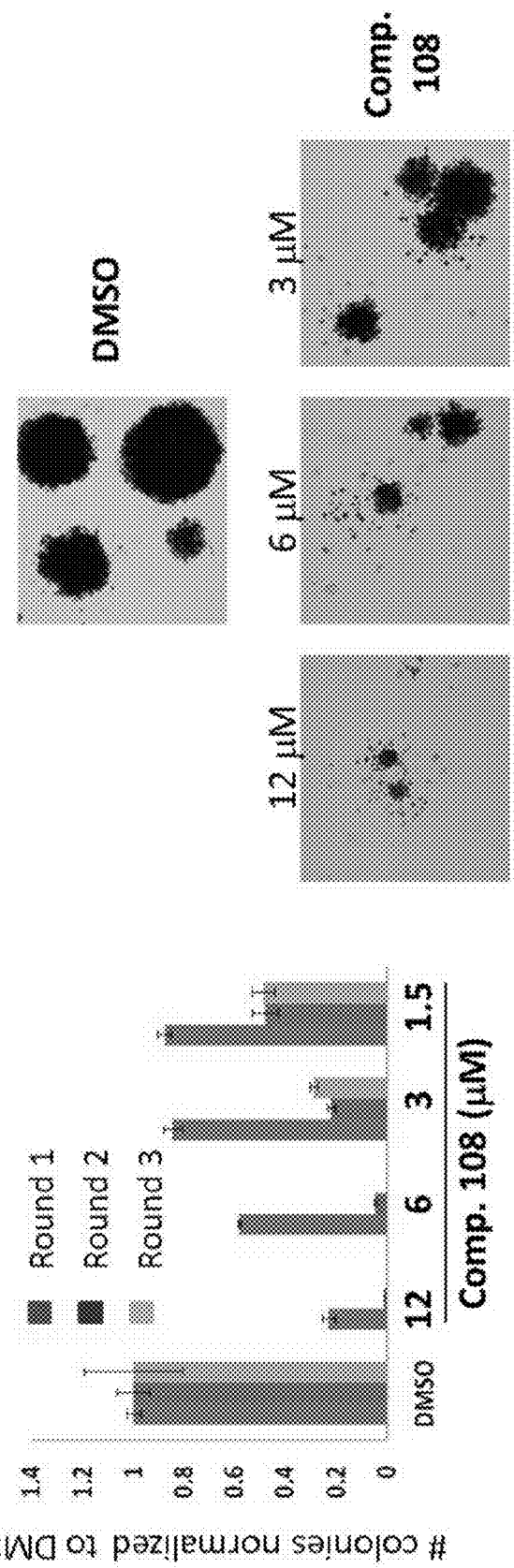
FIG. 7. Compound 108 reduces colony number (left) and changes morphology of colonies (right) as assessed in colony formation assay performed in MLL-AF9 BMC. Each round takes 7 days.
Figure 8:
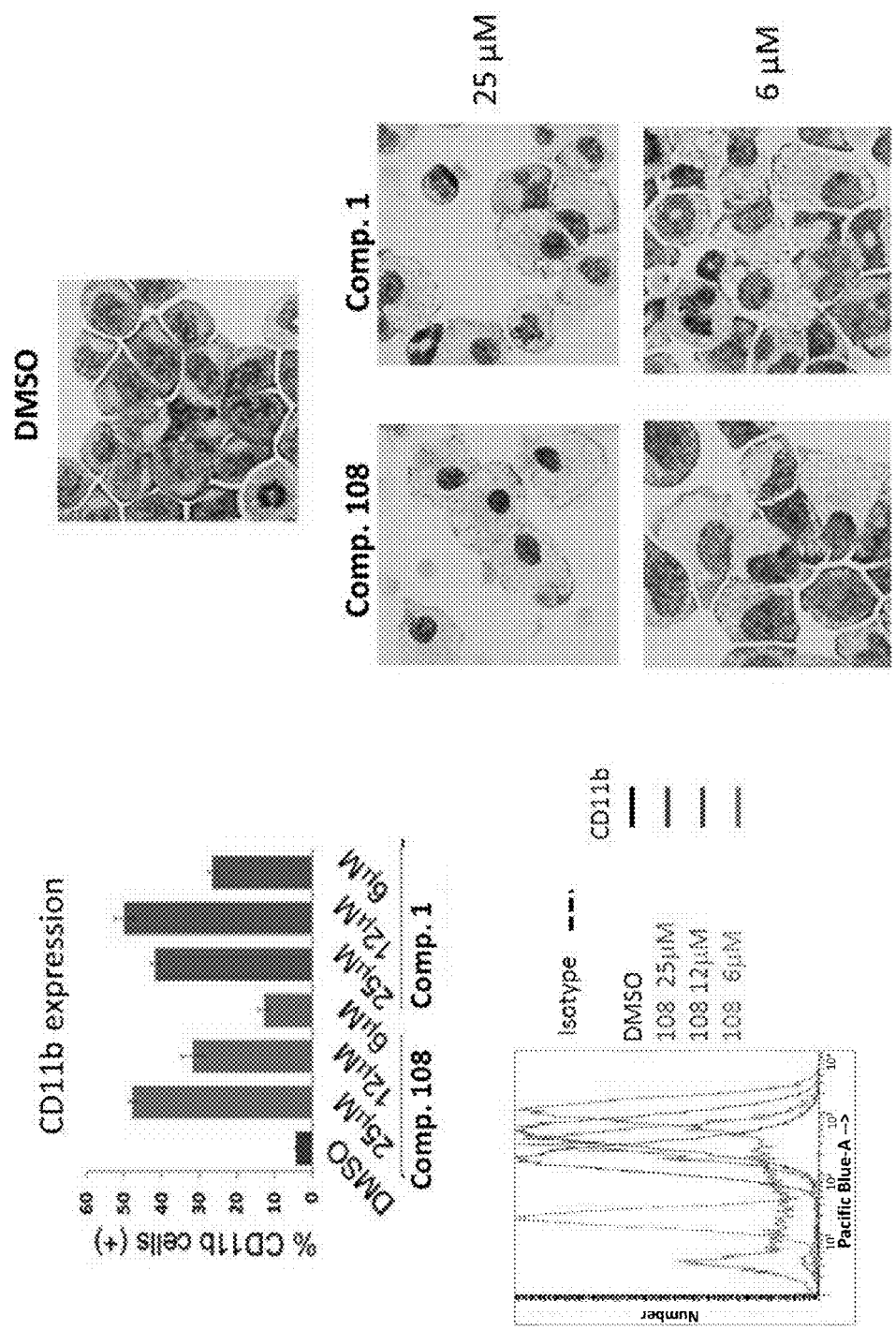
FIG. 8. Menin-MLL inhibitors induce differentiation in MLL-AF9 BMC as assessed by change in expression level of CD11b differentiation marker (left) and change in cell morphology (right).
Figure 9:
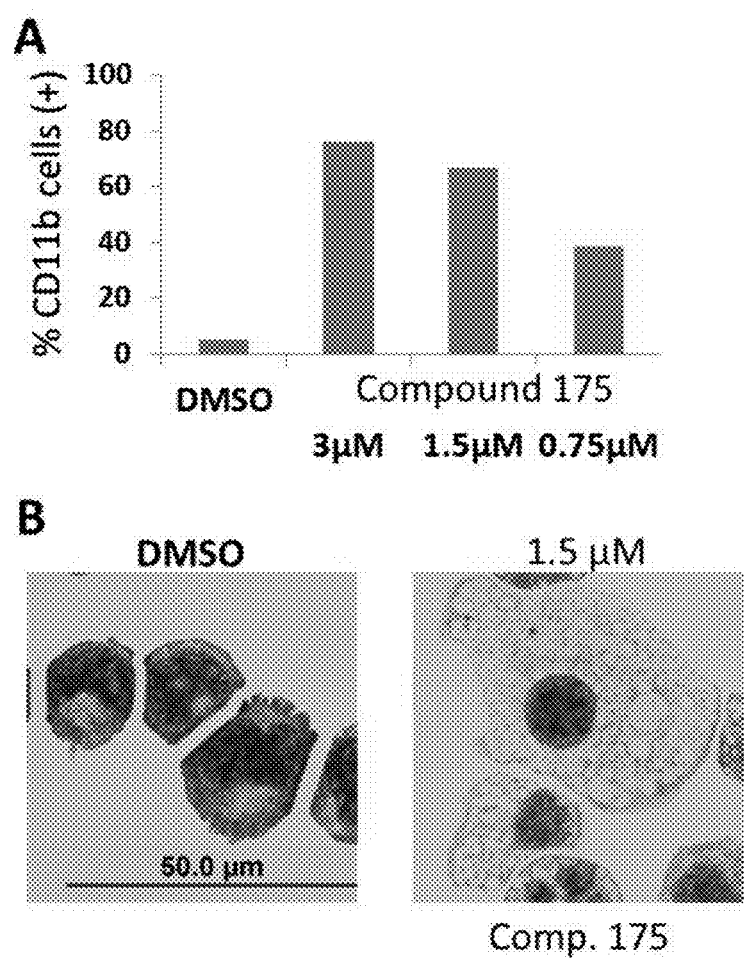
FIG. 9. Differentiation induced in MLL-AF9 BMC upon treatment with Compound 175: A. Change in expression level of CD11b, B. Change in cell morphology.
Figure 10:
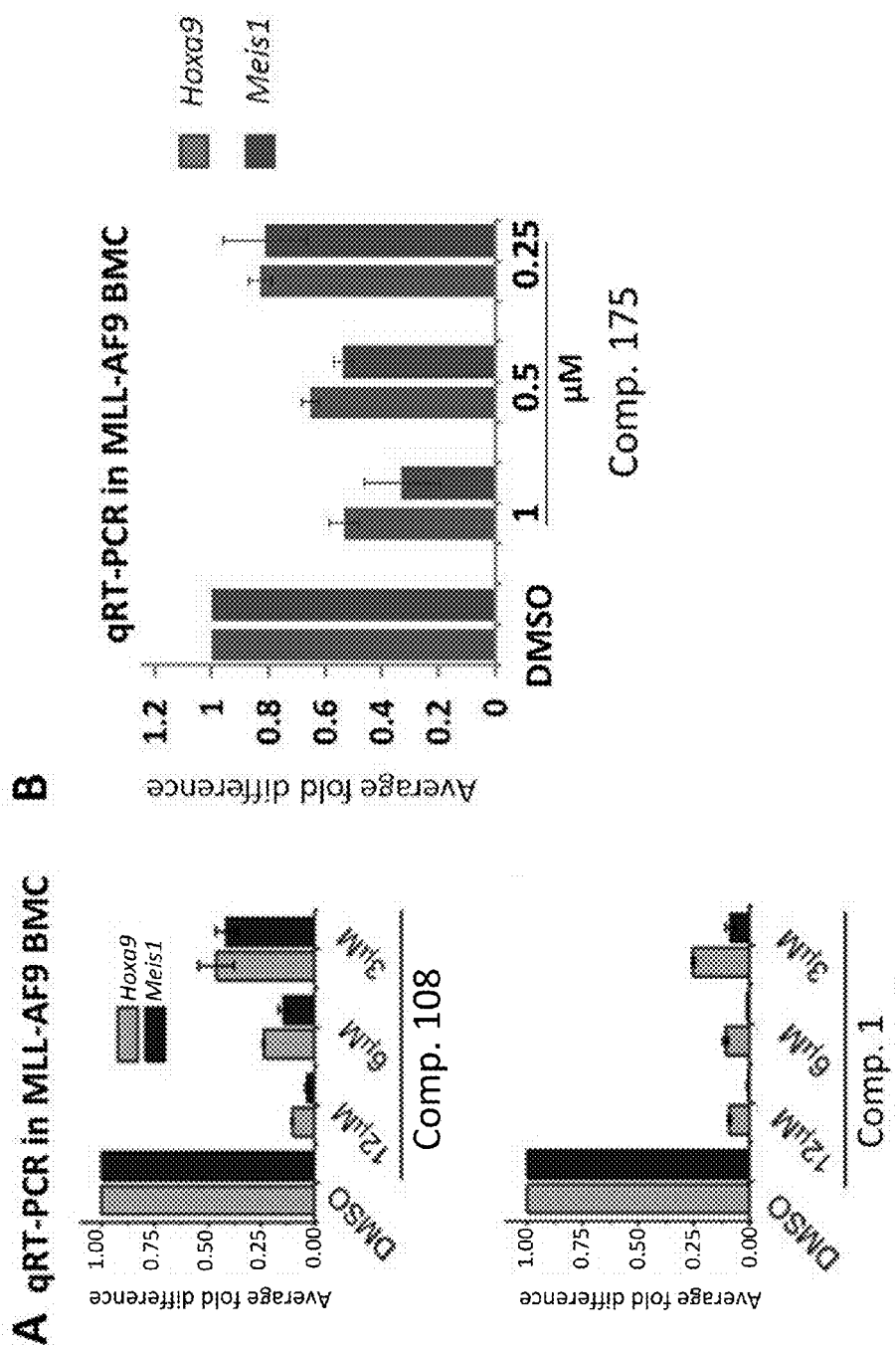
FIG. 10. Menin-MLL inhibitors downregulate expression of downstream targets of MLL fusion proteins: Hoxa9 and Meis1. A. qRT-PCR performed in MLL-AF9 BMC for Compounds 1 and 108. B. qRT-PCR performed in MLL-AF9 BMC for Compound 175.
Figure 11:
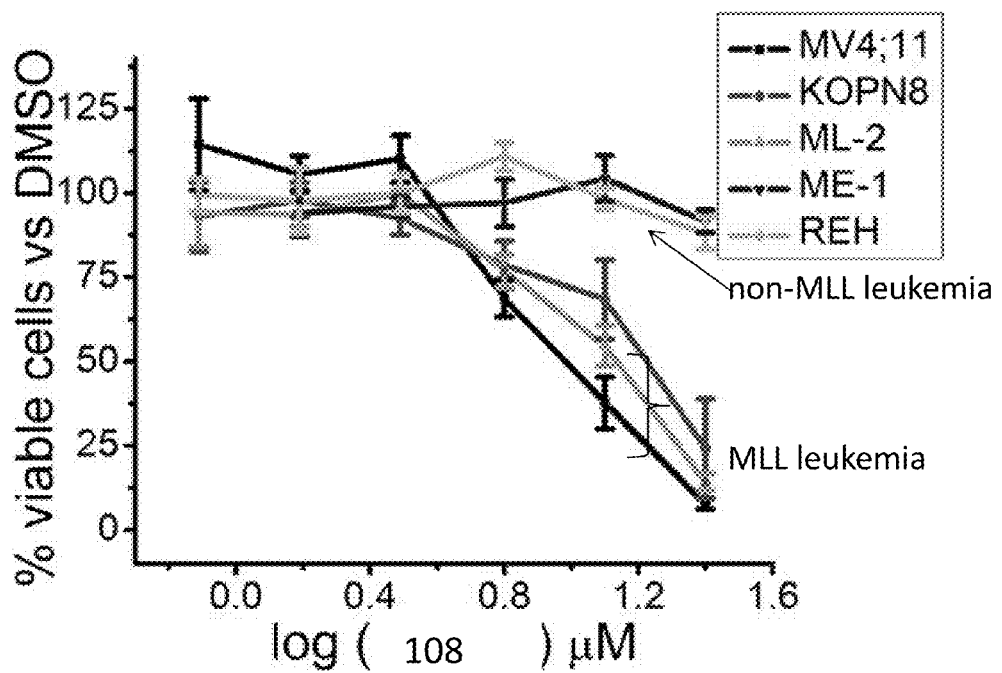
FIG. 11. Menin-MLL inhibitors selectively inhibit growth of human MLL leukemia cell lines as shown by MTT cell viability assay performed for Compound 108 after 3 days of incubation in different human leukemia cell lines.
Figure 12:
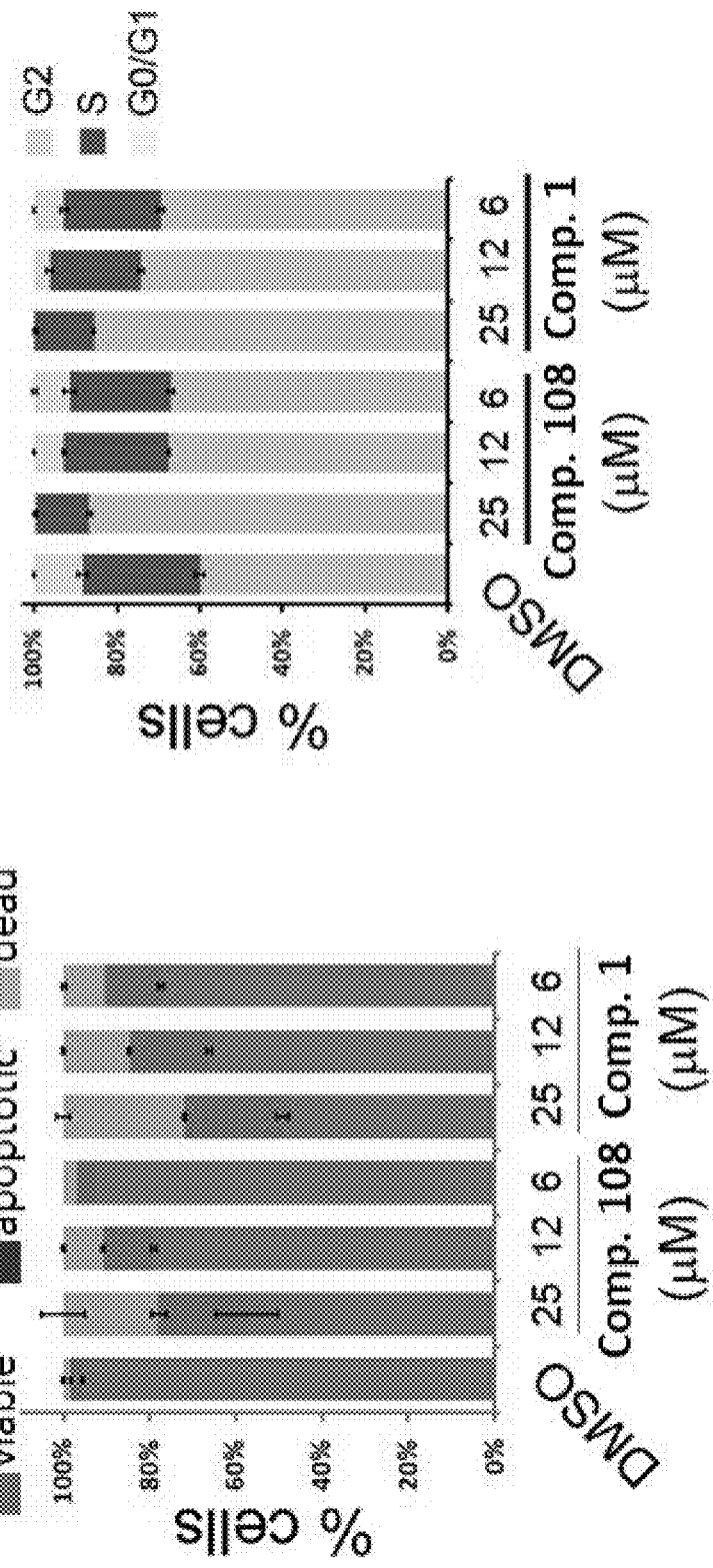
FIG. 12. Thienopyrimidine compounds induce apoptosis (A) and cell cycle arrest (B) in human MLL leukemia cell lines (e.g. MV4; 11 with MLL-AF4 translocation).
Figure 13:
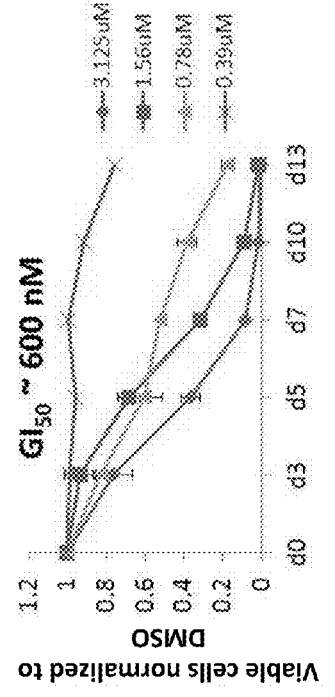
FIG. 13. Thienopyrimidine compound 175 selectively inhibits growth of human MLL leukemia cell lines (A) and has a limited effect in non-MLL leukemia cell lines (B).
Figure 13:
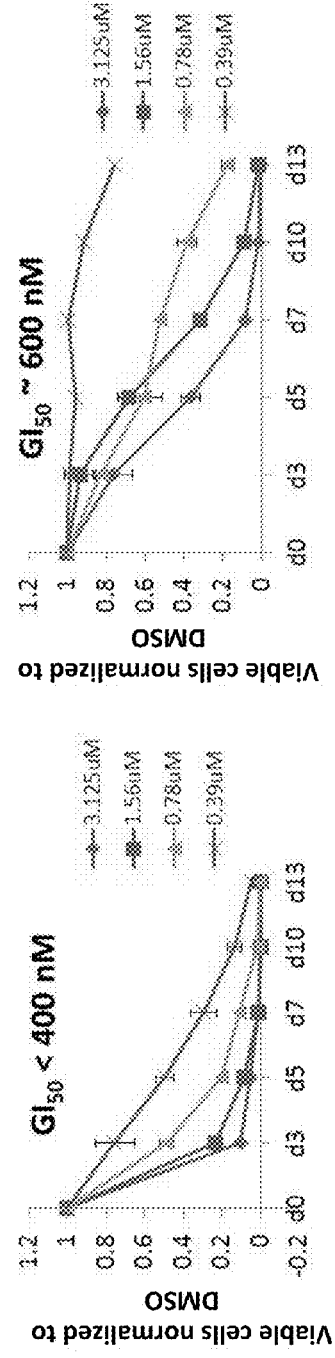
Figure 13:
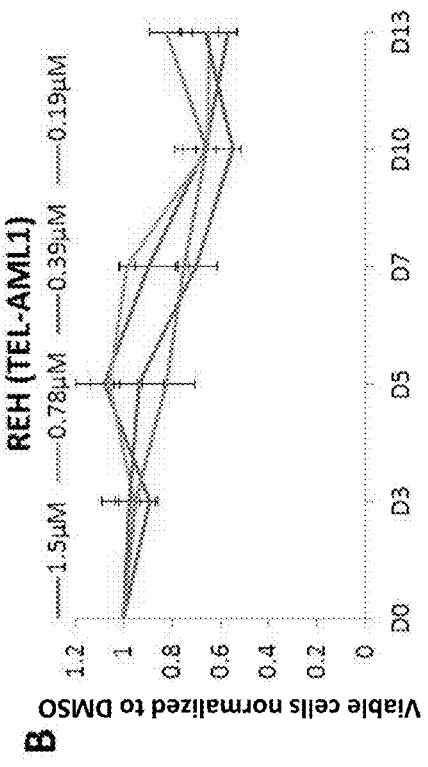
Figure 14:
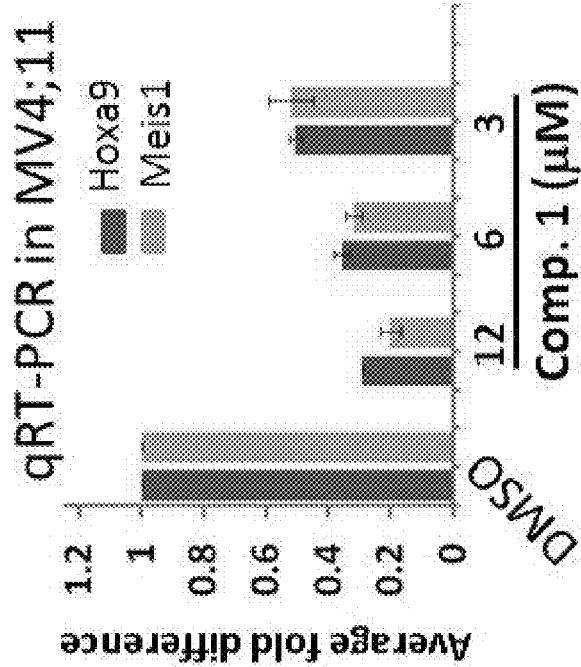
FIG. 14. Thienopyrimidine compounds downregulate expression of downstream targets of MLL fusion proteins (Hoxa9 and Meis1) in human MLL leukemia cell lines.
Figure 14:
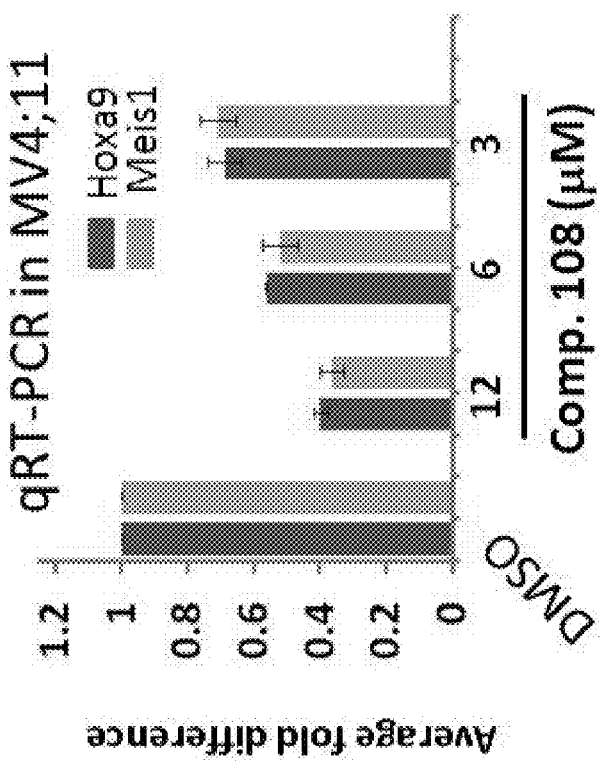
Figure 15:
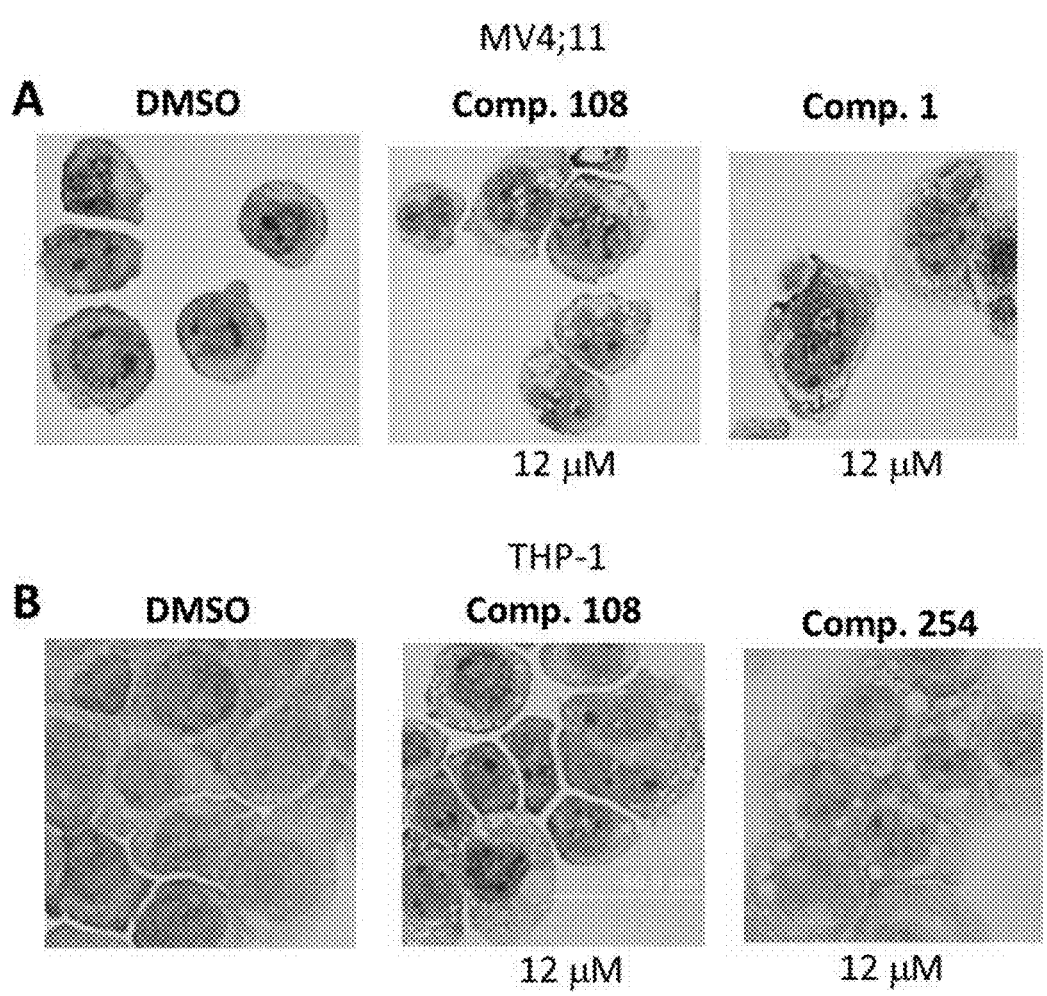
FIG. 15. Thienopyrimidine compounds induce differentiation in human MLL leukemia cell lines: MV4; 11 (A) and THP-1 (B).
Figure 16:
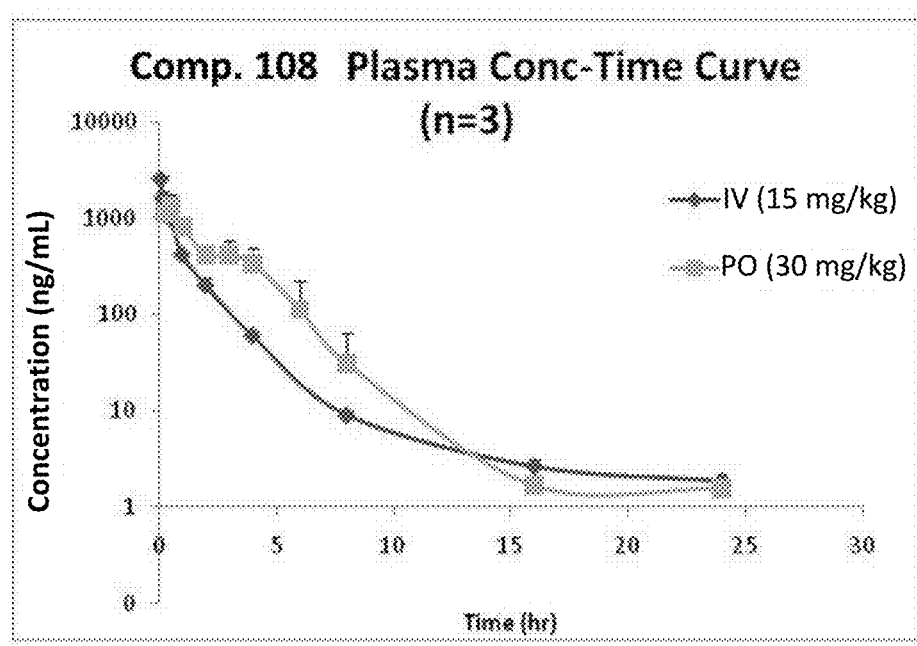
FIG. 16. Pharmacokinetic (PK) profile of compound 108 after oral (p.o.) and intravenous (i.v.) injections of the compound to mice.
Figure 17:
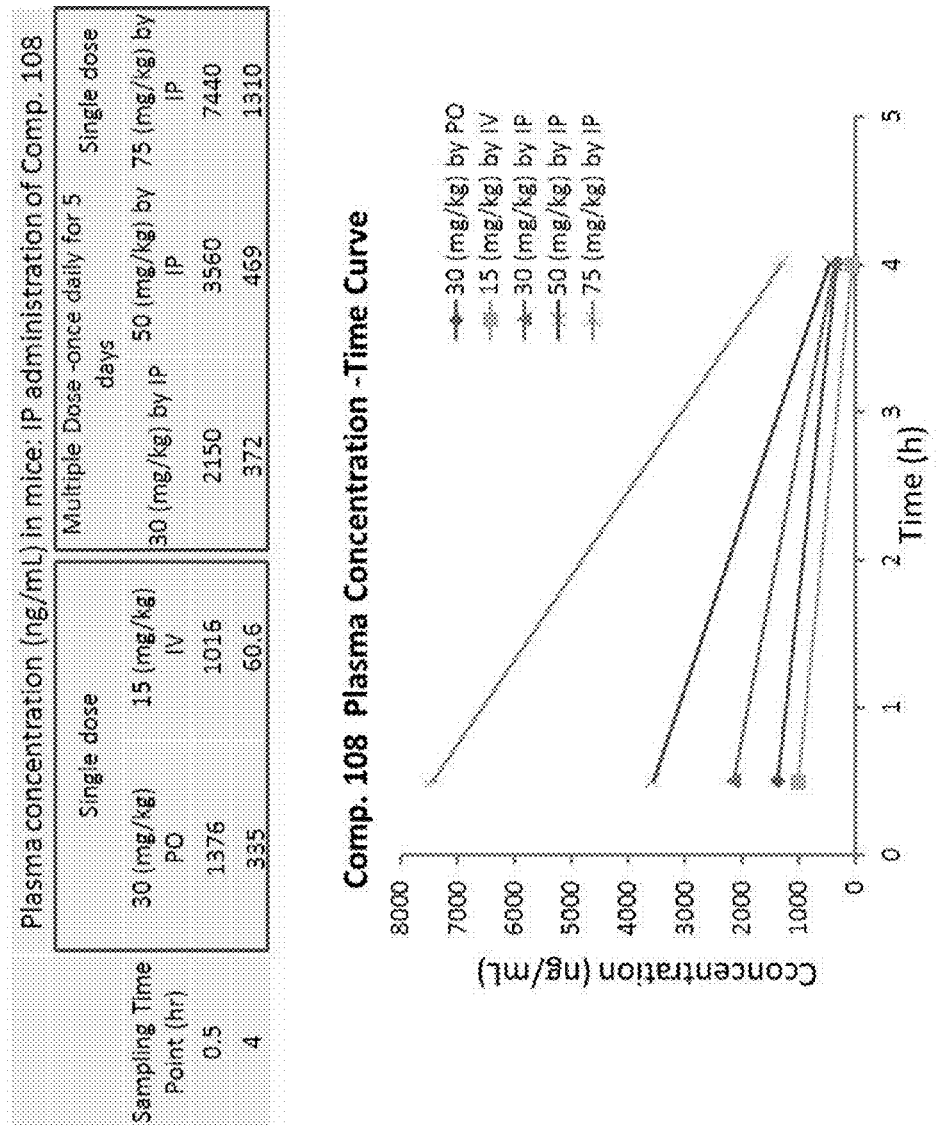
FIG. 17. MTD (Maximum Tolerated Dose) studies with compound 108 in mice after i.p. (intraperitoneal) injections of the compound.
Figure 18:
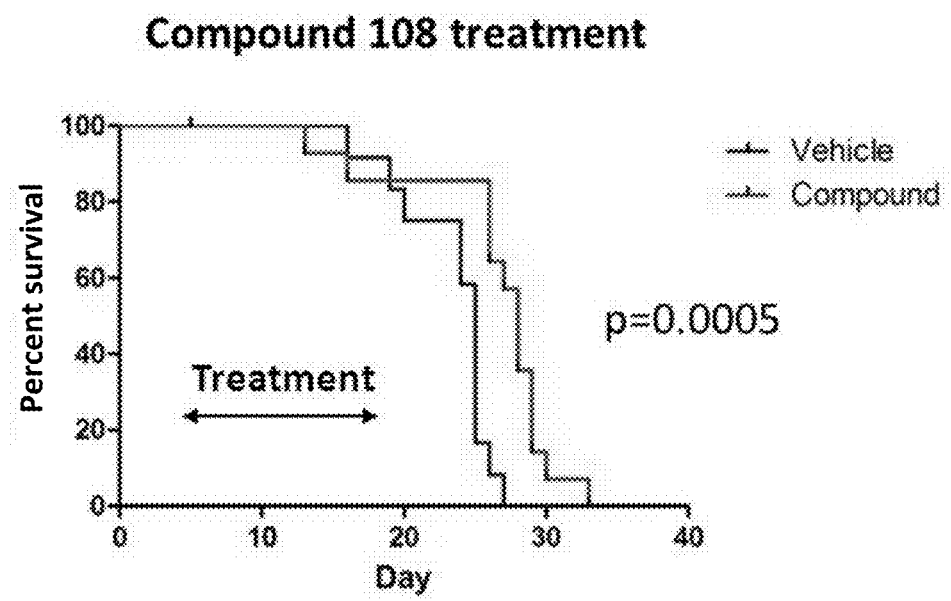
FIG. 18. In vivo efficacy studies with compound 108 in mice model of MLL-AF9 leukemia. Increase in survival of leukemic mice was observed after once daily i.p. injections of 75 mg/kg dose.
Figure 19:
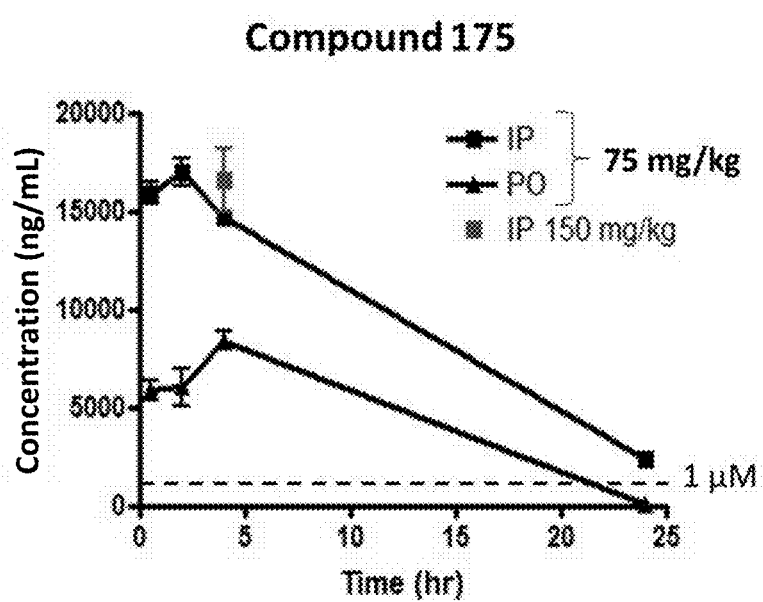
FIG. 19. PK profile in mice for compound 175 after i.p. and oral administration of the compound.

Biological activity of menin-MLL inhibitors is demonstrated in FIGS. 1-19. The $IC_{50}$ values shown in Tables 1-8 were measured using the above fluorescence polarization (FP) assay.

What is claimed is:

1. A compound of Formula 2:

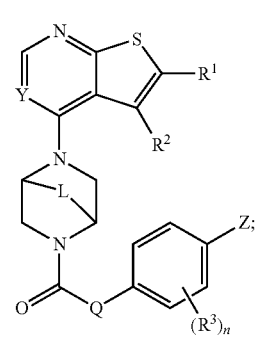

Formula 2 or a pharmaceutically acceptable salt thereof, wherein:

each of R¹ and R² is independently H, alkyl, substituted alkyl, alcohol, ether, amine, thioalkyl, halogen, ketone, carbocyclic ring, aryl, substituted aryl, heteroaryl, substituted heteroaryl, heterocycloalkyl, substituted heterocycloalkyl, thiol, disulfide, sulfoxide, or sulfone;

Y is N, C—H, or C—Rᵃ;

Rᵃ is alkyl, heteroalkyl, alkyl-substituted aryl, substituted alkyl, alcohol, ether, amino, cyano, aldehyde, heterocycloalkyl, or aromatic group;

L is alkylene, oxalkylene, or absent;

wherein when L is absent the bonds attached to L do not exist;

Q is alkylene or heteroalkylene;

each R³ is independently H, alkyl, substituted alkyl, alcohol, ether, amine, thioalkyl, halogen, ketone, carbocyclic ring, aryl, substituted aryl, heteroaryl, substituted heteroaryl, heterocycloalkyl, or substituted heterocycloalkyl;

n is 1, 2, 3, or 4; and

Z is CHR⁴SO₂R⁵ or —NR⁴SO₂R⁵, wherein R⁴ is H, alkyl, substituted alkyl, alcohol, ether, amine, or carbocyclic ring and R⁵ is H, alkyl, substituted alkyl, alcohol, ether, amine, thioalkyl, ketone, carbocyclic ring, aryl, substituted aryl, heteroaryl, substituted heteroaryl, heterocycloalkyl, or substituted heterocycloalkyl.

2. The compound or pharmaceutically acceptable salt of claim 1, wherein R¹ is alkyl or substituted alkyl.

3. The compound or pharmaceutically acceptable salt of claim 2, wherein R¹ is a halogen-substituted alkyl group.

4. The compound or pharmaceutically acceptable salt of claim 1, wherein R² is H, alkyl, substituted alkyl, halogen, alcohol, ether, or amine.

5. The compound or pharmaceutically acceptable salt of claim 4, wherein R² is H.

6. The compound or pharmaceutically acceptable salt of claim 1, wherein Y is N.

7. The compound or pharmaceutically acceptable salt of claim 1, wherein Y is C—Rᵃ.

8. The compound or pharmaceutically acceptable salt of claim 1, wherein L is absent.

9. The compound or pharmaceutically acceptable salt of claim 1, wherein Q is alkylene.

10. The compound or pharmaceutically acceptable salt of claim 9, wherein Q is C₁-C₅ alkylene.

11. The compound or pharmaceutically acceptable salt of claim 10, wherein Q is C₁ alkylene.

12. The compound or pharmaceutically acceptable salt of claim 1, wherein Q is heteroalkylene.

13. The compound or pharmaceutically acceptable salt of claim 1, wherein R³ is H, alkyl, haloalkyl, alcohol, ether, amine, halogen, or methyl-sulfonyl-amine.

14. The compound or pharmaceutically acceptable salt of claim 13, wherein R³ is H, alcohol, ether, or halogen.

15. The compound or pharmaceutically acceptable salt of claim 1, wherein n is 1.

16. The compound or pharmaceutically acceptable salt of claim 1, wherein n is 2, 3, or 4.

17. The compound or pharmaceutically acceptable salt of claim 1, comprising an R³ at an ortho position of a benzene ring.

18. The compound or pharmaceutically acceptable salt of claim 1, comprising an R³ at a meta position of a benzene ring.

19. The compound or pharmaceutically acceptable salt of claim 1, wherein Z is —CHR⁴SO₂R⁵ or —NR⁴SO₂R⁵, wherein R⁴ is H, alkyl, or substituted alkyl and R⁵ is H, alkyl, or substituted alkyl.

20. The compound or pharmaceutically acceptable salt of claim 19, wherein Y is N.

21. The compound or pharmaceutically acceptable salt of claim 20, wherein R¹ is alkyl or substituted alkyl.

22. The compound or pharmaceutically acceptable salt of claim 21, wherein R² is H, alkyl, substituted alkyl, halogen, alcohol, ether, or amine.

23. The compound or pharmaceutically acceptable salt of claim 1, wherein the compound is selected from:

Compound 43

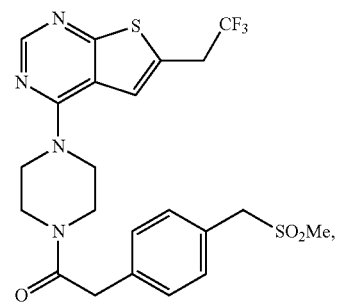

Compound 44

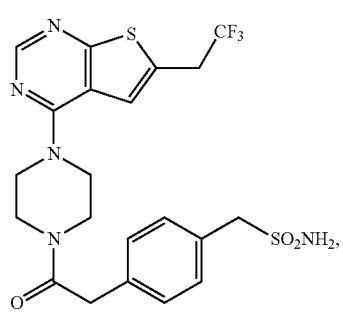

Compound 45

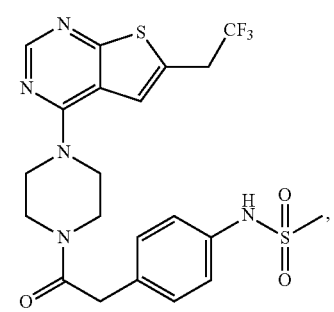

Compound 46

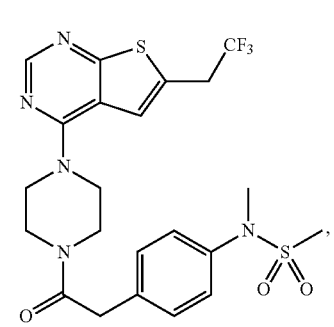

Compound 47

Compound 48

Compound 49

Compound 50

Compound 51

Compound 52

Compound 53

Compound 54

Compound 55

Compound 56
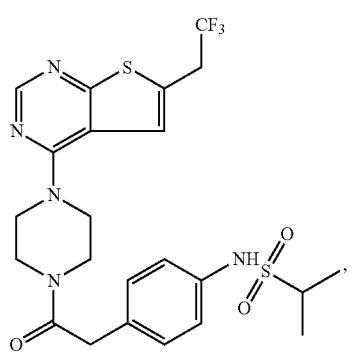
Compound 57
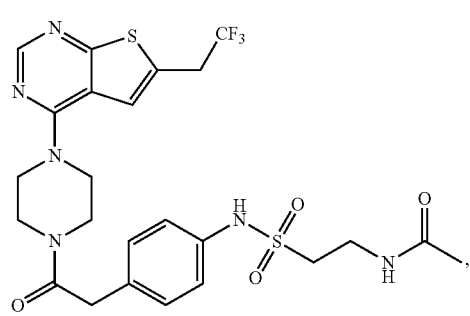
Compound 58
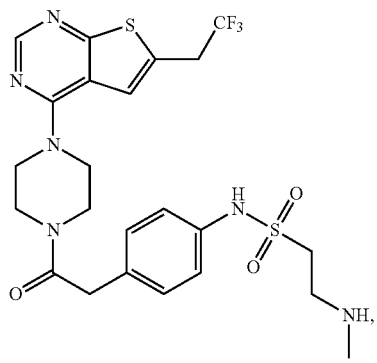
Compound 59
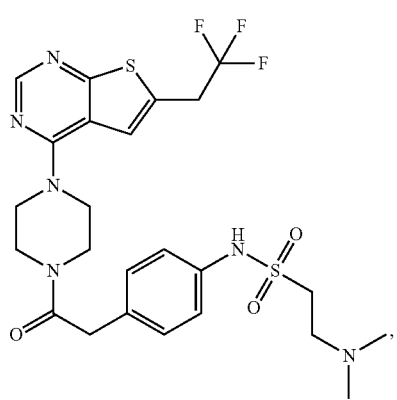
Compound 60
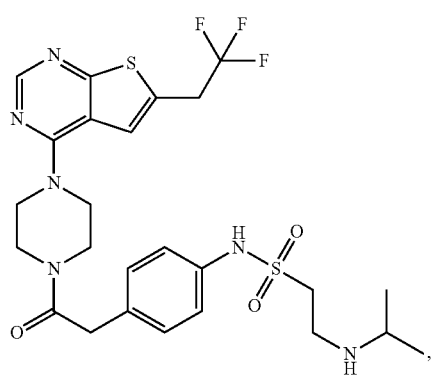
Compound 61
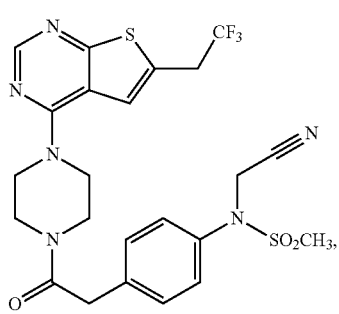
Compound 62
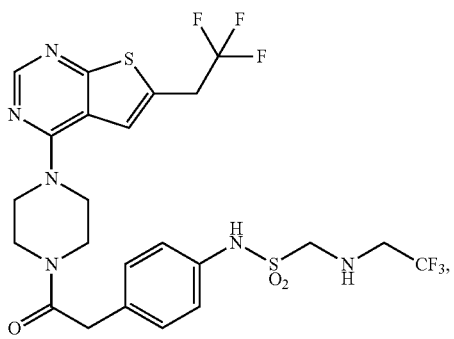
Compound 63
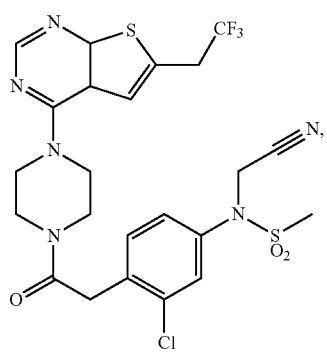

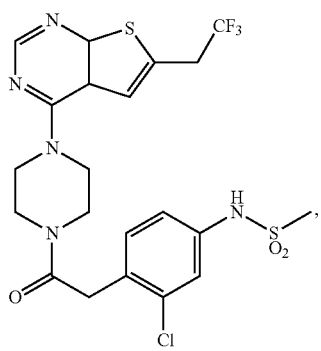
Compound 64
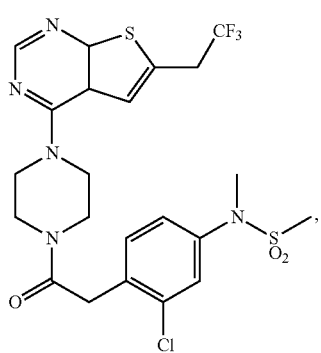
Compound 65
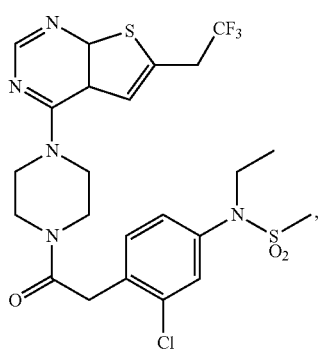
Compound 66
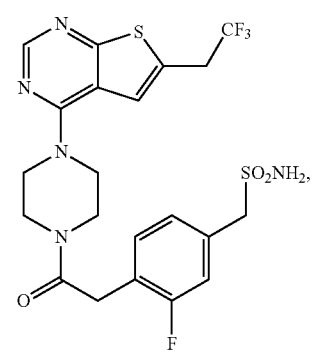
Compound 78
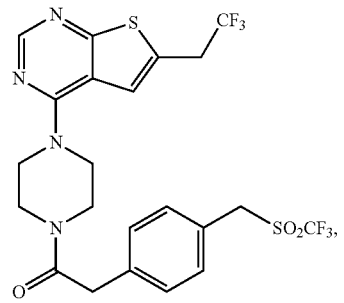
Compound 79
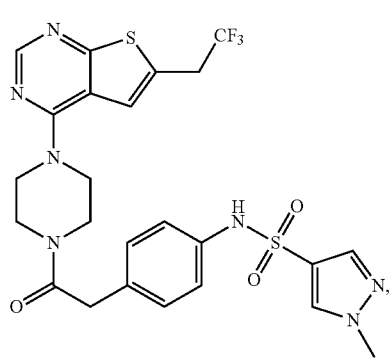
Compound 83
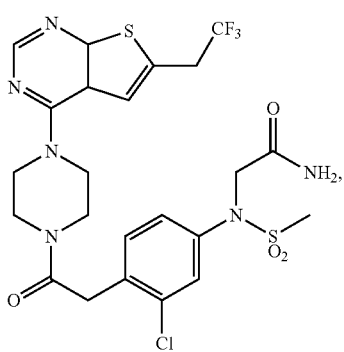
Compound 84
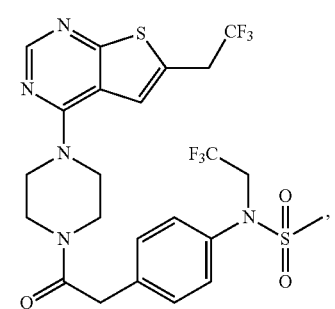
Compound 85
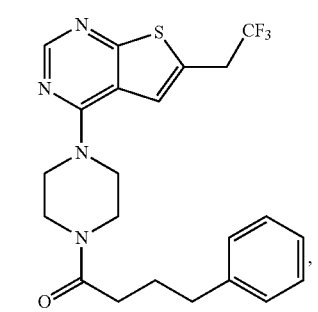
Compound 93

Compound 94

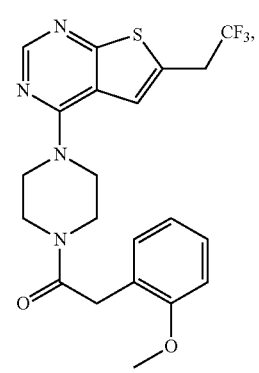

Compound 95

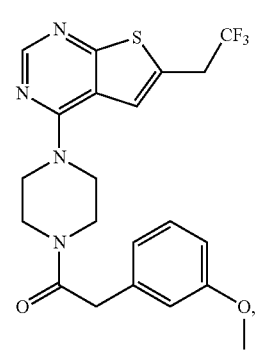

Compound 100

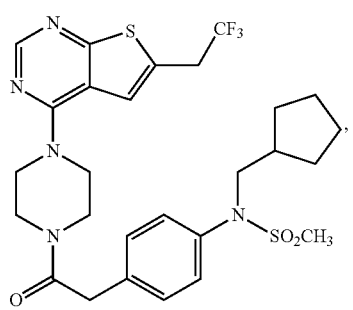

Compound 101

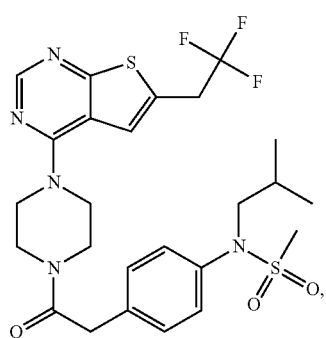

Compound 102

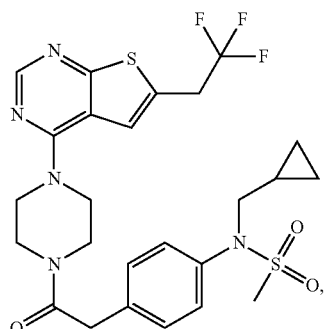

Compound 103

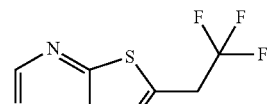 and

Compound 104

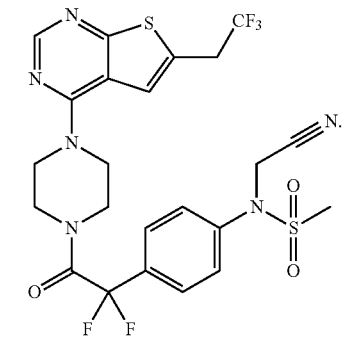

24. A method for the treatment of leukemia comprising administering the compound or pharmaceutically acceptable salt of claim 1 to a subject suffering from leukemia.

25. The method of claim 24, wherein said leukemia comprises AML or ALL.

26. A method of inhibiting the interaction of MLL and menin comprising administering the compound or pharmaceutically acceptable salt of claim 1 to a sample comprising MLL or MLL fusion protein and menin.

* * * * *

UNITED STATES PATENT AND TRADEMARK OFFICE
CERTIFICATE OF CORRECTION

PATENT NO. : 9,505,782 B2
APPLICATION NO. : 14/937421
DATED : November 29, 2016
INVENTOR(S) : Grembecka et al.

It is certified that error appears in the above-identified patent and that said Letters Patent is hereby corrected as shown below:

On the Title Page

Item (72), should be corrected to read:
Jolanta Grembecka, Ann Arbor, MI (US);
Tomasz Cierpicki, Ann Arbor, MI (US);
Dmitry Borkin, Ann Arbor, MI (US);
Jay L. Hess, Ann Arbor, MI (US);
Duxin Sun, Ann Arbor, MI (US);
Xiaoqin Li, Ann Arbor, MI (US);
Mohamed Ibrahim, Santa Clara, CA (US);
Artem Plekhov, Santa Clara, CA (US);
Kevin Greenman, Santa Clara, CA (US).

Signed and Sealed this
Twenty-fifth Day of October, 2022

Katherine Kelly Vidal
*Director of the United States Patent and Trademark Office*